(12) United States Patent
Liu et al.

(10) Patent No.: US 11,667,702 B2
(45) Date of Patent: *Jun. 6, 2023

(54) STABLE AQUEOUS FORMULATIONS OF AFLIBERCEPT

(71) Applicant: Coherus BioSciences Inc., Redwood City, CA (US)

(72) Inventors: Jun Liu, Redwood City, CA (US); Mark Manning, Redwood City, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/297,387

(22) Filed: Mar. 8, 2019

(65) Prior Publication Data

US 2019/0276528 A1    Sep. 12, 2019

Related U.S. Application Data

(60) Provisional application No. 62/640,411, filed on Mar. 8, 2018.

(51) Int. Cl.
| | | |
|---|---|---|
| *A61K 39/395* | (2006.01) | |
| *C07K 16/22* | (2006.01) | |
| *A61K 38/17* | (2006.01) | |
| *A61K 9/00* | (2006.01) | |
| *A61K 47/02* | (2006.01) | |
| *A61K 47/18* | (2017.01) | |
| *A61P 27/02* | (2006.01) | |
| *A61K 47/26* | (2006.01) | |
| *A61K 47/12* | (2006.01) | |
| *A61K 9/08* | (2006.01) | |
| *C07K 14/71* | (2006.01) | |
| *A61K 47/10* | (2017.01) | |

(52) U.S. Cl.
CPC ............ *C07K 16/22* (2013.01); *A61K 9/0019* (2013.01); *A61K 9/0048* (2013.01); *A61K 9/08* (2013.01); *A61K 38/179* (2013.01); *A61K 47/02* (2013.01); *A61K 47/10* (2013.01); *A61K 47/12* (2013.01); *A61K 47/183* (2013.01); *A61K 47/26* (2013.01); *A61P 27/02* (2018.01); *C07K 14/71* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,070,959 | B1 | 7/2006 | Papadopoulos |
| 7,425,542 | B2 | 9/2008 | Maggio |
| 7,608,261 | B2 | 10/2009 | Furfine |
| 7,807,164 | B2 | 10/2010 | Furfine |
| 7,998,927 | B2 | 8/2011 | Maggio |
| 8,084,022 | B2 | 12/2011 | Maggio |
| 8,092,803 | B2 | 1/2012 | Furfine |
| 8,226,949 | B2 | 7/2012 | Maggio |
| 8,349,321 | B2 | 1/2013 | Burke |
| 8,481,046 | B2 | 7/2013 | Furfine |
| 8,802,107 | B2 | 8/2014 | Furfine |
| 8,846,044 | B2 | 9/2014 | Maggio |
| 9,340,594 | B2 | 5/2016 | Furfine |
| 9,446,134 | B2 | 9/2016 | Maggio |
| 9,580,480 | B2 | 2/2017 | Lu |
| 9,580,489 | B2 | 2/2017 | Furfine |
| 10,046,025 | B2 | 8/2018 | Maggio |
| 11,426,446 | B2 | 8/2022 | Liu et al. |
| 2006/0210566 | A1 | 9/2006 | Holash |
| 2016/0144025 | A1 | 5/2016 | Vitti |
| 2018/0043020 | A1 | 2/2018 | Ogez |
| 2018/0325728 | A1 | 11/2018 | Weikart |
| 2019/0000919 | A1 | 1/2019 | Brockmeyer |
| 2020/0246423 | A1 | 8/2020 | Liu et al. |

FOREIGN PATENT DOCUMENTS

| | | |
|---|---|---|
| WO | WO 2006/104852 | 10/2006 |
| WO | WO 2007/149334 | 12/2007 |
| WO | WO 2016/196367 | 12/2016 |
| WO | WO 2016/208989 | 12/2016 |
| WO | WO 2017/087798 | 5/2017 |
| WO | WO 2017/177120 | 10/2017 |
| WO | WO 2018/063963 | 4/2018 |
| WO | WO 2018/194918 | 10/2018 |
| WO | WO 2018/217995 | 11/2018 |
| WO | WO 2018/218013 | 11/2018 |
| WO | WO 2019/055902 | 3/2019 |
| WO | WO 2019/099921 | 5/2019 |
| WO | WO 2019/173767 | 9/2019 |
| WO | WO 2020/055123 | 3/2020 |
| WO | WO 2020/087003 | 4/2020 |

OTHER PUBLICATIONS

Bahrenburg et al., Biotechnology Journal, vol. 10, pp. 610-622 (Year: 2015).*
Anonymous: "Zaltrap—aflibercept—Annex I Summary of Product Characteristics", Zaltrap—aflibercept—EMEA/H/C/002532-R/0037, Sep. 21, 2017, 45 pages, Retrieved from the Internet: URL:https://www.ema.europa.eu/en/documents/product-information/zaltrap-epar-productinformation_en.pdf [retrieved on May 27, 2019].
Holash et al., "VEGF-Trap: A VEGF blocker with potent antitumor effects," *Proc. Natl. Acad. Sci. U.S.A.* 99:11393-11398, 2002.
International Search Report and Written Opinion in Application No. PCT/US2019/021443, dated Jul. 24, 2019, 27 pages.
Jones, "Analysis of polypeptides and proteins," *Adv Drug Delivery Rev.* 10:29-90, 1993.

(Continued)

*Primary Examiner* — Yunsoo Kim
(74) *Attorney, Agent, or Firm* — Fish & Richardson P.C.

(57) ABSTRACT

A stable aqueous pharmaceutical formulation comprising a therapeutically effective amount of aflibercept, wherein the formulation is free of organic co-solvent and/or free of buffer; methods for making such a formulation; and methods of using such a formulation.

30 Claims, 46 Drawing Sheets
(46 of 46 Drawing Sheet(s) Filed in Color)

(56) References Cited

OTHER PUBLICATIONS

Merrifield, "Solid Phase Peptide Synthesis. I. The Synthesis of a Tetrapeptide," *J. Am. Chem. Soc.* 85:2149-2154, 1963.

Pożarowska et al., "The era of anti-vascular endothelial growth factor (VEGF) drugs in ophthalmology, VEGF and anti-VEGF therapy," *Cent. Eur. J. Immunol.* 41(3):311-316, 2016.

Vincent Lee, "Peptide and Protein Drug Delivery," pp. 247-301, New York, NY, 1991.

Wang et al., "Antibody Structure, Instability, and Formulation," *J. Pharm. Sci.* 96(1):1-26, 2007.

Wang et al., "Instability, stabilization, and formulation of liquid protein pharmaceuticals," *Int. J. Pharm.* 185(2):129-188, 1999.

PCT International Preliminary Report on Patentability in International Appln. No. PCT/US2019/021443, dated Sep. 17, 2020, 17 Pages.

Bodratti et al., "Formulation of Poloxamers for Drug Delivery", J Funct Biomater., Mar. 2018, 9(1):11, 24 pages.

Giannos et al., "Formulation stabilization and disaggregation of bevacizumab, ranibizumab and aflibercept in dilute solutions," Pharmaceutical research, Apr. 1, 2018, 35(4):78 pp. 1-15.

PCT International Search Report and Written Opinion in International Appln. No. PCT/US2020/050141, dated Feb. 3, 2021, 23 pages.

PCT Invitation to Pay Additional Fees in International Appln. No. PCT/US2020/050141, date Nov. 27, 2020, 19 Pages.

socratic.org [online], Anonymous: "What are amino acids? How can an amino acid act as buffer," Jan. 1, 2019, retrieved on Dec. 18, 2020, retrieved from URL:https://socratic.org/questions/what-are-amino-acids-how-can-an-amino-acid-act-as-buffer-.

Sharma et al., "Biosimilars in ophthalmology: "Is there a big change on the horizon?"" Clinical ophthalmology, 2018, 12:2137, 7 pages.

\* cited by examiner

STABLE AQUEOUS FORMULATIONS OF AFLIBERCEPT

CROSS-REFERENCE TO RELATED APPLICATIONS

This application claims priority to U.S. Provisional Patent Application Ser. No. 62/640,411, filed Mar. 8, 2018; the entire contents of which are herein incorporated by reference.

FIELD OF THE INVENTION

The present invention relates to stable aqueous pharmaceutical compositions of aflibercept, including compositions that are considered or intended to be a "biosimilar" of commercially available aflibercept products, methods of manufacture of the compositions, methods of their administration, and kits containing the same.

BACKGROUND OF THE INVENTION

Vascular endothelial growth factor (VEGF) and its receptors (VEGFR) regulates angiogenesis. Drugs that target VEGF-VEGFR interactions have demonstrated efficacy in treating ocular diseases. See Pożarowska et al. (2016) Cent Eur J Immunol 41(3): 311-316. A soluble VEGF-specific fusion protein antagonist, termed a "VEGF trap" was developed that interferes with binding of VEGF with its receptors. See, Holash et al. (2002) Proc. Natl. Acad. Sci. USA 99:11393-8.

Aflibercept, developed by Regeneron Pharmaceuticals, Inc. is a 115 kDa recombinant fusion protein. It consists of an IgG backbone fused to extracellular Vascular Endothelial Growth Factor receptor sequences of the human VEGFR1 and VEGFR2 receptors. Aflibercept is a soluble decoy receptor that binds vascular endothelial growth factor-A (VEGF-A), VEGF-B, and placental growth factor (PlGF) with a greater affinity than the body's native receptors. Aflibercept's high affinity for VEGF prevents the subsequent binding and activation of native VEGF receptors. Reduced VEGF activity leads to decreased angiogenesis and vascular permeability. Inhibition of VEGF-B may also aid in the treatment of angiogenic conditions. VEGF-B overexpression has recently been connected with breakdown of the blood-retinal battier retinal angiogenesis. Aflibercept products have been approved by the FDA and are commercially available under the brand names of Eylea® and Zaltrap®.

Various formulations of aflibercept are known in the art. See, for example, Eylea®, Zaltrap®, U.S. Pat. Nos. 7,608,261; 7,807,164; 8,092,803; 8,481,046; 8,802,107; 9,340,594; and 9,580,489. There is still need for stable liquid formulations of aflibercept suitable for ophthalmic administration.

BRIEF SUMMARY OF THE INVENTION

The invention provides stable aqueous formulations comprising aflibercept.

In general, the invention provides several types of aflibercept formulations: buffer-free formulations; formulations free of an organic co-solvent; and formulations that are free of both buffers and organic co-solvents.

In all embodiments of the invention, aflibercept can be present at concentrations of about 1 mg/mL to about 200 mg/mL, e.g., a concentration of about 1 mg/mL to about 190 mg/mL, about 1 mg/mL to about 180 mg/mL, about 1 mg/mL to about 170 mg/mL, about 1 mg/mL to about 160 mg/mL, about 1 mg/mL to about 150 mg/mL, about 1 mg/mL to about 140 mg/mL, about 1 mg/mL to about 130 mg/mL, about 1 mg/mL to about 120 mg/mL, about 1 mg/mL to about 110 mg/mL, about 1 mg/mL to about 100 mg/mL, about 1 mg/mL to about 90 mg/mL, about 1 mg/mL to about 80 mg/mL, about 1 mg/mL to about 70 mg/mL, about 1 mg/mL to about 60 mg/mL, about 1 mg/mL to about 50 mg/mL, about 1 mg/mL to about 45 mg/mL, about 1 mg/mL to about 40 mg/mL, about 1 mg/mL to about 35 mg/mL, about 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 8 mg/mL, about 1 mg/mL to about 6 mg/mL, about 1 mg/mL to about 4 mg/mL, about 1 mg/mL to about 2 mg/mL, about 2 mg/mL to about 200 mg/mL, about 2 mg/mL to about 190 mg/mL, about 2 mg/mL to about 180 mg/mL, about 2 mg/mL to about 170 mg/mL, about 2 mg/mL to about 160 mg/mL, about 2 mg/mL to about 150 mg/mL, about 2 mg/mL to about 140 mg/mL, about 2 mg/mL to about 130 mg/mL, about 2 mg/mL to about 120 mg/mL, about 2 mg/mL to about 110 mg/mL, about 2 mg/mL to about 100 mg/mL, about 2 mg/mL to about 90 mg/mL, about 2 mg/mL to about 80 mg/mL, about 2 mg/mL to about 70 mg/mL, about 2 mg/mL to about 60 mg/mL, about 2 mg/mL to about 50 mg/mL, about 2 mg/mL to about 45 mg/mL, about 2 mg/mL to about 40 mg/mL, about 2 mg/mL to about 35 mg/mL, about 2 mg/mL to about 30 mg/mL, about 2 mg/mL to about 25 mg/mL, about 2 mg/mL to about 20 mg/mL, about 2 mg/mL to about 15 mg/mL, about 2 mg/mL to about 10 mg/mL, about 2 mg/mL to about 8 mg/mL, about 2 mg/mL to about 6 mg/mL, about 2 mg/mL to about 4 mg/mL, about 4 mg/mL to about 200 mg/mL, about 4 mg/mL to about 190 mg/mL, about 4 mg/mL to about 180 mg/mL, about 4 mg/mL to about 170 mg/mL, about 4 mg/mL to about 160 mg/mL, about 4 mg/mL to about 150 mg/mL, about 4 mg/mL to about 140 mg/mL, about 4 mg/mL to about 130 mg/mL, about 4 mg/mL to about 120 mg/mL, about 4 mg/mL to about 110 mg/mL, about 4 mg/mL to about 100 mg/mL, about 4 mg/mL to about 90 mg/mL, about 4 mg/mL to about 80 mg/mL, about 4 mg/mL to about 70 mg/mL, about 4 mg/mL to about 60 mg/mL, about 4 mg/mL to about 50 mg/mL, about 4 mg/mL to about 45 mg/mL, about 4 mg/mL to about 40 mg/mL, about 4 mg/mL to about 35 mg/mL, about 4 mg/mL to about 30 mg/mL, about 4 mg/mL to about 25 mg/mL, about 4 mg/mL to about 20 mg/mL, about 4 mg/mL to about 15 mg/mL, about 4 mg/mL to about 10 mg/mL, about 4 mg/mL to about 8 mg/mL, about 4 mg/mL to about 6 mg/mL, about 6 mg/mL to about 200 mg/mL, about 6 mg/mL to about 190 mg/mL, about 6 mg/mL to about 180 mg/mL, about 6 mg/mL to about 170 mg/mL, about 6 mg/mL to about 160 mg/mL, about 6 mg/mL to about 150 mg/mL, about 6 mg/mL to about 140 mg/mL, about 6 mg/mL to about 130 mg/mL, about 6 mg/mL to about 120 mg/mL, about 6 mg/mL to about 110 mg/mL, about 6 mg/mL to about 100 mg/mL, about 6 mg/mL to about 90 mg/mL, about 6 mg/mL to about 80 mg/mL, about 6 mg/mL to about 70 mg/mL, about 6 mg/mL to about 60 mg/mL, about 6 mg/mL to about 50 mg/mL, about 6 mg/mL to about 45 mg/mL, about 6 mg/mL to about 40 mg/mL, about 6 mg/mL to about 35 mg/mL, about 6 mg/mL to about 30 mg/mL, about 6 mg/mL to about 25 mg/mL, about 6 mg/mL to about 20 mg/mL, about 6 mg/mL to about 15 mg/mL, about 6 mg/mL to about 10 mg/mL, about 6 mg/mL to about 8 mg/mL, about 8 mg/mL to about 200 mg/mL, about 8 mg/mL to about 190 mg/mL, about 8 mg/mL to about 180 mg/mL, about 8 mg/mL to about 170 mg/mL, about 8 mg/mL to about 160 mg/mL, about 8 mg/mL to about 150 mg/mL, about 8 mg/mL to about 140 mg/mL, about 8 mg/mL to about 130 mg/mL, about 8 mg/mL to about 120 mg/mL, about 8 mg/mL to about 110 mg/mL, about 8 mg/mL to about 100 mg/mL, about 8 mg/mL to about 90 mg/mL, about 8 mg/mL to about 80 mg/mL, about 8 mg/mL to about 70 mg/mL, about 8 mg/mL to about 60 mg/mL, about 8 mg/mL to about 50 mg/mL, about 8 mg/mL to about 45 mg/mL, about 8 mg/mL to about 40 mg/mL, about 8 mg/mL to about 35 mg/mL, about 8 mg/mL to about 30 mg/mL, about 8 mg/mL to about 25 mg/mL, about 8 mg/mL to about 20 mg/mL, about 8 mg/mL to about 15 mg/mL, about 8 mg/mL to about 10 mg/mL, about 10 mg/mL to about 200 mg/mL, about 10 mg/mL to about 190 mg/mL, about 10 mg/mL to about 180 mg/mL, about 10 mg/mL to about 170 mg/mL, about 10 mg/mL to about 160 mg/mL, about 10 mg/mL to about 150 mg/mL, about 10 mg/mL to about 140 mg/mL, about 10 mg/mL to about 130 mg/mL, about 10 mg/mL to about 120 mg/mL, about 10 mg/mL to about 110 mg/mL, about 10 mg/mL to about 100 mg/mL, about 10 mg/mL to about 90 mg/mL, about 10 mg/mL to about 80 mg/mL, about 10 mg/mL to about 70 mg/mL, about 10 mg/mL to about 60 mg/mL, about 10 mg/mL to about 50 mg/mL, about 10 mg/mL to about 45 mg/mL, about 10 mg/mL to about 40 mg/mL, about 10 mg/mL to about 35 mg/mL, about 10 mg/mL to about 30 mg/mL, about 10 mg/mL to about 25 mg/mL, about 10 mg/mL to about 20 mg/mL, about 10 mg/mL to about 15 mg/mL, about 15 mg/mL to about 200 mg/mL, about 15 mg/mL to about 190 mg/mL, about 15 mg/mL to about 180 mg/mL, about 15 mg/mL to about 170 mg/mL, about 15 mg/mL to about 160 mg/mL, about 15 mg/mL to about 150 mg/mL, about 15 mg/mL to about 140 mg/mL, about 15 mg/mL to about 130 mg/mL, about 15 mg/mL to about 120 mg/mL, about 15 mg/mL to about 110 mg/mL, about 15 mg/mL to about 100 mg/mL, about 15 mg/mL to about 90 mg/mL, about 15 mg/mL to about 80 mg/mL, about 15 mg/mL to about 70 mg/mL, about 15 mg/mL to about 60 mg/mL, about 15 mg/mL to about 50 mg/mL, about 15 mg/mL to about 45 mg/mL, about 15 mg/mL to about 40 mg/mL, about 15 mg/mL to about 35 mg/mL, about 15 mg/mL to about 30 mg/mL, about 15 mg/mL to about 25 mg/mL, about 15 mg/mL to about 20 mg/mL, about 20 mg/mL to about 200 mg/mL, about 20 mg/mL to about 190 mg/mL, about 20 mg/mL to about 180 mg/mL, about 20 mg/mL to about 170 mg/mL, about 20 mg/mL to about 160 mg/mL, about 20 mg/mL to about 150 mg/mL, about 20 mg/mL to about 140 mg/mL, about 20 mg/mL to about 130 mg/mL, about 20 mg/mL to about 120 mg/mL, about 20 mg/mL to about 110 mg/mL, about 20 mg/mL to about 100 mg/mL, about 20 mg/mL to about 90 mg/mL, about 20 mg/mL to about 80 mg/mL, about 20 mg/mL to about 70 mg/mL, about 20 mg/mL to about 60 mg/mL, about 20 mg/mL to about 50 mg/mL, about 20 mg/mL to about 45 mg/mL, about 20 mg/mL to about 40 mg/mL, about 20 mg/mL to about 35 mg/mL, about 20 mg/mL to about 30 mg/mL, about 20 mg/mL to about 25 mg/mL, about 25 mg/mL to about 200 mg/mL, about 25 mg/mL to about 190 mg/mL, about 25 mg/mL to about 180 mg/mL, about 25 mg/mL to about 170 mg/mL, about 25 mg/mL to about 160 mg/mL, about 25 mg/mL to about 150 mg/mL, about 25 mg/mL to about 140 mg/mL, about 25 mg/mL to about 130 mg/mL, about 25 mg/mL to about 120 mg/mL, about 25 mg/mL to about 110 mg/mL, about 25 mg/mL to about 100 mg/mL, about 25 mg/mL to about 90 mg/mL, about 25 mg/mL to about 80 mg/mL, about 25 mg/mL to about 70 mg/mL, about 25 mg/mL to about 60 mg/mL, about 25 mg/mL to about 50 mg/mL, about 25 mg/mL to about 45 mg/mL, about 25 mg/mL to about 40 mg/mL, about 25 mg/mL to about 35 mg/mL, about 25 mg/mL to about 30 mg/mL, about 30 mg/mL to about 200 mg/mL, about 30 mg/mL to about 190 mg/mL, about 30 mg/mL to about 180 mg/mL, about 30 mg/mL to about 170 mg/mL, about 30 mg/mL to about 160 mg/mL, about 30 mg/mL to about 150 mg/mL, about 30 mg/mL to about 140 mg/mL, about 30 mg/mL to about 130 mg/mL, about 30 mg/mL to about 120 mg/mL, about 30 mg/mL to about 110 mg/mL, about 30 mg/mL to about 100 mg/mL, about 30 mg/mL to about 90 mg/mL, about 30 mg/mL to about 80 mg/mL, about 30 mg/mL to about 70 mg/mL, about 30 mg/mL to about 60 mg/mL, about 30 mg/mL to about 50 mg/mL, about 30 mg/mL to about 45 mg/mL, about 30 mg/mL to about 40 mg/mL, about 30 mg/mL to about 35 mg/mL, about 35 mg/mL to about 200 mg/mL, about 35 mg/mL to about 190 mg/mL, about 35 mg/mL to about 180 mg/mL, about 35 mg/mL to about 170 mg/mL, about 35 mg/mL to about 160 mg/mL, about 35 mg/mL to about 150 mg/mL, about 35 mg/mL to about 140 mg/mL, about 35 mg/mL to about 130 mg/mL, about 35 mg/mL to about 120 mg/mL, about 35 mg/mL to about 110 mg/mL, about 35 mg/mL to about 100 mg/mL, about 35 mg/mL to about 90 mg/mL, about 35 mg/mL to about 80 mg/mL, about 35 mg/mL to about 70 mg/mL, about 35 mg/mL to about 60 mg/mL, about 35 mg/mL to about 50 mg/mL, about 35 mg/mL to about 45 mg/mL, about 35 mg/mL to about 40 mg/mL, about 40 mg/mL to about 200 mg/mL, about 40 mg/mL to about 190 mg/mL, about 40 mg/mL to about 180 mg/mL, about 40 mg/mL to about 170 mg/mL, about 40 mg/mL to about 160 mg/mL, about 40 mg/mL to about 150 mg/mL, about 40 mg/mL to about 140 mg/mL, about 40 mg/mL to about 130 mg/mL, about 40 mg/mL to about 120 mg/mL, about 40 mg/mL to about 110 mg/mL, about 40 mg/mL to about 100 mg/mL, about 40 mg/mL to about 90 mg/mL, about 40 mg/mL to about 80 mg/mL, about 40 mg/mL to about 70 mg/mL, about 40 mg/mL to about 60 mg/mL, about 40 mg/mL to about 50 mg/mL, about 40 mg/mL to about 45 mg/mL, about 45 mg/mL to about 200 mg/mL, about 45 mg/mL to about 190 mg/mL, about 45 mg/mL to about 180 mg/mL, about 45 mg/mL to about 170 mg/mL, about 45 mg/mL to about 160 mg/mL, about 45 mg/mL to about 150 mg/mL, about 45 mg/mL to about 140 mg/mL, about 45 mg/mL to about 130 mg/mL, about 45 mg/mL to about 120 mg/mL, about 45 mg/mL to about 110 mg/mL, about 45 mg/mL to about 100 mg/mL, about 45 mg/mL to about 90 mg/mL, about 45 mg/mL to about 80 mg/mL, about 45 mg/mL to about 70 mg/mL, about 45 mg/mL to about 60 mg/mL, about 45 mg/mL to about 50 mg/mL, about 50 mg/mL to about 200 mg/mL, about 50 mg/mL to about 190 mg/mL, about 50 mg/mL to about 180 mg/mL, about 50 mg/mL to about 170 mg/mL, about 50 mg/mL to about 160 mg/mL, about 50 mg/mL to about 150 mg/mL, about 50 mg/mL to about 140 mg/mL, about 50 mg/mL to about 130 mg/mL, about 50 mg/mL to about 120 mg/mL, about 50 mg/mL to about 110 mg/mL, about 50 mg/mL to about 100 mg/mL, about 50 mg/mL to about 90 mg/mL, about 50 mg/mL to about 80 mg/mL, about 50 mg/mL to about 70 mg/mL, about 50 mg/mL to about 60 mg/mL, about 60 mg/mL to about 200 mg/mL, about 60 mg/mL to about 190 mg/mL, about 60 mg/mL to about 180 mg/mL, about 60 mg/mL to about 170 mg/mL, about 60 mg/mL to about 160 mg/mL, about 60 mg/mL to about 150 mg/mL, about 60 mg/mL to about 140 mg/mL, about 60 mg/mL to about 130 mg/mL, about 60 mg/mL to about 120 mg/mL, about 60 mg/mL to about 110 mg/mL, about 60 mg/mL to about 100 mg/mL, about 60 mg/mL to about 90 mg/mL, about 60 mg/mL to about 80 mg/mL, about 60 mg/mL to about 70 mg/mL, about 70 mg/mL to about 200 mg/mL, about 70 mg/mL to about 190 mg/mL, about 70 mg/mL to about 180 mg/mL, about 70 mg/mL to about 170 mg/mL, about 70 mg/mL to about 160 mg/mL, about 70 mg/mL to about 150 mg/mL, about 70 mg/mL to about 140 mg/mL, about 70 mg/mL to about 130 mg/mL, about 70 mg/mL to about 120 mg/mL, about 70 mg/mL to about 110 mg/mL, about 70 mg/mL to about 100 mg/mL, about 70 mg/mL to about 90 mg/mL, about 70 mg/mL to about 80 mg/mL, about 80 mg/mL to about 200 mg/mL, about 80 mg/mL to about 190 mg/mL, about 80 mg/mL to about 180 mg/mL, about 80 mg/mL to about 170 mg/mL, about 80 mg/mL to about 160 mg/mL, about 80 mg/mL to about 150 mg/mL, about 80 mg/mL to about 140 mg/mL, about 80 mg/mL to about 130 mg/mL, about 80 mg/mL to about 120 mg/mL, about 80 mg/mL to about 110 mg/mL, about 80 mg/mL to about 100 mg/mL, about 80 mg/mL to about 90 mg/mL, about 90 mg/mL to about 200 mg/mL, about 90 mg/mL to about 190 mg/mL, about 90 mg/mL to about 180 mg/mL, about 90 mg/mL to about 170 mg/mL, about 90 mg/mL to about 160 mg/mL, about 90 mg/mL to about 150 mg/mL, about 90 mg/mL to about 140 mg/mL, about 90 mg/mL to about 130 mg/mL, about 90 mg/mL to about 120 mg/mL, about 90 mg/mL to about 110 mg/mL, about 90 mg/mL to about 100 mg/mL, about 100 mg/mL to about 200 mg/mL, about 100 mg/mL to about 190 mg/mL, about 100 mg/mL to about 180 mg/mL, about 100 mg/mL to about 170 mg/mL, about 100 mg/mL to about 160 mg/mL, about 100 mg/mL to about 150 mg/mL, about 100 mg/mL to about 140 mg/mL, about 100 mg/mL to about 130 mg/mL, about 100 mg/mL to about 120 mg/mL, about 100 mg/mL to about 110 mg/mL, about 110 mg/mL to about 200 mg/mL, about 110 mg/mL to about 190 mg/mL, about 110 mg/mL to about 180 mg/mL, about 110 mg/mL to about 170 mg/mL, about 110 mg/mL to about 160 mg/mL, about 110 mg/mL to about 150 mg/mL, about 110 mg/mL to about 140 mg/mL, about 110 mg/mL to about 130 mg/mL, about 110 mg/mL to about 120 mg/mL, about 120 mg/mL to about 200 mg/mL, about 120 mg/mL to about 190 mg/mL, about 120 mg/mL to about 180 mg/mL, about 120 mg/mL to about 170 mg/mL, about 120 mg/mL to about 160 mg/mL, about 120 mg/mL to about 150 mg/mL, about 120 mg/mL to about 140 mg/mL, about 120 mg/mL to about 130 mg/mL, about 130 mg/mL to about 200 mg/mL, about 130 mg/mL to about 190 mg/mL, about 130 mg/mL to about 180 mg/mL, about 130 mg/mL to about 170 mg/mL, about 130 mg/mL to about 160 mg/mL, about 130 mg/mL to about 150 mg/mL, about 130 mg/mL to about 140 mg/mL, about 140 mg/mL to about 200 mg/mL, about 140 mg/mL to about 190 mg/mL, about 140 mg/mL to about 180 mg/mL, about 140 mg/mL to about 170 mg/mL, about 140 mg/mL to about 160 mg/mL, about 140 mg/mL to about 150 mg/mL, about 150 mg/mL to about 200 mg/mL, about 150 mg/mL to about 190 mg/mL, about 150 mg/mL to about 180 mg/mL, about 150 mg/mL to about 170 mg/mL, about 150 mg/mL to about 160 mg/mL, about 160 mg/mL to about 200 mg/mL, about 160 mg/mL to about 190 mg/mL, about 160 mg/mL to about 180 mg/mL, about 160 mg/mL to about 170 mg/mL, about 170 mg/mL to about 200 mg/mL, about 170 mg/mL to about 190 mg/mL, about 170 mg/mL to about 180 mg/mL, about 180 mg/mL to about 200 mg/mL, about 180 mg/mL to about 190 mg/mL, or about 190 mg/mL to about 200 mg/mL, or a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, or 200 mg/mL.

Buffer-Free Formulations

In one embodiment, the invention provides an aqueous formulation comprising aflibercept, a stabilizer and an organic co-solvent, wherein the formulation is free of buffer.

In one embodiment, the formulation has a pH of about 5.5 to about 7.0 (e.g., about 5.5 to about 6.9, about 5.5 to about 6.8, about 5.5 to about 6.7, about 5.5 to about 6.6, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.6 to about 7.0, about 5.6 to about 6.9, about 5.6 to about 6.8, about 5.6 to about 6.7, about 5.6 to about 6.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.7 to about 7.0, about 5.7 to about 6.9, about 5.7 to about 6.8, about 5.7 to about 6.7, about 5.7 to about 6.6, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.8 to about 7.0, about 5.8 to about 6.9, about 5.8 to about 6.8, about 5.8 to about 6.7, about 5.8 to about 6.6, about 5.8 to about 6.5, about 5.8 to about 6.4, about 5.8 to about 6.3, about 5.8 to about 6.2, about 5.8 to about 6.1, about 5.8 to about 6.0, about 5.9 to about 7.0, about 5.9 to about 6.9, about 5.9 to about 6.8, about 5.9 to about 6.7, about 5.9 to about 6.6, about 5.9 to about 6.5, about 5.9 to about 6.4, about 5.9 to about 6.3, about 5.9 to about 6.2, about 5.9 to about 6.1, about 6.0 to about 7.0, about 6.0 to about 6.9, about 6.0 to about 6.8, about 6.0 to about 6.7, about 6.0 to about 6.6, about 6.0 to about 6.5, about 6.0 to about 6.4, about 6.0 to about 6.3, about 6.0 to about 6.2, about 6.1 to about 7.0, about 6.1 to about 6.9, about 6.1 to about 6.8, about 6.1 to about 6.7, about 6.1 to about 6.6, about 6.1 to about 6.5, about 6.1 to about 6.4, about 6.1 to about 6.3, about 6.2 to about 7.0, about 6.2 to about 6.9, about 6.2 to about 6.8, about 6.2 to about 6.7, about 6.2 to about 6.6, about 6.2 to about 6.5, about 6.2 to about 6.4, about 6.3 to about 7.0, about 6.3 to about 6.9, about 6.3 to about 6.8, about 6.3 to about 6.7, about 6.3 to about 6.6, about 6.3 to about 6.5, about 6.4 to about 7.0, about 6.4 to about 6.9, about 6.4 to about 6.8, about 6.4 to about 6.7, about 6.4 to about 6.6, about 6.5 to about 7.0, about 6.5 to about 6.9, about 6.5 to about 6.8, about 6.5 to about 6.7, about 6.6 to about 7.0, about 6.6 to about 6.9, about 6.6 to about 6.8, about 6.7 to about 7.0, about 6.7 to about 6.9, or about 6.8 to about 7.0).

In another embodiment, the pH is about 6.0 to about 6.5. In yet another embodiment, the pH is about 6.2. In another embodiment, the pH is about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0.

In one embodiment, the stabilizer is selected from the group consisting of amino acids, sugars, polyols, polymers, and combinations thereof.

In one embodiment, the organic co-solvent is selected from the group consisting of a surfactant, polyethylene glycol (PEG), propylene glycol.

In one embodiment, the surfactant is selected from the group consisting of polysorbate 20, polysorbate 80, sodium dodecyl sulfate (SDS), n-Dodecyl-β-D-maltoside (DDM) and poloxamer 188 (Pluronic F-68).

In another embodiment, the buffer-free formulations of the invention further comprise a salt. In one embodiment, the salt is selected from the group consisting of sodium chloride, magnesium chloride and calcium chloride. The salts may be present at a concentration of about 10 mM-100 mM (e.g., about 10 mM to about 95 mM, about 10 mM to about 90 mM, about 10 mM to about 85 mM, about 10 mM to about 80 mM, about 10 mM to about 75 mM, about 10 mM to about 70 mM, about 10 mM to about 65 mM, about 10 mM to about 60 mM, about 10 mM to about 55 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 18 mM, about 10 mM to about 16 mM, about 10 mM to about 14 mM, about 10 mM to about 12 mM, about 12 mM to about 100 mM, about 12 mM to about 95 mM, about 12 mM to about 90 mM, about 12 mM to about 85 mM, about 12 mM to about 80 mM, about 12 mM to about 75 mM, about 12 mM to about 70 mM, about 12 mM to about 65 mM, about 12 mM to about 60 mM, about 12 mM to about 55 mM, about 12 mM to about 50 mM, about 12 mM to about 45 mM, about 12 mM to about 40 mM, about 12 mM to about 35 mM, about 12 mM to about 30 mM, about 12 mM to about 25 mM, about 12 mM to about 20 mM, about 12 mM to about 18 mM, about 12 mM to about 16 mM, about 12 mM to about 14 mM, about 14 mM to about 100 mM, about 14 mM to about 95 mM, about 14 mM to about 90 mM, about 14 mM to about 85 mM, about 14 mM to about 80 mM, about 14 mM to about 75 mM, about 14 mM to about 70 mM, about 14 mM to about 65 mM, about 14 mM to about 60 mM, about 14 mM to about 55 mM, about 14 mM to about 50 mM, about 14 mM to about 45 mM, about 14 mM to about 40 mM, about 14 mM to about 35 mM, about 14 mM to about 30 mM, about 14 mM to about 25 mM, about 14 mM to about 20 mM, about 14 mM to about 18 mM, about 14 mM to about 16 mM, about 16 mM to about 100 mM, about 16 mM to about 95 mM, about 16 mM to about 90 mM, about 16 mM to about 85 mM, about 16 mM to about 80 mM, about 16 mM to about 75 mM, about 16 mM to about 70 mM, about 16 mM to about 65 mM, about 16 mM to about 60 mM, about 16 mM to about 55 mM, about 16 mM to about 50 mM, about 16 mM to about 45 mM, about 16 mM to about 40 mM, about 16 mM to about 35 mM, about 16 mM to about 30 mM, about 16 mM to about 25 mM, about 16 mM to about 20 mM, about 16 mM to about 18 mM, about 18 mM to about 100 mM, about 18 mM to about 95 mM, about 18 mM to about 90 mM, about 18 mM to about 85 mM, about 18 mM to about 80 mM, about 18 mM to about 75 mM, about 18 mM to about 70 mM, about 18 mM to about 65 mM, about 18 mM to about 60 mM, about 18 mM to about 55 mM, about 18 mM to about 50 mM, about 18 mM to about 45 mM, about 18 mM to about 40 mM, about 18 mM to about 35 mM, about 18 mM to about 30 mM, about 18 mM to about 25 mM, about 18 mM to about 20 mM, about 20 mM to about 100 mM, about 20 mM to about 95 mM, about 20 mM to about 90 mM, about 20 mM to about 85 mM, about 20 mM to about 80 mM, about 20 mM to about 75 mM, about 20 mM to about 70 mM, about 20 mM to about 65 mM, about 20 mM to about 60 mM, about 20 mM to about 55 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 100 mM, about 25 mM to about 95 mM, about 25 mM to about 90 mM, about 25 mM to about 85 mM, about 25 mM to about 80 mM, about 25 mM to about 75 mM, about 25 mM to about 70 mM, about 25 mM to about 65 mM, about 25 mM to about 60 mM, about 25 mM to about 55 mM, about 25 mM to about 50 mM, about 25 mM to about 45 mM, about 25 mM to about 40 mM, about 25 mM to about 35 mM, about 25 mM to about 30 mM, about 30 mM to about 100 mM, about 30 mM to about 95 mM, about 30 mM to about 90 mM, about 30 mM to about 85 mM, about 30 mM to about 80 mM, about 30 mM to about 75 mM, about 30 mM to about 70 mM, about 30 mM to about 65 mM, about 30 mM to about 60 mM, about 30 mM to about 55 mM, about 30 mM to about 50 mM, about 30 mM to about 45 mM, about 30 mM to about 40 mM, about 30 mM to about 35 mM, about 35 mM to about 100 mM, about 35 mM to about 95 mM, about 35 mM to about 90 mM, about 35 mM to about 85 mM, about 35 mM to about 80 mM, about 35 mM to about 75 mM, about 35 mM to about 70 mM, about 35 mM to about 65 mM, about 35 mM to about 60 mM, about 35 mM to about 55 mM, about 35 mM to about 50 mM, about 35 mM to about 45 mM, about 35 mM to about 40 mM, about 40 mM to about 100 mM, about 40 mM to about 95 mM, about 40 mM to about 90 mM, about 40 mM to about 85 mM, about 40 mM to about 80 mM, about 40 mM to about 75 mM, about 40 mM to about 70 mM, about 40 mM to about 65 mM, about 40 mM to about 60 mM, about 40 mM to about 55 mM, about 40 mM to about 50 mM, about 40 mM to about 45 mM, about 45 mM to about 100 mM, about 45 mM to about 95 mM, about 45 mM to about 90 mM, about 45 mM to about 85 mM, about 45 mM to about 80 mM, about 45 mM to about 75 mM, about 45 mM to about 70 mM, about 45 mM to about 65 mM, about 45 mM to about 60 mM, about 45 mM to about 55 mM, about 45 mM to about 50 mM, about 50 mM to about 100 mM, about 50 mM to about 95 mM, about 50 mM to about 90 mM, about 50 mM to about 85 mM, about 50 mM to about 80 mM, about 50 mM to about 75 mM, about 50 mM to about 70 mM, about 50 mM to about 65 mM, about 50 mM to about 60 mM, about 50 mM to about 55 mM, about 55 mM to about 100 mM, about 55 mM to about 95 mM, about 55 mM to about 90 mM, about 55 mM to about 85 mM, about 55 mM to about 80 mM, about 55 mM to about 75 mM, about 55 mM to about 70 mM, about 55 mM to about 65 mM, about 55 mM to about 60 mM, about 60 mM to about 100 mM, about 60 mM to about 95 mM, about 60 mM to about 90 mM, about 60 mM to about 85 mM, about 60 mM to about 80 mM, about 60 mM to about 75 mM, about 60 mM to about 70 mM, about 60 mM to about 65 mM, about 65 mM to about 100 mM, about 65 mM to about 95 mM, about 65 mM to about 90 mM, about 65 mM to about 85 mM, about 65 mM to about 80 mM, about 65 mM to about 75 mM, about 65 mM to about 70 mM, about 70 mM to about 100 mM, about 70 mM to about 95 mM, about 70 mM to about 90 mM, about 70 mM to about 85 mM, about 70 mM to about 80 mM, about 70 mM to about 75 mM, about 75 mM to about 100 mM, about 75 mM to about 95 mM, about 75 mM to about 90 mM, about 75 mM to about 85 mM, about 75 mM to about 80 mM, about 80 mM to about 100 mM, about 80 mM to about 95 mM, about 80 mM to about 90 mM, about 80 mM to about 85 mM, about 85 mM to about 100 mM, about 85 mM to about 95 mM, about 85 mM to about 90 mM, about 90 mM to about 100 mM, about 90 mM to about 95 mM, or about 95 mM to about 100 mM).

In one embodiment, the stabilizer is a sugar. In another embodiment, the stabilizer is sucrose.

In one embodiment, the stabilizer is an amino acid. In another embodiment, the amino acid is selected from the group consisting of glycine, arginine, and proline or combinations thereof. The amino acids may be present at a concentration of about 25-300 mM.

In some embodiments, the stabilizer is sucrose, the organic co-solvent is polysorbate 20 and the pH of the formulation is about 5.5-7.0 (e.g., about 5.5 to about 6.9, about 5.5 to about 6.8, about 5.5 to about 6.7, about 5.5 to about 6.6, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.6 to about 7.0, about 5.6 to about 6.9, about 5.6 to about 6.8, about 5.6 to about 6.7, about 5.6 to about 6.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.7 to about 7.0, about 5.7 to about 6.9, about 5.7 to about 6.8, about 5.7 to about 6.7, about 5.7 to about 6.6, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.8 to about 7.0, about 5.8 to about 6.9, about 5.8 to about 6.8, about 5.8 to about 6.7, about 5.8 to about 6.6, about 5.8 to about 6.5, about 5.8 to about 6.4, about 5.8 to about 6.3, about 5.8 to about 6.2, about 5.8 to about 6.1, about 5.8 to about 6.0, about 5.9 to about 7.0, about 5.9 to about 6.9, about 5.9 to about 6.8, about 5.9 to about 6.7, about 5.9 to about 6.6, about 5.9 to about 6.5, about 5.9 to about 6.4, about 5.9 to about 6.3, about 5.9 to about 6.2, about 5.9 to about 6.1, about 6.0 to about 7.0, about 6.0 to about 6.9, about 6.0 to about 6.8, about 6.0 to about 6.7, about 6.0 to about 6.6, about 6.0 to about 6.5, about 6.0 to about 6.4, about 6.0 to about 6.3, about 6.0 to about 6.2, about 6.1 to about 7.0, about 6.1 to about 6.9, about 6.1 to about 6.8, about 6.1 to about 6.7, about 6.1 to about 6.6, about 6.1 to about 6.5, about 6.1 to about 6.4, about 6.1 to about 6.3, about 6.2 to about 7.0, about 6.2 to about 6.9, about 6.2 to about 6.8, about 6.2 to about 6.7, about 6.2 to about 6.6, about 6.2 to about 6.5, about 6.2 to about 6.4, about 6.3 to about 7.0, about 6.3 to about 6.9, about 6.3 to about 6.8, about 6.3 to about 6.7, about 6.3 to about 6.6, about 6.3 to about 6.5, about 6.4 to about 7.0, about 6.4 to about 6.9, about 6.4 to about 6.8, about 6.4 to about 6.7, about 6.4 to about 6.6, about 6.5 to about 7.0, about 6.5 to about 6.9, about 6.5 to about 6.8, about 6.5 to about 6.7, about 6.6 to about 7.0, about 6.6 to about 6.9, about 6.6 to about 6.8, about 6.7 to about 7.0, about 6.7 to about 6.9, or about 6.8 to about 7.0, or about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0).

In one embodiment, the formulation is iso-osmolar relative to the vitreous.

Formulations Free of Organic Co-Solvent

In one embodiment, the invention provides an aqueous formulation comprising aflibercept, a stabilizer and a buffer, wherein the formulation is free of an organic co-solvent.

In one embodiment, the formulation has a pH of about 5.5 to about 7.0 (e.g., any of the subranges of described herein or about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In another embodiment, the pH is about 6.0 to about 6.5. In yet another embodiment, the pH is about 6.2.

In one embodiment, the stabilizer is selected from the group consisting of amino acids, sugars, polyols, polymers, and combinations thereof.

In one embodiment, the buffer is selected from the group consisting of acetate, histidine, phosphate, citrate, succinate, tartrate and maleate. In another embodiment, the buffer is present at a concentration of about 1 mM to 150 mM (e.g., about 1 mM to about 140 mM, about 1 mM to about 130 mM, about 1 mM to about 120 mM, about 1 mM to about 110 mM, about 1 mM to about 100 mM, about 1 mM to about 90 mM, about 1 mM to about 80 mM, about 1 mM to about 70 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 18 mM, about 1 mM to about 16 mM, about 1 mM to about 14 mM, about 1 mM to about 12 mM, about 1 mM to about 10 mM, about 1 mM to about 8 mM, about 1 mM to about 6 mM, about 1 mM to about 4 mM, about 1 mM to about 2 mM, about 2 mM to about 150 mM, about 2 mM to about 140 mM, about 2 mM to about 130 mM, about 2 mM to about 120 mM, about 2 mM to about 110 mM, about 2 mM to about 100 mM, about 2 mM to about 90 mM, about 2 mM to about 80 mM, about 2 mM to about 70 mM, about 2 mM to about 60 mM, about 2 mM to about 50 mM, about 2 mM to about 45 mM, about 2 mM to about 40 mM, about 2 mM to about 35 mM, about 2 mM to about 30 mM, about 2 mM to about 25 mM, about 2 mM to about 20 mM, about 2 mM to about 18 mM, about 2 mM to about 16 mM, about 2 mM to about 14 mM, about 2 mM to about 12 mM, about 2 mM to about 10 mM, about 2 mM to about 8 mM, about 2 mM to about 6 mM, about 2 mM to about 4 mM, about 4 mM to about 150 mM, about 4 mM to about 140 mM, about 4 mM to about 130 mM, about 4 mM to about 120 mM, about 4 mM to about 110 mM, about 4 mM to about 100 mM, about 4 mM to about 90 mM, about 4 mM to about 80 mM, about 4 mM to about 70 mM, about 4 mM to about 60 mM, about 4 mM to about 50 mM, about 4 mM to about 45 mM, about 4 mM to about 40 mM, about 4 mM to about 35 mM, about 4 mM to about 30 mM, about 4 mM to about 25 mM, about 4 mM to about 20 mM, about 4 mM to about 18 mM, about 4 mM to about 16 mM, about 4 mM to about 14 mM, about 4 mM to about 12 mM, about 4 mM to about 10 mM, about 4 mM to about 8 mM, about 4 mM to about 6 mM, about 6 mM to about 150 mM, about 6 mM to about 140 mM, about 6 mM to about 130 mM, about 6 mM to about 120 mM, about 6 mM to about 110 mM, about 6 mM to about 100 mM, about 6 mM to about 90 mM, about 6 mM to about 80 mM, about 6 mM to about 70 mM, about 6 mM to about 60 mM, about 6 mM to about 50 mM, about 6 mM to about 45 mM, about 6 mM to about 40 mM, about 6 mM to about 35 mM, about 6 mM to about 30 mM, about 6 mM to about 25 mM, about 6 mM to about 20 mM, about 6 mM to about 18 mM, about 6 mM to about 16 mM, about 6 mM to about 14 mM, about 6 mM to about 12 mM, about 6 mM to about 10 mM, about 6 mM to about 8 mM, about 8 mM to about 150 mM, about 8 mM to about 140 mM, about 8 mM to about 130 mM, about 8 mM to about 120 mM, about 8 mM to about 110 mM, about 8 mM to about 100 mM, about 8 mM to about 90 mM, about 8 mM to about 80 mM, about 8 mM to about 70 mM, about 8 mM to about 60 mM, about 8 mM to about 50 mM, about 8 mM to about 45 mM, about 8 mM to about 40 mM, about 8 mM to about 35 mM, about 8 mM to about 30 mM, about 8 mM to about 25 mM, about 8 mM to about 20 mM, about 8 mM to about 18 mM, about 8 mM to about 16 mM, about 8 mM to about 14 mM, about 8 mM to about 12 mM, about 8 mM to about 10 mM, about 10 mM to about 150 mM, about 10 mM to about 140 mM, about 10 mM to about 130 mM, about 10 mM to about 120 mM, about 10 mM to about 110 mM, about 10 mM to about 100 mM, about 10 mM to about 90 mM, about 10 mM to about 80 mM, about 10 mM to about 70 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 18 mM, about 10 mM to about 16 mM, about 10 mM to about 14 mM, about 10 mM to about 12 mM, about 12 mM to about 150 mM, about 12 mM to about 140 mM, about 12 mM to about 130 mM, about 12 mM to about 120 mM, about 12 mM to about 110 mM, about 12 mM to about 100 mM, about 12 mM to about 90 mM, about 12 mM to about 80 mM, about 12 mM to about 70 mM, about 12 mM to about 60 mM, about 12 mM to about 50 mM, about 12 mM to about 45 mM, about 12 mM to about 40 mM, about 12 mM to about 35 mM, about 12 mM to about 30 mM, about 12 mM to about 25 mM, about 12 mM to about 20 mM, about 12 mM to about 18 mM, about 12 mM to about 16 mM, about 12 mM to about 14 mM, about 14 mM to about 150 mM, about 14 mM to about 140 mM, about 14 mM to about 130 mM, about 14 mM to about 120 mM, about 14 mM to about 110 mM, about 14 mM to about 100 mM, about 14 mM to about 90 mM, about 14 mM to about 80 mM, about 14 mM to about 70 mM, about 14 mM to about 60 mM, about 14 mM to about 50 mM, about 14 mM to about 45 mM, about 14 mM to about 40 mM, about 14 mM to about 35 mM, about 14 mM to about 30 mM, about 14 mM to about 25 mM, about 14 mM to about 20 mM, about 14 mM to about 18 mM, about 14 mM to about 16 mM, about 16 mM to about 150 mM, about 16 mM to about 140 mM, about 16 mM to about 130 mM, about 16 mM to about 120 mM, about 16 mM to about 110 mM, about 16 mM to about 100 mM, about 16 mM to about 90 mM, about 16 mM to about 80 mM, about 16 mM to about 70 mM, about 16 mM to about 60 mM, about 16 mM to about 50 mM, about 16 mM to about 45 mM, about 16 mM to about 40 mM, about 16 mM to about 35 mM, about 16 mM to about 30 mM, about 16 mM to about 25 mM, about 16 mM to about 20 mM, about 16 mM to about 18 mM, about 18 mM to about 150 mM, about 18 mM to about 140 mM, about 18 mM to about 130 mM, about 18 mM to about 120 mM, about 18 mM to about 110 mM, about 18 mM to about 100 mM, about 18 mM to about 90 mM, about 18 mM to about 80 mM, about 18 mM to about 70 mM, about 18 mM to about 60 mM, about 18 mM to about 50 mM, about 18 mM to about 45 mM, about 18 mM to about 40 mM, about 18 mM to about 35 mM, about 18 mM to about 30 mM, about 18 mM to about 25 mM, about 18 mM to about 20 mM, about 20 mM to about 150 mM, about 20 mM to about 140 mM, about 20 mM to about 130 mM, about 20 mM to about 120 mM, about 20 mM to about 110 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 150 mM, about 25 mM to about 140 mM, about 25 mM to about 130 mM, about 25 mM to about 120 mM, about 25 mM to about 110 mM, about 25 mM to about 100 mM, about 25 mM to about 90 mM, about 25 mM to about 80 mM, about 25 mM to about 70 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 150 mM, about 30 mM to about 140 mM, about 30 mM to about 130 mM, about 30 mM to about 120 mM, about 30 mM to about 110 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 45 mM, about 30 mM to about 40 mM, about 30 mM to about 35 mM, about 35 mM to about 150 mM, about 35 mM to about 140 mM, about 35 mM to about 130 mM, about 35 mM to about 120 mM, about 35 mM to about 110 mM, about 35 mM to about 100 mM, about 35 mM to about 90 mM, about 35 mM to about 80 mM, about 35 mM to about 70 mM, about 35 mM to about 60 mM, about 35 mM to about 50 mM, about 35 mM to about 45 mM, about 35 mM to about 40 mM, about 40 mM to about 150 mM, about 40 mM to about 140 mM, about 40 mM to about 130 mM, about 40 mM to about 120 mM, about 40 mM to about 110 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 40 mM to about 45 mM, about 45 mM to about 150 mM, about 45 mM to about 140 mM, about 45 mM to about 130 mM, about 45 mM to about 120 mM, about 45 mM to about 110 mM, about 45 mM to about 100 mM, about 45 mM to about 90 mM, about 45 mM to about 80 mM, about 45 mM to about 70 mM, about 45 mM to about 60 mM, about 45 mM to about 50 mM, about 50 mM to about 150 mM, about 50 mM to about 140 mM, about 50 mM to about 130 mM, about 50 mM to about 120 mM, about 50 mM to about 110 mM, about 50 mM to about 100 mM, about 50 mM to about 90 mM, about 50 mM to about 80 mM, about 50 mM to about 70 mM, about 50 mM to about 60 mM, about 60 mM to about 150 mM, about 60 mM to about 140 mM, about 60 mM to about 130 mM, about 60 mM to about 120 mM, about 60 mM to about 110 mM, about 60 mM to about 100 mM, about 60 mM to about 90 mM, about 60 mM to about 80 mM, about 60 mM to about 70 mM, about 70 mM to about 150 mM, about 70 mM to about 140 mM, about 70 mM to about 130 mM, about 70 mM to about 120 mM, about 70 mM to about 110 mM, about 70 mM to about 100 mM, about 70 mM to about 90 mM, about 70 mM to about 80 mM, about 80 mM to about 150 mM, about 80 mM to about 140 mM, about 80 mM to about 130 mM, about 80 mM to about 120 mM, about 80 mM to about 110 mM, about 80 mM to about 100 mM, about 80 mM to about 90 mM, about 90 mM to about 150 mM, about 90 mM to about 140 mM, about 90 mM to about 130 mM, about 90 mM to about 120 mM, about 90 mM to about 110 mM, about 90 mM to about 100 mM, about 100 mM to about 150 mM, about 100 mM to about 140 mM, about 100 mM to about 130 mM, about 100 mM to about 120 mM, about 100 mM to about 110 mM, about 110 mM to about 150 mM, about 110 mM to about 140 mM, about 110 mM to about 130 mM, about 110 mM to about 120 mM, about 120 mM to about 150 mM, about 120 mM to about 140 mM, about 120 mM to about 130 mM, about 130 mM to about 150 mM, about 130 mM to about 140 mM, or about 140 mM to about 150 mM). In still another embodiment, the buffer concentration is about 5 mM to 20 mM. In yet another embodiment, the buffer concentration is about 10 mM.

In one embodiment, the stabilizer is a sugar. In another embodiment, the stabilizer is sucrose.

In one embodiment, the stabilizer is an amino acid. In another embodiment, the amino acid is selected from the group consisting of glycine, arginine, and proline or combinations thereof. The amino acids may be present at a concentration of about 25-300 mM.

In another embodiment, the co-solvent-free formulations of the invention further comprise a salt. In one embodiment, the salt is selected from the group consisting of sodium chloride, magnesium chloride and calcium chloride. The salts may be present at a concentration of about 10 mM-100 mM (e.g., about 10 mM to about 95 mM, about 10 mM to about 90 mM, about 10 mM to about 85 mM, about 10 mM to about 80 mM, about 10 mM to about 75 mM, about 10 mM to about 70 mM, about 10 mM to about 65 mM, about 10 mM to about 60 mM, about 10 mM to about 55 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 18 mM, about 10 mM to about 16 mM, about 10 mM to about 14 mM, about 10 mM to about 12 mM, about 12 mM to about 100 mM, about 12 mM to about 95 mM, about 12 mM to about 90 mM, about 12 mM to about 85 mM, about 12 mM to about 80 mM, about 12 mM to about 75 mM, about 12 mM to about 70 mM, about 12 mM to about 65 mM, about 12 mM to about 60 mM, about 12 mM to about 55 mM, about 12 mM to about 50 mM, about 12 mM to about 45 mM, about 12 mM to about 40 mM, about 12 mM to about 35 mM, about 12 mM to about 30 mM, about 12 mM to about 25 mM, about 12 mM to about 20 mM, about 12 mM to about 18 mM, about 12 mM to about 16 mM, about 12 mM to about 14 mM, about 14 mM to about 100 mM, about 14 mM to about 95 mM, about 14 mM to about 90 mM, about 14 mM to about 85 mM, about 14 mM to about 80 mM, about 14 mM to about 75 mM, about 14 mM to about 70 mM, about 14 mM to about 65 mM, about 14 mM to about 60 mM, about 14 mM to about 55 mM, about 14 mM to about 50 mM, about 14 mM to about 45 mM, about 14 mM to about 40 mM, about 14 mM to about 35 mM, about 14 mM to about 30 mM, about 14 mM to about 25 mM, about 14 mM to about 20 mM, about 14 mM to about 18 mM, about 14 mM to about 16 mM, about 16 mM to about 100 mM, about 16 mM to about 95 mM, about 16 mM to about 90 mM, about 16 mM to about 85 mM, about 16 mM to about 80 mM, about 16 mM to about 75 mM, about 16 mM to about 70 mM, about 16 mM to about 65 mM, about 16 mM to about 60 mM, about 16 mM to about 55 mM, about 16 mM to about 50 mM, about 16 mM to about 45 mM, about 16 mM to about 40 mM, about 16 mM to about 35 mM, about 16 mM to about 30 mM, about 16 mM to about 25 mM, about 16 mM to about 20 mM, about 16 mM to about 18 mM, about 18 mM to about 100 mM, about 18 mM to about 95 mM, about 18 mM to about 90 mM, about 18 mM to about 85 mM, about 18 mM to about 80 mM, about 18 mM to about 75 mM, about 18 mM to about 70 mM, about 18 mM to about 65 mM, about 18 mM to about 60 mM, about 18 mM to about 55 mM, about 18 mM to about 50 mM, about 18 mM to about 45 mM, about 18 mM to about 40 mM, about 18 mM to about 35 mM, about 18 mM to about 30 mM, about 18 mM to about 25 mM, about 18 mM to about 20 mM, about 20 mM to about 100 mM, about 20 mM to about 95 mM, about 20 mM to about 90 mM, about 20 mM to about 85 mM, about 20 mM to about 80 mM, about 20 mM to about 75 mM, about 20 mM to about 70 mM, about 20 mM to about 65 mM, about 20 mM to about 60 mM, about 20 mM to about 55 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 100 mM, about 25 mM to about 95 mM, about 25 mM to about 90 mM, about 25 mM to about 85 mM, about 25 mM to about 80 mM, about 25 mM to about 75 mM, about 25 mM to about 70 mM, about 25 mM to about 65 mM, about 25 mM to about 60 mM, about 25 mM to about 55 mM, about 25 mM to about 50 mM, about 25 mM to about 45 mM, about 25 mM to about 40 mM, about 25 mM to about 35 mM, about 25 mM to about 30 mM, about 30 mM to about 100 mM, about 30 mM to about 95 mM, about 30 mM to about 90 mM, about 30 mM to about 85 mM, about 30 mM to about 80 mM, about 30 mM to about 75 mM, about 30 mM to about 70 mM, about 30 mM to about 65 mM, about 30 mM to about 60 mM, about 30 mM to about 55 mM, about 30 mM to about 50 mM, about 30 mM to about 45 mM, about 30 mM to about 40 mM, about 30 mM to about 35 mM, about 35 mM to about 100 mM, about 35 mM to about 95 mM, about 35 mM to about 90 mM, about 35 mM to about 85 mM, about 35 mM to about 80 mM, about 35 mM to about 75 mM, about 35 mM to about 70 mM, about 35 mM to about 65 mM, about 35 mM to about 60 mM, about 35 mM to about 55 mM, about 35 mM to about 50 mM, about 35 mM to about 45 mM, about 35 mM to about 40 mM, about 40 mM to about 100 mM, about 40 mM to about 95 mM, about 40 mM to about 90 mM, about 40 mM to about 85 mM, about 40 mM to about 80 mM, about 40 mM to about 75 mM, about 40 mM to about 70 mM, about 40 mM to about 65 mM, about 40 mM to about 60 mM, about 40 mM to about 55 mM, about 40 mM to about 50 mM, about 40 mM to about 45 mM, about 45 mM to about 100 mM, about 45 mM to about 95 mM, about 45 mM to about 90 mM, about 45 mM to about 85 mM, about 45 mM to about 80 mM, about 45 mM to about 75 mM, about 45 mM to about 70 mM, about 45 mM to about 65 mM, about 45 mM to about 60 mM, about 45 mM to about 55 mM, about 45 mM to about 50 mM, about 50 mM to about 100 mM, about 50 mM to about 95 mM, about 50 mM to about 90 mM, about 50 mM to about 85 mM, about 50 mM to about 80 mM, about 50 mM to about 75 mM, about 50 mM to about 70 mM, about 50 mM to about 65 mM, about 50 mM to about 60 mM, about 50 mM to about 55 mM, about 55 mM to about 100 mM, about 55 mM to about 95 mM, about 55 mM to about 90 mM, about 55 mM to about 85 mM, about 55 mM to about 80 mM, about 55 mM to about 75 mM, about 55 mM to about 70 mM, about 55 mM to about 65 mM, about 55 mM to about 60 mM, about 60 mM to about 100 mM, about 60 mM to about 95 mM, about 60 mM to about 90 mM, about 60 mM to about 85 mM, about 60 mM to about 80 mM, about 60 mM to about 75 mM, about 60 mM to about 70 mM, about 60 mM to about 65 mM, about 65 mM to about 100 mM, about 65 mM to about 95 mM, about 65 mM to about 90 mM, about 65 mM to about 85 mM, about 65 mM to about 80 mM, about 65 mM to about 75 mM, about 65 mM to about 70 mM, about 70 mM to about 100 mM, about 70 mM to about 95 mM, about 70 mM to about 90 mM, about 70 mM to about 85 mM, about 70 mM to about 80 mM, about 70 mM to about 75 mM, about 75 mM to about 100 mM, about 75 mM to about 95 mM, about 75 mM to about 90 mM, about 75 mM to about 85 mM, about 75 mM to about 80 mM, about 80 mM to about 100 mM, about 80 mM to about 95 mM, about 80 mM to about 90 mM, about 80 mM to about 85 mM, about 85 mM to about 100 mM, about 85 mM to about 95 mM, about 85 mM to about 90 mM, about 90 mM to about 100 mM, about 90 mM to about 95 mM, or about 95 mM to about 100 mM, or about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM about 95 mM, or about 100 mM).

In one embodiment, the formulation is iso-osmolar relative to the vitreous.

Formulations Free of Buffer and Organic Co-Solvent

In another embodiment, the invention provides an aqueous formulation comprising aflibercept and a stabilizer, wherein the formulation is free of both an organic co-solvent and a buffer.

In one embodiment, the formulation has a pH of about 5.5 to about 7.0 (e.g., or any of the subranges of this range described herein, e.g., about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In another embodiment, the pH is about 6.0 to about 6.5. In yet another embodiment, the pH is about 6.2.

In one embodiment, the stabilizer is selected from the group consisting of amino acids, sugars, polyols, polymers, and combinations thereof.

In one embodiment, the stabilizer is a sugar. In another embodiment, the stabilizer is sucrose.

In one embodiment, the stabilizer is an amino acid. In another embodiment, the amino acid is selected from the group consisting of glycine, arginine, and proline or combinations thereof. The amino acids may be present at a concentration of about 25-300 mM (e.g., about 25 mM to about 280 mM, about 25 mM to about 260 mM, about 25 mM to about 240 mM, about 25 mM to about 220 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 95 mM, about 25 mM to about 90 mM, about 25 mM to about 85 mM, about 25 mM to about 80 mM, about 25 mM to about 75 mM, about 25 mM to about 70 mM, about 25 mM to about 65 mM, about 25 mM to about 60 mM, about 25 mM to about 55 mM, about 25 mM to about 50 mM, about 25 mM to about 45 mM, about 25 mM to about 40 mM, about 25 mM to about 35 mM, about 25 mM to about 30 mM, about 30 mM to about 300 mM, about 30 mM to about 280 mM, about 30 mM to about 260 mM, about 30 mM to about 240 mM, about 30 mM to about 220 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 95 mM, about 30 mM to about 90 mM, about 30 mM to about 85 mM, about 30 mM to about 80 mM, about 30 mM to about 75 mM, about 30 mM to about 70 mM, about 30 mM to about 65 mM, about 30 mM to about 60 mM, about 30 mM to about 55 mM, about 30 mM to about 50 mM, about 30 mM to about 45 mM, about 30 mM to about 40 mM, about 30 mM to about 35 mM, about 35 mM to about 300 mM, about 35 mM to about 280 mM, about 35 mM to about 260 mM, about 35 mM to about 240 mM, about 35 mM to about 220 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 95 mM, about 35 mM to about 90 mM, about 35 mM to about 85 mM, about 35 mM to about 80 mM, about 35 mM to about 75 mM, about 35 mM to about 70 mM, about 35 mM to about 65 mM, about 35 mM to about 60 mM, about 35 mM to about 55 mM, about 35 mM to about 50 mM, about 35 mM to about 45 mM, about 35 mM to about 40 mM, about 40 mM to about 300 mM, about 40 mM to about 280 mM, about 40 mM to about 260 mM, about 40 mM to about 240 mM, about 40 mM to about 220 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 95 mM, about 40 mM to about 90 mM, about 40 mM to about 85 mM, about 40 mM to about 80 mM, about 40 mM to about 75 mM, about 40 mM to about 70 mM, about 40 mM to about 65 mM, about 40 mM to about 60 mM, about 40 mM to about 55 mM, about 40 mM to about 50 mM, about 40 mM to about 45 mM, about 45 mM to about 300 mM, about 45 mM to about 280 mM, about 45 mM to about 260 mM, about 45 mM to about 240 mM, about 45 mM to about 220 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 95 mM, about 45 mM to about 90 mM, about 45 mM to about 85 mM, about 45 mM to about 80 mM, about 45 mM to about 75 mM, about 45 mM to about 70 mM, about 45 mM to about 65 mM, about 45 mM to about 60 mM, about 45 mM to about 55 mM, about 45 mM to about 50 mM, about 50 mM to about 300 mM, about 50 mM to about 280 mM, about 50 mM to about 260 mM, about 50 mM to about 240 mM, about 50 mM to about 220 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 95 mM, about 50 mM to about 90 mM, about 50 mM to about 85 mM, about 50 mM to about 80 mM, about 50 mM to about 75 mM, about 50 mM to about 70 mM, about 50 mM to about 65 mM, about 50 mM to about 60 mM, about 50 mM to about 55 mM, about 55 mM to about 300 mM, about 55 mM to about 280 mM, about 55 mM to about 260 mM, about 55 mM to about 240 mM, about 55 mM to about 220 mM, about 55 mM to about 200 mM, about 55 mM to about 180 mM, about 55 mM to about 160 mM, about 55 mM to about 140 mM, about 55 mM to about 120 mM, about 55 mM to about 100 mM, about 55 mM to about 95 mM, about 55 mM to about 90 mM, about 55 mM to about 85 mM, about 55 mM to about 80 mM, about 55 mM to about 75 mM, about 55 mM to about 70 mM, about 55 mM to about 65 mM, about 55 mM to about 60 mM, about 60 mM to about 300 mM, about 60 mM to about 280 mM, about 60 mM to about 260 mM, about 60 mM to about 240 mM, about 60 mM to about 220 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 95 mM, about 60 mM to about 90 mM, about 60 mM to about 85 mM, about 60 mM to about 80 mM, about 60 mM to about 75 mM, about 60 mM to about 70 mM, about 60 mM to about 65 mM, about 65 mM to about 300 mM, about 65 mM to about 280 mM, about 65 mM to about 260 mM, about 65 mM to about 240 mM, about 65 mM to about 220 mM, about 65 mM to about 200 mM, about 65 mM to about 180 mM, about 65 mM to about 160 mM, about 65 mM to about 140 mM, about 65 mM to about 120 mM, about 65 mM to about 100 mM, about 65 mM to about 95 mM, about 65 mM to about 90 mM, about 65 mM to about 85 mM, about 65 mM to about 80 mM, about 65 mM to about 75 mM, about 65 mM to about 70 mM, about 70 mM to about 300 mM, about 70 mM to about 280 mM, about 70 mM to about 260 mM, about 70 mM to about 240 mM, about 70 mM to about 220 mM, about 70 mM to about 200 mM, about 70 mM to about 180 mM, about 70 mM to about 160 mM, about 70 mM to about 140 mM, about 70 mM to about 120 mM, about 70 mM to about 100 mM, about 70 mM to about 95 mM, about 70 mM to about 90 mM, about 70 mM to about 85 mM, about 70 mM to about 80 mM, about 70 mM to about 75 mM, about 75 mM to about 300 mM, about 75 mM to about 280 mM, about 75 mM to about 260 mM, about 75 mM to about 240 mM, about 75 mM to about 220 mM, about 75 mM to about 200 mM, about 75 mM to about 180 mM, about 75 mM to about 160 mM, about 75 mM to about 140 mM, about 75 mM to about 120 mM, about 75 mM to about 100 mM, about 75 mM to about 95 mM, about 75 mM to about 90 mM, about 75 mM to about 85 mM, about 75 mM to about 80 mM, about 80 mM to about 300 mM, about 80 mM to about 280 mM, about 80 mM to about 260 mM, about 80 mM to about 240 mM, about 80 mM to about 220 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 80 mM to about 95 mM, about 80 mM to about 90 mM, about 80 mM to about 85 mM, about 85 mM to about 300 mM, about 85 mM to about 280 mM, about 85 mM to about 260 mM, about 85 mM to about 240 mM, about 85 mM to about 220 mM, about 85 mM to about 200 mM, about 85 mM to about 180 mM, about 85 mM to about 160 mM, about 85 mM to about 140 mM, about 85 mM to about 120 mM, about 85 mM to about 100 mM, about 85 mM to about 95 mM, about 85 mM to about 90 mM, about 90 mM to about 300 mM, about 90 mM to about 280 mM, about 90 mM to about 260 mM, about 90 mM to about 240 mM, about 90 mM to about 220 mM, about 90 mM to about 200 mM, about 90 mM to about 180 mM, about 90 mM to about 160 mM, about 90 mM to about 140 mM, about 90 mM to about 120 mM, about 90 mM to about 100 mM, about 90 mM to about 95 mM, about 95 mM to about 300 mM, about 95 mM to about 280 mM, about 95 mM to about 260 mM, about 95 mM to about 240 mM, about 95 mM to about 220 mM, about 95 mM to about 200 mM, about 95 mM to about 180 mM, about 95 mM to about 160 mM, about 95 mM to about 140 mM, about 95 mM to about 120 mM, about 95 mM to about 100 mM, about 100 mM to about 300 mM, about 100 mM to about 280 mM, about 100 mM to about 260 mM, about 100 mM to about 240 mM, about 100 mM to about 220 mM, about 100 mM to about 200 mM, about 100 mM to about 180 mM, about 100 mM to about 160 mM, about 100 mM to about 140 mM, about 100 mM to about 120 mM, about 120 mM to about 300 mM, about 120 mM to about 280 mM, about 120 mM to about 260 mM, about 120 mM to about 240 mM, about 120 mM to about 220 mM, about 120 mM to about 200 mM, about 120 mM to about 180 mM, about 120 mM to about 160 mM, about 120 mM to about 140 mM, about 140 mM to about 300 mM, about 140 mM to about 280 mM, about 140 mM to about 260 mM, about 140 mM to about 240 mM, about 140 mM to about 220 mM, about 140 mM to about 200 mM, about 140 mM to about 180 mM, about 140 mM to about 160 mM, about 160 mM to about 300 mM, about 160 mM to about 280 mM, about 160 mM to about 260 mM, about 160 mM to about 240 mM, about 160 mM to about 220 mM, about 160 mM to about 200 mM, about 160 mM to about 180 mM, about 180 mM to about 300 mM, about 180 mM to about 280 mM, about 180 mM to about 260 mM, about 180 mM to about 240 mM, about 180 mM to about 220 mM, about 180 mM to about 200 mM, about 200 mM to about 300 mM, about 200 mM to about 280 mM, about 200 mM to about 260 mM, about 200 mM to about 240 mM, about 200 mM to about 220 mM, about 220 mM to about 300 mM, about 220 mM to about 280 mM, about 220 mM to about 260 mM, about 220 mM to about 240 mM, about 240 mM to about 300 mM, about 240 mM to about 280 mM, about 240 mM to about 260 mM, about 260 mM to about 300 mM, about 260 mM to about 280 mM, or about 280 mM to about 300 mM, or about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM). In another embodiment, the co-solvent-free and buffer-free formulations of the invention further comprise a salt. In one embodiment, the salt is selected from the group consisting of sodium chloride, magnesium chloride and calcium chloride. The salts may be present at a concentration of about 10 mM-100 mM (e.g., or any of the subranges of this range described herein or about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM about 95 mM, or about 100 mM).

In one embodiment, the formulation is iso-osmolar relative to the vitreous.

These and other aspects will become apparent from the following description of the various embodiments, although variations and modifications therein may be affected without departing from the spirit and scope of the novel concepts of the disclosure.

It is to be understood that both the foregoing general description and the following detailed description are exemplary and explanatory only and are not restrictive of the invention, as claimed.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. In the case of conflict, the present document, including definitions will control.

Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

Definitions

Figure 24:
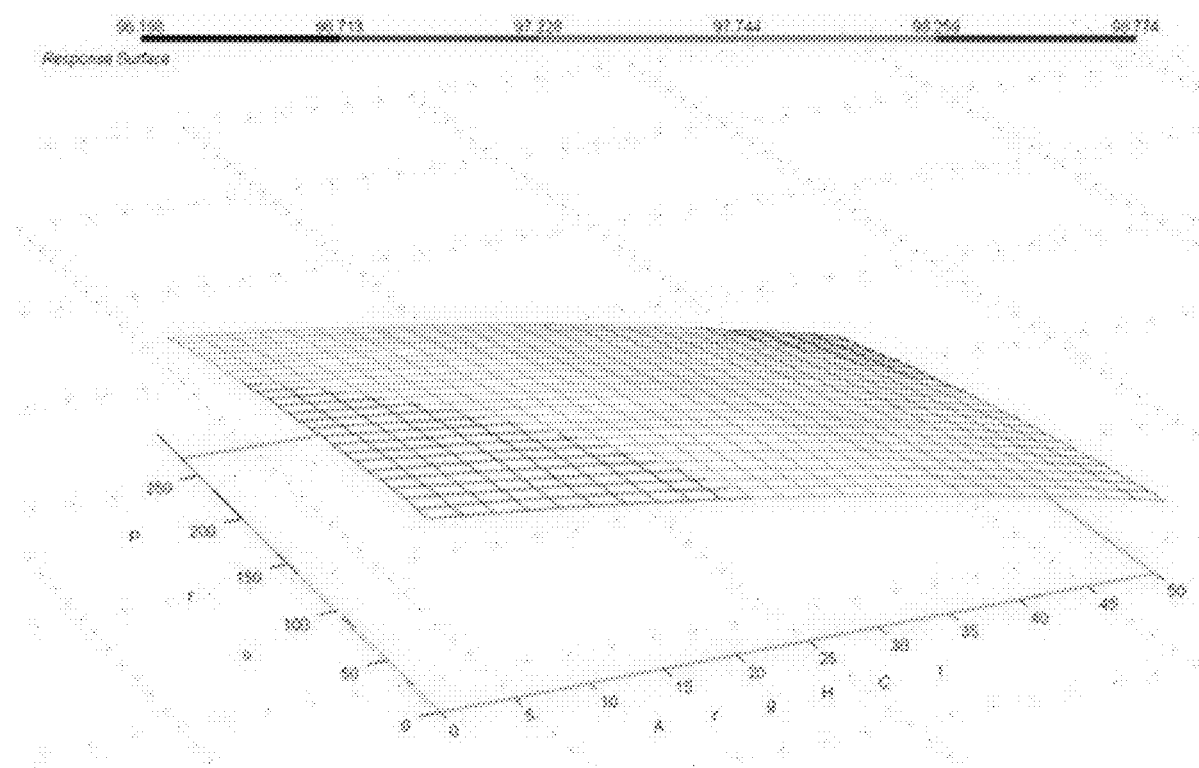
FIG. 24 is a graphic showing the effect of ArgHCl and proline according to the PLS1 model using monomer content after four weeks at 5° C. as the endpoint. The protein concentration was fixed at 40 mg/mL and pH at 6.0.

The term "aflibercept" is intended to be synonymous with the active pharmaceutical ingredient in Eylea® (Regeneron Pharmaceuticals, Inc.) and in Zaltrap® (Sanofi and Regeneron Pharmaceuticals, Inc.). Aflibercept is a recombinant fusion protein consisting of Vascular Endothelial Growth Factor (VEGF)-binding portions from the extracellular domains of human VEGF Receptors 1 and 2 fused to the Fc portion of the human IgG1. Aflibercept is a dimeric glycoprotein with a protein molecular weight of 97 kilodaltons (kDa) and contains glycosylation, constituting an additional 15% of the total molecular mass, resulting in a total molecular weight of 115 kDa. Amino acid and nucleic acid sequences of aflibercept are known in the art. See, U.S. Pat. No. 7,070,959 sequences 15 and 16 (FIG. 24).

The term "aflibercept" encompasses the active pharmaceutical ingredient in products intended to be, or approved as, biosimilar, interchangeable, or bio-better product of commercially available Eylea® and Zaltrap® (also referred to ziv-aflibercept). According the FDA, A biosimilar is a biological product that is highly similar to and has no clinically meaningful differences from an existing FDA-approved reference product. Therefore, a biosimilar for Eylea® or Zaltrap® may have essentially the same pharmacological effects as commercially available Eylea® or Zaltrap® even though the active pharmaceutical product in the biosimilar exhibits certain physical properties, such as glycosylation profile, that may be similar but not identical to Eylea® or Zaltrap®.

For the purposes of the present application, the term "aflibercept" also encompasses aflibercept with minor modifications in the amino acid structure (including deletions, additions, and/or substitutions of amino acids) or in the glycosylation properties, which do not significantly affect the function of the polypeptide.

The term "antibody", as used herein, refers to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "sugar" refers to monosaccharides, disaccharides, and polysaccharides. Examples of sugars include, but are not limited to, sucrose, glucose, dextrose, trehalose, lactose, and maltose.

The term "polyol" refers to an alcohol containing multiple hydroxyl groups. Examples of polyols include, but are not limited to, mannitol, sorbitol, glycerol, xylitol and inositol.

The term "metal ion" refers to a metal atom with a net positive or negative electric charge. For the purposes of the present application, the term "metal ion" also includes sources of metal ions, including but not limited to metal salts.

The term "stable" is understood to mean that aflibercept contained in the formulation or pharmaceutical compositions does not lose more than 20%, or more preferably 15%, or even more preferably 10%, and most preferably 5% of its activity relative to activity of the formulation or composition at the beginning of storage. The term also should be understood to mean that the aflibercept formulations or compositions are at least comparable to, or better than commercially available aflibercept compositions, in terms of their stability and/or ability to resist formation of particulates during storage. In another embodiment, term is understood to mean the aflibercept formulations or compositions is stable when agitated, mixed, or handled.

Stability is also intended to denote the ability of the pharmaceutical aflibercept compositions disclosed herein to resist particulates formation such that the compositions, under storage conditions typical of protein therapeutics, exhibits levels and types of particulates that meet standard guidelines. A reduced tendency to form particulates in formulations disclosed herein results in aflibercept formulations having reduced immunogenicity, and therefore reduced potential to cause harm to patients resulting from such immunogenicity.

The term "long-term storage" in connection with "formulation" or "pharmaceutical composition" is understood to mean that the formulation or pharmaceutical composition can be stored for three months or more, for six months or more, or for one year or more. In one embodiment of long-term storage, the composition is stored at about 2-8° C. In another embodiment of long-term storage, the composition is stored at about 0° C. In another embodiment of long-term storage, the composition is stored at about −20° C. In yet another embodiment of long-term storage, the composition is stored at about −40° C. In another embodiment of long-term storage, the composition is stored at about −70° C. In still another embodiment of long-term storage, the composition is stored at about −80° C. Generally speaking, the terms "long term storage" and "long term stability" further include stable storage durations that are at least comparable to or better than the stability of currently available commercial formulations of aflibercept, without losses in stability that would render the formulation unsuitable for its intended pharmaceutical application. It is also contemplated that the composition can be frozen and thawed more than once.

Stability of a protein in an aqueous formulation may also be defined as the percentage of monomer, aggregate, or fragment, or combinations thereof, of the protein in the formulation. A protein "retains its physical stability" in a formulation if it shows substantially no signs of aggregation, precipitation and/or denaturation upon visual examination of color and/or clarity, or as measured by UV light scattering or by size exclusion chromatography. In one aspect of the invention, a stable aqueous formulation is a formulation having less than about 10%, or less than about 5% of the protein being present as aggregate in the formulation.

A protein in an aqueous formulation can be stable at frozen storage temperatures, liquid storage temperatures such as refrigeration (e.g. 2-8° C.) and room temperature (about 25° C.), and under accelerated liquid stability testing temperatures (e.g. 40° C.).

Various analytical techniques for measuring protein stability, including techniques for measuring the type and degree of particulates that may be present in protein formulations, are available in the art and are reviewed in PEPTIDE AND PROTEIN DRUG DELIVERY, 247-301 (Vincent Lee ed., New York, N.Y., 1991) and Jones, 1993 Adv. Drug Delivery Rev. 10: 29-90, for examples. Stability can be measured at a selected temperature for a selected time period, e.g., as described in the examples below.

The term "mammal" includes, but is not limited to, a human.

The term "ophthalmically suitable" or "suitable for ophthalmic administration" means a composition as a whole, or the individual components (e.g. excipients) of a composition are safe for administration to a subject in, on, or around the subject's eye. Examples of such excipients are found in products already approved by the FDA for administration to a person's eye and are known to person of skill in the art. In one embodiment, a composition suitable for ophthalmic administration has a non-stinging formulation. In one embodiment, a composition suitable for ophthalmic administration is iso-osmolar relative to the vitreous. In one embodiment, a composition suitable for ophthalmic administration has an osmolality is between about 200 and about 350 mOsM. In another embodiment, a composition suitable for ophthalmic administration can be administered intravitreously. In one embodiment, a composition suitable for ophthalmic administration is administered by intravitreal injection. In one embodiment, a composition suitable for ophthalmic administration is administered topically. In one embodiment, a composition suitable for ophthalmic administration is administered via a port. In one embodiment, a composition suitable for ophthalmic administration has a volume of about 0.1 mL or less. In one embodiment, a composition suitable for ophthalmic administration has a volume of about 0.05 mL or less. In one embodiment, a composition suitable for ophthalmic administration has a volume of about 0.025 mL or less.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "pharmaceutical composition" or "formulation" as used herein refers to a mixture of a protein, such as a fusion protein, e.g., aflibercept, together with one or more additional components. In some embodiments, the additional component is water or a buffer. In other embodiments, the additional components may include, e.g., one or more excipients, such as a stabilizer, tonicity modifier, surfactant, and the like, e.g., a pharmaceutically acceptable carrier or excipient that is conventional in the art and which is suitable for administration to a subject for therapeutic, diagnostic, or prophylactic purposes. In one embodiment, the additional component is suitable for ophthalmic administration. For example, pharmaceutical compositions/formulations according to the present invention may be aqueous formulation suitable for intravitreal administration.

The term "substantially free" of a particular substance means that either the substance is not present or only minimal, trace amounts of the substance are present which do not have any substantial impact on the properties of the composition. If reference is made to no amount of a substance (or that the substance is not present), it should be understood as "no detectable amount."

By "iso-osmolar relative to the vitreous" is meant that the formulation of interest has essentially the same osmotic pressure as vitreous.

As used herein, "buffer" refers to a buffered solution that resists changes in pH by the action of its acid-base conjugate components. In one example, a buffer consists of a weak acid and a conjugate salt or a weak base and a conjugate salt (e.g sodium acetate). Buffers suitable for use in connection with this invention may have a pH in the range from about 4.0 to about 9.0; from about pH 4.0 to about 7.0; or from about pH 4.5 to about 6.5. A pH of any point in between the above ranges is also contemplated.

As used herein, the terms "buffer-free" or "free of buffer" are synonymous and intend to exclude components traditionally used to introduce buffer capacity in the formulation in addition to any buffering capacity present in the formulation absent the buffer component. For example, proteins are known to provide buffering capacity to a formulation. Hence, these terms do not mean a formulation cannot have any buffering capacity. In one embodiment, a buffer-free protein formulation is self-buffering.

As used herein, "purified" means that a molecule is present in a sample at a concentration of at least 95% by weight, or at least 98% by weight of the sample in which it is contained.

The term "organic co-solvent" is used herein in the same sense as it is used in U.S. Pat. No. 9,580,489. See, for example, column 2, lines 25-38. U.S. Pat. No. 9,580,489 states "organic co-solvent may be polysorbate, for example, polysorbate 20 or polysorbate 80, polyethylene glycol (PEG), for example, PEG 3350, or propylene glycol, or a combination thereof." An organic co-solvent is an organic (i.e., carbon-based) substance that is added to composition primarily to keep the ingredients of the composition in solution (i.e. dissolved). This includes preventing precipitation, aggregation, and adsorption of composition ingredients.

Substances defined or recited separately from "organic co-solvent" in U.S. Pat. No. 9,580,489 are excluded from term "organic co-solvent" in the present application. For example, U.S. Pat. No. 9,580,489 lists types of substances, and gives examples thereof, as distinct from an "organic co-solvent." See, column 2, lines 25-38. In particular, U.S. Pat. No. 9,580,489 provides the following examples of substances that are not organic co-solvents: a tonicity agent for example sodium chloride or potassium chloride; a stabilizing agent for example sucrose, sorbitol, glycerol, trehalose, or mannitol; and a buffering agent for example phosphate buffer. Examples of compounds that are not an "organic co-solvent," as used herein, include salt (e.g. sodium chloride, magnesium chloride), sugar (e.g. dextran or other polysaccharides), polyol (e.g. sorbitol, glycerol, mannitol), and amino acid (e.g. arginine, glycine, proline).

When pharmaceutical compositions containing aflibercept are stored, the activity of aflibercept can be lost or decreased due to aggregation and/or degradation. Thus, the present invention provides aqueous formulations of aflibercept that allow stable storage of aflibercept, so that aflibercept is stable over the course of storage either in liquid or frozen states. The provided formulations do not require any extra steps such as rehydrating.

Numerous embodiments of the present invention are explained in a greater detail below.

A. Aflibercept

Aflibercept suitable for storage in one of the present pharmaceutical compositions or formulations can be produced by standard methods known in the art. For example, U.S. Pat. No. 9,580,480 and WO 2006/104852 describe various methods that a skilled artisan could use to prepare aflibercept protein for use in the formulations of the present invention. These methods are incorporated by reference herein.

Aflibercept can also be produced by purifying and/or diluting from commercially-available Eylea® and/or Zaltrap® preparations using standard methods Purification of the expressed aflibercept can be performed by standard methods known in the art. When aflibercept is produced intracellularly by host cells, the host cells are lysed and particulate debris is removed, for example, by centrifugation or ultrafiltration. When aflibercept is secreted into the medium by host cells, supernatants from such expression systems can be first concentrated using standard polypeptide concentration filters. Protease inhibitors can also be added to inhibit proteolysis and antibiotics can be included to prevent the growth of microorganisms.

For example, aflibercept can be purified using, for example, hydroxyapatite chromatography, gel electrophoresis, dialysis, ion exchange chromatography and affinity chromatography, and any combination of known or yet to be discovered purification techniques, including but not limited to Protein A chromatography, fractionation on an ion-exchange column, hydrophobic interaction chromatography (HIC), ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

B. pH/Buffer Selection for Aflibercept Formulations

The formulations of the invention may include buffers, tonicity modifiers, excipients, pharmaceutically acceptable carriers and other commonly used inactive ingredients of the pharmaceutical compositions. However, formulations that indicate that an ingredient is excluded (e.g. buffer-free formulations) do not include such ingredient.

Buffers maintain pH in a desired range, e.g., between pH 4 and pH 9. Buffers may also serve to stabilize aflibercept by a variety of other mechanisms, meaning they may be used outside of the nominal buffer capacity range indicated by their respective pKa values. Examples of suitable buffers include acetate (e.g., at pH 4 to 5.5), citrate (e.g., at pH 5 to 6.5), histidine (e.g., at pH 5 to 7), phosphate (e.g., at about pH 6 and 8), Tris (e.g., at pH 7 to 8), and glycine (e.g., at pH 8 to 9). Specific embodiments include, without limitation, sodium or potassium phosphate, sodium or potassium citrate, ammonium acetate, tris-(hydroxymethyl)-aminomethane (tris), various forms of acetate and diethanolamine. Other suitable buffers include succinate, histidine, tartrate, bicarbonate, borate, and maleate. In one embodiment, the concentration of the buffer in the formulation is between about 1 mM to about 1M (e.g., about 1 mM to about 950 mM, about 1 mM to about 900 mM, about 1 mM to about 850 mM, about 1 mM to about 800 mM, about 1 mM to about 750 mM, about 1 mM to about 700 mM, about 1 mM to about 650 mM, about 1 mM to about 600 mM, about 1 mM to about 550 mM, about 1 mM to about 500 mM, about 1 mM to about 450 mM, about 1 mM to about 400 mM, about 1 mM to about 350 mM, about 1 mM to about 300 mM, about 1 mM to about 250 mM, about 1 mM to about 200 mM, about 1 mM to about 180 mM, about 1 mM to about 160 mM, about 1 mM to about 140 mM, about 1 mM to about 120 mM, about 1 mM to about 100 mM, about 1 mM to about 90 mM, about 1 mM to about 80 mM, about 1 mM to about 70 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 1 mM to about 5 mM, about 5 mM to about 1 M, about 5 mM to about 950 mM, about 5 mM to about 900 mM, about 5 mM to about 850 mM, about 5 mM to about 800 mM, about 5 mM to about 750 mM, about 5 mM to about 700 mM, about 5 mM to about 650 mM, about 5 mM to about 600 mM, about 5 mM to about 550 mM, about 5 mM to about 500 mM, about 5 mM to about 450 mM, about 5 mM to about 400 mM, about 5 mM to about 350 mM, about 5 mM to about 300 mM, about 5 mM to about 250 mM, about 5 mM to about 200 mM, about 5 mM to about 180 mM, about 5 mM to about 160 mM, about 5 mM to about 140 mM, about 5 mM to about 120 mM, about 5 mM to about 100 mM, about 5 mM to about 90 mM, about 5 mM to about 80 mM, about 5 mM to about 70 mM, about 5 mM to about 60 mM, about 5 mM to about 50 mM, about 5 mM to about 45 mM, about 5 mM to about 40 mM, about 5 mM to about 35 mM, about 5 mM to about 30 mM, about 5 mM to about 25 mM, about 5 mM to about 20 mM, about 5 mM to about 15 mM, about 5 mM to about 10 mM, about 10 mM to about 1 M, about 10 mM to about 950 mM, about 10 mM to about 900 mM, about 10 mM to about 850 mM, about 10 mM to about 800 mM, about 10 mM to about 750 mM, about 10 mM to about 700 mM, about 10 mM to about 650 mM, about 10 mM to about 600 mM, about 10 mM to about 550 mM, about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 180 mM, about 10 mM to about 160 mM, about 10 mM to about 140 mM, about 10 mM to about 120 mM, about 10 mM to about 100 mM, about 10 mM to about 90 mM, about 10 mM to about 80 mM, about 10 mM to about 70 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 1 M, about 15 mM to about 950 mM, about 15 mM to about 900 mM, about 15 mM to about 850 mM, about 15 mM to about 800 mM, about 15 mM to about 750 mM, about 15 mM to about 700 mM, about 15 mM to about 650 mM, about 15 mM to about 600 mM, about 15 mM to about 550 mM, about 15 mM to about 500 mM, about 15 mM to about 450 mM, about 15 mM to about 400 mM, about 15 mM to about 350 mM, about 15 mM to about 300 mM, about 15 mM to about 250 mM, about 15 mM to about 200 mM, about 15 mM to about 180 mM, about 15 mM to about 160 mM, about 15 mM to about 140 mM, about 15 mM to about 120 mM, about 15 mM to about 100 mM, about 15 mM to about 90 mM, about 15 mM to about 80 mM, about 15 mM to about 70 mM, about 15 mM to about 60 mM, about 15 mM to about 50 mM, about 15 mM to about 45 mM, about 15 mM to about 40 mM, about 15 mM to about 35 mM, about 15 mM to about 30 mM, about 15 mM to about 25 mM, about 15 mM to about 20 mM, about 20 mM to about 1 M, about 20 mM to about 950 mM, about 20 mM to about 900 mM, about 20 mM to about 850 mM, about 20 mM to about 800 mM, about 20 mM to about 750 mM, about 20 mM to about 700 mM, about 20 mM to about 650 mM, about 20 mM to about 600 mM, about 20 mM to about 550 mM, about 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 180 mM, about 20 mM to about 160 mM, about 20 mM to about 140 mM, about 20 mM to about 120 mM, about 20 mM to about 100 mM, about 20 mM to about 90 mM, about 20 mM to about 80 mM, about 20 mM to about 70 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 1 M, about 25 mM to about 950 mM, about 25 mM to about 900 mM, about 25 mM to about 850 mM, about 25 mM to about 800 mM, about 25 mM to about 750 mM, about 25 mM to about 700 mM, about 25 mM to about 650 mM, about 25 mM to about 600 mM, about 25 mM to about 550 mM, about 25 mM to about 500 mM, about 25 mM to about 450 mM, about 25 mM to about 400 mM, about 25 mM to about 350 mM, about 25 mM to about 300 mM, about 25 mM to about 250 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 90 mM, about 25 mM to about 80 mM, about 25 mM to about 70 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 1 M, about 30 mM to about 950 mM, about 30 mM to about 900 mM, about 30 mM to about 850 mM, about 30 mM to about 800 mM, about 30 mM to about 750 mM, about 30 mM to about 700 mM, about 30 mM to about 650 mM, about 30 mM to about 600 mM, about 30 mM to about 550 mM, about 30 mM to about 500 mM, about 30 mM to about 450 mM, about 30 mM to about 400 mM, about 30 mM to about 350 mM, about 30 mM to about 300 mM, about 30 mM to about 250 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 90 mM, about 30 mM to about 80 mM, about 30 mM to about 70 mM, about 30 mM to about 60 mM, about 30 mM to about 50 mM, about 30 mM to about 45 mM, about 30 mM to about 40 mM, about 30 mM to about 35 mM, about 35 mM to about 1 M, about 35 mM to about 950 mM, about 35 mM to about 900 mM, about 35 mM to about 850 mM, about 35 mM to about 800 mM, about 35 mM to about 750 mM, about 35 mM to about 700 mM, about 35 mM to about 650 mM, about 35 mM to about 600 mM, about 35 mM to about 550 mM, about 35 mM to about 500 mM, about 35 mM to about 450 mM, about 35 mM to about 400 mM, about 35 mM to about 350 mM, about 35 mM to about 300 mM, about 35 mM to about 250 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 90 mM, about 35 mM to about 80 mM, about 35 mM to about 70 mM, about 35 mM to about 60 mM, about 35 mM to about 50 mM, about 35 mM to about 45 mM, about 35 mM to about 40 mM, about 40 mM to about 1 M, about 40 mM to about 950 mM, about 40 mM to about 900 mM, about 40 mM to about 850 mM, about 40 mM to about 800 mM, about 40 mM to about 750 mM, about 40 mM to about 700 mM, about 40 mM to about 650 mM, about 40 mM to about 600 mM, about 40 mM to about 550 mM, about 40 mM to about 500 mM, about 40 mM to about 450 mM, about 40 mM to about 400 mM, about 40 mM to about 350 mM, about 40 mM to about 300 mM, about 40 mM to about 250 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 90 mM, about 40 mM to about 80 mM, about 40 mM to about 70 mM, about 40 mM to about 60 mM, about 40 mM to about 50 mM, about 40 mM to about 45 mM, about 45 mM to about 1 M, about 45 mM to about 950 mM, about 45 mM to about 900 mM, about 45 mM to about 850 mM, about 45 mM to about 800 mM, about 45 mM to about 750 mM, about 45 mM to about 700 mM, about 45 mM to about 650 mM, about 45 mM to about 600 mM, about 45 mM to about 550 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 90 mM, about 45 mM to about 80 mM, about 45 mM to about 70 mM, about 45 mM to about 60 mM, about 45 mM to about 50 mM, about 50 mM to about 1 M, about 50 mM to about 950 mM, about 50 mM to about 900 mM, about 50 mM to about 850 mM, about 50 mM to about 800 mM, about 50 mM to about 750 mM, about 50 mM to about 700 mM, about 50 mM to about 650 mM, about 50 mM to about 600 mM, about 50 mM to about 550 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 90 mM, about 50 mM to about 80 mM, about 50 mM to about 70 mM, about 50 mM to about 60 mM, about 60 mM to about 1 M, about 60 mM to about 950 mM, about 60 mM to about 900 mM, about 60 mM to about 850 mM, about 60 mM to about 800 mM, about 60 mM to about 750 mM, about 60 mM to about 700 mM, about 60 mM to about 650 mM, about 60 mM to about 600 mM, about 60 mM to about 550 mM, about 60 mM to about 500 mM, about 60 mM to about 450 mM, about 60 mM to about 400 mM, about 60 mM to about 350 mM, about 60 mM to about 300 mM, about 60 mM to about 250 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 90 mM, about 60 mM to about 80 mM, about 60 mM to about 70 mM, about 70 mM to about 1 M, about 70 mM to about 950 mM, about 70 mM to about 900 mM, about 70 mM to about 850 mM, about 70 mM to about 800 mM, about 70 mM to about 750 mM, about 70 mM to about 700 mM, about 70 mM to about 650 mM, about 70 mM to about 600 mM, about 70 mM to about 550 mM, about 70 mM to about 500 mM, about 70 mM to about 450 mM, about 70 mM to about 400 mM, about 70 mM to about 350 mM, about 70 mM to about 300 mM, about 70 mM to about 250 mM, about 70 mM to about 200 mM, about 70 mM to about 180 mM, about 70 mM to about 160 mM, about 70 mM to about 140 mM, about 70 mM to about 120 mM, about 70 mM to about 100 mM, about 70 mM to about 90 mM, about 70 mM to about 80 mM, about 80 mM to about 1 M, about 80 mM to about 950 mM, about 80 mM to about 900 mM, about 80 mM to about 850 mM, about 80 mM to about 800 mM, about 80 mM to about 750 mM, about 80 mM to about 700 mM, about 80 mM to about 650 mM, about 80 mM to about 600 mM, about 80 mM to about 550 mM, about 80 mM to about 500 mM, about 80 mM to about 450 mM, about 80 mM to about 400 mM, about 80 mM to about 350 mM, about 80 mM to about 300 mM, about 80 mM to about 250 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 80 mM to about 90 mM, about 90 mM to about 1 M, about 90 mM to about 950 mM, about 90 mM to about 900 mM, about 90 mM to about 850 mM, about 90 mM to about 800 mM, about 90 mM to about 750 mM, about 90 mM to about 700 mM, about 90 mM to about 650 mM, about 90 mM to about 600 mM, about 90 mM to about 550 mM, about 90 mM to about 500 mM, about 90 mM to about 450 mM, about 90 mM to about 400 mM, about 90 mM to about 350 mM, about 90 mM to about 300 mM, about 90 mM to about 250 mM, about 90 mM to about 200 mM, about 90 mM to about 180 mM, about 90 mM to about 160 mM, about 90 mM to about 140 mM, about 90 mM to about 120 mM, about 90 mM to about 100 mM, about 100 mM to about 1 M, about 100 mM to about 950 mM, about 100 mM to about 900 mM, about 100 mM to about 850 mM, about 100 mM to about 800 mM, about 100 mM to about 750 mM, about 100 mM to about 700 mM, about 100 mM to about 650 mM, about 100 mM to about 600 mM, about 100 mM to about 550 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 180 mM, about 100 mM to about 160 mM, about 100 mM to about 140 mM, about 100 mM to about 120 mM, about 120 mM to about 1 M, about 120 mM to about 950 mM, about 120 mM to about 900 mM, about 120 mM to about 850 mM, about 120 mM to about 800 mM, about 120 mM to about 750 mM, about 120 mM to about 700 mM, about 120 mM to about 650 mM, about 120 mM to about 600 mM, about 120 mM to about 550 mM, about 120 mM to about 500 mM, about 120 mM to about 450 mM, about 120 mM to about 400 mM, about 120 mM to about 350 mM, about 120 mM to about 300 mM, about 120 mM to about 250 mM, about 120 mM to about 200 mM, about 120 mM to about 180 mM, about 120 mM to about 160 mM, about 120 mM to about 140 mM, about 140 mM to about 1 M, about 140 mM to about 950 mM, about 140 mM to about 900 mM, about 140 mM to about 850 mM, about 140 mM to about 800 mM, about 140 mM to about 750 mM, about 140 mM to about 700 mM, about 140 mM to about 650 mM, about 140 mM to about 600 mM, about 140 mM to about 550 mM, about 140 mM to about 500 mM, about 140 mM to about 450 mM, about 140 mM to about 400 mM, about 140 mM to about 350 mM, about 140 mM to about 300 mM, about 140 mM to about 250 mM, about 140 mM to about 200 mM, about 140 mM to about 180 mM, about 140 mM to about 160 mM, about 160 mM to about 1 M, about 160 mM to about 950 mM, about 160 mM to about 900 mM, about 160 mM to about 850 mM, about 160 mM to about 800 mM, about 160 mM to about 750 mM, about 160 mM to about 700 mM, about 160 mM to about 650 mM, about 160 mM to about 600 mM, about 160 mM to about 550 mM, about 160 mM to about 500 mM, about 160 mM to about 450 mM, about 160 mM to about 400 mM, about 160 mM to about 350 mM, about 160 mM to about 300 mM, about 160 mM to about 250 mM, about 160 mM to about 200 mM, about 160 mM to about 180 mM, about 180 mM to about 1 M, about 180 mM to about 950 mM, about 180 mM to about 900 mM, about 180 mM to about 850 mM, about 180 mM to about 800 mM, about 180 mM to about 750 mM, about 180 mM to about 700 mM, about 180 mM to about 650 mM, about 180 mM to about 600 mM, about 180 mM to about 550 mM, about 180 mM to about 500 mM, about 180 mM to about 450 mM, about 180 mM to about 400 mM, about 180 mM to about 350 mM, about 180 mM to about 300 mM, about 180 mM to about 250 mM, about 180 mM to about 200 mM, about 200 mM to about 1 M, about 200 mM to about 950 mM, about 200 mM to about 900 mM, about 200 mM to about 850 mM, about 200 mM to about 800 mM, about 200 mM to about 750 mM, about 200 mM to about 700 mM, about 200 mM to about 650 mM, about 200 mM to about 600 mM, about 200 mM to about 550 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 250 mM to about 1 M, about 250 mM to about 950 mM, about 250 mM to about 900 mM, about 250 mM to about 850 mM, about 250 mM to about 800 mM, about 250 mM to about 750 mM, about 250 mM to about 700 mM, about 250 mM to about 650 mM, about 250 mM to about 600 mM, about 250 mM to about 550 mM, about 250 mM to about 500 mM, about 250 mM to about 450 mM, about 250 mM to about 400 mM, about 250 mM to about 350 mM, about 250 mM to about 300 mM, about 300 mM to about 1 M, about 300 mM to about 950 mM, about 300 mM to about 900 mM, about 300 mM to about 850 mM, about 300 mM to about 800 mM, about 300 mM to about 750 mM, about 300 mM to about 700 mM, about 300 mM to about 650 mM, about 300 mM to about 600 mM, about 300 mM to about 550 mM, about 300 mM to about 500 mM, about 300 mM to about 450 mM, about 300 mM to about 400 mM, about 300 mM to about 350 mM, about 350 mM to about 1 M, about 350 mM to about 950 mM, about 350 mM to about 900 mM, about 350 mM to about 850 mM, about 350 mM to about 800 mM, about 350 mM to about 750 mM, about 350 mM to about 700 mM, about 350 mM to about 650 mM, about 350 mM to about 600 mM, about 350 mM to about 550 mM, about 350 mM to about 500 mM, about 350 mM to about 450 mM, about 350 mM to about 400 mM, about 400 mM to about 1 M, about 400 mM to about 950 mM, about 400 mM to about 900 mM, about 400 mM to about 850 mM, about 400 mM to about 800 mM, about 400 mM to about 750 mM, about 400 mM to about 700 mM, about 400 mM to about 650 mM, about 400 mM to about 600 mM, about 400 mM to about 550 mM, about 400 mM to about 500 mM, about 400 mM to about 450 mM, about 450 mM to about 1 M, about 450 mM to about 950 mM, about 450 mM to about 900 mM, about 450 mM to about 850 mM, about 450 mM to about 800 mM, about 450 mM to about 750 mM, about 450 mM to about 700 mM, about 450 mM to about 650 mM, about 450 mM to about 600 mM, about 450 mM to about 550 mM, about 450 mM to about 500 mM, about 500 mM to about 1 M, about 500 mM to about 950 mM, about 500 mM to about 900 mM, about 500 mM to about 850 mM, about 500 mM to about 800 mM, about 500 mM to about 750 mM, about 500 mM to about 700 mM, about 500 mM to about 650 mM, about 500 mM to about 600 mM, about 500 mM to about 550 mM, about 550 mM to about 1 M, about 550 mM to about 950 mM, about 550 mM to about 900 mM, about 550 mM to about 850 mM, about 550 mM to about 800 mM, about 550 mM to about 750 mM, about 550 mM to about 700 mM, about 550 mM to about 650 mM, about 550 mM to about 600 mM, about 600 mM to about 1 M, about 600 mM to about 950 mM, about 600 mM to about 900 mM, about 600 mM to about 850 mM, about 600 mM to about 800 mM, about 600 mM to about 750 mM, about 600 mM to about 700 mM, about 600 mM to about 650 mM, about 650 mM to about 1 M, about 650 mM to about 950 mM, about 650 mM to about 900 mM, about 650 mM to about 850 mM, about 650 mM to about 800 mM, about 650 mM to about 750 mM, about 650 mM to about 700 mM, about 700 mM to about 1 M, about 700 mM to about 950 mM, about 700 mM to about 900 mM, about 700 mM to about 850 mM, about 700 mM to about 800 mM, about 700 mM to about 750 mM, about 750 mM to about 1 M, about 750 mM to about 950 mM, about 750 mM to about 900 mM, about 750 mM to about 850 mM, about 750 mM to about 800 mM, about 800 mM to about 1 M, about 800 mM to about 950 mM, about 800 mM to about 900 mM, about 800 mM to about 850 mM, about 850 mM to about 1 M, about 850 mM to about 950 mM, about 850 mM to about 900 mM, about 900 mM to about 1 M, about 900 mM to about 950 mM, or 950 mM to 1 M). In one embodiment, the concentration of the buffer is between 1 mM to about 150 mM. In one embodiment, the concentration of the buffer is about 5 mM to about 20 mM. In one embodiment, the concentration of the buffer is about 10 mM. Buffers are well known in the art and are manufactured by known methods and available from commercial suppliers. The selection of an appropriate buffer may be informed by data on any interactions of specific buffers with other formulation components. For example, U.S. Pat. No. 8,349,321 discloses that degradation of polysorbate 80 (thought to be due to a metal catalyzed oxidation of polysorbate) is significantly impeded by replacing histidine buffer with phosphate buffer in a tested placebo formulation.

The pH of the pharmaceutical compositions of the invention is generally between 5 and 7 (e.g., about 5.0 to about 6.9, about 5.0 to about 6.8, about 5.0 to about 6.7, about 5.0 to about 6.6, about 5.0 to about 6.5, about 5.0 to about 6.4, about 5.0 to about 6.3, about 5.0 to about 6.2, about 5.0 to about 6.1, about 5.0 to about 6.0, about 5.0 to about 5.9, about 5.0 to about 5.8, about 5.0 to about 5.7, about 5.0 to about 5.6, about 5.0 to about 5.5, about 5.0 to about 5.4, about 5.0 to about 5.3, about 5.0 to about 5.2, about 5.1 to about 7.0, about 5.1 to about 6.9, about 5.1 to about 6.8, about 5.1 to about 6.7, about 5.1 to about 6.6, about 5.1 to about 6.5, about 5.1 to about 6.4, about 5.1 to about 6.3, about 5.1 to about 6.2, about 5.1 to about 6.1, about 5.1 to about 6.0, about 5.1 to about 5.9, about 5.1 to about 5.8, about 5.1 to about 5.7, about 5.1 to about 5.6, about 5.1 to about 5.5, about 5.1 to about 5.4, about 5.1 to about 5.3, about 5.2 to about 7.0, about 5.2 to about 6.9, about 5.2 to about 6.8, about 5.2 to about 6.7, about 5.2 to about 6.6, about 5.2 to about 6.5, about 5.2 to about 6.4, about 5.2 to about 6.3, about 5.2 to about 6.2, about 5.2 to about 6.1, about 5.2 to about 6.0, about 5.2 to about 5.9, about 5.2 to about 5.8, about 5.2 to about 5.7, about 5.2 to about 5.6, about 5.2 to about 5.5, about 5.2 to about 5.4, about 5.3 to about 7.0, about 5.3 to about 6.9, about 5.3 to about 6.8, about 5.3 to about 6.7, about 5.3 to about 6.6, about 5.3 to about 6.5, about 5.3 to about 6.4, about 5.3 to about 6.3, about 5.3 to about 6.2, about 5.3 to about 6.1, about 5.3 to about 6.0, about 5.3 to about 5.9, about 5.3 to about 5.8, about 5.3 to about 5.7, about 5.3 to about 5.6, about 5.3 to about 5.5, about 5.4 to about 7.0, about 5.4 to about 6.9, about 5.4 to about 6.8, about 5.4 to about 6.7, about 5.4 to about 6.6, about 5.4 to about 6.5, about 5.4 to about 6.4, about 5.4 to about 6.3, about 5.4 to about 6.2, about 5.4 to about 6.1, about 5.4 to about 6.0, about 5.4 to about 5.9, about 5.4 to about 5.8, about 5.4 to about 5.7, about 5.4 to about 5.6, about 5.5 to about 7.0, about 5.5 to about 6.9, about 5.5 to about 6.8, about 5.5 to about 6.7, about 5.5 to about 6.6, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.6 to about 7.0, about 5.6 to about 6.9, about 5.6 to about 6.8, about 5.6 to about 6.7, about 5.6 to about 6.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.7 to about 7.0, about 5.7 to about 6.9, about 5.7 to about 6.8, about 5.7 to about 6.7, about 5.7 to about 6.6, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.8 to about 7.0, about 5.8 to about 6.9, about 5.8 to about 6.8, about 5.8 to about 6.7, about 5.8 to about 6.6, about 5.8 to about 6.5, about 5.8 to about 6.4, about 5.8 to about 6.3, about 5.8 to about 6.2, about 5.8 to about 6.1, about 5.8 to about 6.0, about 5.9 to about 7.0, about 5.9 to about 6.9, about 5.9 to about 6.8, about 5.9 to about 6.7, about 5.9 to about 6.6, about 5.9 to about 6.5, about 5.9 to about 6.4, about 5.9 to about 6.3, about 5.9 to about 6.2, about 5.9 to about 6.1, about 6.0 to about 7.0, about 6.0 to about 6.9, about 6.0 to about 6.8, about 6.0 to about 6.7, about 6.0 to about 6.6, about 6.0 to about 6.5, about 6.0 to about 6.4, about 6.0 to about 6.3, about 6.0 to about 6.2, about 6.1 to about 7.0, about 6.1 to about 6.9, about 6.1 to about 6.8, about 6.1 to about 6.7, about 6.1 to about 6.6, about 6.1 to about 6.5, about 6.1 to about 6.4, about 6.1 to about 6.3, about 6.2 to about 7.0, about 6.2 to about 6.9, about 6.2 to about 6.8, about 6.2 to about 6.7, about 6.2 to about 6.6, about 6.2 to about 6.5, about 6.2 to about 6.4, about 6.3 to about 7.0, about 6.3 to about 6.9, about 6.3 to about 6.8, about 6.3 to about 6.7, about 6.3 to about 6.6, about 6.3 to about 6.5, about 6.4 to about 7.0, about 6.4 to about 6.9, about 6.4 to about 6.8, about 6.4 to about 6.7, about 6.4 to about 6.6, about 6.5 to about 7.0, about 6.5 to about 6.9, about 6.5 to about 6.8, about 6.5 to about 6.7, about 6.6 to about 7.0, about 6.6 to about 6.9, about 6.6 to about 6.8, about 6.7 to about 7.0, about 6.7 to about 6.9, or about 6.8 to about 7.0, or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In one embodiment, the pH is between 5.5 and 7.0. In another embodiment, the pH is between 6.0 and 6.5. In another embodiment, the pH is about 6.2.

A person of ordinary skill in the art will understand that the pH can be adjusted as necessary to maximize stability and solubility of aflibercept in a particular formulation. For example, a strong acid (e.g. HCl) or a strong base (NaOH) can be added to a formulation to adjust the pH down or up. Such adjustment to a target pH can be made in buffer-free formulations and such formulations are still considered buffer-free C. Excipients Suitable for Use in Aflibercept Formulations Excipients include components of a pharmaceutical formulation other than the active ingredient and are typically added during formulation development for a specific purpose, such as to stabilize the polypeptide while in solution, change viscosity of the formulation, adjust tonicity, and confer other desired properties to the formulation. Excipients are well known in the art and are manufactured by known methods and available from commercial suppliers. Excipients may include, for example, tonicity modifiers, stabilizers, salts, chelating agents, sacrificial additives and surfactants, and miscellaneous excipients such as ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate, and the like. In one embodiment, the concentration of an excipient in a formulation of the invention is between about 0.001 to 30 weight percent (e.g., about 0.001 to about 28 weight percent, about 0.001 to about 26 weight percent, about 0.001 to about 24 weight percent, about 0.001 to about 22 weight percent, about 0.001 to about 20 weight percent, about 0.001 to about 18 weight percent, about 0.001 to about 16 weight percent, about 0.001 to about 14 weight percent, about 0.001 to about 12 weight percent, about 0.001 to about 10 weight percent, about 0.001 to about 9 weight percent, about 0.001 to about 8 weight percent, about 0.001 to about 7 weight percent, about 0.001 to about 6 weight percent, about 0.001 to about 5 weight percent, about 0.001 to about 4.5 weight percent, about 0.001 to about 4.0 weight percent, about 0.001 to about 3.5 weight percent, about 0.001 to about 3.0 weight percent, about 0.001 to about 2.5 weight percent, about 0.001 to about 2.0 weight percent, about 0.001 to about 1.5 weight percent, about 0.001 to about 1.0 weight percent, about 0.001 to about 0.5 weight percent, about 0.001 to about 0.1 weight percent, about 0.001 to about 0.01 weight percent, about 0.01 to about 30 weight percent, about 0.01 to about 28 weight percent, about 0.01 to about 26 weight percent, about 0.01 to about 24 weight percent, about 0.01 to about 22 weight percent, about 0.01 to about 20 weight percent, about 0.01 to about 18 weight percent, about 0.01 to about 16 weight percent, about 0.01 to about 14 weight percent, about 0.01 to about 12 weight percent, about 0.01 to about 10 weight percent, about 0.01 to about 9 weight percent, about 0.01 to about 8 weight percent, about 0.01 to about 7 weight percent, about 0.01 to about 6 weight percent, about 0.01 to about 5 weight percent, about 0.01 to about 4.5 weight percent, about 0.01 to about 4.0 weight percent, about 0.01 to about 3.5 weight percent, about 0.01 to about 3.0 weight percent, about 0.01 to about 2.5 weight percent, about 0.01 to about 2.0 weight percent, about 0.01 to about 1.5 weight percent, about 0.01 to about 1.0 weight percent, about 0.01 to about 0.5 weight percent, about 0.01 to about 0.1 weight percent, about 0.1 to about 30 weight percent, about 0.1 to about 28 weight percent, about 0.1 to about 26 weight percent, about 0.1 to about 24 weight percent, about 0.1 to about 22 weight percent, about 0.1 to about 20 weight percent, about 0.1 to about 18 weight percent, about 0.1 to about 16 weight percent, about 0.1 to about 14 weight percent, about 0.1 to about 12 weight percent, about 0.1 to about 10 weight percent, about 0.1 to about 9 weight percent, about 0.1 to about 8 weight percent, about 0.1 to about 7 weight percent, about 0.1 to about 6 weight percent, about 0.1 to about 5 weight percent, about 0.1 to about 4.5 weight percent, about 0.1 to about 4.0 weight percent, about 0.1 to about 3.5 weight percent, about 0.1 to about 3.0 weight percent, about 0.1 to about 2.5 weight percent, about 0.1 to about 2.0 weight percent, about 0.1 to about 1.5 weight percent, about 0.1 to about 1.0 weight percent, about 0.1 to about 0.5 weight percent, about 0.5 to about 30 weight percent, about 0.5 to about 28 weight percent, about 0.5 to about 26 weight percent, about 0.5 to about 24 weight percent, about 0.5 to about 22 weight percent, about 0.5 to about 20 weight percent, about 0.5 to about 18 weight percent, about 0.5 to about 16 weight percent, about 0.5 to about 14 weight percent, about 0.5 to about 12 weight percent, about 0.5 to about 10 weight percent, about 0.5 to about 9 weight percent, about 0.5 to about 8 weight percent, about 0.5 to about 7 weight percent, about 0.5 to about 6 weight percent, about 0.5 to about 5 weight percent, about 0.5 to about 4.5 weight percent, about 0.5 to about 4.0 weight percent, about 0.5 to about 3.5 weight percent, about 0.5 to about 3.0 weight percent, about 0.5 to about 2.5 weight percent, about 0.5 to about 2.0 weight percent, about 0.5 to about 1.5 weight percent, about 0.5 to about 1.0 weight percent, about 1.0 to about 30 weight percent, about 1.0 to about 28 weight percent, about 1.0 to about 26 weight percent, about 1.0 to about 24 weight percent, about 1.0 to about 22 weight percent, about 1.0 to about 20 weight percent, about 1.0 to about 18 weight percent, about 1.0 to about 16 weight percent, about 1.0 to about 14 weight percent, about 1.0 to about 12 weight percent, about 1.0 to about 10 weight percent, about 1.0 to about 9 weight percent, about 1.0 to about 8 weight percent, about 1.0 to about 7 weight percent, about 1.0 to about 6 weight percent, about 1.0 to about 5 weight percent, about 1.0 to about 4.5 weight percent, about 1.0 to about 4.0 weight percent, about 1.0 to about 3.5 weight percent, about 1.0 to about 3.0 weight percent, about 1.0 to about 2.5 weight percent, about 1.0 to about 2.0 weight percent, about 1.0 to about 1.5 weight percent, about 1.5 to about 30 weight percent, about 1.5 to about 28 weight percent, about 1.5 to about 26 weight percent, about 1.5 to about 24 weight percent, about 1.5 to about 22 weight percent, about 1.5 to about 20 weight percent, about 1.5 to about 18 weight percent, about 1.5 to about 16 weight percent, about 1.5 to about 14 weight percent, about 1.5 to about 12 weight percent, about 1.5 to about 10 weight percent, about 1.5 to about 9 weight percent, about 1.5 to about 8 weight percent, about 1.5 to about 7 weight percent, about 1.5 to about 6 weight percent, about 1.5 to about 5 weight percent, about 1.5 to about 4.5 weight percent, about 1.5 to about 4.0 weight percent, about 1.5 to about 3.5 weight percent, about 1.5 to about 3.0 weight percent, about 1.5 to about 2.5 weight percent, about 1.5 to about 2.0 weight percent, about 2.0 to about 30 weight percent, about 2.0 to about 28 weight percent, about 2.0 to about 26 weight percent, about 2.0 to about 24 weight percent, about 2.0 to about 22 weight percent, about 2.0 to about 20 weight percent, about 2.0 to about 18 weight percent, about 2.0 to about 16 weight percent, about 2.0 to about 14 weight percent, about 2.0 to about 12 weight percent, about 2.0 to about 10 weight percent, about 2.0 to about 9 weight percent, about 2.0 to about 8 weight percent, about 2.0 to about 7 weight percent, about 2.0 to about 6 weight percent, about 2.0 to about 5 weight percent, about 2.0 to about 4.5 weight percent, about 2.0 to about 4.0 weight percent, about 2.0 to about 3.5 weight percent, about 2.0 to about 3.0 weight percent, about 2.0 to about 2.5 weight percent, about 2.5 to about 30 weight percent, about 2.5 to about 28 weight percent, about 2.5 to about 26 weight percent, about 2.5 to about 24 weight percent, about 2.5 to about 22 weight percent, about 2.5 to about 20 weight percent, about 2.5 to about 18 weight percent, about 2.5 to about 16 weight percent, about 2.5 to about 14 weight percent, about 2.5 to about 12 weight percent, about 2.5 to about 10 weight percent, about 2.5 to about 9 weight percent, about 2.5 to about 8 weight percent, about 2.5 to about 7 weight percent, about 2.5 to about 6 weight percent, about 2.5 to about 5 weight percent, about 2.5 to about 4.5 weight percent, about 2.5 to about 4.0 weight percent, about 2.5 to about 3.5 weight percent, about 2.5 to about 3.0 weight percent, about 3.0 to about 30 weight percent, about 3.0 to about 28 weight percent, about 3.0 to about 26 weight percent, about 3.0 to about 24 weight percent, about 3.0 to about 22 weight percent, about 3.0 to about 20 weight percent, about 3.0 to about 18 weight percent, about 3.0 to about 16 weight percent, about 3.0 to about 14 weight percent, about 3.0 to about 12 weight percent, about 3.0 to about 10 weight percent, about 3.0 to about 9 weight percent, about 3.0 to about 8 weight percent, about 3.0 to about 7 weight percent, about 3.0 to about 6 weight percent, about 3.0 to about 5 weight percent, about 3.0 to about 4.5 weight percent, about 3.0 to about 4.0 weight percent, about 3.0 to about 3.5 weight percent, about 3.5 to about 30 weight percent, about 3.5 to about 28 weight percent, about 3.5 to about 26 weight percent, about 3.5 to about 24 weight percent, about 3.5 to about 22 weight percent, about 3.5 to about 20 weight percent, about 3.5 to about 18 weight percent, about 3.5 to about 16 weight percent, about 3.5 to about 14 weight percent, about 3.5 to about 12 weight percent, about 3.5 to about 10 weight percent, about 3.5 to about 9 weight percent, about 3.5 to about 8 weight percent, about 3.5 to about 7 weight percent, about 3.5 to about 6 weight percent, about 3.5 to about 5 weight percent, about 3.5 to about 4.5 weight percent, about 3.5 to about 4.0 weight percent, about 4.0 to about 30 weight percent, about 4.0 to about 28 weight percent, about 4.0 to about 26 weight percent, about 4.0 to about 24 weight percent, about 4.0 to about 22 weight percent, about 4.0 to about 20 weight percent, about 4.0 to about 18 weight percent, about 4.0 to about 16 weight percent, about 4.0 to about 14 weight percent, about 4.0 to about 12 weight percent, about 4.0 to about 10 weight percent, about 4.0 to about 9 weight percent, about 4.0 to about 8 weight percent, about 4.0 to about 7 weight percent, about 4.0 to about 6 weight percent, about 4.0 to about 5 weight percent, about 4.0 to about 4.5 weight percent, about 4.5 to about 30 weight percent, about 4.5 to about 28 weight percent, about 4.5 to about 26 weight percent, about 4.5 to about 24 weight percent, about 4.5 to about 22 weight percent, about 4.5 to about 20 weight percent, about 4.5 to about 18 weight percent, about 4.5 to about 16 weight percent, about 4.5 to about 14 weight percent, about 4.5 to about 12 weight percent, about 4.5 to about 10 weight percent, about 4.5 to about 9 weight percent, about 4.5 to about 8 weight percent, about 4.5 to about 7 weight percent, about 4.5 to about 6 weight percent, about 4.5 to about 5 weight percent, about 5 to about 30 weight percent, about 5 to about 28 weight percent, about 5 to about 26 weight percent, about 5 to about 24 weight percent, about 5 to about 22 weight percent, about 5 to about 20 weight percent, about 5 to about 18 weight percent, about 5 to about 16 weight percent, about 5 to about 14 weight percent, about 5 to about 12 weight percent, about 5 to about 10 weight percent, about 5 to about 9 weight percent, about 5 to about 8 weight percent, about 5 to about 7 weight percent, about 5 to about 6 weight percent, about 6 to about 30 weight percent, about 6 to about 28 weight percent, about 6 to about 26 weight percent, about 6 to about 24 weight percent, about 6 to about 22 weight percent, about 6 to about 20 weight percent, about 6 to about 18 weight percent, about 6 to about 16 weight percent, about 6 to about 14 weight percent, about 6 to about 12 weight percent, about 6 to about 10 weight percent, about 6 to about 9 weight percent, about 6 to about 8 weight percent, about 6 to about 7 weight percent, about 7 to about 30 weight percent, about 7 to about 28 weight percent, about 7 to about 26 weight percent, about 7 to about 24 weight percent, about 7 to about 22 weight percent, about 7 to about 20 weight percent, about 7 to about 18 weight percent, about 7 to about 16 weight percent, about 7 to about 14 weight percent, about 7 to about 12 weight percent, about 7 to about 10 weight percent, about 7 to about 9 weight percent, about 7 to about 8 weight percent, about 8 to about 30 weight percent, about 8 to about 28 weight percent, about 8 to about 26 weight percent, about 8 to about 24 weight percent, about 8 to about 22 weight percent, about 8 to about 20 weight percent, about 8 to about 18 weight percent, about 8 to about 16 weight percent, about 8 to about 14 weight percent, about 8 to about 12 weight percent, about 8 to about 10 weight percent, about 8 to about 9 weight percent, about 9 to about 30 weight percent, about 9 to about 28 weight percent, about 9 to about 26 weight percent, about 9 to about 24 weight percent, about 9 to about 22 weight percent, about 9 to about 20 weight percent, about 9 to about 18 weight percent, about 9 to about 16 weight percent, about 9 to about 14 weight percent, about 9 to about 12 weight percent, about 9 to about 10 weight percent, about 10 to about 30 weight percent, about 10 to about 28 weight percent, about 10 to about 26 weight percent, about 10 to about 24 weight percent, about 10 to about 22 weight percent, about 10 to about 20 weight percent, about 10 to about 18 weight percent, about 10 to about 16 weight percent, about 10 to about 14 weight percent, about 10 to about 12 weight percent, about 12 to about 30 weight percent, about 12 to about 28 weight percent, about 12 to about 26 weight percent, about 12 to about 24 weight percent, about 12 to about 22 weight percent, about 12 to about 20 weight percent, about 12 to about 18 weight percent, about 12 to about 16 weight percent, about 12 to about 14 weight percent, about 14 to about 30 weight percent, about 14 to about 28 weight percent, about 14 to about 26 weight percent, about 14 to about 24 weight percent, about 14 to about 22 weight percent, about 14 to about 20 weight percent, about 14 to about 18 weight percent, about 14 to about 16 weight percent, about 16 to about 30 weight percent, about 16 to about 28 weight percent, about 16 to about 26 weight percent, about 16 to about 24 weight percent, about 16 to about 22 weight percent, about 16 to about 20 weight percent, about 16 to about 18 weight percent, about 18 to about 30 weight percent, about 18 to about 28 weight percent, about 18 to about 26 weight percent, about 18 to about 24 weight percent, about 18 to about 22 weight percent, about 18 to about 20 weight percent, about 20 to about 30 weight percent, about 20 to about 28 weight percent, about 20 to about 26 weight percent, about 20 to about 24 weight percent, about 20 to about 22 weight percent, about 22 to about 30 weight percent, about 22 to about 28 weight percent, about 22 to about 26 weight percent, about 22 to about 24 weight percent, about 24 to about 30 weight percent, about 24 to about 28 weight percent, about 24 to about 26 weight percent, about 26 to about 30 weight percent, about 26 to about 28 weight percent, or about 28 to about 30 weight percent).

In another embodiment, the concentration of the excipient is about 0.01 to 10 weight percent.

In one embodiment, the concentration of an excipient in the provided formulations is between about 1 mM and about 500 mM (e.g., about 1 mM to about 450 mM, about 1 mM to about 400 mM, about 1 mM to about 350 mM, about 1 mM to about 300 mM, about 1 mM to about 250 mM, about 1 mM to about 200 mM, about 1 mM to about 180 mM, about 1 mM to about 160 mM, about 1 mM to about 140 mM, about 1 mM to about 120 mM, about 1 mM to about 100 mM, about 1 mM to about 80 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 1 mM to about 8 mM, about 1 mM to about 6 mM, about 1 mM to about 4 mM, about 1 mM to about 2 mM, about 2 mM to about 500 mM, about 2 mM to about 450 mM, about 2 mM to about 400 mM, about 2 mM to about 350 mM, about 2 mM to about 300 mM, about 2 mM to about 250 mM, about 2 mM to about 200 mM, about 2 mM to about 180 mM, about 2 mM to about 160 mM, about 2 mM to about 140 mM, about 2 mM to about 120 mM, about 2 mM to about 100 mM, about 2 mM to about 80 mM, about 2 mM to about 60 mM, about 2 mM to about 50 mM, about 2 mM to about 45 mM, about 2 mM to about 40 mM, about 2 mM to about 35 mM, about 2 mM to about 30 mM, about 2 mM to about 25 mM, about 2 mM to about 20 mM, about 2 mM to about 15 mM, about 2 mM to about 10 mM, about 2 mM to about 8 mM, about 2 mM to about 6 mM, about 2 mM to about 4 mM, about 4 mM to about 500 mM, about 4 mM to about 450 mM, about 4 mM to about 400 mM, about 4 mM to about 350 mM, about 4 mM to about 300 mM, about 4 mM to about 250 mM, about 4 mM to about 200 mM, about 4 mM to about 180 mM, about 4 mM to about 160 mM, about 4 mM to about 140 mM, about 4 mM to about 120 mM, about 4 mM to about 100 mM, about 4 mM to about 80 mM, about 4 mM to about 60 mM, about 4 mM to about 50 mM, about 4 mM to about 45 mM, about 4 mM to about 40 mM, about 4 mM to about 35 mM, about 4 mM to about 30 mM, about 4 mM to about 25 mM, about 4 mM to about 20 mM, about 4 mM to about 15 mM, about 4 mM to about 10 mM, about 4 mM to about 8 mM, about 4 mM to about 6 mM, about 6 mM to about 500 mM, about 6 mM to about 450 mM, about 6 mM to about 400 mM, about 6 mM to about 350 mM, about 6 mM to about 300 mM, about 6 mM to about 250 mM, about 6 mM to about 200 mM, about 6 mM to about 180 mM, about 6 mM to about 160 mM, about 6 mM to about 140 mM, about 6 mM to about 120 mM, about 6 mM to about 100 mM, about 6 mM to about 80 mM, about 6 mM to about 60 mM, about 6 mM to about 50 mM, about 6 mM to about 45 mM, about 6 mM to about 40 mM, about 6 mM to about 35 mM, about 6 mM to about 30 mM, about 6 mM to about 25 mM, about 6 mM to about 20 mM, about 6 mM to about 15 mM, about 6 mM to about 10 mM, about 6 mM to about 8 mM, about 8 mM to about 500 mM, about 8 mM to about 450 mM, about 8 mM to about 400 mM, about 8 mM to about 350 mM, about 8 mM to about 300 mM, about 8 mM to about 250 mM, about 8 mM to about 200 mM, about 8 mM to about 180 mM, about 8 mM to about 160 mM, about 8 mM to about 140 mM, about 8 mM to about 120 mM, about 8 mM to about 100 mM, about 8 mM to about 80 mM, about 8 mM to about 60 mM, about 8 mM to about 50 mM, about 8 mM to about 45 mM, about 8 mM to about 40 mM, about 8 mM to about 35 mM, about 8 mM to about 30 mM, about 8 mM to about 25 mM, about 8 mM to about 20 mM, about 8 mM to about 15 mM, about 8 mM to about 10 mM, about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 180 mM, about 10 mM to about 160 mM, about 10 mM to about 140 mM, about 10 mM to about 120 mM, about 10 mM to about 100 mM, about 10 mM to about 80 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 500 mM, about 15 mM to about 450 mM, about 15 mM to about 400 mM, about 15 mM to about 350 mM, about 15 mM to about 300 mM, about 15 mM to about 250 mM, about 15 mM to about 200 mM, about 15 mM to about 180 mM, about 15 mM to about 160 mM, about 15 mM to about 140 mM, about 15 mM to about 120 mM, about 15 mM to about 100 mM, about 15 mM to about 80 mM, about 15 mM to about 60 mM, about 15 mM to about 50 mM, about 15 mM to about 45 mM, about 15 mM to about 40 mM, about 15 mM to about 35 mM, about 15 mM to about 30 mM, about 15 mM to about 25 mM, about 15 mM to about 20 mM, about 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 180 mM, about 20 mM to about 160 mM, about 20 mM to about 140 mM, about 20 mM to about 120 mM, about 20 mM to about 100 mM, about 20 mM to about 80 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 500 mM, about 25 mM to about 450 mM, about 25 mM to about 400 mM, about 25 mM to about 350 mM, about 25 mM to about 300 mM, about 25 mM to about 250 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 80 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 500 mM, about 30 mM to about 450 mM, about 30 mM to about 400 mM, about 30 mM to about 350 mM, about 30 mM to about 300 mM, about 30 mM to about 250 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 80 mM, about 30 mM to about 60 mM, about 30 mM to about 50 mM, about 30 mM to about 45 mM, about 30 mM to about 40 mM, about 30 mM to about 35 mM, about 35 mM to about 500 mM, about 35 mM to about 450 mM, about 35 mM to about 400 mM, about 35 mM to about 350 mM, about 35 mM to about 300 mM, about 35 mM to about 250 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 80 mM, about 35 mM to about 60 mM, about 35 mM to about 50 mM, about 35 mM to about 45 mM, about 35 mM to about 40 mM, about 40 mM to about 500 mM, about 40 mM to about 450 mM, about 40 mM to about 400 mM, about 40 mM to about 350 mM, about 40 mM to about 300 mM, about 40 mM to about 250 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 80 mM, about 40 mM to about 60 mM, about 40 mM to about 50 mM, about 40 mM to about 45 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 80 mM, about 45 mM to about 60 mM, about 45 mM to about 50 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 80 mM, about 50 mM to about 60 mM, about 60 mM to about 500 mM, about 60 mM to about 450 mM, about 60 mM to about 400 mM, about 60 mM to about 350 mM, about 60 mM to about 300 mM, about 60 mM to about 250 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 80 mM, about 80 mM to about 500 mM, about 80 mM to about 450 mM, about 80 mM to about 400 mM, about 80 mM to about 350 mM, about 80 mM to about 300 mM, about 80 mM to about 250 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 180 mM, about 100 mM to about 160 mM, about 100 mM to about 140 mM, about 100 mM to about 120 mM, about 120 mM to about 500 mM, about 120 mM to about 450 mM, about 120 mM to about 400 mM, about 120 mM to about 350 mM, about 120 mM to about 300 mM, about 120 mM to about 250 mM, about 120 mM to about 200 mM, about 120 mM to about 180 mM, about 120 mM to about 160 mM, about 120 mM to about 140 mM, about 140 mM to about 500 mM, about 140 mM to about 450 mM, about 140 mM to about 400 mM, about 140 mM to about 350 mM, about 140 mM to about 300 mM, about 140 mM to about 250 mM, about 140 mM to about 200 mM, about 140 mM to about 180 mM, about 140 mM to about 160 mM, about 160 mM to about 500 mM, about 160 mM to about 450 mM, about 160 mM to about 400 mM, about 160 mM to about 350 mM, about 160 mM to about 300 mM, about 160 mM to about 250 mM, about 160 mM to about 200 mM, about 160 mM to about 180 mM, about 180 mM to about 500 mM, about 180 mM to about 450 mM, about 180 mM to about 400 mM, about 180 mM to about 350 mM, about 180 mM to about 300 mM, about 180 mM to about 250 mM, about 180 mM to about 200 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 250 mM to about 500 mM, about 250 mM to about 450 mM, about 250 mM to about 400 mM, about 250 mM to about 350 mM, about 250 mM to about 300 mM, about 300 mM to about 500 mM, about 300 mM to about 450 mM, about 300 mM to about 400 mM, about 300 mM to about 350 mM, about 350 mM to about 500 mM, about 350 mM to about 450 mM, about 350 mM to about 400 mM, about 400 mM to about 500 mM, about 400 mM to about 450 mM, or about 450 mM to about 500 mM).

I. Tonicity Modifiers

A tonicity modifier is an ingredient that contributes to the osmolality of a solution. A tonicity modifier may also provide some degree of conformational or colloidal stabilization as well. The osmolality of a pharmaceutical composition is adjusted to minimize discomfort to the patient upon administration. Additionally, osmolality of a composition may impact the active ingredient's stability and can be adjusted to improve the stability. It is generally preferred that a pharmaceutical composition for intravitreal administration to a patient be isotonic with vitreous, i.e., have the same or similar osmolality, which is achieved by addition of a tonicity modifier. However, hypertonic formulations which would then be diluted in an isotonic vehicle are also within the scope of this invention.

In one embodiment, the osmolality of the provided formulations is from about 180 to about 500 mOsM (e.g., about 180 to about 450 mOsM, about 180 to about 400 mOsM, about 180 to about 350 mOsM, about 180 to about 300 mOsM, about 180 to about 250 mOsM, about 180 to about 200 mOsM, about 200 to about 500 mOsM, about 200 to about 450 mOsM, about 200 to about 400 mOsM, about 200 to about 350 mOsM, about 200 to about 300 mOsM, about 200 to about 250 mOsM, about 250 to about 500 mOsM, about 250 to about 450 mOsM, about 250 to about 400 mOsM, about 250 to about 350 mOsM, about 250 to about 300 mOsM, about 300 to about 500 mOsM, about 300 to about 450 mOsM, about 300 to about 400 mOsM, about 300 to about 350 mOsM, about 350 to about 500 mOsM, about 350 to about 450 mOsM, about 350 to about 400 mOsM, about 400 to about 500 mOsM, about 400 to about 450 mOsM, or about 450 to about 500 mOsM).

In one embodiment, the osmolality is between about 200 and about 300 mOsM. However, it is to be understood that the osmolality can be either higher or lower as specific conditions require.

Examples of tonicity modifiers suitable for modifying osmolality include, but are not limited to amino acids (e.g., cysteine, arginine, histidine and glycine), salts (e.g., sodium chloride, potassium chloride and sodium citrate) and/or nonelectrolytes (e.g., sugars or polyols, such as, for example, sucrose, glucose and mannitol).

In one embodiment, the concentration of the tonicity modifier in the formulation is between about 1 mM to about 1 M (e.g., any of the subranges of this range described herein). In another embodiment, the concentration is about 50 mM to about 500 mM.

In one embodiment, the concentration of the tonicity modifier in the provided formulations is between about 1 mM and about 500 mM (e.g., about 1 mM to about 450 mM, about 1 mM to about 400 mM, about 1 mM to about 350 mM, about 1 mM to about 300 mM, about 1 mM to about 250 mM, about 1 mM to about 200 mM, about 1 mM to about 180 mM, about 1 mM to about 160 mM, about 1 mM to about 140 mM, about 1 mM to about 120 mM, about 1 mM to about 100 mM, about 1 mM to about 80 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 1 mM to about 8 mM, about 1 mM to about 6 mM, about 1 mM to about 4 mM, about 1 mM to about 2 mM, about 2 mM to about 500 mM, about 2 mM to about 450 mM, about 2 mM to about 400 mM, about 2 mM to about 350 mM, about 2 mM to about 300 mM, about 2 mM to about 250 mM, about 2 mM to about 200 mM, about 2 mM to about 180 mM, about 2 mM to about 160 mM, about 2 mM to about 140 mM, about 2 mM to about 120 mM, about 2 mM to about 100 mM, about 2 mM to about 80 mM, about 2 mM to about 60 mM, about 2 mM to about 50 mM, about 2 mM to about 45 mM, about 2 mM to about 40 mM, about 2 mM to about 35 mM, about 2 mM to about 30 mM, about 2 mM to about 25 mM, about 2 mM to about 20 mM, about 2 mM to about 15 mM, about 2 mM to about 10 mM, about 2 mM to about 8 mM, about 2 mM to about 6 mM, about 2 mM to about 4 mM, about 4 mM to about 500 mM, about 4 mM to about 450 mM, about 4 mM to about 400 mM, about 4 mM to about 350 mM, about 4 mM to about 300 mM, about 4 mM to about 250 mM, about 4 mM to about 200 mM, about 4 mM to about 180 mM, about 4 mM to about 160 mM, about 4 mM to about 140 mM, about 4 mM to about 120 mM, about 4 mM to about 100 mM, about 4 mM to about 80 mM, about 4 mM to about 60 mM, about 4 mM to about 50 mM, about 4 mM to about 45 mM, about 4 mM to about 40 mM, about 4 mM to about 35 mM, about 4 mM to about 30 mM, about 4 mM to about 25 mM, about 4 mM to about 20 mM, about 4 mM to about 15 mM, about 4 mM to about 10 mM, about 4 mM to about 8 mM, about 4 mM to about 6 mM, about 6 mM to about 500 mM, about 6 mM to about 450 mM, about 6 mM to about 400 mM, about 6 mM to about 350 mM, about 6 mM to about 300 mM, about 6 mM to about 250 mM, about 6 mM to about 200 mM, about 6 mM to about 180 mM, about 6 mM to about 160 mM, about 6 mM to about 140 mM, about 6 mM to about 120 mM, about 6 mM to about 100 mM, about 6 mM to about 80 mM, about 6 mM to about 60 mM, about 6 mM to about 50 mM, about 6 mM to about 45 mM, about 6 mM to about 40 mM, about 6 mM to about 35 mM, about 6 mM to about 30 mM, about 6 mM to about 25 mM, about 6 mM to about 20 mM, about 6 mM to about 15 mM, about 6 mM to about 10 mM, about 6 mM to about 8 mM, about 8 mM to about 500 mM, about 8 mM to about 450 mM, about 8 mM to about 400 mM, about 8 mM to about 350 mM, about 8 mM to about 300 mM, about 8 mM to about 250 mM, about 8 mM to about 200 mM, about 8 mM to about 180 mM, about 8 mM to about 160 mM, about 8 mM to about 140 mM, about 8 mM to about 120 mM, about 8 mM to about 100 mM, about 8 mM to about 80 mM, about 8 mM to about 60 mM, about 8 mM to about 50 mM, about 8 mM to about 45 mM, about 8 mM to about 40 mM, about 8 mM to about 35 mM, about 8 mM to about 30 mM, about 8 mM to about 25 mM, about 8 mM to about 20 mM, about 8 mM to about 15 mM, about 8 mM to about 10 mM, about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 180 mM, about 10 mM to about 160 mM, about 10 mM to about 140 mM, about 10 mM to about 120 mM, about 10 mM to about 100 mM, about 10 mM to about 80 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 500 mM, about 15 mM to about 450 mM, about 15 mM to about 400 mM, about 15 mM to about 350 mM, about 15 mM to about 300 mM, about 15 mM to about 250 mM, about 15 mM to about 200 mM, about 15 mM to about 180 mM, about 15 mM to about 160 mM, about 15 mM to about 140 mM, about 15 mM to about 120 mM, about 15 mM to about 100 mM, about 15 mM to about 80 mM, about 15 mM to about 60 mM, about 15 mM to about 50 mM, about 15 mM to about 45 mM, about 15 mM to about 40 mM, about 15 mM to about 35 mM, about 15 mM to about 30 mM, about 15 mM to about 25 mM, about 15 mM to about 20 mM, about 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 180 mM, about 20 mM to about 160 mM, about 20 mM to about 140 mM, about 20 mM to about 120 mM, about 20 mM to about 100 mM, about 20 mM to about 80 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 500 mM, about 25 mM to about 450 mM, about 25 mM to about 400 mM, about 25 mM to about 350 mM, about 25 mM to about 300 mM, about 25 mM to about 250 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 80 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 500 mM, about 30 mM to about 450 mM, about 30 mM to about 400 mM, about 30 mM to about 350 mM, about 30 mM to about 300 mM, about 30 mM to about 250 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 80 mM, about 30 mM to about 60 mM, about 30 mM to about 50 mM, about 30 mM to about 45 mM, about 30 mM to about 40 mM, about 30 mM to about 35 mM, about 35 mM to about 500 mM, about 35 mM to about 450 mM, about 35 mM to about 400 mM, about 35 mM to about 350 mM, about 35 mM to about 300 mM, about 35 mM to about 250 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 80 mM, about 35 mM to about 60 mM, about 35 mM to about 50 mM, about 35 mM to about 45 mM, about 35 mM to about 40 mM, about 40 mM to about 500 mM, about 40 mM to about 450 mM, about 40 mM to about 400 mM, about 40 mM to about 350 mM, about 40 mM to about 300 mM, about 40 mM to about 250 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 80 mM, about 40 mM to about 60 mM, about 40 mM to about 50 mM, about 40 mM to about 45 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 80 mM, about 45 mM to about 60 mM, about 45 mM to about 50 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 80 mM, about 50 mM to about 60 mM, about 60 mM to about 500 mM, about 60 mM to about 450 mM, about 60 mM to about 400 mM, about 60 mM to about 350 mM, about 60 mM to about 300 mM, about 60 mM to about 250 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 80 mM, about 80 mM to about 500 mM, about 80 mM to about 450 mM, about 80 mM to about 400 mM, about 80 mM to about 350 mM, about 80 mM to about 300 mM, about 80 mM to about 250 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 180 mM, about 100 mM to about 160 mM, about 100 mM to about 140 mM, about 100 mM to about 120 mM, about 120 mM to about 500 mM, about 120 mM to about 450 mM, about 120 mM to about 400 mM, about 120 mM to about 350 mM, about 120 mM to about 300 mM, about 120 mM to about 250 mM, about 120 mM to about 200 mM, about 120 mM to about 180 mM, about 120 mM to about 160 mM, about 120 mM to about 140 mM, about 140 mM to about 500 mM, about 140 mM to about 450 mM, about 140 mM to about 400 mM, about 140 mM to about 350 mM, about 140 mM to about 300 mM, about 140 mM to about 250 mM, about 140 mM to about 200 mM, about 140 mM to about 180 mM, about 140 mM to about 160 mM, about 160 mM to about 500 mM, about 160 mM to about 450 mM, about 160 mM to about 400 mM, about 160 mM to about 350 mM, about 160 mM to about 300 mM, about 160 mM to about 250 mM, about 160 mM to about 200 mM, about 160 mM to about 180 mM, about 180 mM to about 500 mM, about 180 mM to about 450 mM, about 180 mM to about 400 mM, about 180 mM to about 350 mM, about 180 mM to about 300 mM, about 180 mM to about 250 mM, about 180 mM to about 200 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 250 mM to about 500 mM, about 250 mM to about 450 mM, about 250 mM to about 400 mM, about 250 mM to about 350 mM, about 250 mM to about 300 mM, about 300 mM to about 500 mM, about 300 mM to about 450 mM, about 300 mM to about 400 mM, about 300 mM to about 350 mM, about 350 mM to about 500 mM, about 350 mM to about 450 mM, about 350 mM to about 400 mM, about 400 mM to about 500 mM, about 400 mM to about 450 mM, or about 450 mM to about 500 mM).

Tonicity modifiers are well known in the art and are manufactured by known methods and available from commercial suppliers.

II. Stabilizers

Stabilizers are a class of excipients that may stabilize a composition, and the active pharmaceutical ingredient, in various way including providing physical stability, conformational stability, and chemical stability. Examples of types of excipients that are used as a stabilizer include sugars, polymers, polyols and amino acids. Specific examples of sugars include sucrose, dextrose, maltose, lactose, raffinose, and trehalose. Examples of polyols include sorbitol, maltitol, xylitol, and mannitol. Examples of amino acids include glycine, arginine, glutamate, and proline (either as the free base form or as a salt form). The invention further includes specific combinations of stabilizers that have particularly desirable properties. Examples include combinations of amino acids, e.g., Arg and Glu, as well as combinations of one or more amino acids with one or more polyols (e.g., Gly together with sorbitol or mannitol).

Improvements in formulation stability, due to such stabilizers, may be observed over a period of hours, days, months, or may last for extended periods, e.g., 6 months, 9 months, a year, or up to two years or more. Stabilizers may improve stability of a formulation over free-thaw cycles.

a. Aflibercept Formulations Stabilized with Sugars

In one embodiment, the invention provides a stable aqueous formulation comprising aflibercept and a sugar. Optionally, the formulation may further comprise a polyol and/or an amino acid. Examples of sugars include sucrose, lactose, maltose, trehalose, raffinose, and glucose. The composition may be a buffer-free and/or free of an organic co-solvent.

Inclusion of a sugar in the formulation improves the physical stability and other properties of specific aflibercept formulations (e.g., reduce tendency of aflibercept to associate in an undesirable conformation, and therefore reduce aggregation in aflibercept formulations). Thus, a sugar may stabilize aqueous pharmaceutical compositions containing aflibercept.

In one embodiment, the concentration of a sugar in the provided formulations is between about 0.01% (w/v) to 40% (e.g., about 0.01% to about 35% w/v, about 0.01% to about 30% w/v, about 0.01% to about 25% w/v, about 0.01% to about 20% w/v, about 0.01% to about 18% w/v, about 0.01% to about 16% w/v, about 0.01% to about 14% w/v, about 0.01% to about 12% w/v, about 0.01% to about 10% w/v, about 0.01% to about 9% w/v, about 0.01% to about 8% w/v, about 0.01% to about 7% w/v, about 0.01% to about 6% w/v, about 0.01% to about 5% w/v, about 0.01% to about 4% w/v, about 0.01% to about 3% w/v, about 0.01% to about 2% w/v, about 0.01% to about 1% w/v, about 0.01% to about 0.5% w/v, about 0.01% to about 0.1% w/v, about 0.1% to about 40% w/v, about 0.1% to about 35% w/v, about 0.1% to about 30% w/v, about 0.1% to about 25% w/v, about 0.1% to about 20% w/v, about 0.1% to about 18% w/v, about 0.1% to about 16% w/v, about 0.1% to about 14% w/v, about 0.1% to about 12% w/v, about 0.1% to about 10% w/v, about 0.1% to about 9% w/v, about 0.1% to about 8% w/v, about 0.1% to about 7% w/v, about 0.1% to about 6% w/v, about 0.1% to about 5% w/v, about 0.1% to about 4% w/v, about 0.1% to about 3% w/v, about 0.1% to about 2% w/v, about 0.1% to about 1% w/v, about 0.1% to about 0.5% w/v, about 0.5% to about 40% w/v, about 0.5% to about 35% w/v, about 0.5% to about 30% w/v, about 0.5% to about 25% w/v, about 0.5% to about 20% w/v, about 0.5% to about 18% w/v, about 0.5% to about 16% w/v, about 0.5% to about 14% w/v, about 0.5% to about 12% w/v, about 0.5% to about 10% w/v, about 0.5% to about 9% w/v, about 0.5% to about 8% w/v, about 0.5% to about 7% w/v, about 0.5% to about 6% w/v, about 0.5% to about 5% w/v, about 0.5% to about 4% w/v, about 0.5% to about 3% w/v, about 0.5% to about 2% w/v, about 0.5% to about 1% w/v, about 1% to about 40% w/v, about 1% to about 35% w/v, about 1% to about 30% w/v, about 1% to about 25% w/v, about 1% to about 20% w/v, about 1% to about 18% w/v, about 1% to about 16% w/v, about 1% to about 14% w/v, about 1% to about 12% w/v, about 1% to about 10% w/v, about 1% to about 9% w/v, about 1% to about 8% w/v, about 1% to about 7% w/v, about 1% to about 6% w/v, about 1% to about 5% w/v, about 1% to about 4% w/v, about 1% to about 3% w/v, about 1% to about 2% w/v, about 2% to about 40% w/v, about 2% to about 35% w/v, about 2% to about 30% w/v, about 2% to about 25% w/v, about 2% to about 20% w/v, about 2% to about 18% w/v, about 2% to about 16% w/v, about 2% to about 14% w/v, about 2% to about 12% w/v, about 2% to about 10% w/v, about 2% to about 9% w/v, about 2% to about 8% w/v, about 2% to about 7% w/v, about 2% to about 6% w/v, about 2% to about 5% w/v, about 2% to about 4% w/v, about 2% to about 3% w/v, about 3% to about 40% w/v, about 3% to about 35% w/v, about 3% to about 30% w/v, about 3% to about 25% w/v, about 3% to about 20% w/v, about 3% to about 18% w/v, about 3% to about 16% w/v, about 3% to about 14% w/v, about 3% to about 12% w/v, about 3% to about 10% w/v, about 3% to about 9% w/v, about 3% to about 8% w/v, about 3% to about 7% w/v, about 3% to about 6% w/v, about 3% to about 5% w/v, about 3% to about 4% w/v, about 4% to about 40% w/v, about 4% to about 35% w/v, about 4% to about 30% w/v, about 4% to about 25% w/v, about 4% to about 20% w/v, about 4% to about 18% w/v, about 4% to about 16% w/v, about 4% to about 14% w/v, about 4% to about 12% w/v, about 4% to about 10% w/v, about 4% to about 9% w/v, about 4% to about 8% w/v, about 4% to about 7% w/v, about 4% to about 6% w/v, about 4% to about 5% w/v, about 5% to about 40% w/v, about 5% to about 35% w/v, about 5% to about 30% w/v, about 5% to about 25% w/v, about 5% to about 20% w/v, about 5% to about 18% w/v, about 5% to about 16% w/v, about 5% to about 14% w/v, about 5% to about 12% w/v, about 5% to about 10% w/v, about 5% to about 9% w/v, about 5% to about 8% w/v, about 5% to about 7% w/v, about 5% to about 6% w/v, about 6% to about 40% w/v, about 6% to about 35% w/v, about 6% to about 30% w/v, about 6% to about 25% w/v, about 6% to about 20% w/v, about 6% to about 18% w/v, about 6% to about 16% w/v, about 6% to about 14% w/v, about 6% to about 12% w/v, about 6% to about 10% w/v, about 6% to about 9% w/v, about 6% to about 8% w/v, about 6% to about 7% w/v, about 7% to about 40% w/v, about 7% to about 35% w/v, about 7% to about 30% w/v, about 7% to about 25% w/v, about 7% to about 20% w/v, about 7% to about 18% w/v, about 7% to about 16% w/v, about 7% to about 14% w/v, about 7% to about 12% w/v, about 7% to about 10% w/v, about 7% to about 9% w/v, about 7% to about 8% w/v, about 8% to about 40% w/v, about 8% to about 35% w/v, about 8% to about 30% w/v, about 8% to about 25% w/v, about 8% to about 20% w/v, about 8% to about 18% w/v, about 8% to about 16% w/v, about 8% to about 14% w/v, about 8% to about 12% w/v, about 8% to about 10% w/v, about 8% to about 9% w/v, about 9% to about 40% w/v, about 9% to about 35% w/v, about 9% to about 30% w/v, about 9% to about 25% w/v, about 9% to about 20% w/v, about 9% to about 18% w/v, about 9% to about 16% w/v, about 9% to about 14% w/v, about 9% to about 12% w/v, about 9% to about 10% w/v, about 10% to about 40% w/v, about 10% to about 35% w/v, about 10% to about 30% w/v, about 10% to about 25% w/v, about 10% to about 20% w/v, about 10% to about 18% w/v, about 10% to about 16% w/v, about 10% to about 14% w/v, about 10% to about 12% w/v, about 12% to about 40% w/v, about 12% to about 35% w/v, about 12% to about 30% w/v, about 12% to about 25% w/v, about 12% to about 20% w/v, about 12% to about 18% w/v, about 12% to about 16% w/v, about 12% to about 14% w/v, about 14% to about 40% w/v, about 14% to about 35% w/v, about 14% to about 30% w/v, about 14% to about 25% w/v, about 14% to about 20% w/v, about 14% to about 18% w/v, about 14% to about 16% w/v, about 16% to about 40% w/v, about 16% to about 35% w/v, about 16% to about 30% w/v, about 16% to about 25% w/v, about 16% to about 20% w/v, about 16% to about 18% w/v, about 18% to about 40% w/v, about 18% to about 35% w/v, about 18% to about 30% w/v, about 18% to about 25% w/v, about 18% to about 20% w/v, about 20% to about 40% w/v, about 20% to about 35% w/v, about 20% to about 30% w/v, about 20% to about 25% w/v, about 25% to about 40% w/v, about 25% to about 35% w/v, about 25% to about 30% w/v, about 30% to about 40% w/v, about 30% to about 35% w/v, or about 35% to about 40% w/v), for example about 1% to about 20%, about 2% to about 10%, or about 5% to 9%.

In one embodiment, the concentration of the sugar in the provided formulations is between about 1 mM and about 500 mM (e.g., about 1 mM to about 450 mM, about 1 mM to about 400 mM, about 1 mM to about 350 mM, about 1 mM to about 300 mM, about 1 mM to about 250 mM, about 1 mM to about 200 mM, about 1 mM to about 180 mM, about 1 mM to about 160 mM, about 1 mM to about 140 mM, about 1 mM to about 120 mM, about 1 mM to about 100 mM, about 1 mM to about 80 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 1 mM to about 8 mM, about 1 mM to about 6 mM, about 1 mM to about 4 mM, about 1 mM to about 2 mM, about 2 mM to about 500 mM, about 2 mM to about 450 mM, about 2 mM to about 400 mM, about 2 mM to about 350 mM, about 2 mM to about 300 mM, about 2 mM to about 250 mM, about 2 mM to about 200 mM, about 2 mM to about 180 mM, about 2 mM to about 160 mM, about 2 mM to about 140 mM, about 2 mM to about 120 mM, about 2 mM to about 100 mM, about 2 mM to about 80 mM, about 2 mM to about 60 mM, about 2 mM to about 50 mM, about 2 mM to about 45 mM, about 2 mM to about 40 mM, about 2 mM to about 35 mM, about 2 mM to about 30 mM, about 2 mM to about 25 mM, about 2 mM to about 20 mM, about 2 mM to about 15 mM, about 2 mM to about 10 mM, about 2 mM to about 8 mM, about 2 mM to about 6 mM, about 2 mM to about 4 mM, about 4 mM to about 500 mM, about 4 mM to about 450 mM, about 4 mM to about 400 mM, about 4 mM to about 350 mM, about 4 mM to about 300 mM, about 4 mM to about 250 mM, about 4 mM to about 200 mM, about 4 mM to about 180 mM, about 4 mM to about 160 mM, about 4 mM to about 140 mM, about 4 mM to about 120 mM, about 4 mM to about 100 mM, about 4 mM to about 80 mM, about 4 mM to about 60 mM, about 4 mM to about 50 mM, about 4 mM to about 45 mM, about 4 mM to about 40 mM, about 4 mM to about 35 mM, about 4 mM to about 30 mM, about 4 mM to about 25 mM, about 4 mM to about 20 mM, about 4 mM to about 15 mM, about 4 mM to about 10 mM, about 4 mM to about 8 mM, about 4 mM to about 6 mM, about 6 mM to about 500 mM, about 6 mM to about 450 mM, about 6 mM to about 400 mM, about 6 mM to about 350 mM, about 6 mM to about 300 mM, about 6 mM to about 250 mM, about 6 mM to about 200 mM, about 6 mM to about 180 mM, about 6 mM to about 160 mM, about 6 mM to about 140 mM, about 6 mM to about 120 mM, about 6 mM to about 100 mM, about 6 mM to about 80 mM, about 6 mM to about 60 mM, about 6 mM to about 50 mM, about 6 mM to about 45 mM, about 6 mM to about 40 mM, about 6 mM to about 35 mM, about 6 mM to about 30 mM, about 6 mM to about 25 mM, about 6 mM to about 20 mM, about 6 mM to about 15 mM, about 6 mM to about 10 mM, about 6 mM to about 8 mM, about 8 mM to about 500 mM, about 8 mM to about 450 mM, about 8 mM to about 400 mM, about 8 mM to about 350 mM, about 8 mM to about 300 mM, about 8 mM to about 250 mM, about 8 mM to about 200 mM, about 8 mM to about 180 mM, about 8 mM to about 160 mM, about 8 mM to about 140 mM, about 8 mM to about 120 mM, about 8 mM to about 100 mM, about 8 mM to about 80 mM, about 8 mM to about 60 mM, about 8 mM to about 50 mM, about 8 mM to about 45 mM, about 8 mM to about 40 mM, about 8 mM to about 35 mM, about 8 mM to about 30 mM, about 8 mM to about 25 mM, about 8 mM to about 20 mM, about 8 mM to about 15 mM, about 8 mM to about 10 mM, about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 180 mM, about 10 mM to about 160 mM, about 10 mM to about 140 mM, about 10 mM to about 120 mM, about 10 mM to about 100 mM, about 10 mM to about 80 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 500 mM, about 15 mM to about 450 mM, about 15 mM to about 400 mM, about 15 mM to about 350 mM, about 15 mM to about 300 mM, about 15 mM to about 250 mM, about 15 mM to about 200 mM, about 15 mM to about 180 mM, about 15 mM to about 160 mM, about 15 mM to about 140 mM, about 15 mM to about 120 mM, about 15 mM to about 100 mM, about 15 mM to about 80 mM, about 15 mM to about 60 mM, about 15 mM to about 50 mM, about 15 mM to about 45 mM, about 15 mM to about 40 mM, about 15 mM to about 35 mM, about 15 mM to about 30 mM, about 15 mM to about 25 mM, about 15 mM to about 20 mM, about 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 180 mM, about 20 mM to about 160 mM, about 20 mM to about 140 mM, about 20 mM to about 120 mM, about 20 mM to about 100 mM, about 20 mM to about 80 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 500 mM, about 25 mM to about 450 mM, about 25 mM to about 400 mM, about 25 mM to about 350 mM, about 25 mM to about 300 mM, about 25 mM to about 250 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 80 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 500 mM, about 30 mM to about 450 mM, about 30 mM to about 400 mM, about 30 mM to about 350 mM, about 30 mM to about 300 mM, about 30 mM to about 250 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 80 mM, about 30 mM to about 60 mM, about 30 mM to about 50 mM, about 30 mM to about 45 mM, about 30 mM to about 40 mM, about 30 mM to about 35 mM, about 35 mM to about 500 mM, about 35 mM to about 450 mM, about 35 mM to about 400 mM, about 35 mM to about 350 mM, about 35 mM to about 300 mM, about 35 mM to about 250 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 80 mM, about 35 mM to about 60 mM, about 35 mM to about 50 mM, about 35 mM to about 45 mM, about 35 mM to about 40 mM, about 40 mM to about 500 mM, about 40 mM to about 450 mM, about 40 mM to about 400 mM, about 40 mM to about 350 mM, about 40 mM to about 300 mM, about 40 mM to about 250 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 80 mM, about 40 mM to about 60 mM, about 40 mM to about 50 mM, about 40 mM to about 45 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 80 mM, about 45 mM to about 60 mM, about 45 mM to about 50 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 80 mM, about 50 mM to about 60 mM, about 60 mM to about 500 mM, about 60 mM to about 450 mM, about 60 mM to about 400 mM, about 60 mM to about 350 mM, about 60 mM to about 300 mM, about 60 mM to about 250 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 80 mM, about 80 mM to about 500 mM, about 80 mM to about 450 mM, about 80 mM to about 400 mM, about 80 mM to about 350 mM, about 80 mM to about 300 mM, about 80 mM to about 250 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 180 mM, about 100 mM to about 160 mM, about 100 mM to about 140 mM, about 100 mM to about 120 mM, about 120 mM to about 500 mM, about 120 mM to about 450 mM, about 120 mM to about 400 mM, about 120 mM to about 350 mM, about 120 mM to about 300 mM, about 120 mM to about 250 mM, about 120 mM to about 200 mM, about 120 mM to about 180 mM, about 120 mM to about 160 mM, about 120 mM to about 140 mM, about 140 mM to about 500 mM, about 140 mM to about 450 mM, about 140 mM to about 400 mM, about 140 mM to about 350 mM, about 140 mM to about 300 mM, about 140 mM to about 250 mM, about 140 mM to about 200 mM, about 140 mM to about 180 mM, about 140 mM to about 160 mM, about 160 mM to about 500 mM, about 160 mM to about 450 mM, about 160 mM to about 400 mM, about 160 mM to about 350 mM, about 160 mM to about 300 mM, about 160 mM to about 250 mM, about 160 mM to about 200 mM, about 160 mM to about 180 mM, about 180 mM to about 500 mM, about 180 mM to about 450 mM, about 180 mM to about 400 mM, about 180 mM to about 350 mM, about 180 mM to about 300 mM, about 180 mM to about 250 mM, about 180 mM to about 200 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 250 mM to about 500 mM, about 250 mM to about 450 mM, about 250 mM to about 400 mM, about 250 mM to about 350 mM, about 250 mM to about 300 mM, about 300 mM to about 500 mM, about 300 mM to about 450 mM, about 300 mM to about 400 mM, about 300 mM to about 350 mM, about 350 mM to about 500 mM, about 350 mM to about 450 mM, about 350 mM to about 400 mM, about 400 mM to about 500 mM, about 400 mM to about 450 mM, or about 450 mM to about 500 mM).

In one embodiment, a formulation of the invention comprises about 10 to about 200 mg/mL (e.g., any of the subranges of this range described herein) of aflibercept; about 10 mM to about 350 mM (e.g., any of the subranges of this range described herein) sucrose; about 0.01 mM to about 100 mM (e.g., any of the subranges of this range described herein) sodium chloride; about 0.0001% to about 0.1% (e.g., about 0.0001% to about 0.05%, about 0.0001% to about 0.01%, about 0.0001% to about 0.0005%, about 0.0005% to about 0.1%, about 0.0005% to about 0.05%, about 0.0005% to about 0.01%, about 0.01% to about 0.1%, about 0.01% to about 0.05%, or about 0.05% to about 0.1%) surfactant; and about 0.1 to about 5% (e.g., about 0.1% to about 4.5%, about 0.1% to about 4.0%, about 0.1% to about 3.5%, about 0.1% to about 3.0%, about 0.1% to about 2.5%, about 0.1% to about 2.0%, about 0.1% to about 1.5%, about 0.1% to about 1.0%, about 0.1% to about 0.5%, about 0.5% to about 5.0%, about 0.5% to about 4.5%, about 0.5% to about 4.0%, about 0.5% to about 3.5%, about 0.5% to about 3.0%, about 0.5% to about 2.5%, about 0.5% to about 2.0%, about 0.5% to about 1.5%, about 0.5% to about 1.0%, about 1.0% to about 5.0%, about 1.0% to about 4.5%, about 1.0% to about 4.0%, about 1.0% to about 3.5%, about 1.0% to about 3.0%, about 1.0% to about 2.5%, about 1.0% to about 2.0%, about 1.0% to about 1.5%, about 1.5% to about 5.0%, about 1.5% to about 4.5%, about 1.5% to about 4.0%, about 1.5% to about 3.5%, about 1.5% to about 3.0%, about 1.5% to about 2.5%, about 1.5% to about 2.0%, about 2.0% to about 5.0%, about 2.0% to about 4.5%, about 2.0% to about 4.0%, about 2.0% to about 3.5%, about 2.0% to about 3.0%, about 2.0% to about 2.5%, about 2.5% to about 5.0%, about 2.5% to about 4.5%, about 2.5% to about 4.0%, about 2.5% to about 3.5%, about 2.5% to about 3.0%, about 3.0% to about 5.0%, about 3.0% to about 4.5%, about 3.0% to about 4.0%, about 3.0% to about 3.5%, about 3.5% to about 5.0%, about 3.5% to about 4.5%, about 3.5% to about 4.0%, about 4.0% to about 5.0%, about 4.0% to about 4.5%, or about 4.0% to about 5.0%) polyethylene glycol, at about pH 5 to about pH 7 (e.g., any of the subranges of this range described herein or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0).

In another embodiment, sucrose can be replaced with another sugar such as trehalose (at about 10 mM to about 350 mM, or any of the subranges of this range described herein) in the formulation. In yet another embodiment, sodium chloride can be replaced with another salt such as magnesium chloride (at about 0.01 mM to about 100 mM, e.g., any of the subranges of this range described herein or about 0.01 mM, about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM about 95 mM, or about 100 mM)) in the formulation.

In another embodiment, a formulation of the invention comprises about 10 to about 200 mg/mL (e.g., any of the subranges of this range described herein) of aflibercept; about 10 mM to about 350 mM (e.g., any of the subranges of this range described herein) sucrose; about 0.01 mM to about 100 mM (e.g., any of the subranges of this range described herein) sodium chloride; about 0.01 mM to about 10 mM buffer (e.g., about 0.01 mM to about 8 mM, about 0.01 mM to about 6 mM, about 0.01 mM to about 5 mM, about 0.01 mM to about 4 mM, about 0.01 mM to about 3 mM, about 0.01 mM to about 2 mM, about 0.01 mM to about 1 mM, about 0.01 mM to about 0.5 mM, about 0.01 mM to about 0.1 mM, about 0.1 mM to about 10 mM, about 0.1 mM to about 8 mM, about 0.1 mM to about 6 mM, about 0.1 mM to about 5 mM, about 0.1 mM to about 4 mM, about 0.1 mM to about 3 mM, about 0.1 mM to about 2 mM, about 0.1 mM to about 1 mM, about 0.1 mM to about 0.5 mM, about 0.5 mM to about 10 mM, about 0.5 mM to about 8 mM, about 0.5 mM to about 6 mM, about 0.5 mM to about 5 mM, about 0.5 mM to about 4 mM, about 0.5 mM to about 3 mM, about 0.5 mM to about 2 mM, about 0.5 mM to about 1 mM, about 1 mM to about 10 mM, about 1 mM to about 8 mM, about 1 mM to about 6 mM, about 1 mM to about 5 mM, about 1 mM to about 4 mM, about 1 mM to about 3 mM, about 1 mM to about 2 mM, about 2 mM to about 10 mM, about 2 mM to about 8 mM, about 2 mM to about 6 mM, about 2 mM to about 5 mM, about 2 mM to about 4 mM, about 2 mM to about 3 mM, about 3 mM to about 10 mM, about 3 mM to about 8 mM, about 3 mM to about 6 mM, about 3 mM to about 5 mM, about 3 mM to about 4 mM, about 4 mM to about 10 mM, about 4 mM to about 8 mM, about 4 mM to about 6 mM, about 4 mM to about 5 mM, about 5 mM to about 10 mM, about 5 mM to about 8 mM, about 5 mM to about 6 mM, about 6 mM to about 10 mM, about 6 mM to about 8 mM, or about 8 mM to about 10 mM); at about pH 5 to about pH 7 (e.g., any of the subranges of this range described herein or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0).

The formulations of the invention may also include buffering agents, tonicity modifiers, excipients, and other commonly used inactive ingredients of the pharmaceutical compositions.

b. Aflibercept Formulations Stabilized with Polyol

In one embodiment, the invention provides a stable aqueous formulation comprising aflibercept and a polyol. Optionally, the formulation may further comprise a sugar and/or an amino acid. Examples of polyols include glycerol, sorbitol, mannitol, xylitol, and maltitol. The composition may be a buffer-free and/or free of an organic co-solvent.

In one embodiment, the concentration of a polyol in the provided formulations is between about 0.1% to 30% (e.g., about 0.1% to about 28%, about 0.1% to about 26%, about 0.1% to about 24%, about 0.1% to about 22%, about 0.1% to about 20%, about 0.1% to about 18%, about 0.1% to about 16%, about 0.1% to about 14%, about 0.1% to about 12%, about 0.1% to about 10%, about 0.1% to about 8%, about 0.1% to about 6%, about 0.1% to about 4%, about 0.1% to about 2%, about 0.1% to about 1%, about 0.1% to about 0.5%, about 0.5% to about 30%, about 0.5% to about 28%, about 0.5% to about 26%, about 0.5% to about 24%, about 0.5% to about 22%, about 0.5% to about 20%, about 0.5% to about 18%, about 0.5% to about 16%, about 0.5% to about 14%, about 0.5% to about 12%, about 0.5% to about 10%, about 0.5% to about 8%, about 0.5% to about 6%, about 0.5% to about 4%, about 0.5% to about 2%, about 0.5% to about 1%, about 1% to about 30%, about 1% to about 28%, about 1% to about 26%, about 1% to about 24%, about 1% to about 22%, about 1% to about 20%, about 1% to about 18%, about 1% to about 16%, about 1% to about 14%, about 1% to about 12%, about 1% to about 10%, about 1% to about 8%, about 1% to about 6%, about 1% to about 4%, about 1% to about 2%, about 2% to about 30%, about 2% to about 28%, about 2% to about 26%, about 2% to about 24%, about 2% to about 22%, about 2% to about 20%, about 2% to about 18%, about 2% to about 16%, about 2% to about 14%, about 2% to about 12%, about 2% to about 10%, about 2% to about 8%, about 2% to about 6%, about 2% to about 4%, about 4% to about 30%, about 4% to about 28%, about 4% to about 26%, about 4% to about 24%, about 4% to about 22%, about 4% to about 20%, about 4% to about 18%, about 4% to about 16%, about 4% to about 14%, about 4% to about 12%, about 4% to about 10%, about 4% to about 8%, about 4% to about 6%, about 6% to about 30%, about 6% to about 28%, about 6% to about 26%, about 6% to about 24%, about 6% to about 22%, about 6% to about 20%, about 6% to about 18%, about 6% to about 16%, about 6% to about 14%, about 6% to about 12%, about 6% to about 10%, about 6% to about 8%, about 8% to about 30%, about 8% to about 28%, about 8% to about 26%, about 8% to about 24%, about 8% to about 22%, about 8% to about 20%, about 8% to about 18%, about 8% to about 16%, about 8% to about 14%, about 8% to about 12%, about 8% to about 10%, about 10% to about 30%, about 10% to about 28%, about 10% to about 26%, about 10% to about 24%, about 10% to about 22%, about 10% to about 20%, about 10% to about 18%, about 10% to about 16%, about 10% to about 14%, about 10% to about 12%, about 12% to about 30%, about 12% to about 28%, about 12% to about 26%, about 12% to about 24%, about 12% to about 22%, about 12% to about 20%, about 12% to about 18%, about 12% to about 16%, about 12% to about 14%, about 14% to about 30%, about 14% to about 28%, about 14% to about 26%, about 14% to about 24%, about 14% to about 22%, about 14% to about 20%, about 14% to about 18%, about 14% to about 16%, about 16% to about 30%, about 16% to about 28%, about 16% to about 26%, about 16% to about 24%, about 16% to about 22%, about 16% to about 20%, about 16% to about 18%, about 18% to about 30%, about 18% to about 28%, about 18% to about 26%, about 18% to about 24%, about 18% to about 22%, about 18% to about 20%, about 20% to about 30%, about 20% to about 28%, about 20% to about 26%, about 20% to about 24%, about 20% to about 22%, about 22% to about 30%, about 22% to about 28%, about 22% to about 26%, about 22% to about 24%, about 24% to about 30%, about 24% to about 28%, about 24% to about 26%, about 26% to about 30%, about 26% to about 28%, or about 28% to about 30%), for example about 1% to about 10%, or about 2% to about 5%.

In one embodiment, the concentration of the polyol in the provided formulations is between about 1 mM and about 500 mM (e.g., about 1 mM to about 450 mM, about 1 mM to about 400 mM, about 1 mM to about 350 mM, about 1 mM to about 300 mM, about 1 mM to about 250 mM, about 1 mM to about 200 mM, about 1 mM to about 180 mM, about 1 mM to about 160 mM, about 1 mM to about 140 mM, about 1 mM to about 120 mM, about 1 mM to about 100 mM, about 1 mM to about 80 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 1 mM to about 8 mM, about 1 mM to about 6 mM, about 1 mM to about 4 mM, about 1 mM to about 2 mM, about 2 mM to about 500 mM, about 2 mM to about 450 mM, about 2 mM to about 400 mM, about 2 mM to about 350 mM, about 2 mM to about 300 mM, about 2 mM to about 250 mM, about 2 mM to about 200 mM, about 2 mM to about 180 mM, about 2 mM to about 160 mM, about 2 mM to about 140 mM, about 2 mM to about 120 mM, about 2 mM to about 100 mM, about 2 mM to about 80 mM, about 2 mM to about 60 mM, about 2 mM to about 50 mM, about 2 mM to about 45 mM, about 2 mM to about 40 mM, about 2 mM to about 35 mM, about 2 mM to about 30 mM, about 2 mM to about 25 mM, about 2 mM to about 20 mM, about 2 mM to about 15 mM, about 2 mM to about 10 mM, about 2 mM to about 8 mM, about 2 mM to about 6 mM, about 2 mM to about 4 mM, about 4 mM to about 500 mM, about 4 mM to about 450 mM, about 4 mM to about 400 mM, about 4 mM to about 350 mM, about 4 mM to about 300 mM, about 4 mM to about 250 mM, about 4 mM to about 200 mM, about 4 mM to about 180 mM, about 4 mM to about 160 mM, about 4 mM to about 140 mM, about 4 mM to about 120 mM, about 4 mM to about 100 mM, about 4 mM to about 80 mM, about 4 mM to about 60 mM, about 4 mM to about 50 mM, about 4 mM to about 45 mM, about 4 mM to about 40 mM, about 4 mM to about 35 mM, about 4 mM to about 30 mM, about 4 mM to about 25 mM, about 4 mM to about 20 mM, about 4 mM to about 15 mM, about 4 mM to about 10 mM, about 4 mM to about 8 mM, about 4 mM to about 6 mM, about 6 mM to about 500 mM, about 6 mM to about 450 mM, about 6 mM to about 400 mM, about 6 mM to about 350 mM, about 6 mM to about 300 mM, about 6 mM to about 250 mM, about 6 mM to about 200 mM, about 6 mM to about 180 mM, about 6 mM to about 160 mM, about 6 mM to about 140 mM, about 6 mM to about 120 mM, about 6 mM to about 100 mM, about 6 mM to about 80 mM, about 6 mM to about 60 mM, about 6 mM to about 50 mM, about 6 mM to about 45 mM, about 6 mM to about 40 mM, about 6 mM to about 35 mM, about 6 mM to about 30 mM, about 6 mM to about 25 mM, about 6 mM to about 20 mM, about 6 mM to about 15 mM, about 6 mM to about 10 mM, about 6 mM to about 8 mM, about 8 mM to about 500 mM, about 8 mM to about 450 mM, about 8 mM to about 400 mM, about 8 mM to about 350 mM, about 8 mM to about 300 mM, about 8 mM to about 250 mM, about 8 mM to about 200 mM, about 8 mM to about 180 mM, about 8 mM to about 160 mM, about 8 mM to about 140 mM, about 8 mM to about 120 mM, about 8 mM to about 100 mM, about 8 mM to about 80 mM, about 8 mM to about 60 mM, about 8 mM to about 50 mM, about 8 mM to about 45 mM, about 8 mM to about 40 mM, about 8 mM to about 35 mM, about 8 mM to about 30 mM, about 8 mM to about 25 mM, about 8 mM to about 20 mM, about 8 mM to about 15 mM, about 8 mM to about 10 mM, about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 180 mM, about 10 mM to about 160 mM, about 10 mM to about 140 mM, about 10 mM to about 120 mM, about 10 mM to about 100 mM, about 10 mM to about 80 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 500 mM, about 15 mM to about 450 mM, about 15 mM to about 400 mM, about 15 mM to about 350 mM, about 15 mM to about 300 mM, about 15 mM to about 250 mM, about 15 mM to about 200 mM, about 15 mM to about 180 mM, about 15 mM to about 160 mM, about 15 mM to about 140 mM, about 15 mM to about 120 mM, about 15 mM to about 100 mM, about 15 mM to about 80 mM, about 15 mM to about 60 mM, about 15 mM to about 50 mM, about 15 mM to about 45 mM, about 15 mM to about 40 mM, about 15 mM to about 35 mM, about 15 mM to about 30 mM, about 15 mM to about 25 mM, about 15 mM to about 20 mM, about 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 180 mM, about 20 mM to about 160 mM, about 20 mM to about 140 mM, about 20 mM to about 120 mM, about 20 mM to about 100 mM, about 20 mM to about 80 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 500 mM, about 25 mM to about 450 mM, about 25 mM to about 400 mM, about 25 mM to about 350 mM, about 25 mM to about 300 mM, about 25 mM to about 250 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 80 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 500 mM, about 30 mM to about 450 mM, about 30 mM to about 400 mM, about 30 mM to about 350 mM, about 30 mM to about 300 mM, about 30 mM to about 250 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 80 mM, about 30 mM to about 60 mM, about 30 mM to about 50 mM, about 30 mM to about 45 mM, about 30 mM to about 40 mM, about 30 mM to about 35 mM, about 35 mM to about 500 mM, about 35 mM to about 450 mM, about 35 mM to about 400 mM, about 35 mM to about 350 mM, about 35 mM to about 300 mM, about 35 mM to about 250 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 80 mM, about 35 mM to about 60 mM, about 35 mM to about 50 mM, about 35 mM to about 45 mM, about 35 mM to about 40 mM, about 40 mM to about 500 mM, about 40 mM to about 450 mM, about 40 mM to about 400 mM, about 40 mM to about 350 mM, about 40 mM to about 300 mM, about 40 mM to about 250 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 80 mM, about 40 mM to about 60 mM, about 40 mM to about 50 mM, about 40 mM to about 45 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 80 mM, about 45 mM to about 60 mM, about 45 mM to about 50 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 80 mM, about 50 mM to about 60 mM, about 60 mM to about 500 mM, about 60 mM to about 450 mM, about 60 mM to about 400 mM, about 60 mM to about 350 mM, about 60 mM to about 300 mM, about 60 mM to about 250 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 80 mM, about 80 mM to about 500 mM, about 80 mM to about 450 mM, about 80 mM to about 400 mM, about 80 mM to about 350 mM, about 80 mM to about 300 mM, about 80 mM to about 250 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 180 mM, about 100 mM to about 160 mM, about 100 mM to about 140 mM, about 100 mM to about 120 mM, about 120 mM to about 500 mM, about 120 mM to about 450 mM, about 120 mM to about 400 mM, about 120 mM to about 350 mM, about 120 mM to about 300 mM, about 120 mM to about 250 mM, about 120 mM to about 200 mM, about 120 mM to about 180 mM, about 120 mM to about 160 mM, about 120 mM to about 140 mM, about 140 mM to about 500 mM, about 140 mM to about 450 mM, about 140 mM to about 400 mM, about 140 mM to about 350 mM, about 140 mM to about 300 mM, about 140 mM to about 250 mM, about 140 mM to about 200 mM, about 140 mM to about 180 mM, about 140 mM to about 160 mM, about 160 mM to about 500 mM, about 160 mM to about 450 mM, about 160 mM to about 400 mM, about 160 mM to about 350 mM, about 160 mM to about 300 mM, about 160 mM to about 250 mM, about 160 mM to about 200 mM, about 160 mM to about 180 mM, about 180 mM to about 500 mM, about 180 mM to about 450 mM, about 180 mM to about 400 mM, about 180 mM to about 350 mM, about 180 mM to about 300 mM, about 180 mM to about 250 mM, about 180 mM to about 200 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 250 mM to about 500 mM, about 250 mM to about 450 mM, about 250 mM to about 400 mM, about 250 mM to about 350 mM, about 250 mM to about 300 mM, about 300 mM to about 500 mM, about 300 mM to about 450 mM, about 300 mM to about 400 mM, about 300 mM to about 350 mM, about 350 mM to about 500 mM, about 350 mM to about 450 mM, about 350 mM to about 400 mM, about 400 mM to about 500 mM, about 400 mM to about 450 mM, or about 450 mM to about 500 mM).

c. Aflibercept Stabilized with Amino Acids

Amino acids, e.g., proline, serine, sodium glutamic acid, glutamate, alanine, histidine, tryptophan, tyrosine, arginine, glycine, lysine, methionine, threonine, glutamic acid, aspartic acid, sarcosine, glycine betaine, and mixtures of the foregoing may be employed as stabilizers in certain aflibercept formulations.

These compositions may use the free base form of the amino acid or any conjugate acid form such as a hydrochloride salt. Such amino acids are readily available from commercial suppliers. For example, in one embodiment, the invention provides a stable aqueous pharmaceutical composition comprising aflibercept and one or more amino acids, wherein the amino acid(s) is selected from the group consisting of serine, proline, glycine, alanine, glutamate, arginine and combinations thereof. The composition may further optionally include a sugar and/or polyol. The composition may be a buffer-free and/or free of an organic co-solvent.

Such additives may improve the properties of the aflibercept formulations, e.g., by reducing aggregation or tendency for aflibercept to associate in undesired ternary or quaternary complexes. Without wishing to be bound to a particular theory, it is believed that amino acids such as serine, proline and glutamate are able to stabilize aqueous pharmaceutical compositions containing aflibercept because they are excluded from the surface of the protein, resulting in net conformation stabilization.

In one embodiment, the concentration of the amino acids in the provided formulations is between about 1 mM and about 500 mM (e.g., about 1 mM to about 450 mM, about 1 mM to about 400 mM, about 1 mM to about 350 mM, about 1 mM to about 300 mM, about 1 mM to about 250 mM, about 1 mM to about 200 mM, about 1 mM to about 180 mM, about 1 mM to about 160 mM, about 1 mM to about 140 mM, about 1 mM to about 120 mM, about 1 mM to about 100 mM, about 1 mM to about 80 mM, about 1 mM to about 60 mM, about 1 mM to about 50 mM, about 1 mM to about 45 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 1 mM to about 8 mM, about 1 mM to about 6 mM, about 1 mM to about 4 mM, about 1 mM to about 2 mM, about 2 mM to about 500 mM, about 2 mM to about 450 mM, about 2 mM to about 400 mM, about 2 mM to about 350 mM, about 2 mM to about 300 mM, about 2 mM to about 250 mM, about 2 mM to about 200 mM, about 2 mM to about 180 mM, about 2 mM to about 160 mM, about 2 mM to about 140 mM, about 2 mM to about 120 mM, about 2 mM to about 100 mM, about 2 mM to about 80 mM, about 2 mM to about 60 mM, about 2 mM to about 50 mM, about 2 mM to about 45 mM, about 2 mM to about 40 mM, about 2 mM to about 35 mM, about 2 mM to about 30 mM, about 2 mM to about 25 mM, about 2 mM to about 20 mM, about 2 mM to about 15 mM, about 2 mM to about 10 mM, about 2 mM to about 8 mM, about 2 mM to about 6 mM, about 2 mM to about 4 mM, about 4 mM to about 500 mM, about 4 mM to about 450 mM, about 4 mM to about 400 mM, about 4 mM to about 350 mM, about 4 mM to about 300 mM, about 4 mM to about 250 mM, about 4 mM to about 200 mM, about 4 mM to about 180 mM, about 4 mM to about 160 mM, about 4 mM to about 140 mM, about 4 mM to about 120 mM, about 4 mM to about 100 mM, about 4 mM to about 80 mM, about 4 mM to about 60 mM, about 4 mM to about 50 mM, about 4 mM to about 45 mM, about 4 mM to about 40 mM, about 4 mM to about 35 mM, about 4 mM to about 30 mM, about 4 mM to about 25 mM, about 4 mM to about 20 mM, about 4 mM to about 15 mM, about 4 mM to about 10 mM, about 4 mM to about 8 mM, about 4 mM to about 6 mM, about 6 mM to about 500 mM, about 6 mM to about 450 mM, about 6 mM to about 400 mM, about 6 mM to about 350 mM, about 6 mM to about 300 mM, about 6 mM to about 250 mM, about 6 mM to about 200 mM, about 6 mM to about 180 mM, about 6 mM to about 160 mM, about 6 mM to about 140 mM, about 6 mM to about 120 mM, about 6 mM to about 100 mM, about 6 mM to about 80 mM, about 6 mM to about 60 mM, about 6 mM to about 50 mM, about 6 mM to about 45 mM, about 6 mM to about 40 mM, about 6 mM to about 35 mM, about 6 mM to about 30 mM, about 6 mM to about 25 mM, about 6 mM to about 20 mM, about 6 mM to about 15 mM, about 6 mM to about 10 mM, about 6 mM to about 8 mM, about 8 mM to about 500 mM, about 8 mM to about 450 mM, about 8 mM to about 400 mM, about 8 mM to about 350 mM, about 8 mM to about 300 mM, about 8 mM to about 250 mM, about 8 mM to about 200 mM, about 8 mM to about 180 mM, about 8 mM to about 160 mM, about 8 mM to about 140 mM, about 8 mM to about 120 mM, about 8 mM to about 100 mM, about 8 mM to about 80 mM, about 8 mM to about 60 mM, about 8 mM to about 50 mM, about 8 mM to about 45 mM, about 8 mM to about 40 mM, about 8 mM to about 35 mM, about 8 mM to about 30 mM, about 8 mM to about 25 mM, about 8 mM to about 20 mM, about 8 mM to about 15 mM, about 8 mM to about 10 mM, about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 180 mM, about 10 mM to about 160 mM, about 10 mM to about 140 mM, about 10 mM to about 120 mM, about 10 mM to about 100 mM, about 10 mM to about 80 mM, about 10 mM to about 60 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 500 mM, about 15 mM to about 450 mM, about 15 mM to about 400 mM, about 15 mM to about 350 mM, about 15 mM to about 300 mM, about 15 mM to about 250 mM, about 15 mM to about 200 mM, about 15 mM to about 180 mM, about 15 mM to about 160 mM, about 15 mM to about 140 mM, about 15 mM to about 120 mM, about 15 mM to about 100 mM, about 15 mM to about 80 mM, about 15 mM to about 60 mM, about 15 mM to about 50 mM, about 15 mM to about 45 mM, about 15 mM to about 40 mM, about 15 mM to about 35 mM, about 15 mM to about 30 mM, about 15 mM to about 25 mM, about 15 mM to about 20 mM, about 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 180 mM, about 20 mM to about 160 mM, about 20 mM to about 140 mM, about 20 mM to about 120 mM, about 20 mM to about 100 mM, about 20 mM to about 80 mM, about 20 mM to about 60 mM, about 20 mM to about 50 mM, about 20 mM to about 45 mM, about 20 mM to about 40 mM, about 20 mM to about 35 mM, about 20 mM to about 30 mM, about 20 mM to about 25 mM, about 25 mM to about 500 mM, about 25 mM to about 450 mM, about 25 mM to about 400 mM, about 25 mM to about 350 mM, about 25 mM to about 300 mM, about 25 mM to about 250 mM, about 25 mM to about 200 mM, about 25 mM to about 180 mM, about 25 mM to about 160 mM, about 25 mM to about 140 mM, about 25 mM to about 120 mM, about 25 mM to about 100 mM, about 25 mM to about 80 mM, about 25 mM to about 60 mM, about 25 mM to about 50 mM, about 25 mM to about 45 mM, about 25 mM to about 40 mM, about 25 mM to about 35 mM, about 25 mM to about 30 mM, about 30 mM to about 500 mM, about 30 mM to about 450 mM, about 30 mM to about 400 mM, about 30 mM to about 350 mM, about 30 mM to about 300 mM, about 30 mM to about 250 mM, about 30 mM to about 200 mM, about 30 mM to about 180 mM, about 30 mM to about 160 mM, about 30 mM to about 140 mM, about 30 mM to about 120 mM, about 30 mM to about 100 mM, about 30 mM to about 80 mM, about 30 mM to about 60 mM, about 30 mM to about 50 mM, about 30 mM to about 45 mM, about 30 mM to about 40 mM, about 30 mM to about 35 mM, about 35 mM to about 500 mM, about 35 mM to about 450 mM, about 35 mM to about 400 mM, about 35 mM to about 350 mM, about 35 mM to about 300 mM, about 35 mM to about 250 mM, about 35 mM to about 200 mM, about 35 mM to about 180 mM, about 35 mM to about 160 mM, about 35 mM to about 140 mM, about 35 mM to about 120 mM, about 35 mM to about 100 mM, about 35 mM to about 80 mM, about 35 mM to about 60 mM, about 35 mM to about 50 mM, about 35 mM to about 45 mM, about 35 mM to about 40 mM, about 40 mM to about 500 mM, about 40 mM to about 450 mM, about 40 mM to about 400 mM, about 40 mM to about 350 mM, about 40 mM to about 300 mM, about 40 mM to about 250 mM, about 40 mM to about 200 mM, about 40 mM to about 180 mM, about 40 mM to about 160 mM, about 40 mM to about 140 mM, about 40 mM to about 120 mM, about 40 mM to about 100 mM, about 40 mM to about 80 mM, about 40 mM to about 60 mM, about 40 mM to about 50 mM, about 40 mM to about 45 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 160 mM, about 45 mM to about 140 mM, about 45 mM to about 120 mM, about 45 mM to about 100 mM, about 45 mM to about 80 mM, about 45 mM to about 60 mM, about 45 mM to about 50 mM, about 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 180 mM, about 50 mM to about 160 mM, about 50 mM to about 140 mM, about 50 mM to about 120 mM, about 50 mM to about 100 mM, about 50 mM to about 80 mM, about 50 mM to about 60 mM, about 60 mM to about 500 mM, about 60 mM to about 450 mM, about 60 mM to about 400 mM, about 60 mM to about 350 mM, about 60 mM to about 300 mM, about 60 mM to about 250 mM, about 60 mM to about 200 mM, about 60 mM to about 180 mM, about 60 mM to about 160 mM, about 60 mM to about 140 mM, about 60 mM to about 120 mM, about 60 mM to about 100 mM, about 60 mM to about 80 mM, about 80 mM to about 500 mM, about 80 mM to about 450 mM, about 80 mM to about 400 mM, about 80 mM to about 350 mM, about 80 mM to about 300 mM, about 80 mM to about 250 mM, about 80 mM to about 200 mM, about 80 mM to about 180 mM, about 80 mM to about 160 mM, about 80 mM to about 140 mM, about 80 mM to about 120 mM, about 80 mM to about 100 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 180 mM, about 100 mM to about 160 mM, about 100 mM to about 140 mM, about 100 mM to about 120 mM, about 120 mM to about 500 mM, about 120 mM to about 450 mM, about 120 mM to about 400 mM, about 120 mM to about 350 mM, about 120 mM to about 300 mM, about 120 mM to about 250 mM, about 120 mM to about 200 mM, about 120 mM to about 180 mM, about 120 mM to about 160 mM, about 120 mM to about 140 mM, about 140 mM to about 500 mM, about 140 mM to about 450 mM, about 140 mM to about 400 mM, about 140 mM to about 350 mM, about 140 mM to about 300 mM, about 140 mM to about 250 mM, about 140 mM to about 200 mM, about 140 mM to about 180 mM, about 140 mM to about 160 mM, about 160 mM to about 500 mM, about 160 mM to about 450 mM, about 160 mM to about 400 mM, about 160 mM to about 350 mM, about 160 mM to about 300 mM, about 160 mM to about 250 mM, about 160 mM to about 200 mM, about 160 mM to about 180 mM, about 180 mM to about 500 mM, about 180 mM to about 450 mM, about 180 mM to about 400 mM, about 180 mM to about 350 mM, about 180 mM to about 300 mM, about 180 mM to about 250 mM, about 180 mM to about 200 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 250 mM to about 500 mM, about 250 mM to about 450 mM, about 250 mM to about 400 mM, about 250 mM to about 350 mM, about 250 mM to about 300 mM, about 300 mM to about 500 mM, about 300 mM to about 450 mM, about 300 mM to about 400 mM, about 300 mM to about 350 mM, about 350 mM to about 500 mM, about 350 mM to about 450 mM, about 350 mM to about 400 mM, about 400 mM to about 500 mM, about 400 mM to about 450 mM, or about 450 mM to about 500 mM). In another embodiment, the concentration of the amino acid(s) is between about 10 mM and about 350 mM; in related embodiments, the concentration of the amino acid(s) is about 50 mM, 100 mM, 150 mM, 200 mM, 220 mM, 240 mM, 260 mM, 280 mM, 300 mM, 320 mM and 340 mM, for example, 50-100 mM, 100-150 mM, 150-200 mM, 200-300 mM, 200-250 mM, 250-300 mM, and 300-350 mM.

AFLIBERCEPT Stabilized with Combinations of Stabilizers

In some embodiments, combinations of stabilizers may act in concert to stabilize aflibercept. In one embodiment, an aflibercept formulation comprises a sugar and a polyol. In another example, amino acids, such as proline, serine, or glutamate maybe used together with a sugar to achieve a stability profile better than either excipient could provide on its own. In one embodiment, the ratio of a sugar to a polyol (or amino acid) in the formulation is between 5:1 and 1:5 (e.g., about 5:1, about 4:1, about 3:1, about 2:1, about 1:1, about 1:2, about 1:3, about 1:4, or about 1:5). In another embodiment, a formulation with a combination of stabilizers has better stability than a formulation with just one of the stabilizers. In another embodiment, a formulation with a combination of stabilizers has better stability than a formulation with just one of the stabilizers where the formulation with the combination of stabilizers has a lower total amount of stabilizers than the formulation with the single stabilizer (e.g. a formulation with 100 mM of sucrose and 50 mM arginine has better stability than a formulation with 200 mM sucrose).

III. Salts

Salts, e.g., NaCl, are often part of protein (e.g., antibody) formulations. For instance, salts such as NaCl, $Na_2SO_4$, $CaCl_2$, $MgCl_2$, and KCl, together with specific buffer combinations as described above, can confer particularly advantageous stability properties. Such salts may be used with as well as without a sugar added (e.g., sucrose and NaCl) or a polyol added (e.g., mannitol and NaCl). For example, concentrations as low as 20 to 50 mM can provide decreased levels of proteolysis (such as hinge region hydrolysis), oxidation, deamidation, or other chemical instabilities. Furthermore, low levels of salt (<50 mM) may lead to improved colloidal stability. Likewise, it is known that high concentrations of certain salts (up to 400 mM or more) can increase conformational stability. The specific effects of NaCl and other salts on aflibercept is dependent on pH, buffer composition, and stress condition.

In specific embodiments, sodium chloride may be replaced with $Na_2SO_4$, KCl, $MgCl_2$, $CaCl_2$, $MgSO_4$, $ZnCl_2$, or other physiologically-acceptable salts.

IV. Surfactants

Surfactants can confer protection against agitation and freeze/thaw damage, as well as stabilizing a formulation during storage. Surfactants which may be employed with aflibercept formulations of the present invention include Tween®-80 (polysorbate 80, PS 80), Tween®-20 (polysorbate 20, PS 20), SDS, polysorbate, polyoxyethylene copolymer, Brij 35, Triton X-10, poloxamer 188 (Pluronic F-68), Pluronic F127, and Maltosides, e.g., n-Decyl-β-D-maltopyranoside (DM), n-Dodecyl-β-D-maltopyranoside (DDM), and 6-Cyclohexyl-1-hexyl-β-D-maltopyranoside (Cymal-6). In certain embodiments, surfactants that may be particularly advantageous include PS 20, PS 40, PS 60, and PS 80 at different concentrations, as well as DMM and poloxamer 188 (Pluronic F-68). Other zwitterionic or nonionic surfactants may be used as well.

In the embodiments of the invention where organic co-solvents are excluded, surfactants cannot be present.

As above, optimal formulation employing such surfactants may also employ specific buffers at specific pH ranges, and may optionally include other tonicity modifier such as NaCl, polyol, or amino acid(s).

V. Polymers

Polymers, such as dextrans, starches (e.g., hydroxyl ethyl starch (HETA)), poly(ethylene glycols (PEGs), e.g., PEG-3350 or PEG-4000, may also provide stabilization to aflibercept, presumably by being excluded from the surface of the protein due to steric effects arising from their higher molecular weight. In particular, hydrophilic polymers, such as polyethylene glycols (PEGs), polysaccharides, and inert proteins, and may be used to stabilize proteins and enhance protein assembly. Examples include dextran, hydroxyl ethyl starch (HETA), PEG-4000, and gelatin. Additionally, nonpolar moieties on certain polymers such as PEGs and Pluronics can decrease water surface tension rendering them as surfactants that suppress surface adsorption induced aggregation. In one embodiment, the concentration of polymer is between 0.01% and 40% (e.g., about 0.01% to about 35%, about 0.01% to about 30%, about 0.01% to about 25%, about 0.01% to about 20%, about 0.01% to about 18%, about 0.01% to about 16%, about 0.01% to about 14%, about 0.01% to about 12%, about 0.01% to about 10%, about 0.01% to about 8%, about 0.01% to about 6%, about 0.01% to about 5%, about 0.01% to about 4.5%, about 0.01% to about 4.0%, about 0.01% to about 3.5%, about 0.01% to about 3.0%, about 0.01% to about 2.5%, about 0.01% to about 2.0%, about 0.01% to about 1.5%, about 0.01% to about 1.0%, about 0.01% to about 0.5%, about 0.01% to about 0.1%, about 0.01% to about 0.05%, about 0.05% to about 40%, about 0.05% to about 35%, about 0.05% to about 30%, about 0.05% to about 25%, about 0.05% to about 20%, about 0.05% to about 18%, about 0.05% to about 16%, about 0.05% to about 14%, about 0.05% to about 12%, about 0.05% to about 10%, about 0.05% to about 8%, about 0.05% to about 6%, about 0.05% to about 5%, about 0.05% to about 4.5%, about 0.05% to about 4.0%, about 0.05% to about 3.5%, about 0.05% to about 3.0%, about 0.05% to about 2.5%, about 0.05% to about 2.0%, about 0.05% to about 1.5%, about 0.05% to about 1.0%, about 0.05% to about 0.5%, about 0.05% to about 0.1%, about 0.1% to about 40%, about 0.1% to about 35%, about 0.1% to about 30%, about 0.1% to about 25%, about 0.1% to about 20%, about 0.1% to about 18%, about 0.1% to about 16%, about 0.1% to about 14%, about 0.1% to about 12%, about 0.1% to about 10%, about 0.1% to about 8%, about 0.1% to about 6%, about 0.1% to about 5%, about 0.1% to about 4.5%, about 0.1% to about 4.0%, about 0.1% to about 3.5%, about 0.1% to about 3.0%, about 0.1% to about 2.5%, about 0.1% to about 2.0%, about 0.1% to about 1.5%, about 0.1% to about 1.0%, about 0.1% to about 0.5%, about 0.5% to about 40%, about 0.5% to about 35%, about 0.5% to about 30%, about 0.5% to about 25%, about 0.5% to about 20%, about 0.5% to about 18%, about 0.5% to about 16%, about 0.5% to about 14%, about 0.5% to about 12%, about 0.5% to about 10%, about 0.5% to about 8%, about 0.5% to about 6%, about 0.5% to about 5%, about 0.5% to about 4.5%, about 0.5% to about 4.0%, about 0.5% to about 3.5%, about 0.5% to about 3.0%, about 0.5% to about 2.5%, about 0.5% to about 2.0%, about 0.5% to about 1.5%, about 0.5% to about 1.0%, about 1.0% to about 40%, about 1.0% to about 35%, about 1.0% to about 30%, about 1.0% to about 25%, about 1.0% to about 20%, about 1.0% to about 18%, about 1.0% to about 16%, about 1.0% to about 14%, about 1.0% to about 12%, about 1.0% to about 10%, about 1.0% to about 8%, about 1.0% to about 6%, about 1.0% to about 5%, about 1.0% to about 4.5%, about 1.0% to about 4.0%, about 1.0% to about 3.5%, about 1.0% to about 3.0%, about 1.0% to about 2.5%, about 1.0% to about 2.0%, about 1.0% to about 1.5%, about 1.5% to about 40%, about 1.5% to about 35%, about 1.5% to about 30%, about 1.5% to about 25%, about 1.5% to about 20%, about 1.5% to about 18%, about 1.5% to about 16%, about 1.5% to about 14%, about 1.5% to about 12%, about 1.5% to about 10%, about 1.5% to about 8%, about 1.5% to about 6%, about 1.5% to about 5%, about 1.5% to about 4.5%, about 1.5% to about 4.0%, about 1.5% to about 3.5%, about 1.5% to about 3.0%, about 1.5% to about 2.5%, about 1.5% to about 2.0%, about 2.0% to about 40%, about 2.0% to about 35%, about 2.0% to about 30%, about 2.0% to about 25%, about 2.0% to about 20%, about 2.0% to about 18%, about 2.0% to about 16%, about 2.0% to about 14%, about 2.0% to about 12%, about 2.0% to about 10%, about 2.0% to about 8%, about 2.0% to about 6%, about 2.0% to about 5%, about 2.0% to about 4.5%, about 2.0% to about 4.0%, about 2.0% to about 3.5%, about 2.0% to about 3.0%, about 2.0% to about 2.5%, about 2.5% to about 40%, about 2.5% to about 35%, about 2.5% to about 30%, about 2.5% to about 25%, about 2.5% to about 20%, about 2.5% to about 18%, about 2.5% to about 16%, about 2.5% to about 14%, about 2.5% to about 12%, about 2.5% to about 10%, about 2.5% to about 8%, about 2.5% to about 6%, about 2.5% to about 5%, about 2.5% to about 4.5%, about 2.5% to about 4.0%, about 2.5% to about 3.5%, about 2.5% to about 3.0%, about 3.0% to about 40%, about 3.0% to about 35%, about 3.0% to about 30%, about 3.0% to about 25%, about 3.0% to about 20%, about 3.0% to about 18%, about 3.0% to about 16%, about 3.0% to about 14%, about 3.0% to about 12%, about 3.0% to about 10%, about 3.0% to about 8%, about 3.0% to about 6%, about 3.0% to about 5%, about 3.0% to about 4.5%, about 3.0% to about 4.0%, about 3.0% to about 3.5%, about 3.5% to about 40%, about 3.5% to about 35%, about 3.5% to about 30%, about 3.5% to about 25%, about 3.5% to about 20%, about 3.5% to about 18%, about 3.5% to about 16%, about 3.5% to about 14%, about 3.5% to about 12%, about 3.5% to about 10%, about 3.5% to about 8%, about 3.5% to about 6%, about 3.5% to about 5%, about 3.5% to about 4.5%, about 3.5% to about 4.0%, about 4.0% to about 40%, about 4.0% to about 35%, about 4.0% to about 30%, about 4.0% to about 25%, about 4.0% to about 20%, about 4.0% to about 18%, about 4.0% to about 16%, about 4.0% to about 14%, about 4.0% to about 12%, about 4.0% to about 10%, about 4.0% to about 8%, about 4.0% to about 6%, about 4.0% to about 5%, about 4.0% to about 4.5%, about 4.5% to about 40%, about 4.5% to about 35%, about 4.5% to about 30%, about 4.5% to about 25%, about 4.5% to about 20%, about 4.5% to about 18%, about 4.5% to about 16%, about 4.5% to about 14%, about 4.5% to about 12%, about 4.5% to about 10%, about 4.5% to about 8%, about 4.5% to about 6%, about 4.5% to about 5%, about 5% to about 40%, about 5% to about 35%, about 5% to about 30%, about 5% to about 25%, about 5% to about 20%, about 5% to about 18%, about 5% to about 16%, about 5% to about 14%, about 5% to about 12%, about 5% to about 10%, about 5% to about 8%, about 5% to about 6%, about 6% to about 40%, about 6% to about 35%, about 6% to about 30%, about 6% to about 25%, about 6% to about 20%, about 6% to about 18%, about 6% to about 16%, about 6% to about 14%, about 6% to about 12%, about 6% to about 10%, about 6% to about 8%, about 8% to about 40%, about 8% to about 35%, about 8% to about 30%, about 8% to about 25%, about 8% to about 20%, about 8% to about 18%, about 8% to about 16%, about 8% to about 14%, about 8% to about 12%, about 8% to about 10%, about 10% to about 40%, about 10% to about 35%, about 10% to about 30%, about 10% to about 25%, about 10% to about 20%, about 10% to about 18%, about 10% to about 16%, about 10% to about 14%, about 10% to about 12%, about 12% to about 40%, about 12% to about 35%, about 12% to about 30%, about 12% to about 25%, about 12% to about 20%, about 12% to about 18%, about 12% to about 16%, about 12% to about 14%, about 14% to about 40%, about 14% to about 35%, about 14% to about 30%, about 14% to about 25%, about 14% to about 20%, about 14% to about 18%, about 14% to about 16%, about 16% to about 40%, about 16% to about 35%, about 16% to about 30%, about 16% to about 25%, about 16% to about 20%, about 16% to about 18%, about 18% to about 40%, about 18% to about 35%, about 18% to about 30%, about 18% to about 25%, about 18% to about 20%, about 20% to about 40%, about 20% to about 35%, about 20% to about 30%, about 20% to about 25%, about 25% to about 40%, about 25% to about 35%, about 25% to about 30%, about 30% to about 40%, about 30% to about 35%, or about 35% to about 40%). In another embodiment, the concentration of polymer is between 1 and 15%. The formulations of the invention may include combination of polymers with sugars, polyols, or amino acids in any combination.

In the embodiments of the invention where organic co-solvents are excluded, polymers cannot be present if they are organic co-solvents (for example, PEGs).

Under certain conditions, aflibercept may be stable even in the absence of surfactants, and/or may be stabilized with surfactants other than PS80 and at lower surfactant concentrations. For example, certain polymers, e.g., PEG, can exhibit surfactant-like properties and may be employed to stabilize aflibercept formulations in the absence of surfactants according to the present invention. Additional polymers which may be employed in specific aflibercept formulations include serum albumin (bovine serum albumin (BSA), human SA or recombinant HA), dextrans, poly(vinyl alcohol) (PVA), hydroxypropyl methylcellulose (HPMC), polyethyleneimine, gelatin, polyvinylpyrrolidone (PVP), hydroxyethylcellulose (HEC), and 2-Hydroxypropyl-beta-cyclodextrin (HP-beta-CD).

VI. Chelating Agents

Chelating agents such as EDTA, DPTA, etc., and/or sacrificial additives (e.g., ascorbate, Met), may be employed at specific pH values and with and without buffers (that may also acts as chelating agents, e.g., citrate, phosphate) to enhance the formulation properties, especially in cases where there may be some level of oxidative damage (under certain conditions, certain metals can catalyze the degradation of antibodies, especially at the hinge region). The addition of a chelating agent, such EDTA and DPTA, may be beneficial at improving the storage stability of aflibercept. Such approaches may be employed to stabilize aflibercept formulations according to the present invention.

Certain buffers, such as citrate, may also function as chelating agents and can serve multiple purposes in stabilization of aflibercept.

Sacrificial additives are well known to diminish certain oxidation events, such as oxidation of methionine residues. Addition of the free amino acid, methionine, or some derivative, can lead to decreased oxidation of aflibercept. Ascorbate and various thiol derivatives can serve the same purpose. Likewise, Trp and its derivatives can also serve as a sacrificial additive, even in the case of photolytic oxidation.

VII. Preparing Formulations

In on embodiment, the formulations of the invention can be prepared by isolating or purifying aflibercept or ziv-aflibercept from commercially available Eylea® or Zaltrap® or by modifying commercial aflibercept (Eylea®) or ziv-aflibercept (Zaltrap®) formulations to arrive at the formulations of the invention. In another embodiment, the formulation is prepared with aflibercept purified from a host cell that produces aflibercept. In another embodiment, the formulation of the invention is a biosimilar of Eylea.

The pharmaceutical compositions of the invention may be prepared by combining aflibercept and an excipient such as a stabilizer (e.g. sugar, amino acid). Further, a buffer (except in buffer-free formulations), an organic co-solvent, such as a surfactant (except in formulations free of organic co-solvents), a tonicity modifier and an additional excipient may be added as needed. A person of ordinary skill in the art will understand that the combining of the various components to be included in the composition can be done in any appropriate order. For example, the buffer can be added first, middle or last, and the tonicity modifier can also be added first, middle or last.

A person of ordinary skill in the art will also understand that some of these chemicals can be incompatible in certain combinations, and accordingly, must be substituted with different chemicals that have similar properties but are compatible in the relevant mixture. While a person of skill in the art may look to the art for clues on how to create new formulations for aflibercept, due to the complexity of proteins, and the unpredictability of effects of chemicals on proteins (including differing effects a chemical may have on one protein versus another protein), care must be taken when creating new formulations as the differing effects of excipients may not produce stable formulations.

VIII. Formulations Free of Excipients

In accordance with the FDA approval to market Eylea, Eylea is a stable formulation of aflibercept. Eylea has a pH of 6.2 and contains 40 mg/mL aflibercept, 10 mM sodium phosphate, 40 mM sodium chloride, 0.03% polysorbate 20, and 5% sucrose. Since this formulation is stable, it is surprising if an aflibercept formulation that is free of at least one of the specific excipients in Eylea, or a class of excipients that one of the Eylea excipients belongs to, is stable.

In one embodiment, the invention provides a stable aqueous pharmaceutical composition comprising aflibercept, wherein the composition is free or substantially free of a buffer. In a further embodiment, the buffer is a phosphate buffer.

In one embodiment, the invention provides a stable aqueous pharmaceutical composition comprising aflibercept, wherein the composition is free or substantially free of a tonicity agent. In a further embodiment, the tonicity agent is a salt. In a further embodiment, the salt is sodium chloride.

In one embodiment, the invention provides a stable aqueous pharmaceutical composition comprising aflibercept, wherein the composition is free or substantially free of an organic co-solvent. In a further embodiment, the organic co-solvent is a surfactant. In a further embodiment, the surfactant is polysorbate 20.

In one embodiment, the invention provides a stable aqueous pharmaceutical composition comprising aflibercept, wherein the composition is free or substantially free of a stabilizer. In a further embodiment, the stabilizer is a sugar. In a further embodiment, the sugar is sucrose.

In another embodiment of the invention, if a stable aflibercept formulation contains an excipient, it is free of other functionally similar excipients. For instance, in one embodiment, a stable aflibercept formulation containing trehalose is free of sucrose. In another embodiment, a stable aflibercept formulation containing acetate buffer is free of phosphate buffer. Likewise, in another embodiment, a stable aflibercept formulation containing acetate buffer is free of histidine buffer. Thus, the formulations of the present invention can be free of one or more excipients.

D. Stability Characteristics

In one embodiment, the invention provides stable aqueous pharmaceutical composition comprising aflibercept, wherein the composition comprises at least 90% monomer aflibercept. In another embodiment, the amount of monomer aflibercept is at least 91%, at least 92%, at least 93%, at least 94%, at least 95%, at least 96%, at least 96.5%, at least 97%, at least 97.5%, at least 98%, at least 98.5%, at least 99%, or at least 99.5%. In another embodiment, the amount of monomer aflibercept is determined by SEC.

In one embodiment, the invention provides stable aqueous pharmaceutical composition comprising aflibercept, wherein the pH of the composition is stable. In one embodiment the pH does not change more than 20%, 15%, 10%, 9%, 8%, 7%, 6%, 5%, 4%, 3%, 2%, or 1% during storage.

In one embodiment, the invention provides stable aqueous pharmaceutical composition comprising aflibercept, wherein the composition has no more total sub-visible particles than Eylea. In another embodiment, the invention provides stable aqueous pharmaceutical composition comprising aflibercept, wherein the composition has no more sub-visible particles ≥10 µm in diameter than Eylea. In another embodiment, the invention provides stable aqueous pharmaceutical composition comprising aflibercept, wherein the composition has no more sub-visible particles ≥25 µm in diameter than Eylea. In another embodiment, the invention provides stable aqueous pharmaceutical composition comprising aflibercept, wherein the composition has no more sub-visible particles ≥50 µm in diameter than Eylea.

In one embodiment, the invention provides stable aqueous pharmaceutical composition comprising aflibercept, wherein the composition meets the requirements of USP <789>, which is incorporated herein by reference in its entirety. In one embodiment, the invention provides stable aqueous pharmaceutical composition comprising aflibercept, wherein the composition has no more than 50 particles per mL of particles that are ≥10 µm in diameter, wherein the particles are counted by a light obscuration test. In one embodiment, the invention provides stable aqueous pharmaceutical composition comprising aflibercept, wherein the composition has no more than 5 particles per mL of particles that are ≥25 µm in diameter, wherein the particles are counted by a light obscuration test. In one embodiment, the invention provides stable aqueous pharmaceutical composition comprising aflibercept, wherein the composition has no more than 50 particles per mL of particles that are ≥10 µm in diameter, wherein the particles are counted by a microscopic method. In one embodiment, the invention provides stable aqueous pharmaceutical composition comprising aflibercept, wherein the composition has no more than 5 particles per mL of particles that are ≥25 µm in diameter, wherein the particles are counted by a microscopic method. In one embodiment, the invention provides stable aqueous pharmaceutical composition comprising aflibercept, wherein the composition has no more than 2 particles per mL of particles that are ≥50 µm in diameter, wherein the particles are counted by a microscopic method.

E. Aflibercept Formulations

I. Formulations of Aflibercept which Exclude Buffer (Buffer-Free Formulations)

In a one embodiment, the invention provides a stable aqueous pharmaceutical composition comprising aflibercept, wherein the composition is free or substantially free of a buffer. The term "free of buffer" should be understood to allow inclusion of the inherent buffering effect of the protein itself. Such "self-buffering" or "buffer-free" protein formulations comprise a protein, e.g., a pharmaceutical protein, and are buffered by the protein itself, i.e., the formulations do not require additional buffering agents to maintain a desired pH. The protein is substantially the only buffering agent in such formulations (i.e., other ingredients, if any, do not act substantially as buffering agents in the formulation).

In another embodiment, the buffer-free aflibercept composition further comprises a stabilizer, a tonicity agent, an organic co-solvent, or combinations thereof.

In one embodiment, the buffer-free formulation has a pH of about 5.0 to about 7.0 (e.g., or any of the subranges of this range described herein or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In another embodiment, the pH is about 5.0 to about 5.8. In another embodiment, the PH is about 5.5.

In one embodiment, the stabilizer is selected from the group consisting of amino acids, sugars, polyols, polymers, and combinations thereof.

In one embodiment, the organic co-solvent is selected from the group consisting of a surfactant, polyethylene glycol (PEG), propylene glycol, and combinations thereof.

In one embodiment, the surfactant is selected from the group consisting of polysorbate 20, polysorbate 80, SDS, DDM and poloxamer 188 (Pluronic F-68).

In one embodiment, the buffer-free formulations of the invention may comprise a salt, which may be selected from the group consisting of sodium chloride, magnesium chloride and calcium chloride. In one embodiment, the salt is present at a concentration of about 10 mM-100 mM (e.g., any of the subranges of this range described herein or about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM about 95 mM, or about 100 mM).

In one embodiment, the stabilizer is sucrose.

In one embodiment, the stabilizer is an amino acid, which may be selected from the group consisting of glycine, arginine, and proline or combinations thereof. The amino acids may be present at a concentration of about 25-300 mM (e.g., any of the subranges of this range described herein or about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM).

In some embodiments, the stabilizer is sucrose, the organic co-solvent is polysorbate 20 and the pH of the formulation is about 5.0 to about 7.0 (e.g., or any of the subranges of this range described herein or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In another embodiment, the pH is about 5.0 to about 5.8. In another embodiment, the PH is about 5.5.

In one embodiment, the formulation is iso-osmolar relative to the vitreous.

In a one embodiment, the invention provides a stable aqueous pharmaceutical composition comprising aflibercept, wherein the composition is free or substantially free of a buffer and the composition has an osmolality of about 200 to 400 mOsm. In another embodiment, the composition is suitable for administration to a subject as a single dose. In still another embodiment, the single dose is about 2 mg of aflibercept. In another embodiment, the aflibercept is present at about 40 mg/mL.

In a one embodiment, the invention provides a stable aqueous pharmaceutical composition comprising aflibercept, wherein the composition is substantially free of a buffer the composition has an osmolality of about 200 to 400 mOsm, the composition is suitable for administration to a subject as a single dose, and the single dose is about 2 mg of aflibercept. In another embodiment the single dose of aflibercept has a volume of about 0.05 mL.

II. Formulations of Aflibercept which Exclude Organic Co-Solvent

In another embodiment, the invention provides a stable aqueous pharmaceutical composition comprising aflibercept, wherein the composition is free or substantially free of an organic co-solvent. In another embodiment, the co-solvent-free aflibercept composition further comprises a buffer, a stabilizer, a tonicity agent, or combinations thereof.

In one embodiment, the formulation has a pH of about 5.0 to about 7.0 (e.g., or any of the subranges of this range described herein or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In another embodiment, the pH is about 5.5 to about 6.3. In another embodiment, the PH is about 6.2.

In one embodiment, the buffer is selected from the group consisting of acetate, histidine, phosphate, citrate, succinate, tartrate and maleate. In one embodiment, the buffer is present at a concentration of about 1 mM to 150 mM (e.g., any of the subranges of this range described herein). In another embodiment, the buffer is present at a concentration of about 5 mM to 20 mM. In another embodiment, the buffer is present at a concentration at about 10 mM.

In one embodiment, the stabilizer is selected from the group consisting of amino acids, sugars, polyols, polymers, and combinations thereof.

In some organic co-solvent-free formulations, the stabilizer is sucrose.

In other organic co-solvent-free formulations, the stabilizer is an amino acid, which may be selected from the group consisting of glycine, arginine, and proline or combinations thereof. The amino acid may be present at a concentration of about 25-300 mM (e.g., any of the subranges of this range described herein or about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM).

In one embodiment, the formulation may comprise a salt, which may be selected from the group consisting of sodium chloride, magnesium chloride and calcium chloride. In one embodiment, the salt is present at a concentration of about 10 mM-100 mM (e.g., any of the subranges of this range described herein or about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM about 95 mM, or about 100 mM).

In one embodiment, the formulation is iso-osmolar relative to the vitreous.

In a one embodiment, the invention provides a stable aqueous pharmaceutical composition comprising aflibercept, wherein the composition is free or substantially free of an organic co-solvent and the composition has an osmolality of about 200 to 400 mOsm. In another embodiment, the composition is suitable for administration to a subject as a single dose. In still another embodiment, the single dose is about 2 mg of aflibercept. In another embodiment, the aflibercept is present at about 40 mg/mL.

In a one embodiment, the invention provides a stable aqueous pharmaceutical composition comprising aflibercept, wherein the composition is free or substantially free of an organic co-solvent, the composition has an osmolality of about 200 to 400 mOsm, the composition is suitable for administration to a subject as a single dose, and the single dose is about 2 mg of aflibercept. In another embodiment the single dose of aflibercept has a volume of about 0.05 mL.

II. Formulations of Aflibercept which Exclude Both a Buffer and an Organic Co-Solvent In a further embodiment, the invention provides a stable aqueous pharmaceutical composition comprising aflibercept, wherein the composition is substantially free of both an organic co-solvent and a buffer. In another embodiment, the buffer-free and co-solvent-free aflibercept composition further comprises a stabilizer, a tonicity agent, or combinations thereof.

In one embodiment, the formulation has a pH of about 5.0 to about 7.0 (e.g., or any of the subranges of this range described herein or about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0). In another embodiment, the pH is about 5.0 to about 6.2. In another embodiment, the pH is about 5.5.

In one embodiment, the stabilizer is selected from the group consisting of amino acids, sugars, polyols, polymers, and combinations thereof.

In one embodiment, the stabilizer is sucrose.

In one embodiment, the stabilizer is an amino acid, which may be selected from the group consisting of glycine, arginine, and proline or combinations thereof. The amino acids may be present at a concentration of about 25-300 mM (e.g., any of the subranges of this range described herein or about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM).

In one embodiment, the formulation may comprise a salt, which may be selected from the group consisting of sodium chloride, magnesium chloride and calcium chloride. In one embodiment, the salt is present at a concentration of about 10 mM-100 mM (e.g., any of the subranges of this range described herein or about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM about 95 mM, or about 100 mM).

In one embodiment, the formulation is iso-osmolar relative to the vitreous.

In a one embodiment, the invention provides a stable aqueous pharmaceutical composition comprising aflibercept, wherein the composition is free or substantially free of both a buffer and an organic co-solvent and the composition has an osmolality of about 200 to 400 mOsm. In another embodiment, the composition is suitable for administration to a subject as a single dose. In still another embodiment, the single dose is about 2 mg of aflibercept. In another embodiment, the aflibercept is present at about 40 mg/mL. In another embodiment the single dose of aflibercept has a volume of about 0.05 mL.

In a one embodiment, the invention provides a stable aqueous pharmaceutical composition comprising aflibercept, wherein the composition is free or substantially free of both a buffer and an organic co-solvent, the composition has an osmolality of about 200 to 400 mOsm, the composition is suitable for administration to a subject as a single dose, and the single dose is about 2 mg of aflibercept.

IV. Exemplary Aflibercept Formulations

In one embodiment, the invention provides a stable aqueous pharmaceutical composition comprising aflibercept, a stabilizer, and an organic co-solvent, wherein the composition has a pH of about 5.0 to about 5.8 and is free or substantially free of a buffer. In one embodiment, the stabilizer is a sugar, polyol, amino acid, salt, or a combination thereof. In another embodiment, the sugar is sucrose. In another embodiment, the salt is NaCl or $CaCl_2$). In another embodiment, the amino acid is glycine. In another embodiment, the organic so-solvent is a surfactant. In a further embodiment, the surfactant is a polysorbate. In a further embodiment, the polysorbate is polysorbate 20 or polysorbate 80.

In one embodiment, the invention provides a stable aqueous pharmaceutical composition comprising aflibercept, sucrose, and a polysorbate, wherein the composition has a pH of about 5.0 to about 5.8 and is free or substantially free of a buffer. In one embodiment, the invention provides a stable aqueous pharmaceutical composition comprising aflibercept, sucrose, a salt selected from the group consisting of NaCl and $CaCl_2$, and a polysorbate, wherein the composition has a pH of about 5.0 to about 5.8 and is free or substantially free of a buffer. In one embodiment, the invention provides a stable aqueous pharmaceutical composition comprising aflibercept, an amino acid, a salt selected from the group consisting of NaCl and $CaCl_2$), and a polysorbate, wherein the composition has a pH of about 5.0 to about 5.8 and is free or substantially free of a buffer. In a further embodiment the amino acid is glycine. In one embodiment, the invention provides a stable aqueous pharmaceutical composition comprising aflibercept, sucrose, $CaCl_2$), and a polysorbate, wherein the composition has a pH of about 5.0 to about 5.8 and is free or substantially free of a buffer. In a further embodiment, the composition is free of NaCl.

In one embodiment, the invention provides a stable aqueous pharmaceutical composition comprising aflibercept, a buffer, and a stabilizer, wherein the composition has a pH of about 5.5 to about 6.3 and is free or substantially free of an organic co-solvent. In one embodiment, the buffer is histidine or acetate. In one embodiment, the stabilizer is a sugar, polyol, amino acid, or a combination thereof. In another embodiment, the sugar is sucrose. In another embodiment, the amino acid is glycine.

In one embodiment, the invention provides a stable aqueous pharmaceutical composition comprising aflibercept, a buffer, and sucrose, wherein the composition has a pH of about 5.5 to about 6.3 and is free or substantially free of an organic co-solvent. In one embodiment, the invention provides a stable aqueous pharmaceutical composition comprising aflibercept, a buffer, and an amino acid, wherein the composition has a pH of about 5.5 to about 6.3 and is free or substantially free of an organic co-solvent. In a further embodiment, the amino acid is glycine. In one embodiment, the invention provides a stable aqueous pharmaceutical composition comprising aflibercept, histidine, and sucrose, wherein the composition has a pH of about 5.5 to about 6.3 and is free or substantially free of an organic co-solvent. In one embodiment, the invention provides a stable aqueous pharmaceutical composition comprising aflibercept, histidine, and glycine, wherein the composition has a pH of about 5.5 to about 6.3 and is free or substantially free of an organic co-solvent. In another embodiment, a co-solvent-free composition further comprises a salt. In one embodiment, the salt is selected from the group consisting of NaCl and $CaCl_2$).

In a further embodiment, exemplary aflibercept formulations are listed in Table 1 below. Formulations in Table 1 include formulations that are buffer free, co-solvent free, and buffer-free and co-solvent-free. All formulations Table 1 contain 40 mg/mL aflibercept.

TABLE 1

| Form No. | pH | Buffer (mM) | Sucrose (mM) | Salt (mM) | PS 20 |
|---|---|---|---|---|---|
| 1-1 | 5.7 | 0 | 180 | 40 mM NaCl | 0.03% |
| 1-2 | 6.2 | 0 | 180 | 40 mM NaCl | 0.03% |
| 1-3 | 6.7 | 0 | 180 | 40 mM NaCl | 0.03% |
| 1-4 | 5.7 | 10 mM Phosphate | 180 | 40 mM NaCl | 0 |
| 1-5 | 6.2 | 10 mM Phosphate | 180 | 40 mM NaCl | 0 |
| 1-6 | 6.7 | 10 mM Phosphate | 180 | 40 mM NaCl | 0 |
| 1-7 | 5.7 | 10 mM Histidine | 180 | 40 mM NaCl | 0 |
| 1-8 | 6.7 | 10 mM Histidine | 180 | 40 mM NaCl | 0 |
| 1-9 | 5.7 | 10 mM Succinate | 180 | 40 mM NaCl | 0 |
| 1-10 | 6.7 | 10 mM Succinate | 180 | 40 mM NaCl | 0 |
| 1-11 | 6.2 | 0 | 180 | 40 mM NaCl | 0 |
| 1-12 | 5.2 | 0 | 180 | 0 | 0.03% |
| 1-13 | 5.5 | 0 | 180 | 0 | 0.03% |
| 1-14 | 5.8 | 0 | 180 | 0 | 0.03% |
| 1-15 | 5.2 | 0 | 180 | 10 mM $CaCl_2$ | 0.03% |
| 1-16 | 5.5 | 0 | 180 | 10 mM $CaCl_2$ | 0.03% |
| 1-17 | 5.8 | 0 | 180 | 10 mM $CaCl_2$ | 0.03% |
| 1-18 | 5.5 | 10 mM Histidine | 180 | 0 | 0 |
| 1-19 | 6.0 | 10 mM Histidine | 180 | 0 | 0 |
| 1-20 | 6.3 | 10 mM Histidine | 180 | 0 | 0 |
| 1-21 | 5.5 | 10 mM Histidine | 180 | 10 mM $CaCl_2$ | 0 |
| 1-22 | 6.0 | 10 mM Histidine | 180 | 10 mM $CaCl_2$ | 0 |
| 1-23 | 6.3 | 10 mM Histidine | 180 | 10 mM $CaCl_2$ | 0 |
| 1-24 | 5.2 | 0 | 180 | 10 mM $CaCl_2$ | 0 |
| 1-25 | 5.5 | 0 | 180 | 10 mM $CaCl_2$ | 0 |
| 1-26 | 5.8 | 0 | 180 | 10 mM $CaCl_2$ | 0 |

F. Analytical Methods

The chemical and physical stability of the aflibercept protein in a formulation is measured using, e.g., SEC, CEX, HPLC, RP, UV, pH, MFI, Flow-CAM, icIEF, CE-IEF and CE-SDS. However, other analytical methods may also be employed, for example, biophysical techniques such as those described by Jiskoot and Crommelin (Methods for Structural Analysis of Protein Pharmaceuticals, Springer, New York, 2005). Specific examples of such techniques include spectroscopic analyses (e.g., second derivative ultraviolet spectroscopy, circular dichroism, Fourier Transform infrared spectroscopy, Raman spectroscopy, fluorescence and phosphorescence spectroscopy), thermal analyses (e.g., differential scanning calorimetry), and size-based analyses (e.g., analytical ultracentrifuge, light scattering).

One of skill in the art can readily determine which of these or other suitable techniques may be used in specific situations when assessing the physical characteristics (e.g., stability, aggregation, oxidation, etc.) of the aflibercept protein in particular formulations.

G. Methods of Treatment

Formulations of the present invention may be used in methods of treating an ocular condition in a subject in need thereof. In one embodiment, the subject is a human patient. In another embodiment, treating comprises administering a therapeutically effective amount of the formulations of the invention to the subject. In another embodiment, the subject has an ocular disease or disorder that can be beneficially treated with aflibercept, for example any ocular disease or disorder that can benefit from an anti-VEGF injection.

In one embodiment, the ocular disease or disorder is a vascular eye disease or disorder. Ocular diseases or disorders that can be treated with the formulations of the present invention includes, but is not limited to, those which can be treated with Eylea®, such as macular degeneration (AMD), diabetic macular edema (DME), retinal vein occlusion (RVO), diabetic retinopathy (DR).

In one embodiment, the formulations of the present invention are administered intravitreally.

As used herein, the terms "treat", "treating", or the like, mean to alleviate symptoms, eliminate the causation of symptoms either on a temporary or permanent basis, or to prevent or slow the appearance of symptoms of an eye disease. In certain embodiments, the present methods are useful for treating or ameliorating at least one symptom or indication including, but not limited to, retinal angiogenesis, neovascularization, vascular leak, retinal thickening within 500 µm of the center of the fovea, hard, yellow exudates within 500 µm of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision. In the context of methods for treating a vascular eye disease such as AMD or DME, the term means that, from the initiation of treatment, the patient exhibits gain of one or more (e.g., 1, 2, 3, 4, 5, 6, 7, 8, 9, 10 or more) letters on the Early Treatment Diabetic Retinopathy Study (EDTRS) visual acuity chart. In certain embodiments, the term means that, from initiation of treatment, vision loss of greater than or equal to 15 letters is prevented in the patient.

As used herein, the terms "prevent", "preventing", or the like, mean to prevent development of a symptom, indication or a complication of a vascular eye disease. In the context of methods for treating a vascular eye disease such as AMD or DME, the term means, from initiation of treatment, moderate or severe vision loss is prevented in a patient.

As used herein, a "vascular eye disease or disorder" refers to eye disease or disorders that affect blood vessels in the eye. The diseases may be caused due to abnormal angiogenesis (formation of new blood vessels) or occlusion or blockage of blood vessels. The term, as used herein, includes eye diseases or disorders associated with angiogenesis. The term includes, but is not limited to, eye disease or disorder selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization. In certain embodiments, the term "neovascular eye disease or disorder" may be used interchangeably with the term "eye disease or disorder associated with angiogenesis."

In certain embodiments, the present invention includes methods for treating, preventing, or ameliorating at least one symptom or indication of an eye disease or disorder associated with angiogenesis in a subject, wherein the disease or disorder is selected from the group consisting of diabetic retinopathy, diabetic macular edema, age-related macular degeneration, retinal neovascularization, polypoidal choroidal vasculopathy, and choroidal neovascularization.

"Diabetic Macular Edema" (DME), as used herein, refers to a serious eye condition that affects people with diabetes (type 1 or 2). Macular edema occurs when blood vessels in the retina leak into the macula and fluid and protein deposits collect on or under the macula of the eye (a yellow central area of the retina) and causes it to thicken and swell (edema). The swelling may distort a person's central vision, as the macula is near the center of the retina at the back of the eyeball. The primary symptoms of DME include, but are not limited to, blurry vision, floaters, loss of contrast, double vision, and eventual loss of vision. The pathology of DME is characterized by breakdown of the blood-retinal barrier, normally preventing water movement in the retina, thus allowing fluid to accumulate in the retinal tissue, and presence of retinal thickening. DME is presently diagnosed during an eye examination consisting of a visual acuity test, which determines the smallest letters a person can read on a standardized chart, a dilated eye exam to check for signs of the disease, imaging tests such as optical coherence tomography (OCT) or fluorescein angiography (FA) and tonometry, an instrument that measures pressure inside the eye. The following studies are also performed to determine treatment: optical coherence tomography (OCT), fluorescein angiography, and color stereo fundus photography. DME can be broadly characterized into two main categories— Focal and Diffuse. Focal DME is characterized by specific areas of separate and distinct leakage in the macula with sufficient macular blood flow. Diffuse DME results from leakage of the entire capillary bed surrounding the macula, resulting from a breakdown of the inner blood-retina barrier of the eye. In addition to Focal and Diffuse, DME is also categorized based on clinical exam findings into clinically significant macular edema (CSME), non-CSME and CSME with central involvement (CSME-CI), which involves the fovea. The present invention includes methods to treat the above-mentioned categories of DME.

Age-related macular degeneration (AMD), as used herein, refers to a serious eye condition when the small central portion of the retina, known as the macula, deteriorates. The wet form of AMD is characterized by the growth of abnormal blood vessels from the choroid underneath the macula. This is called choroidal neovascularization. These blood vessels leak blood and fluid into the retina, causing distortion of vision that makes straight lines look wavy, as well as blind spots and loss of central vision. These abnormal blood vessels eventually scar, leading to permanent loss of central vision. The symptoms of AMD include dark, blurry areas in the center of vision; and diminished or changed color perception. AMD can be detected in a routine eye exam. One of the most common early signs of macular degeneration is the presence of drusen—tiny yellow deposits under the retina—or pigment clumping.

As used herein, the expression "a subject in need thereof" means a human or non-human mammal that exhibits one or more symptoms or indications of, and/or who has been diagnosed with an eye disease or disorder associated angiogenesis. The term "a subject in need thereof" may also include, e.g., subjects who, prior to treatment, exhibit (or have exhibited) one or more indications of a neovascular eye disease such as, e.g., retinal angiogenesis, neovascularization, vascular leak, retinal thickening within 500 μm of the center of the fovea, hard, yellow exudates within 500 μm of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision.

In the context of the invention, a "subject in need thereof" also includes human or non-human mammal who has a vascular eye disease or disorder selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization.

In the context of the present invention, "a subject in need thereof" may include a subset of population which is more susceptible to DME or AMD or may show an elevated level of a DME-associated or an AMD-associated biomarker. For example, "a subject in need thereof" may include a subject suffering from diabetes for more than 10 years, have frequent high blood sugar levels or high fasting blood glucose levels. In certain embodiments, the term "a subject in need thereof" includes a subject who, prior to or at the time of administration of the formulations of the invention, has or is diagnosed with diabetes. In certain embodiments, the term "a subject in need thereof" includes a subject who, prior to or at the time of administration of the formulations of the invention, is more than 50 years old. In some embodiments, the term "a subject in need thereof" includes subjects who are smokers, or subjects with high blood pressure or high cholesterol.

The present invention includes methods for treating, preventing or reducing the severity of a vascular eye disease comprising administering a therapeutically effective amount of a formulation of the present invention to a subject in need thereof, wherein the formulation is administered to the subject as a single dose or in multiple doses, e.g., as part of a specific therapeutic dosing regimen. For example, the therapeutic dosing regimen may comprise administering multiple doses of the formulation to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the therapeutic dosing regimen may comprise administering multiple doses of the formulation to the subject at a frequency of once a day or 2 times a day or more.

In one embodiment, methods of treating include administering to a subject in need thereof an aflibercept composition of the present invention according to the dosing and administration regimen for Eylea®. See, Eylea® package insert.

In one embodiment, a subject with Neovascular (Wet) Age-Related Macular Degeneration (AMD) is administered 2 mg of aflibercept by intravitreal injection every 4 weeks (approximately every 28 days, monthly) for the first 3 months, followed by 2 mg (0.05 mL) via intravitreal injection once every 8 weeks (2 months). In another embodiment, a subject with Neovascular (Wet) Age-Related Macular Degeneration (AMD) is administered 2 mg of aflibercept by intravitreal injection every 4 weeks (approximately every 25 days, monthly). In another embodiment, a subject with Neovascular (Wet) Age-Related Macular Degeneration (AMD) is administered 2 mg of aflibercept by intravitreal injection every 4 week (monthly) dosing after the first 12 weeks (3 months). In another embodiment, a subject with Neovascular (Wet) Age-Related Macular Degeneration (AMD) is administered 2 mg of aflibercept by intravitreal injection every 12 weeks after one year of effective therapy.

In one embodiment, a subject with Macular Edema Following Retinal Vein Occlusion (RVO) is administered 2 mg of aflibercept by intravitreal injection once every 4 weeks (approximately every 25 days, monthly).

In one embodiment, a subject with Diabetic Macular Edema (DME) or Diabetic Retinopathy (DR) in Patients with Diabetic Macular Edema is administered 2 mg of aflibercept by intravitreal injection every 4 weeks (approximately every 28 days, monthly) for the first 5 injections followed by 2 mg via intravitreal injection once every 8 weeks (2 months). In another embodiment, a subject with Diabetic Macular Edema (DME) or Diabetic Retinopathy (DR) in Patients with Diabetic Macular Edema is administered 2 mg of aflibercept by intravitreal injection every 4 weeks (approximately every 25 days, monthly). In another embodiment, a subject with Diabetic Macular Edema (DME) or Diabetic Retinopathy (DR) in Patients with Diabetic Macular Edema is administered 2 mg of aflibercept by intravitreal injection every 4 week (monthly) dosing after the first 20 weeks (5 months).

In some embodiments of the invention, the formulations of the invention may be administered in combination with other ocular therapy, for example, laser treatment. As used herein, the phrase 'in combination with' means that the formulations of the invention may be administered to the subject at the same time as, just before, or just after other therapy including laser treatment.

The present invention also includes methods for inhibiting or reducing or suppressing vascular leak in a subject. In certain embodiments, the methods according to this aspect of the invention comprise administering to the subject one or more doses of a pharmaceutical formulation of the invention to reduce or inhibit vascular leak in the eye of a subject. In certain other embodiments, the methods comprise administering to the subject one or more doses of a formulation of the invention. In certain embodiments, the vascular leak is inhibited for more than 3 weeks, more than 4 weeks, more than 8 weeks, or more than 10 weeks than in a subject who has not been administered the formulations of the invention.

In certain embodiments, the methods comprise administering an initial dose of the pharmaceutical composition, followed by one or more secondary doses, wherein each secondary dose is administered 1 to 4 weeks after the immediately preceding dose. In certain embodiments, one or more tertiary doses of the pharmaceutical composition are administered, wherein each tertiary dose is administered 5 to 12 weeks after the immediately preceding dose. In certain embodiments, each dose of the pharmaceutical composition may comprise about 2 mg of the VEGF antagonist.

The methods of the present invention are useful for treating or preventing vascular eye disorders in patients that have been diagnosed with or are at risk of being afflicted with a vascular eye disorder. Generally, the methods of the present invention demonstrate efficacy within 36 weeks of the initiation of the treatment regimen (with the initial dose administered at "week 0"), e.g., by the end of week 6, by the end of week 12, by the end of week 18, by the end of week 24, etc. In the context of methods for treating angiogenic eye disorders such as AMD, and DME, "efficacy" means that, from the initiation of treatment, the patient exhibits a loss of 10 or fewer letters on the Early Treatment Diabetic Retinopathy Study (ETDRS) visual acuity chart. In certain embodiments, "efficacy" means a gain of one or more (e.g., 1, 2, 3, 4, 5, 6, 7, 8, 9, 10, 11 or more) letters on the ETDRS chart from the time of initiation of treatment.

In one embodiment, the formulations of the invention may be intravitreally administered to a subject (e.g., a human) with an aflibercept concentration of about 0.01 mg/mL to about 200 mg/mL. In another embodiment, the concentration of aflibercept is about 0.1 mg/mL to about 100 mg/mL. In another embodiment, the concentration of aflibercept is about 1 mg/mL to about 60 mg/mL. In another embodiment, the concentration of aflibercept is about 40 mg/mL.

In certain embodiments, the formulations of the invention may be prepared in a bulk formulation, and as such, the components of the bulk formulation are adjusted to be higher than would be required for administration and then diluted appropriately prior to administration.

In one embodiment, the invention includes a container comprising a formulation of the present invention. In one embodiment the container is a vial. In another embodiment, the container is a syringe. In one embodiment, the syringe is silicone free. In another embodiment, the internal surface of the syringe is coated with baked-on silicone.

In some embodiments, the invention includes pre-filled syringes suitable for intravitreal administration wherein the pre-filled syringes comprise the formulations of the invention. In one embodiment the pre-filled syringe is filled a volume of a formulation that delivers 2 mg of aflibercept upon administration. One one embodiment, the 2 mg of aflibercept is delivered in 0.05 mL. In a further embodiment, the syringe is over-filled.

In another embodiment, the syringe is coupled to a needle. In one embodiment, the needle is a 30-gauge needle.

In another embodiment, the pre-filled syringe is a glass syringe. In another embodiment, the pre-filled syringe is a plastic syringe. In another embodiment, the pre-filled syringe is a glass syringe with an internal non-glass coating. Syringes, non-glass coatings, and syringes with internal non-glass coatings are known in the art. See, WO2017087798, US20180325728, WO2017177120, WO2018194918, WO2018217995, WO2018218013, and US20190000919 which are hereby incorporated by reference in their entirety.

In one embodiment, a formulation of the present invention is in a container that has no headspace. By providing the formulation in a closed container with no headspace interfacial stress on the formulation is reduced and the formulation is stabilized. Such containers and methods of preparing a container with no headspace that comprises a formulation are known in the art. See, US 20180043020 which is hereby incorporated by reference in its entirety.

In some embodiments, the methods of administration include administering the formulations of the invention to a subject in need thereof every four weeks for the first three months, and then once every eight weeks. In one embodiment, dose is about 2 mg of aflibercept (for example 0.05 mL of an aqueous solution containing 40 mg/mL aflibercept)

Treatment for longer periods may be necessary to induce the desired degree of improvement. For incurable chronic conditions the regimen may be continued indefinitely.

The pharmaceutical compositions may be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

In some embodiments, the formulations of the invention can be administered in ways other than intravitreal administration, for example parenteral, oral, buccal, nasal, rectal, intraperitoneal, intradermal, transdermal, subcutaneous, intravenous, intra-arterial, intracardiac, intraventricular, intracranial, intratracheal, intrathecal administration, intramuscular injection, and topical application.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (μg/ml) of aqueous formulation. The kit can also be accompanied by instructions for use.

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

EXAMPLES

Aflibercept formulations may be prepared as described more fully below. The formulations are typically grouped into blocks, where each block is described in the context of one Example or portion of one Example. The formulations are exposed to storage conditions, for example, 1 week at 40° C., 2 weeks at 25° C., and 4 weeks at 5° C. Storage at 40° C. is an accelerated model which indicates that a formulation will be stable at lower temperatures for longer period of times. Aflibercept formulations of the present invention are compared to the aflibercept formulation for Elyea®. Eylea® has a pH of 6.2 and contains 40 mg/mL aflibercept, 10 mM sodium phosphate, 40 mM sodium chloride, 0.03% polysorbate 20, and 5% sucrose.

For each time point, the chemical and physical stability of the aflibercept protein may be measured by, e.g., SEC, HIC, CEX, AF4, RP, UV, pH, CE-IEF and CE-SDS. However, studies using other durations, as well as other temperatures, may also be conducted following the guidance herein. Unless specified otherwise, all formulations contain 40 mg/ml aflibercept.

In the experimental disclosure which follows, the following abbreviations apply: SEC (size exclusion chromatography); HIC (Hydrophobic Interaction Chromatography); CEX (Cation Exchange Chromatography); AF4 (Asymmetrical flow field-flow fractionation); RP (reverse phase chromatography); UV (Ultra-violet spectroscopy); CE-IEF (Capillary Isoelectric Focusing); CE-SDS (Capillary Electrophoresis Sodium Dodecyl Sulfate); eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

Materials and Methods

A. Representative Equipment Useful in Formulation Studies

| Equipment | Manufacture | Model |
|---|---|---|
| Balance | Sartorius | CPA124S |
| pH meter | DenverInstrument | Model 250 |
| pH meter | Mettler Toledo | Seven Excellence |
| UV | Cary | Bio 100 |
| HPLC | Dionex 3 | Ultimate 3000 UPLC |
| HPLC | Dionex 2 | Ultimate 3000, UPLC |
| BeckmanCE | Beckman | P/ACE |
| Agilent CE | Agilent | 3DCE 1600A |
| RockerPlate | Labnet | Orbit P4 |

B. Representative Chemicals and Materials Useful in Formulation Studies

| Chemicals | Manufacture |
|---|---|
| 2-mercaptoethanol | Fisher |
| Acetate | Mallinckrodt |
| Arginine | Spectrum |
| Bicarbonate | EMD |
| CaCl2 | J. T. Baker |
| Citrate | Mallinckrodt |
| Dextran (40,000 MW) | Alfa Aesar |
| Di Phosphate | J. T. Baker |
| EDTA | Sigma |
| F-68 | Sigma |
| Glacial acetic acid | Macron |
| Glycerol | Sigma/Aldrich |
| Glycine | Emprove |
| Glycine | Spectrum |
| Glycine | Fisher |
| Histidine | Spectrum |
| L-Arginine HCl | J. T Baker |
| L-Histidine | J. T. Baker |
| L-Histidine (HA) | J. T. Baker |
| L-Histidine HCl | J. T. Baker |
| L-Histidine monohydrate (H2A+) | J. T. Baker |
| L-Proline | Emprove |
| Lactose | J. T Baker |
| Magnesium Chloride | J. T Baker |
| Maleate | TCI |
| Mannitol | BDH |
| Methionine | Spectrum |
| Mono Phosphate | J. T. Baker |
| PEG 3350 | Spectrum |
| PG | J. T Baker |
| Phosphate | Fisher |
| Polysorbate 20 | Spectrum |
| Polysorbate 80 | Sigma-Aldrich |
| Sodium Acetate | Emprove |
| Sodium Acetate Anhydrous | Emprove |
| Sodium biphosphate monohydrate | J. T Baker |
| Sodium Chloride | J. T. Baker |
| Sodium Chloride | Mallinckrodt |
| Sodium Chloride | Macron |
| Sodium Citrate Di hyrdate | Emprove |
| Sodium dodecyl sulfate | Fluka |
| Sodium phosphate dibasic | J. T Baker |
| Sorbitol | Emprove |
| Sorbitol | Spectrum |
| Succinate | Spectrum |
| Sucrose | Emprove |
| Tartrate | Spectrum |
| Trehalose | Pfanstiehl |
| Trehalose | Spectrum |
| Tris | Emprove |
| Tris base | Fisher |
| Xylitol | Spectrum |

| Materials |
|---|
| Vials, Schott, PN: 450006939 |
| Caps S2-F451 D777-1 R B2-40 |
| Serial Filters, Millex-GV, PVDF 0.22 µm |
| Pellicon ® 3 |
| Slide-A-Lyzer ® Mini Dialysis 20K MWCO, 2 ML |
| Amicon Ultra-15, Ultracel ® 30K |
| SoloVP Fibrette |
| SoloVP Small UV Disposable Vessels |

C. Representative Reagents Useful in Formulation Studies

| Material/Reagents | Part Number | Supplier |
|---|---|---|
| Slide-A-Lyzers 7K cutoff | 66373 | Thermo |
| Mini Dialysis Units | 69550 | Thermo |
| Millex ®-GV 0.22 µM, Filter | SLGV004SL | Millipore |
| 1 mL Vials | 4500050375 | SCHOTT |
| cIEF Gel Polymer Solution | 477497 | Beckman Coulter |
| pI Marker Kit | A58481 | Beckman Coulter |
| Pharmalyte 3-10 ampholyte | 17-0456-01 | GE Healthcare |
| Fused silica capillary (50 µmi.d.) | TSP050375 | Polymicro |
| SDS-MW gel buffer | A10663 | Beckman |
| 10 kD internal standard | A26487 | Beckman |

D. Representative HPLC Columns Useful in Formulation Studies

| Column | Company | Part # |
|---|---|---|
| Poroshell 300SB- C8, 2.1 × 75 mm, 5 um | Agilent | 660750-906 |
| Poroshell 300SB- C8, 2.1 × 75 mm, 5 um | Agilent | 660750-906 |
| ACQUITY UPLC BEH200 SEC, 1.7 um Column, 4.6 × 150 mm | Waters | 186005225 |
| ACQUITY UPLC BEH200 SEC, 1.7 um Column, 4.6 × 150 mm | Waters | 186005225 |

E. Tangential Flow Filtration (TFF)

Tween 20 was removed from Zaltrap (commercially available aflibercept formulation) using a protein A column. The processed material was buffer exchanged into 10 mM sodium phosphate at pH 6.2. TFF was used to buffer exchange the bulk material and the concentrate sample. The parameters below were used to process the material by TFF for buffer exchange and concentration.

The TFF system was stored in 0.1% NaoH, this was washed out with the exchange buffer which was 10 mM sodium phosphate, pH 6.2. To ensure that sodium hydroxide was been flushed from the system and the lines, the pH was checked in the tank and the waste line. After flushing the system the material was added to the tank and the flow was changed to pass through the Pellicon® 3.

The processed material was added the tank and diluted with the dialysis buffer to 500 mL. After buffer exchange the sample volume was reduced to 100 mL, concentrating aflibercept. The material was UF/DF vs 2000 mL of 10 mM phosphate, pH 6.2, using the following parameters: Stir 30%; Pump 30%; TMP target 14.1 pSI; DP target 28.1 pSI.

F. Fluorescence Micelle Assay (FMA)

FMA is a method that quantifies polysorbates (Tweens) by the interaction of a fluorescence dye with the surfactant micelles. Below is the basic method used for the quantification of polysorbate 20 (PS20). It turned out that this method is extremely dependent on the sample matrix.

Stock NPN Solution was prepared by weighing out 219 mg of NPN in a glass volumetric container and 100 mL of Acetonitrile. The solution needs to be protected from light and is stable for 3 months at room temperature.

NPN Mobile Phase.
    50 mM TRIS, 150 mM NaCl, 50 μg/mL Brij 35, 5 μM NPN.
    7.9 g, Tris HCl, 8.8 grams NaCl dissolve in water and adjust to pH 8.
    Q.S. to 1 L, Filter and then add 500 uL of 10 mM NPN stock solution and add 165 μL of Brij 35

HPLC Analysis Parameters.
    Column Temperature: 25° C.
    Flow Rate: 1 mL/min
    Injection Vol: 50 uL
    Fluorescence Parameters: Excitation Wavelength: 350 nm Emission Wavelength: 395 nm
    Separation Device: Supelco Knitted reaction coil, 5 m by 0.5 mm, Product ID 57405 (The coil is used to allow for enough time for the dye to interact with micelle)

G. Dialysis

The UF/DF processed bulk aflibercept material was formulated by dialysis using a Slide-A-Lyzer® Mini Dialysis 20K MWCO, 2 ML. The Slide-A-Lyzer® Mini Dialysis was prepared by hydrating the membrane using the formulation buffer. After the membrane was hydrated the liquid was removed and replaced UF/DF processed bulk aflibercept material. Slide-A-Lyzer then shacked using an orbital rotator set to 300 rpm for 48 to 72 hours at 5-8° C. The dialysis buffer was changed out 3 times during this procedure at 4, 24 and 48 hours.

H. Spin Concentration

After the pH of the sample was within ±0.1 pH units of the target value the sample was concentrated by spin concentrator. The spin concentrator was first hydrated by 4 mL of water pass through the membrane. The sample was then loaded into the spin concentrator and rotated at 2,000 g for 7 to 13 minutes. The sample was concentrated above the target concentration of 40 mg/mL and was then diluted to be within 10% of the target protein concentration for the formulation.

I. UV Analysis

In order to prevent sample loss and the error due to preparing the UV sample, the concentration of each formulation was measured using the Solo VP. The concentration of the sample was measured by added 50 to 100 μL of material into a SoloVP small UV disposable vessel. A new fibrette was installed and the sample absorbance was measured by the instrument, using an extinction coefficient of 1.55 mL. $mg^{-1}$ $cm^{-1}$, and correcting background scattering. After analysis the sample is removed with a pipette the disposable vessel and fibrette are both disposed. This procedure is repeated for each sample.

J. pH Analysis

After sample preparation the pH will be checked for each formulation and be within ±0.1 of the target pH. Before the start of analysis, the pH probe was calibrated with three pH standards ordered from fisher. The pH of the formulation will be measured by inserting the pH probe in to the sample and waiting until the measured value has stabilized, which can take up to 1 to 2 minutes. After the analysis the pH probe is washed with 18 (water for one minute and stored in the pH storage solution.

K. Osmotic Analysis

The osmotic analysis was performed using an Advanced Instruments, Osmo 1. At the start of analysis, a reference standard at 290 mOsm is analyzed to insure the instrument is working properly. After the reference standard has passed the samples are then analyzed. 20 uL of material is removed and analyzed by the Osmo 1, after analysis the chamber is cleared by a using a chamber cleaner. This procedure is repeated for each sample.

L. Formulating

The bulk processed aflibercept material was formulated following the procedures below. The aflibercept material was buffered exchanged following the dialysis procedure. After dialysis the osmotic pressure and the pH was checked, if the pH of the sample was not within ±0.1 pH units, the formulation buffer was made more acidic or basic, by repeat dialysis or by addition of HCl or NaOH, until the pH target was reached. Following pH adjustment if needed, the sample was concentrated above the target formulation concentration. The pH, osmotic pressure and the protein concentration was then measured once more. The sample was then diluted with the formulation buffer to reached the target formulation protein concentration within 10%. The protein concentration was then measured once more to insure the diluted sample was within 10% of the target concentration. The last step was the addition of the 20% PS 20 (diluted in water) to the sample based on weight, if required.

M. Sterile Filtering and Sample Filling

The samples were sterile filtered in a clean hood that was wiped down with 70% ethanol. Each formulation was loaded into a sterile syringe with sterile filter attached. The sample was then slowly pushed through filter into a sterile container. After the samples had been sterile filtered, they were loaded into autoclaved vials and caps N. Size Exclusion Chromatography Method Size exclusion chromatography (SEC) analyses were conducted on formulations to measure the changes in colloidal stability. SEC can quantify oligomers and soluble aggregates, as well as detect fragmentation of proteins.

The SEC analysis parameters are described below
    Column: ACQUITY UPLC BEH SEC (CAT. 186005225), 220 Å 1.7 μm, 4.6 mm×150 mm
    Mobile Phase: 20 mM Sodium Phosphate, 250 mM Sodium Chloride, pH 7.55*
    Autosampler Temp: 5° C.±3° C.
    Column Temp.: 30° C.±2° C.
    Flow Rate: 0.25 mL/minute
    Injection Vol: 5 μL
    UV Setting: 280 nm
    Data Collection Time: 15 minutes O. Sub-Visible Particle Evaluation by MFI In the examples below, screening studies were conducted to identify formulations with particle counts indicating that the formulation is sufficiently stable and therefore suitable as commercial aflibercept product. Formulations with exceptionally high particle counts (e.g. >1,000,000) may not be sufficiently stable. The particle counts reported in the examples below for a formulation may not be the particle counts for a commercialized aflibercept product. For example, a commercialized product is manufactured under strict GMP conditions which is expected to reduce the number of particles found in the formulation. Moreover, USP guidelines (e.g. USP <788>, <789>, which are hereby incorporated by reference in their entirety) limit the number of particles that can be present in certain products. When manufactured and handled under GMP conditions, it is expected that the formulations herein that are identified to be sufficiently stable based on the screening test of sub-visible particles will be suitable for a commercial aflibercept product.

To evaluate sub-visible particles in formulations Micro Flow Imaging analysis was conducted. The MFI analysis was performed on a MFI 5200 Protein Simple system following the procedure described below.

MFI System Suitability.

In order to ensure the MFI was counting and assessing particle size accurately, 5 uM size/concentration standards (5 um polystyrene beads for MFI system suitability Countcal Cat #CC05) and 10 uM size standards (10 um polystyrene beads for MFI system suitability Duke Std Cat #4210A) were used. Triplicate analyses for each standard were performed and the average of each standard were within 10% of true/given manufacture value.

Sample Preparation.

Samples were placed in the BSC and allowed to equilibrate to room temperature for about 30 minutes. Using Neptune Barrier Tips (1000 uL Barrier Tip, Cat #1000.96N), samples were diluted 1:1 with MilliQ Water, specifically 190 uL MilliQ water+190 uL Samples. All samples were degassed for 20 min @ 70 cmHg.

MFI Analysis.

Prior to analysis, approximately 10 mL of MilliQ water was flushed through the MFI system using a 100 uM FlowCell (FlowCell, 100 uM, 1.6 mm, Silane Coating). For each sample, 350 μL was pipetted and sample-filled pipette was placed in the MFI inlet port. 0.03-0.05 mL manual purge (by volume) was performed followed by selecting "Optimize illumination" to calibrate and set the background. Analysis was started by selecting "Start analysis". A total of 180 ul of sample was analyzed for each measurement. After each measurement, 1-4 ml of MilliQ water was flushed through the flow-cell.

For the example below, the levels of subvisible particles (SVPs) were monitored for each of the formulations in Blocks A through G at all of the time points using micro-flow imaging (MFI). Total particle levels are reported, along with a corrected particle concentration once the circular particles likely due to air bubbles and oil droplets are removed. In addition, the levels of subvisible particles in four different size bins (≥2 μm, ≥5 μm, ≥10 μm, and ≥20 μm) are reported as well. Due to volume limitations, all samples were diluted two-fold to allow better quantitation. Particles ≥2 μm in size are rarely associated with protein aggregates, so the focus of subsequent analysis was mostly on the amounts of larger particles and on the corrected total number of particles per mL.

P. Imaged Capillary Isoelectric Focusing (icIEF, ICE)

Imaged capillary isoelectric focusing was used to quantify the charge distribution for the formulations. The icIEF analysis was performed on aniCE3 Protein Simple system following the procedure described below.

Materials:

| Reagent/Supply | Manufacturer | Cat# |
|---|---|---|
| TTM Reagent | ProteinSimple | 102672 |
| Electrolyte Kit | ProteinSimple | 102506 |
| 0.5% MC | ProteinSimple | 102505 |
| FC Cartridge | ProteinSimple | 101701 |

Working Sample Preparation.

Samples were diluted with MilliQ Water to 5 mg/mL with a working volume of 20 uL (e.g. 2.5 uL of 40 mg/mL Sample+17.5 uL MilliQ Water.

icIEF Matrix Preparation.

The icIEF reagents were removed from 5° C. storage and placed at ambient temperatures for 30 minutes. The following icIEF Matrix preparation was prepared for N+1 samples and all preparations were thoroughly mixed.

| icIEF Reagent | Single Sample Preparation |
|---|---|
| 1% MC (Protein Simple, 1% MC, 101876) | 70 uL |
| MilliQ Water | 106 uL |
| Pharmalyte pH 3-10 (Pharmalyte pH 3-10, GE, 17-0456-01) | 1 uL |
| Pharmalyte pH 5-8 (Pharmalyte pH 5-8, GE, 17-0453-01) | 1 uL |
| pI Marker 5.85 (pI Marker 5.85, ProteinSimple, 102225) | 1 uL |
| pI Marker 8.40 (pI Marker 8.40, ProteinSimple, 102229) | 1 uL |
| Total | 180 uL | icIEF Sample Preparation and icIEF Analysis.

For each sample and reference standard, 180 uL of iciEF Matrix was added to 20 uL of working sample. For blank preparation, 20 uL of MilliQ water was combined with 180 uL of icIEF matrix. Prepared sample was thoroughly mixed and centrifuge for at 3000 g for 10-15 seconds. The sample was analyzed by the iCE3 instrument with a Pre-Focus of 1500V for 1 minute and a Focus of 3000V for 15 minutes.

In the formulations evaluated by ICE below, twelve distinct features were observed. The measured relative areas of each of these twelve peaks for each sample are tabulated in the examples below. The average pI values for these twelve peaks within each block are determined. From these data, the average pI value for any given sample is calculated. Compared to the values T=0, the differences for each of the stored samples were calculated. These values are quite small, but fairly reproducible. This was the basis for the PLS model to evaluate chemical stability of formulations.

Q. Shipment Test

To evaluate the physical stability of aflibercept in formulations, a shipment test is performed. Formulations are filled into containers (e.g. a syringe) then packed into cardboard containers separated by corrugated cardboard. The containers are then shipped at least 1,000 miles by truck over paved roads. During shipment, the containers are kept at a constant temperature or within a suitable temperature range (e.g. +/−10% of target temperature). The temperature may be 25° C., 2-8° C., 0° C., or freezing (i.e. below 0° C.). After reaching their destination the formulations in the containers are inspected for particles (e.g. visible particles and sub-visible particles).

R. Drop Test

To evaluate the physical stability of aflibercept in formulations, a drop test is performed. Formulations are filled into containers (e.g. a syringe) then packed into cardboard containers separated by corrugated cardboard. The containers are then subjected to a dropping test. The dropping test may be conducted at 2-8° C. or around room temperature (e.g. 25° C.). For the dropping test, the container is dropped in various orientations. In one example of a dropping test, a cardboard container holding a pre-filled syringe containing a formulation is dropped a total of 16 times from a height of 36 inches. The 16 drops include: 1) dropping the container on each of its 6 faces; 2) dropping the container on each of the 4 edges with the needle (or needle connector) pointing in the horizontal position (i.e. perpendicular to surface the container is being dropped on); 3) dropping the container on 1 edge with the needle pointing upward; 4) dropping the container on 1 edge with the needle pointing downward; 5) dropping the container on 2 separate corners with the needle generally pointing downward; and 6) dropping the container on 2 separate corners with the needle generally pointing upward. Following the dropping test the formulations in the containers are inspected for particles (e.g. visible particles and sub-visible particles).

S. Multivariate Statistical Modeling: Partial Least-Squares (PLS)

Partial least squares regression (PLS) was used to shed additional light on the effects of the various formulation parameters on stability of the formulations. For any large matrix of values, where there are a reasonable number of samples (together forming the so-called X-matrix), mathematical models can be constructed that explain the largest amount of variance in the dependent variable(s) of interest (the Y-matrix). The best single description of the relationship between the variation in the X-matrix and the endpoint (the Y matrix) is called the first principal component, PC1. The next important (in terms of describing the variance in the Y-matrix) component is called the second principal component, PC2, and so on. Quite often, only one or two PCs are required to explain most of the variance in the Y-matrix. Each of these PCs contains some contribution from each of the variables in the X-matrix. If a variable within the X-matrix contributes heavily to the construction of a given PC, then it is ranked as being significant. In fact, regression coefficients can be calculated for each variable in the X-matrix for a given model, where a model is the composite of a certain number of PCs in order to provide an adequate description of the Y-matrix. In summary, PLS takes information from the X-matrix, calculates the desired number of PCs, and constructs a suitable model. The model that includes all of the samples is termed a calibration model. The overall coefficient of determination ($r^2$) indicates the quality of the model. All PLS calculations were conducted using Unscrambler® software (CAMO, Corvallis, Oreg.). A PLS analysis done with a single variable in the Y-matrix is termed PLS1 analysis. Building a model that fits multiple variables in the Y-matrix is called PLS2 analysis.

A full cross validation was performed on all calibration models using standard techniques. Briefly, one sample is removed at a time, the data set is recalibrated, and a new model is constructed. This process is repeated until all of the calibration samples are removed once and quantified as a validation model. Therefore, the first set, containing all samples is referred to as the calibration set and the one after cross-validation as the validation set. The jack-knife algorithm was used to determine statistical significance for any factor used in constructing the PLS models described above.

Stability Testing Conditions

Unless otherwise indicated, formulations may be maintained at an indicated temperature, e.g., 40° C., 25° C., 2-8° C., or a freezing temperature (e.g. 0° C. and below) for a period of time, e.g., days, weeks, or months, and assessed for stability and/or other parameters. For example, the pH, conductivity and/or viscosity of the samples may be measured at time zero and periodically throughout the experiment. The material may be analyzed for stability and other properties using, e.g., chromatography or other methods; non-limiting examples include SEC, RP, HIC, CEX, AF4 and/or CE-SDS. These analyses are typically carried out at time zero and then periodically during the experiment.

The samples may also be assessed by starting the experiment at one temperature, e.g., 40° C., and then stepping or ramping to a different temperature, e.g., 25° C., and/or 2-8° C., for a selected period of time. For example, the samples may be stored at −20° C. or 2 months; and/or at 40° C. for 1 and 2 weeks; and/or at 25° C. for 2 and 4 weeks, and/or at 2-8° C. for 2 months. A drop test can be carried out at 25° C.

Example 1—Preparation of Aflibercept

Aflibercept may be prepared either de novo or through purification/isolation from a commercially available source. The steps below describe production of aflibercept by culturing cells transformed or transfected with a vector containing aflibercept nucleic acid. Alternative methods, which are well known in the art, may also be employed to prepare aflibercept. For instance, the appropriate amino acid sequence, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of aflibercept may be chemically synthesized separately and combined using chemical or enzymatic methods to produce aflibercept.

A. Recombinant Production

DNA encoding aflibercept is inserted into an expression vector appropriate for the host cell to express aflibercept.

Host cells transfected or transformed with expression or cloning vectors described herein for aflibercept production is cultured in nutrient media modified as appropriate for inducing promoters, selecting transformants, and/or amplifying the genes encoding the desired sequences. The culture conditions, such as media, temperature, pH and the like, are selected by the skilled artisan using well-known approaches without undue experimentation. For example, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation, which means introduction of DNA into the host so that the DNA is replicable, either as an extrachromosomal or by chromosomal integrant, are known to the ordinarily skilled artisan, for example, CaCl$_2$), CaPO$_4$, liposome-mediated, polyethylene-glycol/DMSO and electroporation.

Aflibercept may be expressed in a mammalian cell line, such as a CHO cell and may be modified post-translationally.

Aflibercept is recovered from culture medium or from host cell lysates. If membrane-bound, it can be released from the membrane using a suitable detergent solution (e.g Triton-X 100) or by enzymatic cleavage. Cells employed in expression of aflibercept can be disrupted by various physical or chemical means, such as freeze-thaw cycling, sonication, mechanical disruption, or cell lysing agents.

It may be desired to purify aflibercept from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SD S-PAGE; ammonium sulfate precipitation; gel filtration using, for example, Sephadex G-75; protein A Sepharose columns to remove contaminants such as IgG. Various methods of protein purification may be employed and such methods are known in the art and described for example in Deutscher, Methods in Enzymology, 182 (1990); Scopes, Protein Purification: Principles and Practice, Springer-Verlag, New York (1982).

The aflibercept composition prepared from the cells can be purified using, for example, hydroxylapatite chromatography, gel electrophoresis, dialysis, and affinity chromatography.

Following any preliminary purification step(s), the mixture comprising aflibercept and contaminants may be subjected to low pH hydrophobic interaction chromatography using an elution buffer at a pH between about 2.5-4.5. The HIC may be performed at low salt concentrations (e.g., from about 0-0.25M salt).

B. Purifying Aflibercept from a Commercially-Available Formulation

Alternatively, aflibercept is purified from a commercially available preparation such as Eylea® or Zaltrap®. Aflibercept is purified away from other formulation components in Eylea® or Zaltrap® using, for example, hydroxyapatite chromatography, gel electrophoresis, dialysis, affinity chromatography, and/or any other applicable purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

In another alternative, compositions of the present invention are prepared by buffer exchange. Here, using techniques known to one of skill in the art, commercially available Eylea® or Zaltrap® is subjected to a buffer exchange wherein the ingredients, other than aflibercept, of the Eylea® or Zaltrap® formulation are removed and replaced with the ingredients of a formulation of the present invention.

Example 2—Effects of pH and Buffers on Aflibercept Formulations

This example describes experiments to evaluate the effects of various pH levels and different buffering agents on aflibercept formulations (Block A). Block A formulations are listed in Table 2.

TABLE 2

| Form No. | aflibercept | pH | Buffer (20 mM) |
|---|---|---|---|
| A-1 | 40 mg/ml | 5.0 | Acetate |
| A-2 | 40 mg/ml | 5.0 | Citrate |
| A-3 | 40 mg/ml | 5.5 | Acetate |
| A-4 | 40 mg/ml | 5.5 | Histidine |
| A-5 | 40 mg/ml | 6.0 | Histidine |
| A-6 | 40 mg/ml | 6.0 | Phosphate |
| A-7 | 40 mg/ml | 6.2 | Phosphate |
| A-8 | 40 mg/ml | 6.2 | Histidine |
| A-9 | 40 mg/ml | 6.2 | Citrate |
| A-10 | 40 mg/ml | 6.5 | Phosphate |
| A-11 | 40 mg/ml | 6.5 | Histidine |
| A-12 | 40 mg/ml | 7.0 | Phosphate |
| A-13 | 40 mg/ml | 7.0 | Tris |
| A-14 | 40 mg/ml | 7.5 | Phosphate |
| A-15 | 40 mg/ml | 7.5 | Tris |
| A-16 | 40 mg/ml | 8.0 | Tris |
| A-17 | 40 mg/ml | 8.0 | Bicarbonate |

Concentration, pH, and Osmolality

The aflibercept concentration (mg/mL), pH, and osmolality (mOSm) of the Block A formulations were evaluated at t0. Results are reported in Table 3 below.

TABLE 3

| Form No. | Final pH | Final Osmolality (mOsm/Kg) | Final Concentration (mg/mL) |
|---|---|---|---|
| A-1 | 4.99 | 35 | 40.27 |
| A-2 | 5.06 | 90 | 40.22 |
| A-3 | 5.48 | 37 | 39.79 |
| A-4 | 5.55 | 38 | 39.72 |
| A-5 | 6.08 | 33 | 38.91 |
| A-6 | 5.99 | 44 | 39.97 |
| A-7 | 6.18 | 45 | 40.05 |
| A-8 | 6.29 | 29 | 41.24 |
| A-9 | 6.20 | 71 | 40.84 |
| A-10 | 6.48 | 44 | 40.24 |
| A-11 | 6.56 | 25 | 40.31 |
| A-12 | 6.98 | 47 | 39.94 |
| A-13 | 7.00 | 42 | 39.38 |
| A-14 | 7.48 | 52 | 40.02 |
| A-15 | 7.48 | 37 | 40.18 |
| A-16 | 7.96 | 30 | 40.2 |
| A-17 | 8.01 | 38 | 40.99 |
| Eylea | 6.20 | 239 | 40.99 |

Size Exclusion Chromatography

The stability of the Block A formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Tables 4-7 below.

TABLE 4

| SEC results for Block A formulations at T = 0 | | | |
|---|---|---|---|
| Form No. | Rel. Area (%), Before Main Peak | Rel. Area (%), Main Peak | Rel. Area (%), After Main Peak |
| A-1 | 0.88 | 99.12 | 0.00 |
| A-2 | 0.87 | 99.13 | 0.00 |
| A-3 | 0.89 | 99.11 | 0.00 |
| A-4 | 0.88 | 99.12 | 0.00 |
| A-5 | 0.90 | 99.10 | 0.00 |
| A-6 | 1.02 | 98.98 | 0.00 |
| A-7 | 1.07 | 98.93 | 0.00 |
| A-8 | 0.98 | 99.02 | 0.00 |
| A-9 | 1.03 | 98.97 | 0.00 |

TABLE 4-continued

SEC results for Block A formulations at T = 0

| Form No. | Rel. Area (%), Before Main Peak | Rel. Area (%), Main Peak | Rel. Area (%), After Main Peak |
|---|---|---|---|
| A-10 | 1.19 | 98.81 | 0.00 |
| A-11 | 1.09 | 98.91 | 0.00 |
| A-12 | 1.32 | 98.68 | 0.00 |
| A-13 | 1.31 | 98.69 | 0.00 |
| A-14 | 1.49 | 98.51 | 0.00 |
| A-15 | 1.33 | 98.67 | 0.00 |
| A-16 | 1.36 | 98.64 | 0.00 |
| A-17 | 1.78 | 98.22 | 0.00 |
| Eylea | 1.08 | 98.92 | 0.00 |

TABLE 5

SEC results for Block A formulations after one week at 40° C.

| Form No. | Rel. Area (%), Before Main Peak | Rel. Area (%), Main Peak | Rel. Area (%), After Main Peak |
|---|---|---|---|
| A-1 | 1.88 | 98.12 | 0.00 |
| A-2 | 10.13 | 89.87 | 0.00 |
| A-3 | 2.16 | 97.84 | 0.00 |
| A-4 | 2.07 | 97.93 | 0.00 |
| A-5 | 2.31 | 97.69 | 0.00 |
| A-6 | 2.93 | 97.07 | 0.00 |
| A-7 | 3.07 | 96.93 | 0.00 |
| A-8 | 2.59 | 97.41 | 0.00 |
| A-9 | 4.10 | 95.90 | 0.00 |
| A-10 | 3.30 | 96.70 | 0.00 |
| A-11 | 2.99 | 97.01 | 0.00 |
| A-12 | 3.65 | 96.35 | 0.00 |
| A-13 | 3.52 | 96.48 | 0.00 |
| A-14 | 3.88 | 96.12 | 0.00 |
| A-15 | 3.55 | 96.45 | 0.00 |
| A-16 | 3.88 | 96.12 | 0.00 |
| A-17 | 5.25 | 94.75 | 0.00 |
| Eylea | 2.53 | 97.47 | 0.00 |

TABLE 6

SEC results for Block A formulations two weeks at 25° C.

| Form No. | Rel. Area (%), Before Main Peak | Rel. Area (%), Main Peak | Rel. Area (%), After Main Peak |
|---|---|---|---|
| A-1 | 0.96 | 99.04 | 0.00 |
| A-2 | 1.13 | 98.87 | 0.00 |
| A-3 | 1.03 | 98.97 | 0.00 |
| A-4 | 0.92 | 99.08 | 0.00 |
| A-5 | 1.02 | 98.98 | 0.00 |
| A-6 | 1.16 | 98.84 | 0.00 |
| A-7 | 1.26 | 98.74 | 0.00 |
| A-8 | 1.08 | 98.92 | 0.00 |
| A-9 | 1.19 | 98.81 | 0.00 |
| A-10 | 1.40 | 98.60 | 0.00 |
| A-11 | 1.22 | 98.78 | 0.00 |
| A-12 | 1.56 | 98.44 | 0.00 |
| A-13 | 1.48 | 98.52 | 0.00 |
| A-14 | 1.72 | 98.28 | 0.00 |
| A-15 | 1.55 | 98.45 | 0.00 |
| A-16 | 1.58 | 98.42 | 0.00 |
| A-17 | 2.11 | 97.89 | 0.00 |
| Eylea | 1.23 | 98.77 | 0.00 |

TABLE 7

SEC results for Block A formulations after four weeks at 5° C.

| Form No. | Rel. Area (%), Before Main Peak | Rel. Area (%), Main Peak | Rel. Area (%), After Main Peak |
|---|---|---|---|
| A-1 | 0.94 | 99.06 | 0.00 |
| A-2 | 0.93 | 99.07 | 0.00 |
| A-3 | 0.96 | 99.04 | 0.00 |
| A-4 | 0.89 | 99.11 | 0.00 |
| A-5 | 0.95 | 99.05 | 0.00 |
| A-6 | 1.02 | 98.98 | 0.00 |
| A-7 | 1.09 | 98.91 | 0.00 |
| A-8 | 1.04 | 98.96 | 0.00 |
| A-9 | 1.03 | 98.97 | 0.00 |
| A-10 | 1.20 | 98.80 | 0.00 |
| A-11 | 1.10 | 98.90 | 0.00 |
| A-12 | 1.37 | 98.63 | 0.00 |
| A-13 | 1.34 | 98.66 | 0.00 |
| A-14 | 1.53 | 98.47 | 0.00 |
| A-15 | 1.34 | 98.66 | 0.00 |
| A-16 | 1.34 | 98.66 | 0.00 |
| A-17 | 1.72 | 98.28 | 0.00 |
| Eylea | 1.11 | 98.89 | 0.00 |

Initially, at t0, the monomer content by SEC was near 99% for these formulations. After one week at 40° C., most formulations have monomer contents that have decreased to about 97%, although a couple (A-2, A-17) are much less stable. Virtually all of the loss of monomer is due to aggregation (increases in higher molecular weight (HMW) pre-peaks) and none due to fragmentation, as evidenced by the lack of peaks after the main peak. A formulation consisting of the current Eylea formulation was also included in this block.

Likewise, loss at 25° C. is due to aggregation, indicating that this is the primary degradation pathway that will limit shelf-life. Under these conditions (T=2 weeks, 25° C.), almost all of the formulations retained >98.5% monomer. Another set of samples was held at 5° C. for four weeks. These samples showed little loss of monomer, with slightly larger losses at the high pH conditions.

Micro-Flow Imaging

The stability, SVP levels by MFI, of the Block A formulations was evaluated by measuring the particles present in the formulation after being subjected to storage conditions. A few of the Block A samples appear to exhibit elevated particle counts, as noted below. Note that these formulations only contained buffer and no other stabilizers or tonicity modifiers. So, despite being frozen and shipped on dry ice, some damage may have occurred during sample preparation and shipping. Results are reported in Table 8-11 below.

TABLE 8

MFI results for Block A formulations at T = 0

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| A-1 | 114571 | 25825 | 4330 | 811 | 67 |
| A-2 (1) | 156273 | 33187 | 5918 | 1277 | 178 |
| A-3 | 67894 | 16566 | 2298 | 466 | 56 |
| A-4 | 39904 | 9759 | 1133 | 100 | 22 |
| A-5 | 38227 | 8649 | 1554 | 300 | 0 |
| A-6 | 58845 | 14711 | 2698 | 577 | 22 |
| A-7 | 151144 | 36062 | 4275 | 844 | 33 |
| A-8 | 111895 | 26092 | 3797 | 855 | 100 |
| A-9 | 106854 | 26403 | 3409 | 500 | 33 |
| A-10 (2) | 118268 | 23116 | 2898 | 588 | 22 |

TABLE 8-continued

MFI results for Block A formulations at T = 0

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| A-11 (3) | 174060 | 41158 | 7506 | 1110 | 56 |
| A-12 | 58812 | 12402 | 1987 | 411 | 33 |
| A-13 | 110984 | 27036 | 4030 | 711 | 78 |
| A-14 | 63819 | 15477 | 2876 | 899 | 78 |
| A-15 | 54282 | 11625 | 1854 | 433 | 44 |
| A-16 | 72779 | 15511 | 2642 | 622 | 100 |
| A-17 (4) | 194400 | 43756 | 9537 | 2465 | 200 |
| Eylea | 33131 | 9537 | 1987 | 244 | 11 |

Note:
(1) Schlieren Lines in middle during purge,
(2) Faint Schlieren line during analysis (Top of screen)- MVSS Not detected
(3) High Particle counts
(4) High Particle counts
n.a.—not applicable

TABLE 9

MFI results for Block A formulations stored for one week at 40° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| A-1 | 67128 | 11269 | 888 | 244 | 33 |
| A-2 | 158216 | 39837 | 6318 | 1066 | 33 |
| A-3 | 53449 | 10625 | 699 | 100 | 22 |
| A-4 | 4663 | 1288 | 222 | 33 | 0 |
| A-5 | 91332 | 22128 | 2820 | 333 | 22 |
| A-6 | 38727 | 8383 | 1310 | 289 | 22 |
| A-7 | 52650 | 11913 | 1155 | 100 | 0 |
| A-8 | 81095 | 19375 | 2143 | 289 | 33 |
| A-9 | 84271 | 21184 | 2598 | 289 | 78 |
| A-10 (1) | 45588 | 9282 | 899 | 78 | 0 |
| A-11 (2) | 104489 | 23805 | 3286 | 555 | 33 |
| A-12 | 70392 | 14700 | 2165 | 378 | 33 |
| A-13 (3) | 78120 | 17043 | 1776 | 200 | 0 |
| A-14 (4) | 127643 | 28721 | 4324 | 546 | 15 |
| A-15 | 62631 | 13090 | 1632 | 322 | 0 |
| A-16 | 55403 | 11158 | 1532 | 311 | 44 |
| A-17 | 134478 | 23005 | 3286 | 677 | 56 |
| Eylea | 7272 | 1421 | 244 | 44 | 0 |

Note:
(1) Faint Schlieren line during analysis (Top of screen)- MVSS Not detected
(2) High Particle counts
(3) Faint Schlieren line during analysis (middle of screen)- MVSS Not detected
(4) Need time stamp after start after 26%

TABLE 10

MFI results for Block A formulations stored for two weeks at 25° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| A-1 | 28434 | 5718 | 555 | 33 | 0 |
| A-2 (1) | 47909 | 10170 | 1010 | 111 | 0 |
| A-3 | 31554 | 7084 | 822 | 233 | 22 |
| A-4 | 30655 | 7550 | 899 | 122 | 0 |
| A-5 | 48575 | 10192 | 1021 | 155 | 11 |
| A-6 | 70381 | 16388 | 1554 | 200 | 0 |
| A-7 | 6728 | 1732 | 366 | 11 | 0 |
| A-8 | 57924 | 13224 | 1121 | 78 | 11 |
| A-9 (2) | 68682 | 16932 | 1610 | 178 | 11 |
| A-10 (3) | 18942 | 4508 | 400 | 22 | 0 |
| A-11 | 20529 | 4719 | 555 | 44 | 11 |
| A-12 | 30333 | 7061 | 1210 | 266 | 89 |
| A-13 (4) | 31410 | 6973 | 899 | 100 | 11 |
| A-14 | 35829 | 8205 | 1166 | 178 | 0 |
| A-15 | 86847 | 20529 | 3464 | 500 | 44 |
| A-16 | 28135 | 4896 | 600 | 100 | 22 |
| A-17 | 27524 | 6495 | 788 | 144 | 0 |
| Eylea | 5041 | 1077 | 122 | 33 | 22 |

Note:
(1) Schlieren Lines in middle during purge
(2) Faint Schlieren line during analysis (Top of screen) - MVSS Not detected
(3) Faint Schlieren line during analysis (Top of screen) - MVSS Not detected
(4) Faint Schlieren line during analysis (middle of screen) - MVSS Not detected

TABLE 11

MFI results for Block A formulations stored for four weeks at 5° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| A-1 | 35130 | 7517 | 866 | 155 | 11 |
| A-2 | 47742 | 10392 | 966 | 67 | 0 |
| A-3 | 15011 | 3042 | 344 | 33 | 11 |
| A-4 | 58645 | 13657 | 1332 | 67 | 0 |
| A-5 | 24915 | 5662 | 422 | 44 | 0 |
| A-6 | 48742 | 10992 | 1244 | 155 | 0 |
| A-7 | 34252 | 7483 | 677 | 100 | 22 |
| A-8 | 41691 | 10237 | 1321 | 189 | 22 |
| A-9 | 24238 | 6417 | 922 | 144 | 0 |
| A-10 (1) | 27302 | 6795 | 677 | 67 | 11 |
| A-11 | 29445 | 7317 | 611 | 67 | 0 |
| A-12 | 16632 | 3409 | 333 | 22 | 0 |
| A-13 (2) | 24759 | 6795 | 977 | 233 | 11 |
| A-14 | 32964 | 6395 | 799 | 122 | 11 |
| A-15 | 20551 | 4175 | 489 | 111 | 11 |
| A-16 | 29345 | 5885 | 655 | 89 | 11 |
| A-17 | 37383 | 9693 | 1044 | 78 | 0 |
| Eylea | 4597 | 1066 | 233 | 22 | 11 |

Note:
(1) Faint Schlieren line during analysis (Top of screen) - MVSS Not detected
(2) Faint Schlieren line during analysis (middle of screen) - MVSS Not detected Imaging Capillary Isoelectric Focusing (icIEF)

The chemical stability of the Block A formulations was evaluated by measuring the charge variants present in the formulation after being subjected to storage conditions. The relative areas for each of the twelve features detected by icIEF are listed for samples from Block A. These samples were frozen and shipped before analysis. Results are reported in Table 12-15 below.

TABLE 12 icIEF results for Block A formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A-1 | 4.6 | 6.4 | 7.4 | 12.5 | 14.8 | 15.5 | 13.1 | 11.4 | 7.9 | 4.2 | 1.7 | 0.5 |
| A-2 | 4.9 | 6.2 | 7.0 | 13.0 | 14.1 | 14.9 | 14.2 | 11.4 | 7.7 | 4.2 | 1.7 | 0.6 |
| A-3 | 4.8 | 6.2 | 8.2 | 11.7 | 14.0 | 15.3 | 14.1 | 11.4 | 7.9 | 4.1 | 1.7 | 0.6 |
| A-4 | 4.4 | 7.0 | 7.8 | 11.4 | 14.7 | 15.1 | 14.5 | 11.2 | 8.3 | 3.4 | 1.7 | 0.5 |
| A-5 | 5.1 | 6.9 | 7.5 | 12.6 | 13.5 | 15.9 | 14.3 | 11.7 | 7.7 | 3.1 | 1.3 | 0.4 |
| A-6 | 4.7 | 6.3 | 7.3 | 12.3 | 14.6 | 15.5 | 14.5 | 10.6 | 8.0 | 4.2 | 1.6 | 0.4 |
| A-7 | 4.7 | 7.6 | 6.2 | 12.5 | 14.1 | 15.5 | 14.4 | 10.6 | 8.0 | 4.1 | 1.7 | 0.5 |
| A-8 | 4.9 | 7.7 | 6.9 | 12.5 | 14.3 | 15.0 | 14.2 | 11.7 | 8.0 | 3.1 | 1.4 | 0.4 |
| A-9 | 4.7 | 7.5 | 6.4 | 12.0 | 14.7 | 15.7 | 14.3 | 11.0 | 7.6 | 4.0 | 1.6 | 0.6 |
| A-10 | 4.8 | 6.1 | 8.4 | 11.8 | 15.1 | 15.3 | 14.0 | 11.5 | 7.0 | 4.1 | 1.4 | 0.6 |
| A-11 | 5.5 | 8.0 | 7.8 | 12.3 | 14.9 | 15.1 | 14.3 | 10.4 | 7.3 | 2.9 | 1.2 | 0.4 |
| A-12 | 7.3 | 9.2 | 7.9 | 12.8 | 14.8 | 15.7 | 11.7 | 10.1 | 6.0 | 3.1 | 1.1 | 0.4 |
| A-13 | 4.4 | 7.0 | 7.5 | 12.3 | 14.5 | 15.6 | 13.9 | 11.1 | 7.5 | 4.1 | 1.6 | 0.6 |
| A-14 | 5.2 | 6.4 | 7.9 | 12.4 | 15.2 | 14.8 | 13.7 | 10.8 | 7.5 | 4.0 | 1.5 | 0.5 |
| A-15 | 4.7 | 8.0 | 7.1 | 11.9 | 14.4 | 15.7 | 13.6 | 10.9 | 7.5 | 4.1 | 1.6 | 0.5 |
| A-16 | 10.7 | 10.4 | 10.7 | 14.2 | 16.1 | 14.0 | 10.3 | 7.3 | 3.8 | 1.8 | 0.6 | 0.2 |
| A-17 | 7.8 | 8.5 | 9.2 | 13.5 | 14.5 | 14.8 | 12.3 | 9.1 | 5.6 | 3.1 | 1.2 | 0.4 |
| Eylea | 4.7 | 6.8 | 7.1 | 12.2 | 15.1 | 15.0 | 13.8 | 11.6 | 7.5 | 4.0 | 1.6 | 0.5 |

TABLE 13 icIEF results for Block A formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A-1 | 4.3 | 6.1 | 7.0 | 13.0 | 14.4 | 14.6 | 14.6 | 10.8 | 8.3 | 4.4 | 1.9 | 0.6 |
| A-2 | 4.6 | 6.8 | 5.4 | 12.1 | 15.0 | 14.4 | 16.6 | 10.6 | 7.7 | 4.2 | 1.9 | 0.7 |
| A-3 | 4.3 | 7.3 | 6.6 | 12.7 | 15.1 | 15.7 | 13.6 | 11.2 | 7.5 | 4.0 | 1.7 | 0.5 |
| A-4 | 4.9 | 6.2 | 7.5 | 12.4 | 14.4 | 14.9 | 14.4 | 11.8 | 8.1 | 3.2 | 1.7 | 0.6 |
| A-5 | 5.3 | 7.1 | 7.5 | 12.2 | 15.3 | 16.1 | 13.4 | 10.8 | 7.4 | 3.0 | 1.4 | 0.4 |
| A-6 | 5.2 | 7.9 | 5.7 | 12.3 | 15.2 | 16.0 | 13.6 | 10.9 | 7.0 | 4.0 | 1.6 | 0.4 |
| A-7 | 5.4 | 8.0 | 6.6 | 11.8 | 15.3 | 15.6 | 13.6 | 10.3 | 7.2 | 4.1 | 1.5 | 0.5 |
| A-8 | 5.6 | 6.8 | 7.3 | 13.0 | 14.9 | 15.9 | 13.3 | 11.0 | 7.6 | 2.9 | 1.3 | 0.4 |
| A-9 | 5.6 | 7.1 | 7.8 | 12.6 | 15.1 | 15.6 | 13.9 | 9.9 | 7.1 | 3.4 | 1.5 | 0.5 |
| A-10 | 4.6 | 6.3 | 8.2 | 12.0 | 14.5 | 15.3 | 14.3 | 11.3 | 7.6 | 4.0 | 1.6 | 0.4 |
| A-11 | 4.1 | 8.1 | 6.5 | 11.8 | 15.0 | 15.5 | 13.8 | 11.6 | 8.9 | 3.0 | 1.4 | 0.3 |
| A-12 | 5.2 | 7.2 | 7.5 | 12.3 | 15.3 | 14.2 | 14.6 | 10.5 | 7.4 | 3.9 | 1.4 | 0.4 |
| A-13 | 6.2 | 8.2 | 7.1 | 13.4 | 15.5 | 15.2 | 12.8 | 10.5 | 6.1 | 3.3 | 1.2 | 0.4 |
| A-14 | 9.7 | 10.4 | 9.9 | 14.2 | 14.5 | 15.3 | 10.9 | 8.0 | 4.0 | 2.2 | 0.6 | 0.2 |
| A-15 | 7.5 | 8.8 | 9.3 | 13.0 | 14.8 | 15.6 | 11.9 | 9.0 | 5.5 | 3.0 | 1.2 | 0.4 |
| A-16 | 7.9 | 9.5 | 8.8 | 13.3 | 15.2 | 15.2 | 12.0 | 8.8 | 5.5 | 2.5 | 1.0 | 0.3 |
| A-17 | 20.8 | 13.5 | 13.0 | 16.6 | 13.3 | 9.8 | 7.1 | 3.3 | 1.6 | 0.7 | 0.2 | 0.2 |
| Eylea | 5.0 | 7.6 | 7.2 | 12.4 | 14.5 | 15.6 | 13.5 | 11.2 | 6.9 | 3.9 | 1.5 | 0.7 |

TABLE 14 icIEF results for Block A formulations after storage for two weeks at 25° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A-1 | 4.5 | 6.1 | 7.3 | 12.1 | 15.3 | 14.6 | 14.4 | 10.8 | 8.0 | 4.3 | 1.8 | 0.6 |
| A-2 | 4.7 | 6.1 | 7.9 | 10.9 | 14.9 | 15.0 | 14.3 | 11.3 | 8.1 | 4.3 | 1.9 | 0.7 |
| A-3 | 4.9 | 6.3 | 7.8 | 11.7 | 14.7 | 15.7 | 13.5 | 11.7 | 7.4 | 4.1 | 1.7 | 0.4 |
| A-4 | 5.0 | 6.2 | 7.3 | 12.6 | 14.3 | 14.6 | 15.2 | 10.7 | 8.3 | 3.4 | 1.8 | 0.6 |
| A-5 | 4.8 | 6.6 | 7.3 | 12.7 | 14.2 | 15.6 | 14.6 | 10.7 | 8.1 | 3.1 | 1.7 | 0.5 |
| A-6 | 4.7 | 6.4 | 7.1 | 12.0 | 15.8 | 14.3 | 14.8 | 10.7 | 8.1 | 4.1 | 1.5 | 0.5 |
| A-7 | 4.6 | 6.8 | 7.1 | 12.3 | 14.8 | 15.9 | 14.0 | 10.8 | 7.4 | 3.9 | 1.6 | 0.6 |
| A-8 | 4.8 | 6.7 | 7.6 | 12.8 | 13.9 | 15.7 | 14.2 | 11.6 | 7.7 | 3.1 | 1.4 | 0.5 |
| A-9 | 4.6 | 7.5 | 7.2 | 12.1 | 14.1 | 16.1 | 13.3 | 11.2 | 8.0 | 4.0 | 1.5 | 0.4 |
| A-10 | 5.1 | 7.6 | 7.5 | 12.9 | 13.9 | 16.4 | 13.5 | 10.5 | 7.1 | 3.7 | 1.2 | 0.5 |
| A-11 | 4.9 | 6.5 | 7.8 | 11.8 | 15.0 | 15.0 | 14.4 | 11.4 | 8.3 | 3.3 | 1.2 | 0.3 |
| A-12 | 4.5 | 5.8 | 7.9 | 12.9 | 14.2 | 15.9 | 13.0 | 11.4 | 8.2 | 4.2 | 1.7 | 0.4 |
| A-13 | 5.0 | 6.6 | 8.7 | 13.0 | 14.4 | 14.6 | 14.4 | 10.1 | 7.6 | 3.8 | 1.3 | 0.5 |
| A-14 | 6.3 | 8.7 | 7.6 | 12.7 | 14.7 | 14.6 | 13.8 | 10.2 | 6.5 | 3.5 | 1.1 | 0.3 |
| A-15 | 6.2 | 7.3 | 9.2 | 12.3 | 15.2 | 14.7 | 13.3 | 10.1 | 6.5 | 3.6 | 1.4 | 0.3 |

TABLE 14-continued icIEF results for Block A formulations after storage for two weeks at 25° C.

| Formulation | Rel. Area (%) Smoothing (Group) | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| A-16 | 6.3 | 7.6 | 7.6 | 13.2 | 14.6 | 15.0 | 13.4 | 10.5 | 6.7 | 3.5 | 1.3 | 0.4 |
| A-17 | 11.5 | 10.3 | 11.1 | 13.8 | 15.5 | 13.4 | 10.1 | 7.6 | 4.0 | 2.0 | 0.6 | 0.2 |
| Eylea | 4.7 | 6.4 | 7.8 | 12.2 | 14.2 | 15.2 | 14.2 | 10.8 | 7.8 | 4.4 | 1.7 | 0.6 |

TABLE 15 icIEF results for Block A formulations after storage for four weeks at 5° C.

| Formulation | Rel. Area (%) Smoothing (Group) | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| A-1 | 4.5 | 7.0 | 6.5 | 12.9 | 14.4 | 15.2 | 14.0 | 11.2 | 8.1 | 4.1 | 1.6 | 0.5 |
| A-2 | 5.0 | 7.8 | 6.0 | 12.1 | 14.9 | 15.0 | 14.1 | 10.8 | 8.0 | 4.1 | 1.6 | 0.6 |
| A-3 | 4.9 | 6.4 | 7.4 | 12.1 | 14.7 | 14.8 | 14.6 | 11.1 | 8.1 | 4.0 | 1.6 | 0.4 |
| A-4 | 5.1 | 6.7 | 7.4 | 12.5 | 14.3 | 15.0 | 14.3 | 11.4 | 8.0 | 3.2 | 1.6 | 0.4 |
| A-5 | 5.0 | 6.3 | 7.8 | 12.4 | 14.1 | 15.2 | 15.0 | 11.0 | 8.1 | 3.2 | 1.6 | 0.5 |
| A-6 | 4.9 | 6.4 | 7.3 | 12.0 | 14.4 | 16.2 | 13.5 | 11.2 | 7.8 | 4.2 | 1.6 | 0.5 |
| A-7 | 4.9 | 7.9 | 6.2 | 12.4 | 14.2 | 15.5 | 13.9 | 10.7 | 8.0 | 4.0 | 1.6 | 0.6 |
| A-8 | 5.0 | 6.2 | 7.4 | 12.6 | 14.8 | 15.0 | 14.7 | 11.2 | 8.2 | 3.0 | 1.3 | 0.5 |
| A-9 | 4.6 | 6.5 | 7.9 | 11.4 | 14.9 | 15.8 | 14.3 | 10.6 | 8.0 | 3.9 | 1.6 | 0.6 |
| A-10 | 5.2 | 6.6 | 8.0 | 12.3 | 14.1 | 15.7 | 13.9 | 10.8 | 7.4 | 4.0 | 1.4 | 0.4 |
| A-11 | 5.2 | 8.2 | 6.3 | 12.6 | 14.6 | 15.7 | 13.6 | 11.1 | 7.8 | 3.4 | 1.2 | 0.4 |
| A-12 | 4.8 | 7.4 | 6.6 | 12.3 | 15.2 | 14.4 | 14.1 | 11.8 | 7.2 | 4.3 | 1.5 | 0.4 |
| A-13 | 4.9 | 7.3 | 7.0 | 12.0 | 14.5 | 14.9 | 14.8 | 10.6 | 7.7 | 4.3 | 1.6 | 0.3 |
| A-14 | 5.2 | 7.7 | 7.1 | 12.3 | 14.6 | 15.8 | 13.2 | 11.1 | 7.1 | 4.0 | 1.4 | 0.4 |
| A-15 | 5.1 | 6.7 | 7.7 | 11.7 | 15.3 | 15.2 | 13.6 | 11.5 | 7.0 | 4.1 | 1.6 | 0.6 |
| A-16 | 6.3 | 7.6 | 7.6 | 13.2 | 14.6 | 15.0 | 13.4 | 10.5 | 6.7 | 3.5 | 1.3 | 0.4 |
| A-17 | 6.8 | 9.0 | 8.0 | 12.9 | 15.2 | 15.1 | 12.9 | 9.7 | 6.0 | 3.1 | 0.9 | 0.4 |
| Eylea | 4.7 | 6.3 | 7.8 | 11.7 | 14.6 | 14.7 | 14.6 | 11.0 | 8.1 | 4.3 | 1.6 | 0.6 |

Discussion

The aflibercept formulations of Block A are physically and chemically stable.

In addition to the formulations listed in Block A, an aflibercept formulation may have a succinate buffer or a tartrate buffer at a pH of 3.2-5.2 or 2.0-5.4, respectively. Thus, a stable formulation for aflibercept can include these buffers within the pH range. Further, an aflibercept formulation with a buffer may further include an excipient such as a stabilizer or a tonicity modifier. An exemplary aflibercept formulation includes a buffer, sucrose, sodium chloride, and a surfactant.

Example 3—Buffer-Free Aflibercept Formulations

This example describes experiments to evaluate aflibercept formulations that are buffer-free (Block B). The target pH ranged from 5.5 to 7.0 and different levels of co-solvents (e.g. surfactants or water-miscible nonaqueous solvents) were included. Table 16, below, shows an exemplary set of such formulations.

TABLE 16

| Form No. | aflibercept | pH | Sucrose (mM) | NaCl (mM) | PS 20 | PEG 3350 (%) |
|---|---|---|---|---|---|---|
| B-1 | 40 mg/ml | 5.5 | 200 | 40 | 0.03% | 0 |
| B-2 | 40 mg/ml | 5.5 | 270 | 0 | 0.03% | 0 |
| B-3 | 40 mg/ml | 6.0 | 200 | 40 | 0.03% | 0 |
| B-4 | 40 mg/ml | 6.0 | 270 | 0 | 0.03% | 0 |
| B-5 | 40 mg/ml | 6.2 | 200 | 40 | 0.03% | 0 |
| B-6 | 40 mg/ml | 6.2 | 0 | 150 | 0.03% | 0 |
| B-7 | 40 mg/ml | 6.2 | 270 | 0 | 0.03% | 0 |
| B-8 | 40 mg/ml | 6.2 | 150 | 75 | 0.03% | 0 |
| B-9 | 40 mg/ml | 6.5 | 200 | 40 | 0.03% | 0 |
| B-10 | 40 mg/ml | 6.5 | 270 | 0 | 0.03% | 0 |
| B-11 | 40 mg/ml | 7.0 | 200 | 40 | 0.03% | 0 |
| B-12 | 40 mg/ml | 7.0 | 270 | 0 | 0.03% | 0 |
| B-13 | 40 mg/ml | 6.2 | 200 | 40 | 0 | 1 |
| B-14 | 40 mg/ml | 6.2 | 200 | 40 | 0 | 5 |
| B-15 | 40 mg/ml | 6.2 | 200 | 40 | 0.03% | 1 |

Concentration, pH, and Osmolality

The aflibercept concentration (mg/mL), pH, and osmolality (mOSm) of the Block B formulations were evaluated at t0. Results are reported in Table 17 below.

TABLE 17

| Form | Final pH | Final Concentration (mg/mL) | Final Osmolality (mOsm/Kg) |
|---|---|---|---|
| B-1 | 5.53 | 41.33 | 290 |
| B-2 | 5.60 | 40.01 | 294 |
| B-3 | 6.09 | 39.43 | 290 |
| B-4 | 6.05 | 40.35 | 286 |
| B-5 | 6.17 | 40.02 | 293 |
| B-6 | 6.20 | 39.84 | 274 |
| B-7 | 6.21 | 40.13 | 300 |
| B-8 | 6.18 | 39.58 | 306 |
| B-9 | 6.45 | 39.39 | 290 |
| B-10 | 6.48 | 39.08 | 291 |

TABLE 17-continued

| Form | Final pH | Final Concentration (mg/mL) | Final Osmolality (mOsm/Kg) |
| --- | --- | --- | --- |
| B-11 | 6.98 | 39.51 | 288 |
| B-12 | 7.02 | 39.49 | 289 |
| B-13 | 6.21 | 40.08 | 289 |
| B-14 | 6.27 | 39.73 | 285 |
| B-15 | 6.19 | 40.15 | 295 |

Size Exclusion Chromatography

The stability of the Block B formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Table 18-21 below.

TABLE 18

SEC results for Block B formulations at T = 0

| Form | Rel. Area (%), Before Main Peak | Rel. Area (%), Main Peak | Rel. Area (%), After Main Peak |
| --- | --- | --- | --- |
| B-1 | 0.98 | 99.02 | 0 |
| B-2 | 0.99 | 99.01 | 0 |
| B-3 | 1.17 | 98.83 | 0 |
| B-4 | 1.14 | 98.86 | 0 |
| B-5 | 1.20 | 98.80 | 0 |
| B-6 | 1.17 | 98.83 | 0 |
| B-7 | 1.25 | 98.75 | 0 |
| B-8 | 1.20 | 98.80 | 0 |
| B-9 | 1.30 | 98.70 | 0 |
| B-10 | 1.29 | 98.71 | 0 |
| B-11 | 1.44 | 98.56 | 0 |
| B-12 | 1.51 | 98.49 | 0 |
| B-13 | 1.28 | 98.72 | 0 |
| B-14 | 1.27 | 98.73 | 0 |
| B-15 | 1.29 | 98.71 | 0 |

TABLE 19

SEC results for Block B formulations after one week at 40° C.

| Form | Rel. Area (%), Before Main Peak | Rel. Area (%), Main Peak | Rel. Area (%), After Main Peak |
| --- | --- | --- | --- |
| B-1 | 2.44 | 97.56 | 0 |
| B-2 | 1.44 | 98.56 | 0 |
| B-3 | 2.53 | 97.47 | 0 |
| B-4 | 2.03 | 97.97 | 0 |
| B-5 | 2.73 | 97.27 | 0 |
| B-6 | 4.26 | 95.74 | 0 |
| B-7 | 2.37 | 97.63 | 0 |
| B-8 | 2.99 | 97.01 | 0 |
| B-9 | 2.90 | 97.10 | 0 |
| B-10 | 3.05 | 96.95 | 0 |
| B-11 | 3.14 | 96.86 | 0 |
| B-12 | 3.35 | 96.65 | 0 |
| B-13 | 2.67 | 97.33 | 0 |
| B-14 | 2.72 | 97.28 | 0 |
| B-15 | 2.79 | 97.21 | 0 |

TABLE 20

SEC results for Block B formulations two weeks at 25° C.

| Form | Rel. Area (%), Before Main Peak | Rel. Area (%), Main Peak | Rel. Area (%), After Main Peak |
| --- | --- | --- | --- |
| B-1 | 1.28 | 98.72 | 0 |
| B-2 | 1.24 | 98.76 | 0 |
| B-3 | 1.61 | 98.39 | 0 |
| B-4 | 1.57 | 98.43 | 0 |
| B-5 | 1.70 | 98.30 | 0 |
| B-6 | 1.60 | 98.40 | 0 |
| B-7 | 1.76 | 98.24 | 0 |
| B-8 | 1.64 | 98.36 | 0 |
| B-9 | 1.84 | 98.16 | 0 |
| B-10 | 1.90 | 98.10 | 0 |
| B-11 | 2.18 | 97.82 | 0 |
| B-12 | 2.39 | 97.61 | 0 |
| B-13 | 1.69 | 98.31 | 0 |
| B-14 | 1.75 | 98.25 | 0 |
| B-15 | 1.74 | 98.26 | 0 |

TABLE 21

SEC results for Block B formulations after four weeks at 5° C.

| Form | Rel. Area (%), Before Main Peak | Rel. Area (%), Main Peak | Rel. Area (%), After Main Peak |
| --- | --- | --- | --- |
| B-1 | 1.40 | 98.60 | 0.00 |
| B-2 | 1.33 | 98.62 | 0.10 |
| B-3 | 1.65 | 98.35 | 0.00 |
| B-4 | 1.60 | 98.40 | 0.00 |
| B-5 | 1.70 | 98.30 | 0.00 |
| B-6 | 1.58 | 98.42 | 0.00 |
| B-7 | 1.70 | 98.30 | 0.00 |
| B-8 | 1.61 | 98.39 | 0.00 |
| B-9 | 1.81 | 98.19 | 0.00 |
| B-10 | 1.81 | 98.19 | 0.00 |
| B-11 | 2.07 | 97.93 | 0.00 |
| B-12 | 2.17 | 97.83 | 0.00 |
| B-13 | 1.61 | 98.39 | 0.00 |
| B-14 | 1.65 | 98.35 | 0.00 |
| B-15 | 1.66 | 98.34 | 0.00 |

The initial monomer contents were 98-99%. After storage for one week at 40° C., monomer contents decreased to about 97%, with small differences being apparent. The losses were entirely due to aggregation and not due to fragmentation, again emphasizing the nature of the primary degradation pathway.

After two weeks at 25° C., the monomer contents were mostly near 98%. The two nominal pH 7 formulations showed the lowest levels of monomer. For samples stored at 5° C. for four weeks, the losses were similar to those seen after two weeks at 25° C.

Micro-Flow Imaging

The stability of the Block B formulations was evaluated by measuring the particles present in the formulation after being subjected to storage conditions. Block B samples, along with those in Block C were shipped on blue ice. This means that they were exposed to interfacial stress during the shipping process. While Block B formulation do not contain a buffer, all of the formulations contain some co-solvent, usually a surfactant, which appears to have provided some level of protection. A couple formulations (e.g., B-10 and B-14) did display elevated levels of SVPs, likely due to shipping stress. Results are reported in Table 22-25 below.

TABLE 22

MFI results for Block B formulations at T = 0

Size Range Summary

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| B-1 | 13434 | 5163 | 1632 | 511 | 122 |
| B-2 | 7983 | 2798 | 910 | 400 | 133 |
| B-3 | 6651 | 1732 | 533 | 233 | 56 |
| B-4 | 17321 | 4597 | 1166 | 444 | 122 |
| B-5 | 7883 | 2043 | 400 | 211 | 44 |
| B-6 | 14301 | 3653 | 922 | 300 | 111 |
| B-7 | 14067 | 3309 | 644 | 222 | 67 |
| B-8 (1) | 10947 | 2798 | 766 | 244 | 67 |
| B-9 | 49907 | 8860 | 1610 | 522 | 200 |
| B-10 (2) | 87657 | 24360 | 12335 | 7494 | 2720 |
| B-11 | 4497 | 1499 | 155 | 67 | 22 |
| B-12 (3) | 30784 | 6748 | 1083 | 319 | 92 |
| B-13 | 75726 | 21990 | 5235 | 967 | 189 |
| B-14 (4) | 49819 | 13645 | 3664 | 966 | 89 |
| B-15 | 10951 | 3104 | 635 | 247 | 71 |

Note:
(1) Schlieren Line
(2) transparent particles, more particles - Possible Contamination
(3) Time stamp Applied
(4) High count - possible contamination
n.a.—not applicable

TABLE 23

MFI results for Block B formulations stored for one week at 40° C.

Dilution Factor Adjusted-Size Range Summary

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| B-1 | 14634 | 3497 | 744 | 300 | 22 |
| B-2 | 4630 | 888 | 67 | 44 | 11 |
| B-3 | 4308 | 977 | 67 | 33 | 0 |
| B-4 | 5452 | 1632 | 278 | 100 | 11 |
| B-5 | 4919 | 1510 | 444 | 266 | 33 |
| B-6 | 5829 | 1332 | 300 | 167 | 67 |
| B-7 | 10692 | 2820 | 300 | 67 | 22 |
| B-8 (1) | 13835 | 3829 | 1078 | 289 | 58 |
| B-9 | 6273 | 1588 | 378 | 167 | 56 |
| B-10 (2) | 251569 | 97095 | 58090 | 37283 | 13879 |
| B-11 | 2987 | 1121 | 311 | 122 | 11 |
| B-12 (3) | 18208 | 3900 | 857 | 307 | 77 |
| B-13 | 7672 | 1310 | 167 | 44 | 11 |
| B-14 | 9293 | 1643 | 244 | 78 | 22 |
| B-15 | 12113 | 2365 | 555 | 233 | 78 |

Note:
(1) Schlieren Line/Time Stamp Applied
(2) transparent particles, more particles
(3) Stop run at 86%

TABLE 24

MFI results for Block B formulations stored for two weeks at 25° C.

Size Range Summary

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| B-1 | 3464 | 1543 | 611 | 189 | 44 |
| B-2 | 2554 | 888 | 255 | 100 | 22 |
| B-3 | 4008 | 1743 | 711 | 167 | 22 |

TABLE 24-continued

MFI results for Block B formulations stored for two weeks at 25° C.

Size Range Summary

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| B-4 | 2987 | 1010 | 189 | 33 | 0 |
| B-5 | 4796 | 1743 | 466 | 89 | 11 |
| B-6 | 5429 | 1343 | 266 | 78 | 0 |
| B-7 | 3298 | 999 | 378 | 111 | 22 |
| B-8 (1) | 4408 | 2487 | 1055 | 333 | 122 |
| B-9 | 5962 | 2942 | 844 | 200 | 33 |
| B-10 (2) | 430614 | 121876 | 33875 | 15056 | 3275 |
| B-11 | 33087 | 5207 | 1166 | 289 | 56 |
| B-12 (3) | 16483 | 4698 | 1486 | 292 | 27 |
| B-13 | 4330 | 1510 | 466 | 100 | 22 |
| B-14 (4) | 503405 | 269467 | 99848 | 30899 | 4152 |
| B-15 | 3275 | 1088 | 511 | 100 | 33 |

Note:
(1) Schlieren Line
(2) transparent particles, more particles
(3) Time stamp Applied
(4) High Count - Possible contamination

TABLE 25

MFI results for Block B formulations stored for four weeks at 5° C.

Size Range Summary

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| B-1 | 1536 | 8527 | 2654 | 544 | 289 |
| B-2 | 1124 | 6240 | 2420 | 611 | 244 |
| B-3 | 484 | 2687 | 877 | 366 | 167 |
| B-4 | 1404 | 16865 | 5452 | 355 | 111 |
| B-5 | 1404 | 7794 | 1743 | 533 | 167 |
| B-6 | 928 | 5152 | 1232 | 289 | 100 |
| B-7 | 558 | 3098 | 1055 | 289 | 111 |
| B-8 (1) | 1276 | 7084 | 1543 | 311 | 111 |
| B-9 | 1608 | 8927 | 1255 | 289 | 111 |
| B-10 (2) | 27694 | 153742 | 72491 | 55792 | 14500 |
| B-11 | 862 | 4785 | 1310 | 433 | 111 |
| B-12 (3) | 3410 | 26236 | 6448 | 1493 | 539 |
| B-13 | 7666 | 87410 | 22554 | 6408 | 2144 |
| B-14 (4) | 4684 | 26003 | 3875 | 555 | 133 |
| B-15 | 830 | 4608 | 1155 | 266 | 89 |

Note:
(1) Schlieren lines observed
(2) Stop run at 86%
(3) Time stamp Applied
(4) Stop run at 60%

Imaging Capillary Isoelectric Focusing (icIEF)

The chemical stability of the Block B formulations was evaluated by measuring the charge variants present in the formulation after being subjected to storage conditions. Results are reported in Table 26-29 below.

TABLE 26

| icIEF results for Block B formulations at T = 0 | | | | | | | | | | | | |
|---|---|---|---|---|---|---|---|---|---|---|---|---|
| Formulation | Rel. Area (%) Smoothing (Group) | | | | | | | | | | | |
| Block | 1 | 2 | 3 | 4 | 5 | 6 | 7 | 8 | 9 | 10 | 11 | 12 |
| B-1 | 4.7 | 5.9 | 7.7 | 11.4 | 14.3 | 14.8 | 14.1 | 11.2 | 8.6 | 4.8 | 2.1 | 0.6 |
| B-2 | 4.2 | 6.4 | 6.9 | 12.0 | 14.4 | 14.7 | 14.8 | 12.1 | 7.7 | 4.5 | 1.8 | 0.5 |
| B-3 | 4.1 | 6.2 | 7.2 | 12.1 | 14.3 | 14.9 | 14.4 | 11.5 | 8.0 | 4.6 | 2.0 | 0.5 |
| B-4 | 4.5 | 6.4 | 7.1 | 11.7 | 14.2 | 14.9 | 14.7 | 11.7 | 7.6 | 4.6 | 1.8 | 0.7 |
| B-5 | 4.1 | 6.6 | 6.8 | 11.4 | 14.6 | 15.4 | 13.6 | 12.7 | 7.8 | 4.6 | 1.9 | 0.6 |
| B-6 | 4.2 | 6.7 | 6.7 | 11.8 | 14.7 | 15.3 | 14.1 | 11.6 | 8.2 | 4.4 | 1.8 | 0.5 |
| B-7 | 4.5 | 6.4 | 7.0 | 11.3 | 15.3 | 15.0 | 14.3 | 12.0 | 7.8 | 4.3 | 1.6 | 0.4 |
| B-8 | 4.3 | 6.7 | 6.7 | 11.7 | 14.8 | 15.0 | 14.2 | 11.7 | 7.9 | 4.5 | 1.9 | 0.6 |
| B-9 | 3.9 | 6.2 | 6.6 | 12.1 | 14.4 | 15.6 | 14.1 | 11.8 | 8.1 | 4.6 | 1.9 | 0.5 |
| B-10 | 4.2 | 6.3 | 6.8 | 12.4 | 14.0 | 15.1 | 14.9 | 12.4 | 7.8 | 4.3 | 1.5 | 0.3 |
| B-11 | 5.0 | 5.9 | 7.9 | 11.6 | 14.5 | 14.8 | 13.7 | 12.1 | 7.7 | 4.6 | 1.8 | 0.5 |
| B-12 | 4.7 | 6.1 | 7.5 | 12.1 | 14.6 | 15.8 | 13.3 | 12.3 | 7.7 | 4.5 | 1.2 | 0.2 |
| B-13 | 4.3 | 6.0 | 7.4 | 11.1 | 14.8 | 14.7 | 14.5 | 12.1 | 8.0 | 4.6 | 1.9 | 0.6 |
| B-14 | 4.4 | 6.4 | 7.1 | 11.2 | 14.8 | 14.8 | 14.3 | 11.8 | 8.1 | 4.7 | 1.9 | 0.6 |
| B-15 | 4.4 | 6.3 | 7.2 | 11.9 | 13.6 | 15.5 | 14.4 | 11.8 | 8.0 | 4.5 | 1.8 | 0.7 |

TABLE 27

| icIEF results for Block B formulations after storage for one week at 40° C. | | | | | | | | | | | | |
|---|---|---|---|---|---|---|---|---|---|---|---|---|
| Formulation | Rel. Area (%) Smoothing (Group) | | | | | | | | | | | |
| Block | 1 | 2 | 3 | 4 | 5 | 6 | 7 | 8 | 9 | 10 | 11 | 12 |
| B-1 | 4.0 | 5.9 | 6.9 | 11.7 | 14.3 | 15.5 | 13.3 | 11.8 | 8.7 | 4.9 | 2.3 | 0.8 |
| B-2 | 4.5 | 6.3 | 7.1 | 12.4 | 13.9 | 15.3 | 14.1 | 11.9 | 7.3 | 4.6 | 1.9 | 0.6 |
| B-3 | 4.5 | 6.5 | 7.5 | 11.2 | 14.7 | 14.9 | 14.2 | 12.2 | 7.4 | 4.5 | 1.9 | 0.5 |
| B-4 | 4.8 | 6.8 | 7.2 | 12.5 | 15.1 | 15.1 | 13.4 | 11.6 | 7.2 | 4.2 | 1.6 | 0.5 |
| B-5 | 4.9 | 6.4 | 6.8 | 12.6 | 14.0 | 15.7 | 14.2 | 11.0 | 7.5 | 4.4 | 1.9 | 0.5 |
| B-6 | 4.5 | 6.7 | 7.1 | 11.9 | 14.9 | 15.3 | 13.6 | 11.6 | 7.6 | 4.2 | 1.9 | 0.7 |
| B-7 | 5.1 | 6.7 | 7.9 | 11.8 | 14.6 | 15.2 | 14.4 | 10.9 | 7.0 | 4.2 | 1.7 | 0.5 |
| B-8 | 4.3 | 8.0 | 6.1 | 11.6 | 14.5 | 15.5 | 14.7 | 11.9 | 7.0 | 4.4 | 1.6 | 0.3 |
| B-9 | 4.7 | 6.8 | 7.3 | 11.7 | 14.5 | 15.2 | 13.3 | 11.8 | 7.3 | 4.5 | 2.1 | 0.7 |
| B-10 | 5.5 | 7.2 | 7.7 | 11.9 | 15.3 | 16.0 | 13.1 | 11.3 | 6.5 | 3.8 | 1.4 | 0.3 |
| B-11 | 5.5 | 7.3 | 7.4 | 12.7 | 15.0 | 15.8 | 13.4 | 10.9 | 6.5 | 3.9 | 1.3 | 0.3 |
| B-12 | 6.0 | 7.9 | 7.7 | 13.7 | 14.4 | 15.3 | 13.7 | 10.5 | 6.2 | 3.4 | 1.1 | 0.2 |
| B-13 | 4.5 | 6.5 | 7.5 | 12.0 | 14.4 | 15.0 | 14.2 | 11.7 | 7.6 | 4.3 | 1.8 | 0.5 |
| B-14 | 4.8 | 6.5 | 7.3 | 12.2 | 14.9 | 14.2 | 14.4 | 11.4 | 7.7 | 4.2 | 1.8 | 0.5 |
| B-15 | 4.7 | 6.7 | 6.8 | 12.0 | 14.7 | 15.4 | 13.8 | 11.7 | 7.4 | 4.4 | 1.8 | 0.6 |

TABLE 28

| icIEF results for Block B formulations after storage for two weeks at 25° C. | | | | | | | | | | | | |
|---|---|---|---|---|---|---|---|---|---|---|---|---|
| Formulation | Rel. Area (%) Smoothing (Group) | | | | | | | | | | | |
| Block | 1 | 2 | 3 | 4 | 5 | 6 | 7 | 8 | 9 | 10 | 11 | 12 |
| B-1 | 4.4 | 6.0 | 7.3 | 11.7 | 14.3 | 15.2 | 13.9 | 11.4 | 8.8 | 4.6 | 2.0 | 0.5 |
| B-2 | 4.3 | 6.4 | 7.4 | 12.4 | 13.8 | 14.7 | 14.1 | 12.2 | 7.9 | 4.6 | 1.9 | 0.5 |
| B-3 | 4.4 | 6.3 | 7.1 | 11.7 | 14.1 | 15.2 | 14.2 | 12.2 | 7.9 | 4.5 | 2.0 | 0.6 |
| B-4 | 4.1 | 6.6 | 7.2 | 11.9 | 14.5 | 15.2 | 14.4 | 12.2 | 7.4 | 4.3 | 1.7 | 0.5 |
| B-5 | 4.9 | 6.3 | 6.8 | 12.3 | 13.8 | 14.7 | 14.5 | 11.8 | 7.6 | 4.7 | 1.9 | 0.6 |
| B-6 | 4.2 | 6.1 | 7.5 | 11.8 | 14.2 | 16.0 | 13.5 | 11.9 | 8.2 | 4.3 | 1.8 | 0.5 |
| B-7 | 4.7 | 6.4 | 7.1 | 12.5 | 14.3 | 15.2 | 14.7 | 11.4 | 7.6 | 4.3 | 1.6 | 0.4 |
| B-8 | 4.8 | 6.2 | 7.6 | 11.7 | 14.0 | 15.0 | 13.7 | 11.4 | 8.3 | 4.6 | 2.0 | 0.7 |
| B-9 | 4.7 | 6.4 | 7.8 | 11.0 | 14.2 | 14.7 | 13.6 | 11.7 | 8.1 | 4.8 | 2.2 | 0.7 |
| B-10 | 4.1 | 6.2 | 6.9 | 12.1 | 14.8 | 15.0 | 14.7 | 11.9 | 7.9 | 4.4 | 1.6 | 0.3 |
| B-11 | 4.8 | 6.1 | 8.1 | 12.4 | 13.5 | 14.8 | 14.2 | 12.4 | 7.3 | 4.3 | 1.7 | 0.5 |
| B-12 | 4.8 | 6.7 | 7.9 | 11.9 | 15.1 | 14.3 | 14.5 | 11.9 | 7.2 | 4.0 | 1.4 | 0.3 |
| B-13 | 4.4 | 6.5 | 7.4 | 11.4 | 14.2 | 15.1 | 14.3 | 11.7 | 7.9 | 4.6 | 1.9 | 0.6 |
| B-14 | 3.8 | 6.8 | 7.0 | 12.2 | 14.1 | 14.8 | 15.2 | 11.5 | 7.9 | 4.5 | 1.8 | 0.4 |
| B-15 | 4.6 | 6.8 | 7.0 | 11.8 | 14.6 | 15.5 | 13.7 | 12.0 | 7.7 | 4.3 | 1.6 | 0.4 |

TABLE 29 icIEF results for Block B formulations after storage for four weeks at 5° C.

| Formulation | Rel. Area (%) Smoothing (Group) | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| B-1 | 4.6 | 5.9 | 7.1 | 11.6 | 14.6 | 15.2 | 13.6 | 12.4 | 7.8 | 4.6 | 2.0 | 0.6 |
| B-2 | 4.2 | 6.1 | 7.2 | 12.2 | 14.2 | 15.3 | 15.1 | 11.3 | 7.6 | 4.5 | 1.8 | 0.4 |
| B-3 | 4.2 | 6.2 | 6.7 | 12.3 | 14.0 | 15.1 | 14.5 | 11.7 | 8.3 | 4.5 | 2.0 | 0.5 |
| B-4 | 4.4 | 6.4 | 7.5 | 11.7 | 14.1 | 15.2 | 14.8 | 11.8 | 7.8 | 4.3 | 1.7 | 0.4 |
| B-5 | 4.2 | 6.2 | 7.1 | 11.7 | 14.7 | 15.4 | 13.9 | 12.3 | 7.8 | 4.5 | 1.8 | 0.4 |
| B-6 | 4.6 | 6.2 | 7.4 | 12.1 | 13.7 | 15.2 | 14.6 | 11.9 | 7.8 | 4.2 | 1.8 | 0.5 |
| B-7 | 4.6 | 6.4 | 6.7 | 12.1 | 14.4 | 14.9 | 14.8 | 11.9 | 8.0 | 4.0 | 1.7 | 0.5 |
| B-8 | 4.3 | 6.1 | 6.9 | 12.1 | 14.0 | 14.7 | 14.5 | 11.8 | 8.2 | 4.5 | 2.1 | 0.7 |
| B-9 | 4.6 | 6.1 | 7.3 | 11.9 | 13.9 | 14.7 | 15.0 | 11.4 | 8.1 | 4.6 | 1.9 | 0.5 |
| B-10 | 4.5 | 7.2 | 6.9 | 12.0 | 14.7 | 15.0 | 14.5 | 11.7 | 7.4 | 4.2 | 1.4 | 0.6 |
| B-11 | 4.2 | 6.1 | 6.8 | 11.9 | 14.6 | 15.8 | 14.3 | 11.7 | 7.8 | 4.4 | 1.8 | 0.5 |
| B-12 | 4.3 | 6.8 | 6.9 | 11.8 | 14.6 | 15.4 | 15.1 | 11.5 | 7.8 | 4.2 | 1.3 | 0.2 |
| B-13 | 4.5 | 6.5 | 7.1 | 11.3 | 14.6 | 15.0 | 14.2 | 11.6 | 8.3 | 4.6 | 1.8 | 0.4 |
| B-14 | 4.7 | 6.4 | 7.4 | 11.4 | 14.2 | 15.4 | 14.0 | 11.9 | 7.9 | 4.4 | 1.8 | 0.4 |
| B-15 | 4.4 | 6.0 | 7.5 | 11.5 | 14.5 | 14.8 | 14.8 | 12.1 | 8.0 | 4.4 | 1.6 | 0.4 |

Discussion

The aflibercept formulations of Block B are physically and chemically stable.

In addition to the formulations listed in Block B, an aflibercept formulation may include additional excipients, including but not limited to, sorbitol and/or mannitol.

Example 4—Aflibercept Formulations Free of Organic Co-Solvents

This example describes experiments to evaluate aflibercept formulations that are free of an organic co-solvent (Block C). The design of Block C centered on removing the co-solvents (e.g., PS 20, PEG 3350) used in Block B, while using buffers, such as acetate, histidine (His), and phosphate across the same pH range of 5.5 to 7.0. Table 30, below, shows an exemplary set of such formulations.

TABLE 30

| Form No. | aflibercept | pH | Sucrose (mM) | NaCl (mM) | Buffer |
|---|---|---|---|---|---|
| C-1 | 40 mg/ml | 5.5 | 200 | 40 | 10 mM acetate |
| C-2 | 40 mg/ml | 5.5 | 270 | 0 | 10 mM acetate |
| C-3 | 40 mg/ml | 6.0 | 200 | 40 | 10 mM His |
| C-4 | 40 mg/ml | 6.0 | 270 | 0 | 10 mM His |
| C-5 | 40 mg/ml | 6.2 | 200 | 40 | 10 mM His |
| C-6 | 40 mg/ml | 6.2 | 0 | 150 | 10 mM His |
| C-7 | 40 mg/ml | 6.2 | 270 | 0 | 10 mM His |
| C-8 | 40 mg/ml | 6.2 | 150 | 75 | 10 mM His |
| C-9 | 40 mg/ml | 6.5 | 200 | 40 | 10 mM His |
| C-10 | 40 mg/ml | 6.5 | 270 | 0 | 10 mM His |
| C-11 | 40 mg/ml | 7.0 | 200 | 40 | 10 mM phosphate |
| C-12 | 40 mg/ml | 7.0 | 270 | 0 | 10 mM phosphate |
| C-13 | 40 mg/ml | 6.2 | 200 | 40 | 10 mM phosphate |
| C-14 | 40 mg/ml | 6.5 | 200 | 40 | 10 mM phosphate |
| C-15 | 40 mg/ml | 6.5 | 150 | 75 | 10 mM His |

Concentration, pH, and Osmolality

The aflibercept concentration (mg/mL), pH, and osmolality (mOSm) of the Block C formulations were evaluated at t0. Results are reported in Table 31 below.

TABLE 31

| Form No. | Final mOsm | Final pH | Final mg/mL |
|---|---|---|---|
| C-1 | 306 | 5.5 | 38.74 |
| C-2 | 319 | 5.5 | 39.74 |

TABLE 31-continued

| Form No. | Final mOsm | Final pH | Final mg/mL |
|---|---|---|---|
| C-3 | 304 | 6.0 | 39.54 |
| C-4 | 314 | 6.0 | 39.62 |
| C-5 | 305 | 6.1 | 39.61 |
| C-6 | 292 | 6.2 | 39.69 |
| C-7 | 307 | 6.1 | 40.07 |
| C-8 | 321 | 6.1 | 39.88 |
| C-9 | 306 | 6.5 | 40.24 |
| C-10 | 340 | 6.4 | 39.31 |
| C-11 | 319 | 6.9 | 39.29 |
| C-12 | 317 | 7.0 | 40.04 |
| C-13 | 312 | 6.2 | 39.44 |
| C-14 | 323 | 6.5 | 39.21 |
| C-15 | 316 | 6.5 | 40.80 |

Size Exclusion Chromatography

The stability of the Block C formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Tables 32-35 below.

TABLE 32

SEC results for Block C formulations at T = 0

| Form No. | Rel. Area (%), Before Main Peak | Rel. Area (%), Main Peak | Rel. Area (%), After Main Peak |
|---|---|---|---|
| C-1 | 1.56 | 98.44 | 0 |
| C-2 | 1.56 | 98.44 | 0 |
| C-3 | 1.54 | 98.46 | 0 |
| C-4 | 1.56 | 98.44 | 0 |
| C-5 | 1.58 | 98.42 | 0 |
| C-6 | 1.55 | 98.45 | 0 |
| C-7 | 1.63 | 98.37 | 0 |
| C-8 | 1.55 | 98.45 | 0 |
| C-9 | 1.69 | 98.31 | 0 |
| C-10 | 1.80 | 98.20 | 0 |
| C-11 | 2.09 | 97.91 | 0 |
| C-12 | 2.20 | 97.80 | 0 |
| C-13 | 1.62 | 98.38 | 0 |
| C-14 | 1.73 | 98.27 | 0 |
| C-15 | n.a | n.a | 0 |

TABLE 33

SEC results for Block C formulations after one week at 40° C.

| Form No. | aflibercept | Rel. Area (%), Before Main Peak | Rel. Area (%), Main Peak | Rel. Area (%), After Main Peak |
|---|---|---|---|---|
| C-1 | 40 | 2.66 | 97.34 | 0 |
| C-2 | 40 | 1.75 | 98.25 | 0 |
| C-3 | 40 | 2.89 | 97.11 | 0 |
| C-4 | 40 | 1.90 | 98.10 | 0 |
| C-5 | 40 | 2.46 | 97.54 | 0 |
| C-6 | 40 | 4.09 | 95.91 | 0 |
| C-7 | 40 | 2.16 | 97.84 | 0 |
| C-8 | 40 | 2.83 | 97.17 | 0 |
| C-9 | 40 | 2.69 | 97.31 | 0 |
| C-10 | 40 | 2.48 | 97.52 | 0 |
| C-11 | 40 | 3.36 | 96.64 | 0 |
| C-12 | 40 | 3.49 | 96.51 | 0 |
| C-13 | 40 | 2.73 | 97.27 | 0 |
| C-14 | 40 | 2.90 | 97.10 | 0 |
| C-15 | 40 | 2.79 | 97.21 | 0 |

TABLE 34

SEC results for Block C formulations two weeks at 25° C.

| Form No. | Rel. Area (%), Before Main Peak | Rel. Area (%), Main Peak | Rel. Area (%), After Main Peak |
|---|---|---|---|
| C-1 | 1.51 | 98.49 | 0 |
| C-2 | 1.45 | 98.55 | 0 |
| C-3 | 1.80 | 98.20 | 0 |
| C-4 | 1.56 | 98.44 | 0 |
| C-5 | 1.60 | 98.40 | 0 |
| C-6 | 1.59 | 98.41 | 0 |
| C-7 | 1.67 | 98.33 | 0 |
| C-8 | 1.63 | 98.37 | 0 |
| C-9 | 1.83 | 98.17 | 0 |
| C-10 | 1.94 | 98.06 | 0 |
| C-11 | 2.29 | 97.71 | 0 |
| C-12 | 2.53 | 97.47 | 0 |
| C-13 | 1.73 | 98.27 | 0 |
| C-14 | 1.91 | 98.09 | 0 |
| C-15 | 1.64 | 98.36 | 0 |

TABLE 35

SEC results for Block C formulations after four weeks at 5° C.

| Form No. | Rel. Area (%), Before Main Peak | Rel. Area (%), Main Peak | Rel. Area (%), After Main Peak |
|---|---|---|---|
| C-1 | 1.17 | 98.83 | 1.17 |
| C-2 | 1.19 | 98.81 | 1.19 |
| C-3 | 1.18 | 98.82 | 1.18 |
| C-4 | 1.19 | 98.78 | 1.19 |
| C-5 | 1.24 | 98.76 | 1.24 |
| C-6 | 1.20 | 98.80 | 1.20 |
| C-7 | 1.27 | 98.73 | 1.27 |
| C-8 | 1.20 | 98.80 | 1.20 |
| C-9 | 1.32 | 98.68 | 1.32 |
| C-10 | 1.39 | 98.61 | 1.39 |
| C-11 | 1.66 | 98.34 | 1.66 |
| C-12 | 1.78 | 98.22 | 1.78 |
| C-13 | 1.27 | 98.73 | 1.27 |
| C-14 | 1.36 | 98.64 | 1.36 |
| C-15 | 1.24 | 98.76 | 1.24 |

At T=0, comparable monomer contents were observed for all formulations, but the T=0 sample for C-15 was lost.

After one week at 40° C., for all but one formulation (C-6, which does not contain a sugar) the monomer contents only decreased to 97-98%, suggesting that sucrose was a potent stabilizer even in the absence of co-solvents across the entire pH range. Similar behavior was seen for the T=2 weeks/25° C. samples, with the pH 7 formulations showing the largest decrease in monomer content.

After four weeks at 5° C., there was little loss in monomer by SEC across nearly all of the formulations. However, in these samples, this is the first time that some measurable amount of fragmentation was observed. This may be due to the quality of the SEC columns, which were found to degrade relatively quickly with these multiple formulations of aflibercept, suggesting that it was mostly due to the inherent properties of the protein.

Micro-Flow Imaging

The stability of the Block C formulations was evaluated by measuring the particles present in the formulation after being subjected to storage conditions. A number of the Block C samples were damaged due to shipping at a refrigerated temperature (5° C.), as they lacked co-solvents (especially surfactants). Most likely, the interfacial stress of agitation with a head space on blue ice led to the dramatic increases in particle counts, especially for formulations C-3 through C-10. Interestingly, there was almost no damage at the pH extremes of 5.5 (formulations C-1 and C-2) and pH 7.0 (formulations C-11 and C-12). It is quite possible that the colloidal stability is improved at these pH conditions, thereby modulating interfacial stress. Results are reported in Table 36-39 below.

TABLE 36

MFI results for Block C formulations at T = 0

| Form. Block | Total Particle Conc. (#/mL) | Size Range Summary | | | |
|---|---|---|---|---|---|
| | | ≥2 µm (#/mL) | ≥5 µm (#/mL) | ≥10 µm (#/mL) | ≥25 µm (#/mL) |
| C-1 | 21995 | 4885 | 955 | 167 | 22 |
| C-2 | 5063 | 966 | 200 | 67 | 11 |
| C-3 (1) | 184529 | 461658 | 115836 | 29001 | 577 |
| C-4 (2) | 36273682 | 5377199 | 378001 | 22561 | 1685 |
| C-5 (3) | 6020581 | 64974 | 1088 | 144 | 33 |
| C-6 (4) | 5726455 | 364452 | 90488 | 15988 | 100 |
| C-7 (5) | 26768962 | 2112561 | 191018 | 29894 | 108 |
| C-8 (6) | 13621858 | 1081903 | 94325 | 16641 | 2858 |
| C-9 (7) | 10419121 | 292683 | 27457 | 8038 | 922 |
| C-10 (8) | 19074213 | 1031283 | 87381 | 30876 | 4537 |
| C-11 | 39193 | 9582 | 1776 | 344 | 22 |
| C-12 | 11158 | 3131 | 866 | 222 | 11 |
| C-13 (9) | 200718 | 30400 | 4519 | 755 | 78 |
| C-14 (10) | 8569481 | 301254 | 6995 | 577 | 56 |
| C-15 | 42002 | 9782 | 1665 | 222 | 33 |

Note:
(1) Possible Contamination- High Particle Count (Semi transparent irreg. particles)
(2) Possible Contamination- ≥1,000,000 Particle Count (Semi transparent irreg. particles) - MFI stop counting at 29% completion due max counting limit reached (3)
(3) Possible Contamination- ≥1,000,000 Particle Count (Semi transparent irreg. particles) - MFI stop counting at 68% completion due max counting limit reached
(4) Possible Contamination- High Particle Count (Semi transparent irreg. particles)
(5) Possible Contamination- ≥1,000,000 Particle Count (Semi transparent irreg. particles) - MFI stop counting at 29% completion due max counting limit reached
(6) Possible Contamination- ≥1,000,000 Particle Count (Semi transparent irreg. particles) - MFI stop counting at 80% completion due max counting limit reached
(7) Possible Contamination- High Particle Count (Semi transparent irreg. particles) // Schlieren Line-at bottom throughout analysis
(8) Possible Contamination- ≥1,000,000 Particle Count (Semi transparent irreg. particles) - MFI stop counting at 56% completion due max counting limit reached
(9) Possible Contamination- High Particle Count (Semi transparent irreg. particles)
(10) Possible Contamination- High Particle Count (Semi transparent irreg. particles)
n.a.—not applicable

TABLE 37

MFI results for Block C formulations stored for one week at 40° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| C-1 | 2409 | 344 | 67 | 11 | 11 |
| C-2 | 3475 | 533 | 144 | 56 | 11 |
| C-3 (1) | 496177 | 185629 | 64985 | 21939 | 2976 |
| C-4 (2) | 20225234 | 1523140 | 119167 | 15821 | 306 |
| C-5 (3) | 18346696 | 1676160 | 172210 | 33947 | 2938 |
| C-6 | 8827 | 1765 | 366 | 89 | 0 |
| C-7 (4) | 21202350 | 1170533 | 77651 | 17875 | 577 |
| C-8 (5) | 5051178 | 49086 | 4652 | 966 | 89 |
| C-9 (6) | 3650028 | 59800 | 7927 | 1321 | 122 |
| C-10 (7) | 17741780 | 779954 | 37039 | 11471 | 1501 |
| C-11 | 3930 | 1510 | 500 | 144 | 33 |
| C-12 | 92753 | 37816 | 10459 | 1876 | 33 |
| C-13 | 34252 | 10459 | 2531 | 455 | 33 |
| C-14 | 14489 | 4397 | 1210 | 122 | 11 |
| C-15 (8) | 6845370 | 81928 | 5107 | 855 | 22 |

Note:
(1) Possible Contamination- High Particle Count (Semi transparent irreg. particles)
(2) Possible Contamination- ≥1,000,000 Particle Count (Semi transparent irreg. particles) - MFI stop counting at 68% completion due max counting limit reached
(3) Possible Contamination- High Particle Count (Semi transparent irreg. particles
(4) Possible Contamination- ≥1,000,000 Particle Count (Semi transparent irreg. particles) - MFI stop counting at 54% completion due max counting limit reached
(5) Possible Contamination- High Particle Count (Semi transparent irreg. particles)
(6) Possible Contamination- High Particle Count (Semi transparent irreg. particles)
(7) Possible Contamination- ≥1,000,000 Particle Count (Semi transparent irreg. particles) - MFI stop counting at 61% completion due max counting limit reached
(8) Possible Contamination- High Particle Count (Semi transparent irreg. particles)

TABLE 38

MFI results for Block C formulations stored for two weeks at 25° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| C-1 | 3964 | 1310 | 311 | 78 | 11 |
| C-2 | 9771 | 2054 | 278 | 33 | 11 |
| C-3 (1) | 4429228 | 847128 | 156240 | 38238 | 3009 |
| C-4 (2) | 15339196 | 710974 | 93158 | 24591 | 896 |
| C-5 (3) | 8953441 | 345233 | 80263 | 21195 | 378 |
| C-6 (4) | 7898334 | 102357 | 3386 | 766 | 56 |
| C-7 (5) | 31138340 | 2840178 | 185284 | 23686 | 94 |
| C-8 (6) | 5266074 | 120355 | 31144 | 10836 | 511 |
| C-9 | 12069 | 3708 | 777 | 155 | 0 |
| C-10 | 6562 | 1521 | 378 | 89 | 11 |
| C-11 | 4008 | 1366 | 355 | 67 | 22 |
| C-12 | 12024 | 4585 | 1310 | 255 | 33 |
| C-13 (7) | 1397620 | 577505 | 173605 | 35118 | 1488 |
| C-14 | 21207 | 5585 | 855 | 178 | 22 |
| C-15 (8) | 1938030 | 50529 | 9249 | 3053 | 611 |

(1) Possible Contamination- High Particle Count (Semi transparent irreg. particles)
(2) Possible Contamination- ≥1,000,000 Particle Count (Semi transparent irreg. particles) - MFI stop counting at 71% completion due max counting limit reached
(3) Possible Contamination- High Particle Count (Semi transparent irreg. particles)
(4) Possible Contamination- High Particle Count (Semi transparent irreg. particles)
(5) Possible Contamination- ≥1,000,000 Particle Count (Semi transparent irreg. particles) - MFI stop counting at 31% completion due max counting limit reached
(6) Possible Contamination- High Particle Count (Semi transparent irreg. particles)
(7) Possible Contamination- High Particle Count (Semi transparent irreg. particles)
(8) Possible Contamination- High Particle Count (Semi transparent irreg. particles)

TABLE 39

MFI results for Block C formulations stored for four weeks at 5° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| C-1 | 9771 | 2698 | 411 | 89 | 11 |
| C-2 | 5407 | 1588 | 233 | 67 | 0 |
| C-3 (1) | 5638309 | 1245577 | 154286 | 29345 | 577 |
| C-4 | 16343 | 4208 | 655 | 100 | 11 |
| C-5 (2) | 326669 | 99193 | 47365 | 19641 | 977 |
| C-6 (3) | 4597825 | 59090 | 10004 | 3930 | 67 |
| C-7 | 9016 | 1954 | 344 | 56 | 0 |
| C-8 | 7850 | 2110 | 311 | 67 | 0 |
| C-9 (4) | 19747267 | 3262161 | 486876 | 69636 | 3230 |
| C-10 (5) | 27048894 | 2264576 | 138961 | 25209 | 5859 |
| C-11 | 16577 | 5396 | 1366 | 255 | 0 |
| C-12 | 31865 | 8916 | 2332 | 489 | 22 |
| C-13 | 18087 | 5185 | 1155 | 300 | 67 |
| C-14 | 12446 | 3053 | 611 | 100 | 22 |
| C-15 | 25648 | 7361 | 266 | 1421 | 266 |

Note:
(1) Possible Contamination- High Particle Count (Semi transparent irreg. particles)
(2) Possible Contamination- High Particle Count (Semi transparent irreg. particles)
(3) Possible Contamination- High Particle Count (Semi transparent irreg. particles)
(4) Possible Contamination- ≥1,000,000 Particle Count (Semi transparent irreg. particles) - MFI stop counting at 55% completion due max counting limit reached
(5) Possible Contamination- ≥1,000,000 Particle Count (Semi transparent irreg. particles) - MFI stop counting at 40% completion due max counting limit reached Imaging Capillary Isoelectric Focusing (icIEF)

The chemical stability of the Block C formulations was evaluated by measuring the charge variants present in the formulation after being subjected to storage conditions. These samples were shipped on blue ice prior to analysis. Results are reported in Tables 40-43 below.

TABLE 40 icIEF results for Block C formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C-1 | 4.2 | 6.4 | 6.5 | 11.2 | 14.8 | 15.5 | 14.4 | 11.8 | 8.0 | 4.6 | 2.0 | 0.6 |
| C-2 | 4.0 | 6.5 | 6.9 | 11.3 | 14.5 | 14.9 | 14.8 | 12.2 | 7.9 | 4.5 | 2.0 | 0.7 |
| C-3 | 4.3 | 6.5 | 7.0 | 11.9 | 14.3 | 15.2 | 14.4 | 11.8 | 8.7 | 3.6 | 1.8 | 0.6 |
| C-4 | 4.6 | 6.4 | 6.9 | 11.4 | 14.5 | 15.3 | 14.2 | 11.7 | 8.7 | 3.7 | 1.9 | 0.7 |
| C-5 | 4.4 | 6.0 | 7.6 | 11.1 | 14.3 | 14.4 | 14.2 | 11.9 | 8.6 | 4.2 | 2.3 | 1.0 |
| C-6 | 4.6 | 6.2 | 7.1 | 10.1 | 15.8 | 14.8 | 14.5 | 11.8 | 8.5 | 4.0 | 2.0 | 0.6 |
| C-7 | 4.2 | 6.0 | 7.7 | 11.8 | 14.2 | 15.1 | 14.5 | 12.0 | 8.7 | 3.8 | 1.8 | 0.4 |
| C-8 | 4.3 | 6.5 | 7.7 | 11.0 | 14.5 | 14.7 | 14.7 | 11.5 | 8.2 | 4.1 | 2.1 | 0.7 |
| C-9 | 4.7 | 6.5 | 7.0 | 11.6 | 13.8 | 14.9 | 14.5 | 11.2 | 8.7 | 4.3 | 2.0 | 0.7 |

TABLE 40-continued icIEF results for Block C formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C-10 | 4.5 | 6.5 | 6.8 | 12.3 | 14.7 | 14.5 | 14.4 | 12.5 | 8.0 | 3.8 | 1.6 | 0.4 |
| C-11 | 4.7 | 6.2 | 6.8 | 11.9 | 15.0 | 14.4 | 14.8 | 11.7 | 7.7 | 4.5 | 1.8 | 0.4 |
| C-12 | 2.8 | 5.8 | 7.5 | 11.6 | 14.5 | 15.8 | 15.2 | 12.0 | 8.1 | 4.8 | 1.7 | 0.3 |
| C-13 | 4.5 | 5.9 | 8.1 | 10.7 | 14.8 | 14.9 | 14.0 | 12.1 | 8.0 | 4.6 | 2.0 | 0.3 |
| C-14 | 4.7 | 6.2 | 7.2 | 11.3 | 14.4 | 15.0 | 13.7 | 12.3 | 8.1 | 4.5 | 2.0 | 0.6 |
| C-15 | 4.4 | 6.2 | 6.4 | 12.3 | 14.6 | 15.2 | 14.1 | 12.0 | 8.6 | 3.9 | 1.8 | 0.5 |

TABLE 41 icIEF results for Block C formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C-1 | 4.3 | 5.9 | 7.0 | 12.0 | 13.9 | 14.6 | 14.6 | 11.3 | 8.3 | 5.0 | 2.2 | 0.8 |
| C-2 | 4.1 | 6.6 | 8.0 | 10.8 | 14.1 | 15.4 | 13.8 | 12.2 | 7.8 | 4.4 | 2.0 | 0.7 |
| C-3 | 5.7 | 7.6 | 7.6 | 11.9 | 15.3 | 15.1 | 13.1 | 10.8 | 7.0 | 3.7 | 1.5 | 0.5 |
| C-4 | 4.5 | 7.1 | 6.2 | 12.4 | 14.9 | 14.3 | 14.7 | 10.9 | 8.3 | 3.8 | 1.9 | 0.9 |
| C-5 | 5.0 | 6.4 | 7.4 | 11.2 | 14.9 | 15.7 | 13.9 | 11.1 | 8.3 | 3.6 | 1.8 | 0.7 |
| C-6 | 4.5 | 6.8 | 7.0 | 11.6 | 15.0 | 15.7 | 14.2 | 11.5 | 7.8 | 3.6 | 1.6 | 0.5 |
| C-7 | 4.4 | 6.7 | 7.5 | 12.5 | 15.1 | 15.0 | 14.1 | 11.5 | 7.6 | 3.5 | 1.5 | 0.6 |
| C-8 | 4.3 | 6.3 | 7.6 | 12.2 | 13.9 | 15.6 | 13.4 | 11.9 | 8.3 | 3.8 | 2.0 | 0.7 |
| C-9 | 4.9 | 7.0 | 7.1 | 11.8 | 14.3 | 15.0 | 14.1 | 10.8 | 8.1 | 3.7 | 2.1 | 1.0 |
| C-10 | 4.7 | 7.3 | 8.0 | 12.7 | 15.1 | 14.5 | 13.9 | 11.3 | 7.2 | 3.4 | 1.4 | 0.5 |
| C-11 | 5.1 | 8.3 | 7.5 | 12.5 | 15.3 | 15.8 | 12.8 | 10.6 | 6.3 | 3.7 | 1.5 | 0.5 |
| C-12 | 6.3 | 8.1 | 8.2 | 14.0 | 14.5 | 15.6 | 12.9 | 9.5 | 6.3 | 3.3 | 1.2 | 0.2 |
| C-13 | 4.5 | 6.9 | 8.1 | 10.4 | 14.7 | 15.8 | 14.2 | 11.5 | 7.6 | 4.3 | 1.7 | 0.4 |
| C-14 | 5.3 | 6.9 | 7.3 | 12.3 | 14.0 | 15.4 | 13.7 | 10.9 | 7.4 | 4.3 | 1.9 | 0.6 |
| C-15 | 5.0 | 6.6 | 7.6 | 12.1 | 14.3 | 15.6 | 13.8 | 11.5 | 7.8 | 3.5 | 1.7 | 0.4 |

TABLE 42 icIEF results for Block C formulations after storage for two weeks at 25° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C-1 | 4.6 | 5.9 | 6.7 | 12.4 | 13.8 | 15.5 | 13.9 | 11.7 | 7.8 | 4.8 | 2.2 | 0.8 |
| C-2 | 4.2 | 6.4 | 6.6 | 12.0 | 14.2 | 15.6 | 14.3 | 11.5 | 8.1 | 4.5 | 1.9 | 0.7 |
| C-3 | 5.1 | 6.5 | 7.8 | 11.5 | 14.6 | 16.2 | 12.9 | 11.0 | 7.8 | 4.2 | 1.9 | 0.5 |
| C-4 | 4.5 | 6.6 | 6.7 | 11.9 | 13.9 | 15.6 | 13.4 | 11.7 | 8.7 | 4.1 | 2.0 | 0.9 |
| C-5 | 4.2 | 6.5 | 7.0 | 11.3 | 14.8 | 15.6 | 13.1 | 12.3 | 8.8 | 3.8 | 2.0 | 0.6 |
| C-6 | 4.7 | 6.9 | 6.7 | 11.9 | 13.8 | 15.7 | 13.9 | 11.6 | 8.3 | 3.9 | 2.0 | 0.6 |
| C-7 | 4.6 | 6.8 | 6.9 | 12.2 | 14.4 | 15.0 | 14.2 | 11.4 | 8.2 | 3.6 | 1.9 | 0.7 |
| C-8 | 4.6 | 6.2 | 7.3 | 11.7 | 14.3 | 15.1 | 14.2 | 11.6 | 8.6 | 3.8 | 2.0 | 0.6 |
| C-9 | 4.9 | 6.3 | 8.1 | 11.2 | 14.9 | 14.7 | 13.3 | 12.2 | 8.1 | 3.9 | 1.8 | 0.7 |
| C-10 | 4.9 | 6.4 | 6.7 | 12.7 | 14.9 | 15.0 | 13.7 | 11.9 | 7.9 | 3.6 | 1.7 | 0.7 |
| C-11 | 4.7 | 6.9 | 7.8 | 11.5 | 14.8 | 15.2 | 14.4 | 11.2 | 7.5 | 4.2 | 1.5 | 0.5 |
| C-12 | 5.0 | 7.5 | 7.8 | 11.8 | 13.9 | 15.2 | 13.1 | 11.2 | 7.6 | 4.3 | 1.9 | 0.6 |
| C-13 | 4.2 | 6.5 | 6.4 | 13.2 | 14.1 | 14.6 | 14.0 | 12.2 | 8.1 | 4.6 | 1.8 | 0.5 |
| C-14 | 4.7 | 6.4 | 7.6 | 11.9 | 14.5 | 14.7 | 13.1 | 12.5 | 7.7 | 4.5 | 1.9 | 0.5 |
| C-15 | 3.5 | 6.6 | 7.2 | 12.3 | 14.2 | 15.0 | 14.7 | 12.1 | 8.4 | 3.8 | 1.8 | 0.4 |

TABLE 43 icIEF results for Block C formulations after storage for four weeks at 5° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C-1 | 4.4 | 7.1 | 6.8 | 11.8 | 14.0 | 15.0 | 13.7 | 11.8 | 8.3 | 4.4 | 2.0 | 0.7 |
| C-2 | 4.1 | 6.3 | 6.5 | 12.2 | 14.4 | 15.5 | 14.1 | 12.2 | 8.0 | 4.4 | 1.8 | 0.5 |
| C-3 | 3.6 | 6.3 | 7.5 | 11.2 | 15.0 | 14.7 | 14.6 | 12.2 | 8.9 | 3.7 | 1.9 | 0.5 |
| C-4 | 4.6 | 6.5 | 6.6 | 12.7 | 13.3 | 15.1 | 14.1 | 12.0 | 8.4 | 4.1 | 1.9 | 0.8 |

TABLE 43-continued icIEF results for Block C formulations after storage for four weeks at 5° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C-5 | 4.4 | 6.0 | 7.5 | 10.8 | 14.9 | 15.0 | 14.3 | 11.4 | 8.7 | 4.0 | 2.1 | 0.9 |
| C-6 | 4.3 | 6.4 | 7.1 | 12.2 | 14.4 | 14.8 | 14.5 | 11.7 | 8.4 | 3.9 | 1.8 | 0.5 |
| C-7 | 4.7 | 6.3 | 7.4 | 11.7 | 14.4 | 14.6 | 14.1 | 12.6 | 8.0 | 4.0 | 1.7 | 0.6 |
| C-8 | 4.4 | 6.0 | 7.1 | 12.3 | 14.2 | 15.5 | 13.5 | 12.1 | 8.4 | 4.0 | 1.9 | 0.6 |
| C-9 | 4.4 | 5.5 | 7.7 | 12.0 | 14.9 | 14.5 | 14.3 | 11.7 | 8.4 | 4.0 | 2.0 | 0.6 |
| C-10 | 4.0 | 5.9 | 7.8 | 11.2 | 14.8 | 14.9 | 15.0 | 12.2 | 8.3 | 3.6 | 1.7 | 0.6 |
| C-11 | 3.1 | 5.5 | 8.6 | 10.8 | 14.6 | 14.7 | 15.3 | 11.8 | 8.4 | 4.5 | 1.9 | 0.5 |
| C-12 | 4.7 | 6.5 | 8.0 | 10.4 | 14.4 | 15.3 | 14.2 | 11.6 | 7.9 | 4.5 | 2.0 | 0.5 |
| C-13 | 4.4 | 5.9 | 6.8 | 12.3 | 13.6 | 15.5 | 14.4 | 12.3 | 8.3 | 4.5 | 1.8 | 0.3 |
| C-14 | 4.2 | 6.4 | 7.5 | 11.1 | 14.9 | 14.7 | 14.4 | 12.1 | 8.0 | 4.4 | 1.8 | 0.6 |
| C-15 | 3.9 | 6.8 | 6.7 | 11.9 | 14.3 | 15.0 | 13.6 | 12.6 | 8.5 | 3.9 | 2.1 | 0.7 |

Discussion

The aflibercept formulations of Block C are physically and chemically stable.

Example 5—Aflibercept Formulations Free of Organic Co-Solvents with Alternative Stabilizers This example describes experiments to evaluate buffer-free aflibercept formulations that have a stabilizer other than sucrose such as amino acids (Gly, Pro, ArgHCl) as well as electrolytes, such NaCl and $MgCl_2$. (Block D). In these samples, no surfactant or co-solvent was included. In addition, dextran, a large polymer was investigated. Table 44, below, shows an exemplary set of such formulations.

TABLE 44

All formulations include 10 mM His buffer

| Form No. | aflibercept | pH | Gly (mM) | Arg (mM) | Pro (mM) | NaCl (mM) | MgCl$_2$ (mM) | Dextran (%) |
|---|---|---|---|---|---|---|---|---|
| D-1 | 40 mg/ml | 6.2 | 270 | 0 | 0 | 0 | 0 | 0 |
| D-2 | 40 mg/ml | 6.2 | 0 | 0 | 270 | 0 | 0 | 0 |
| D-3 | 40 mg/ml | 6.2 | 0 | 25 | 0 | 125 | 0 | 0 |
| D-4 | 40 mg/ml | 6.2 | 0 | 50 | 0 | 75 | 0 | 0 |
| D-5 | 40 mg/ml | 6.2 | 0 | 0 | 0 | 150 | 0 | 1 |
| D-6 | 40 mg/ml | 6.2 | 0 | 0 | 0 | 0 | 100 | 0 |
| D-7 | 40 mg/ml | 6.2 | 270 | 0 | 0 | 0 | 0 | 1 |
| D-8 | 40 mg/ml | 6.2 | 0 | 0 | 0 | 40 | 75 | 0 |
| D-9 | 40 mg/ml | 6.5 | 270 | 0 | 0 | 0 | 0 | 0 |
| D-10 | 40 mg/ml | 6.5 | 0 | 0 | 270 | 0 | 0 | 0 |
| D-11 | 40 mg/ml | 7.0 | 270 | 0 | 0 | 0 | 0 | 0 |
| D-12 | 40 mg/ml | 7.0 | 0 | 0 | 270 | 0 | 0 | 0 |

Concentration, pH, and Osmolality

The aflibercept concentration (mg/mL), pH, and osmolality (mOSm) of the Block D formulations were evaluated at t0. Results are reported in Table 45 below.

TABLE 45

| Form No. | Final Concentration (mg/mL) | Final pH | Final Osmolality (mOsm/Kg) |
|---|---|---|---|
| D-1 | 39.44 | 6.22 | 305 |
| D-2 | 39.89 | 6.23 | 328 |
| D-3 | 40.03 | 6.18 | 309 |
| D-4 | 39.42 | 6.21 | 261 |
| D-5 | 39.6 | 6.16 | 325 |
| D-6 | 40.22 | 6.18 | 294 |
| D-7 | 41.52 | 6.19 | 310 |
| D-8 | 40.04 | 6.18 | 302 |
| D-9 | 39.83 | 6.48 | 298 |

TABLE 45-continued

| Form No. | Final Concentration (mg/mL) | Final pH | Final Osmolality (mOsm/Kg) |
|---|---|---|---|
| D-10 | 39.83 | 6.50 | 319 |
| D-11 | 39.89 | 6.93 | 296 |
| D-12 | 41.55 | 6.95 | 321 |
| Eylea | 39.37 | 6.23 | 2.35 |

Size Exclusion Chromatography

The stability of the Block D formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Tables 46-49 below.

TABLE 46

SEC results for Block D formulations at T = 0

| Form No. | Rel. Area (%), Before Main Peak | Rel. Area (%), Main Peak | Rel. Area (%), After Main Peak |
|---|---|---|---|
| D-1 | 1.07 | 98.93 | 0 |
| D-2 | 1.08 | 98.92 | 0 |
| D-3 | 1.05 | 98.95 | 0 |
| D-4 | 1.03 | 98.97 | 0 |
| D-5 | 1.07 | 98.93 | 0 |
| D-6 | 1.00 | 99.00 | 0 |
| D-7 | 1.04 | 98.96 | 0 |
| D-8 | 0.99 | 99.01 | 0 |
| D-9 | 1.08 | 98.92 | 0 |
| D-10 | 1.09 | 98.91 | 0 |
| D-11 | 1.16 | 98.84 | 0 |
| D-12 | 1.18 | 98.82 | 0 |
| Eylea | 1.09 | 98.91 | 0 |

TABLE 47

SEC results for Block D formulations after one week at 40° C.

| Form No. | Rel. Area (%), Before Main Peak | Rel. Area (%), Main Peak | Rel. Area (%), After Main Peak |
|---|---|---|---|
| D-1 | 1.54 | 98.46 | 0 |
| D-2 | 1.64 | 98.36 | 0 |
| D-3 | 2.93 | 97.07 | 0 |
| D-4 | 2.81 | 97.19 | 0 |
| D-5 | 3.19 | 96.81 | 0 |
| D-6 | 3.03 | 96.97 | 0 |
| D-7 | 1.80 | 98.20 | 0 |

TABLE 47-continued

SEC results for Block D formulations after one week at 40° C.

| Form No. | Rel. Area (%), Before Main Peak | Rel. Area (%), Main Peak | Rel. Area (%), After Main Peak |
|---|---|---|---|
| D-8 | 2.80 | 97.20 | 0 |
| D-9 | 1.72 | 98.28 | 0 |
| D-10 | 2.15 | 97.85 | 0 |
| D-11 | 2.20 | 97.80 | 0 |
| D-12 | 2.50 | 97.50 | 0 |
| Eylea | 1.09 | 98.91 | 0 |

TABLE 48

SEC results for Block D formulations two weeks at 25° C.

| Form No. | Rel. Area (%), Before Main Peak | Rel. Area (%), Main Peak | Rel. Area (%), After Main Peak |
|---|---|---|---|
| D-1 | 1.03 | 98.97 | 0 |
| D-2 | 1.01 | 98.99 | 0 |
| D-3 | 0.96 | 99.04 | 0 |
| D-4 | 0.95 | 99.05 | 0 |
| D-5 | 1.06 | 98.94 | 0 |
| D-6 | 0.94 | 99.06 | 0 |
| D-7 | 1.07 | 98.93 | 0 |
| D-8 | 0.92 | 99.08 | 0 |
| D-9 | 1.06 | 98.94 | 0 |
| D-10 | 1.08 | 98.92 | 0 |
| D-11 | 1.22 | 98.78 | 0 |
| D-12 | 1.28 | 98.72 | 0 |
| Eylea | 0.98 | 99.02 | 0 |

TABLE 49

SEC results for Block D formulations after four weeks at 5° C.

| Form No. | Rel. Area (%), Before Main Peak | Rel. Area (%), Main Peak | Rel. Area (%), After Main Peak |
|---|---|---|---|
| D-1 | 1.13 | 98.87 | 0 |
| D-2 | 1.07 | 98.93 | 0 |
| D-3 | 1.02 | 98.98 | 0 |
| D-4 | 1.00 | 99.00 | 0 |
| D-5 | 1.06 | 98.94 | 0 |
| D-6 | 0.96 | 99.04 | 0 |
| D-7 | 1.08 | 98.92 | 0 |
| D-8 | 0.96 | 99.04 | 0 |
| D-9 | 1.10 | 98.90 | 0 |
| D-10 | 1.08 | 98.92 | 0 |
| D-11 | 1.22 | 98.78 | 0 |
| D-12 | 1.25 | 98.75 | 0 |
| Eylea | 0.98 | 99.02 | 0 |

All of these formulations exhibit monomer contents near 99% at T0, as was seen with other blocks.

After one week at 40° C., the monomer content decreased to 97-98%, similar to what was observed for previous blocks. No fragmentation is noted and the losses are solely due to aggregation. At 25° C. storage there is only slight changes from the initial levels, suggesting that these types of excipients (amino acids, salts) are good stabilizers for aflibercept. For samples stored at 5° C. for four weeks, little degradation is seen as well.

Micro-Flow Imaging

The stability of the Block D formulations was evaluated by measuring the particles present in the formulation after being subjected to storage conditions. These samples were shipped frozen for MFI analysis and seem to have survived the shipping without any significant damage. Results are reported in Tables 50-53 below.

TABLE 50

MFI results for Block D formulations at T = 0

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| D-1 | 17620 | 4075 | 611 | 33 | 11 |
| D-2 | 14012 | 4175 | 955 | 233 | 44 |
| D-3 | 12358 | 3175 | 655 | 211 | 11 |
| D-4 | 10792 | 2554 | 389 | 78 | 0 |
| D-5 | 7605 | 2098 | 355 | 133 | 0 |
| D-6 | 35385 | 9460 | 1876 | 333 | 333 |
| D-7 | 13523 | 3886 | 744 | 144 | 0 |
| D-8 | 6195 | 1510 | 366 | 100 | 0 |
| D-9 | 19141 | 5318 | 966 | 133 | 0 |
| D-10 | 6318 | 1277 | 200 | 33 | 0 |
| D-11 | 10514 | 1887 | 222 | 11 | 11 |
| D-12 | 16632 | 3930 | 655 | 144 | 56 |
| Eylea | 4430 | 844 | 89 | 22 | 0 |

TABLE 51

MFI results for Block D formulations stored for one week at 40° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| D-1 | 48631 | 13967 | 2187 | 433 | 56 |
| D-2 | 43412 | 11403 | 1743 | 167 | 78 |
| D-3 | 51584 | 13412 | 2276 | 444 | 33 |
| D-4 | 42102 | 11192 | 2276 | 333 | 11 |
| D-5 | 4597 | 1388 | 333 | 111 | 22 |
| D-6 | 40403 | 11303 | 2232 | 433 | 11 |
| D-7 | 7939 | 2332 | 455 | 56 | 22 |
| D-8 | 22061 | 4919 | 755 | 189 | 33 |
| D-9 | 45266 | 10603 | 1654 | 233 | 22 |
| D-10 | 30033 | 7528 | 1832 | 500 | 56 |
| D-11 | 28901 | 8161 | 2121 | 522 | 56 |
| D-12 | 28657 | 7583 | 1499 | 400 | 33 |
| Eylea | 10736 | 3453 | 1232 | 366 | 22 |

TABLE 52

MFI results for Block D formulations stored for two weeks at 25° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| D-1 | 79885 | 20751 | 2620 | 31unit1 | 11 |
| D-2 | 35374 | 10592 | 2642 | 566 | 44 |
| D-3 | 31910 | 7317 | 877 | 100 | 11 |
| D-4 | 30477 | 6939 | 844 | 133 | 44 |
| D-5 | 22439 | 5263 | 922 | 200 | 0 |
| D-6 | 21262 | 5329 | 655 | 56 | 0 |
| D-7 | 35163 | 6906 | 833 | 44 | 0 |
| D-8 | 11647 | 2631 | 278 | 44 | 0 |
| D-9 | 2853 | 777 | 222 | 56 | 11 |
| D-10 | 19397 | 4252 | 533 | 33 | 0 |
| D-11 | 17898 | 4208 | 600 | 67 | 0 |
| D-12 | 30233 | 7272 | 1010 | 233 | 33 |
| Eylea | 8305 | 1865 | 433 | 67 | 11 |

TABLE 53

MFI results for Block D formulations stored for four weeks at 5° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| D-1 | 76166 | 22961 | 4474 | 600 | 11 |
| D-2 | 19419 | 6440 | 1454 | 244 | 11 |
| D-3 | 16976 | 4930 | 1188 | 244 | 0 |
| D-4 | 13279 | 3320 | 344 | 78 | 22 |
| D-5 | 27924 | 6728 | 899 | 122 | 11 |
| D-6 | 25481 | 6606 | 1232 | 111 | 11 |
| D-7 (1) | 30135 | 6328 | 542 | 40 | 0 |
| D-8 | 11447 | 2987 | 300 | 67 | 33 |
| D-9 | 26647 | 6540 | 999 | 211 | 11 |
| D-10 | 42147 | 9293 | 1454 | 167 | 0 |
| D-11 (2) | 47938 | 14019 | 2229 | 273 | 29 |
| D-12 | 59289 | 13823 | 2198 | 355 | 33 |
| Eylea | 11170 | 2665 | 455 | 78 | 0 |

Note:
(1) Need Time stamp, 90%- insufficient sample caused bottom right screen schlieren lines due to illumination error
(2) Need Time stamp, 80%- insufficient sample caused bottom right screen schlieren lines due to illumination error Imaging Capillary Isoelectric Focusing (icIEF)

The chemical stability of the Block D formulations was evaluated by measuring the charge variants present in the formulation after being subjected to storage conditions. These samples were frozen and shipped on dry ice prior to analysis. Results are reported in Table 54-57 below.

TABLE 54 icIEF results for Block D formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| D-1 | 4.5 | 6.3 | 8.1 | 11.0 | 14.7 | 15.2 | 14.5 | 12.1 | 7.8 | 3.7 | 1.7 | 0.4 |
| D-2 | 4.2 | 6.5 | 7.8 | 11.7 | 15.1 | 14.8 | 13.7 | 12.3 | 7.9 | 3.8 | 1.8 | 0.4 |
| D-3 | 4.8 | 6.7 | 7.5 | 12.1 | 14.0 | 15.0 | 14.2 | 11.3 | 8.2 | 3.6 | 1.9 | 0.6 |
| D-4 | 4.5 | 6.5 | 7.5 | 11.6 | 14.2 | 15.3 | 14.2 | 11.7 | 8.7 | 3.6 | 1.8 | 0.5 |
| D-5 | 4.8 | 6.6 | 6.8 | 12.3 | 14.8 | 14.9 | 13.7 | 11.9 | 8.4 | 3.5 | 1.9 | 0.5 |
| D-6 | 4.4 | 7.2 | 6.2 | 12.6 | 14.3 | 14.8 | 15.0 | 11.5 | 8.5 | 3.1 | 1.5 | 0.8 |
| D-7 | 4.6 | 6.6 | 7.7 | 12.2 | 14.4 | 15.2 | 14.0 | 11.1 | 8.3 | 3.6 | 1.7 | 0.5 |
| D-8 | 4.4 | 6.7 | 7.1 | 11.9 | 14.5 | 15.4 | 14.1 | 11.6 | 8.0 | 3.5 | 2.0 | 0.7 |
| D-9 | 4.2 | 6.5 | 7.8 | 12.0 | 14.0 | 14.8 | 14.8 | 11.5 | 8.2 | 3.9 | 1.8 | 0.6 |
| D-10 | 4.3 | 6.1 | 8.1 | 12.5 | 13.9 | 15.5 | 14.0 | 11.7 | 8.0 | 3.8 | 1.7 | 0.4 |
| D-11 | 4.4 | 6.6 | 7.5 | 11.9 | 14.5 | 16.1 | 14.3 | 11.5 | 7.9 | 3.5 | 1.5 | 0.4 |
| D-12 | 4.4 | 8.0 | 6.9 | 12.5 | 14.6 | 14.6 | 14.2 | 11.6 | 7.8 | 3.5 | 1.5 | 0.3 |
| Eylea | 4.4 | 7.4 | 6.1 | 11.6 | 14.9 | 14.8 | 14.5 | 11.5 | 8.4 | 4.1 | 1.7 | 0.6 |

TABLE 55 icIEF results for Block D formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| D-1 | 4.7 | 6.4 | 8.7 | 11.5 | 15.4 | 14.7 | 14.1 | 11.5 | 7.6 | 3.4 | 1.6 | 0.3 |
| D-2 | 4.7 | 7.0 | 8.0 | 11.9 | 14.7 | 15.1 | 13.6 | 11.8 | 7.5 | 3.5 | 1.8 | 0.5 |
| D-3 | 4.6 | 8.0 | 5.9 | 12.9 | 14.0 | 15.9 | 13.7 | 11.4 | 7.8 | 3.4 | 1.7 | 0.6 |
| D-4 | 4.6 | 6.7 | 8.0 | 11.2 | 15.8 | 15.6 | 14.1 | 10.7 | 8.0 | 3.2 | 1.6 | 0.5 |
| D-5 | 5.1 | 6.2 | 8.1 | 11.8 | 14.6 | 15.7 | 13.8 | 11.4 | 7.8 | 3.2 | 1.7 | 0.5 |
| D-6 | 4.4 | 7.5 | 6.5 | 12.6 | 14.9 | 15.8 | 13.9 | 11.3 | 7.6 | 3.1 | 1.7 | 0.7 |
| D-7 | 4.8 | 6.9 | 7.6 | 12.1 | 14.9 | 14.7 | 13.6 | 11.7 | 7.7 | 3.7 | 1.8 | 0.6 |
| D-8 | 4.7 | 6.8 | 7.6 | 12.1 | 15.0 | 15.8 | 13.4 | 11.2 | 7.4 | 3.3 | 1.9 | 0.8 |
| D-9 | 4.5 | 7.4 | 7.8 | 12.7 | 14.4 | 15.4 | 14.4 | 10.8 | 7.4 | 3.3 | 1.6 | 0.4 |
| D-10 | 4.6 | 8.4 | 7.1 | 12.0 | 15.2 | 14.5 | 14.0 | 11.4 | 7.2 | 3.4 | 1.6 | 0.5 |
| D-11 | 5.8 | 8.5 | 7.8 | 12.7 | 15.3 | 15.3 | 14.0 | 10.2 | 6.5 | 2.8 | 1.1 | 0.2 |
| D-12 | 5.8 | 7.5 | 8.7 | 13.6 | 15.3 | 15.7 | 12.8 | 9.9 | 6.4 | 2.9 | 1.2 | 0.2 |
| Eylea | 4.8 | 7.2 | 6.8 | 11.6 | 15.3 | 15.0 | 14.3 | 11.5 | 7.2 | 4.1 | 1.7 | 0.6 |

TABLE 56 icIEF results for Block D formulations after storage for two weeks at 25° C.

| Formulation | Rel. Area (%) Smoothing (Group) | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| D-1 | 4.6 | 6.8 | 7.2 | 12.1 | 14.2 | 14.9 | 14.1 | 11.9 | 8.2 | 3.9 | 1.7 | 0.4 |
| D-2 | 5.2 | 6.2 | 7.8 | 11.7 | 15.0 | 15.4 | 13.4 | 11.5 | 7.9 | 3.7 | 1.7 | 0.5 |
| D-3 | 4.4 | 6.6 | 7.5 | 11.6 | 14.6 | 15.8 | 13.5 | 11.9 | 8.4 | 3.4 | 1.7 | 0.5 |
| D-4 | 4.9 | 6.6 | 6.9 | 12.5 | 14.2 | 15.8 | 13.6 | 11.3 | 8.6 | 3.4 | 1.7 | 0.5 |
| D-5 | 4.8 | 6.5 | 8.1 | 11.7 | 14.4 | 14.8 | 13.9 | 12.0 | 8.1 | 3.4 | 1.8 | 0.5 |
| D-6 | 4.5 | 6.6 | 7.7 | 12.1 | 14.4 | 15.5 | 13.8 | 11.4 | 8.1 | 3.4 | 1.9 | 0.8 |
| D-7 | 4.3 | 6.8 | 7.8 | 11.9 | 14.4 | 15.2 | 14.0 | 11.9 | 8.0 | 3.6 | 1.6 | 0.4 |
| D-8 | 4.5 | 7.1 | 7.3 | 11.7 | 14.3 | 15.6 | 13.7 | 11.2 | 8.2 | 3.3 | 2.1 | 0.9 |
| D-9 | 4.5 | 6.2 | 7.8 | 12.1 | 14.6 | 14.9 | 14.2 | 11.6 | 8.0 | 3.8 | 1.7 | 0.5 |
| D-10 | 4.3 | 5.9 | 8.0 | 11.8 | 15.4 | 15.3 | 14.4 | 11.4 | 7.8 | 3.6 | 1.6 | 0.5 |
| D-11 | 4.7 | 7.0 | 8.0 | 13.0 | 13.8 | 16.1 | 13.8 | 11.3 | 7.2 | 3.4 | 1.4 | 0.3 |
| D-12 | 5.0 | 6.9 | 7.3 | 13.4 | 14.1 | 16.0 | 12.9 | 11.9 | 7.4 | 3.4 | 1.5 | 0.2 |
| Eylea | 4.0 | 7.3 | 6.7 | 12.1 | 14.6 | 14.5 | 15.1 | 11.3 | 8.0 | 4.2 | 1.6 | 0.5 |

TABLE 57 icIEF results for Block D formulations after storage for four weeks at 5° C.

| Formulation | Rel. Area (%) Smoothing (Group) | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| D-1 | 4.6 | 6.8 | 7.4 | 11.4 | 13.9 | 15.2 | 14.5 | 11.6 | 8.5 | 3.9 | 1.8 | 0.4 |
| D-2 | 4.5 | 6.2 | 7.8 | 12.1 | 14.6 | 14.9 | 14.2 | 11.6 | 8.0 | 3.8 | 1.8 | 0.5 |
| D-3 | 4.5 | 6.1 | 7.7 | 11.9 | 14.2 | 14.8 | 14.5 | 11.6 | 8.5 | 3.6 | 1.9 | 0.7 |
| D-4 | 4.3 | 6.6 | 7.3 | 12.4 | 14.0 | 15.5 | 14.1 | 11.5 | 8.5 | 3.6 | 1.8 | 0.5 |
| D-5 | 4.8 | 6.3 | 7.3 | 12.5 | 13.9 | 14.7 | 14.9 | 11.6 | 8.2 | 3.5 | 1.9 | 0.5 |
| D-6 | 4.2 | 7.1 | 6.9 | 11.6 | 14.8 | 15.0 | 14.2 | 11.8 | 8.1 | 3.5 | 1.9 | 0.9 |
| D-7 | 4.4 | 6.3 | 8.0 | 12.0 | 14.3 | 14.8 | 14.7 | 11.6 | 8.0 | 3.6 | 1.7 | 0.5 |
| D-8 | 3.9 | 6.5 | 7.2 | 12.1 | 15.1 | 15.0 | 14.1 | 11.2 | 8.3 | 3.7 | 2.1 | 0.8 |
| D-9 | 4.2 | 6.7 | 7.3 | 12.1 | 14.3 | 15.7 | 14.1 | 11.8 | 8.0 | 3.7 | 1.6 | 0.4 |
| D-10 | 4.4 | 6.1 | 8.0 | 11.9 | 14.4 | 15.6 | 14.0 | 11.9 | 7.8 | 3.8 | 1.6 | 0.4 |
| D-11 | 4.8 | 6.8 | 7.4 | 12.3 | 13.8 | 15.7 | 14.1 | 11.6 | 7.9 | 3.6 | 1.6 | 0.3 |
| D-12 | 5.0 | 6.5 | 6.7 | 12.4 | 14.7 | 15.4 | 14.1 | 11.9 | 7.8 | 3.5 | 1.6 | 0.4 |
| Eylea | 4.5 | 6.2 | 7.8 | 12.1 | 14.6 | 14.9 | 14.2 | 11.6 | 8.0 | 3.8 | 1.6 | 0.6 |

Discussion

The aflibercept formulations of Block D are physically and chemically stable.

It is further contemplated that in the formulations of Block D, phosphate could be used instead of histidine buffer. It is also contemplated that $CaCl_2$ could be used instead of, or in addition to, $MgCl_2$.

Example 6—Buffer-Free Aflibercept Formulations with Alternative Stabilizers

This example describes experiments to evaluate buffer-free aflibercept formulations that have a stabilizer other than sucrose (Block E). The design mirrored Block D, except all of these compositions include 0.03% PS 20. This will allow for a direct and detailed examination of the importance PS 20 (and co-solvents in general) for their impact on storage stability. Table 58, below, shows an exemplary set of such formulations.

TABLE 58

All formulations include 0.03% PS 20.

| Form No. | aflibercept | pH | Gly (mM) | Arg (mM) | Pro (mM) | NaCl (mM) | MgCl$_2$ (mM) | Dextran (%) |
|---|---|---|---|---|---|---|---|---|
| E-1 | 40 mg/ml | 6.2 | 270 | 0 | 0 | 0 | 0 | 0 |
| E-2 | 40 mg/ml | 6.2 | 0 | 0 | 270 | 0 | 0 | 0 |
| E-3 | 40 mg/ml | 6.2 | 0 | 25 | 0 | 125 | 0 | 0 |
| E-4 | 40 mg/ml | 6.2 | 0 | 50 | 0 | 75 | 0 | 0 |
| E-5 | 40 mg/ml | 6.2 | 0 | 0 | 0 | 150 | 0 | 1 |
| E-6 | 40 mg/ml | 6.2 | 0 | 0 | 0 | 0 | 100 | 0 |
| E-7 | 40 mg/ml | 6.2 | 270 | 0 | 0 | 0 | 0 | 1 |
| E-8 | 40 mg/ml | 6.2 | 0 | 0 | 0 | 40 | 75 | 0 |
| E-9 | 40 mg/ml | 6.5 | 270 | 0 | 0 | 0 | 0 | 0 |
| E-10 | 40 mg/ml | 6.5 | 0 | 0 | 270 | 0 | 0 | 0 |
| E-11 | 40 mg/ml | 7.0 | 270 | 0 | 0 | 0 | 0 | 0 |
| E-12 | 40 mg/ml | 7.0 | 0 | 0 | 270 | 0 | 0 | 0 |

Concentration, pH, and Osmolality

The aflibercept concentration (mg/mL), pH, and osmolality (mOSm) of the Block E formulations were evaluated at t0. Results are reported in Table 59 below.

TABLE 59

| Form No. | Final Concentration (mg/mL) | Final pH | Final Osmolality (mOsm/Kg) |
|---|---|---|---|
| E-1 | 38.33 | 6.23 | 274 |
| E-2 | 37.88 | 6.21 | 303 |
| E-3 | 39.55 | 6.25 | 284 |
| E-4 | 40.06 | 6.27 | 242 |

TABLE 59-continued

| Form No. | Final Concentration (mg/mL) | Final pH | Final Osmolality (mOsm/Kg) |
|---|---|---|---|
| E-5 | 37.91 | 6.14 | 295 |
| E-6 | 39.63 | 6.11 | 271 |
| E-7 | 39.31 | 6.22 | 287 |
| E-8 | 39.85 | 6.12 | 290 |
| E-9 | 39.57 | 6.44 | 276 |
| E-10 | 42.04 | 6.57 | 297 |
| E-11 | 39.71 | 6.95 | 276 |
| E-12 | 40.42 | 6.94 | 302 |

Size Exclusion Chromatography

The stability of the Block E formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Table 60-63 below.

TABLE 60

SEC results for Block E formulations at T = 0

| Form No. | Rel. Area (%), Before Main Peak | Rel. Area (%), Main Peak | Rel. Area (%), After Main Peak |
|---|---|---|---|
| E-1 | 1.11 | 98.89 | 0 |
| E-2 | 1.14 | 98.86 | 0 |
| E-3 | 1.14 | 98.86 | 0 |
| E-4 | 1.14 | 98.86 | 0 |
| E-5 | 1.18 | 98.82 | 0 |
| E-6 | 1.43 | 98.57 | 0 |
| E-7 | 1.15 | 98.85 | 0 |
| E-8 | 1.09 | 98.91 | 0 |
| E-9 | 1.13 | 98.87 | 0 |
| E-10 | 1.19 | 98.81 | 0 |
| E-11 | 1.29 | 98.71 | 0 |
| E-12 | 1.36 | 98.64 | 0 |

TABLE 61

SEC results for Block E formulations after one week at 40° C.

| Form No. | Rel. Area (%), Before Main Peak | Rel. Area (%), Main Peak | Rel. Area (%), After Main Peak |
|---|---|---|---|
| E-1 | 1.68 | 98.32 | 0 |
| E-2 | 1.86 | 98.14 | 0 |
| E-3 | 2.89 | 97.11 | 0 |
| E-4 | 2.71 | 97.29 | 0 |
| E-5 | 2.79 | 97.21 | 0 |
| E-6 | 3.17 | 96.83 | 0 |
| E-7 | 1.90 | 98.10 | 0 |
| E-8 | 3.27 | 96.73 | 0 |
| E-9 | 2.04 | 97.96 | 0 |
| E-10 | 2.74 | 97.26 | 0 |
| E-11 | 2.48 | 97.52 | 0 |
| E-12 | 3.15 | 96.85 | 0 |

TABLE 62

SEC results for Block E formulations two weeks at 25° C.

| Form No. | Rel. Area (%), Before Main Peak | Rel. Area (%), Main Peak | Rel. Area (%), After Main Peak |
|---|---|---|---|
| E-1 | 1.08 | 98.92 | 0 |
| E-2 | 1.18 | 98.82 | 0 |
| E-3 | 1.18 | 98.82 | 0 |
| E-4 | 1.11 | 98.89 | 0 |
| E-5 | 1.23 | 98.77 | 0 |
| E-6 | 1.42 | 98.58 | 0 |
| E-7 | 1.26 | 98.74 | 0 |
| E-8 | 1.16 | 98.84 | 0 |
| E-9 | 1.15 | 98.85 | 0 |
| E-10 | 1.47 | 98.53 | 0 |
| E-11 | 1.46 | 98.54 | 0 |
| E-12 | 1.64 | 98.36 | 0 |

TABLE 63

SEC results for Block E formulations after four weeks at 5° C.

| Form No. | Rel. Area (%), Before Main Peak | Rel. Area (%), Main Peak | Rel. Area (%), After Main Peak |
|---|---|---|---|
| E-1 | 1.11 | 98.89 | 0 |
| E-2 | 1.12 | 98.88 | 0 |
| E-3 | 1.11 | 98.89 | 0 |
| E-4 | 1.10 | 98.90 | 0 |
| E-5 | 1.14 | 98.86 | 0 |
| E-6 | 1.36 | 98.64 | 0 |
| E-7 | 1.15 | 98.85 | 0 |
| E-8 | 1.08 | 98.92 | 0 |
| E-9 | 1.14 | 98.86 | 0 |
| E-10 | 1.31 | 98.69 | 0 |
| E-11 | 1.33 | 98.67 | 0 |
| E-12 | 1.48 | 98.52 | 0 |

As with nearly all of the previous samples, aggregation is the dominant degradation pathway and no fragmentation is observed.

The SEC results for Block E are comparable to those in Block D, suggesting that PS 20 has only a modest effect on storage stability. The levels of aggregates seem to be slightly higher than for Block D when stored at 5° C., but these differences may be within the error of the SEC method.

Micro-Flow Imaging

The stability of the Block E formulations was evaluated by measuring the particles present in the formulation after being subjected to storage conditions. As with Block D samples, they were shipped for MFI analysis frozen on dry ice. Results are reported in Table 64-67 below.

TABLE 64

MFI results for Block E formulations at T = 0

| Form. Block | Total Particle Conc. (#/mL) | Size Range Summary | | | |
|---|---|---|---|---|---|
| | | ≥2 µm (#/mL) | ≥5 µm (#/mL) | ≥10 µm (#/mL) | ≥25 µm (#/mL) |
| E-1 | 5962 | 1399 | 344 | 78 | 33 |
| E-2 | 8827 | 2343 | 222 | 44 | 22 |
| E-3 | 5885 | 766 | 122 | 11 | 0 |
| E-4 | 14800 | 2243 | 178 | 22 | 0 |
| E-5 | 9504 | 2098 | 111 | 33 | 0 |
| E-6 | 8460 | 1643 | 222 | 56 | 0 |
| E-7 | 2432 | 433 | 67 | 56 | 33 |
| E-8 | 4319 | 933 | 144 | 56 | 0 |
| E-9 | 6018 | 1144 | 89 | 22 | 11 |
| E-10 | 9027 | 1954 | 211 | 11 | 11 |
| E-11 | 6684 | 1432 | 167 | 22 | 0 |
| E-12 | 17287 | 4186 | 899 | 133 | 22 |

TABLE 65

MFI results for Block E formulations stored for one week at 40° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| E-1 | 5796 | 1388 | 200 | 11 | 0 |
| E-2 | 59578 | 3486 | 344 | 44 | 11 |
| E-3(1) | 676465 | 138664 | 40204 | 12358 | 755 |
| E-4(2) | 458538 | 81795 | 17054 | 3486 | 67 |
| E-5(3) | 316743 | 97494 | 30189 | 7239 | 111 |
| E-6 | 17476 | 3220 | 1177 | 555 | 0 |
| E-7 | 12024 | 2043 | 233 | 67 | 0 |
| E-8 | 99460 | 15377 | 1566 | 100 | 0 |
| E-9 | 3731 | 688 | 78 | 11 | 0 |
| E-10 | 47110 | 4186 | 511 | 144 | 33 |
| E-11 | 8438 | 2309 | 333 | 144 | 11 |
| E-12 | 8671 | 1887 | 366 | 78 | 11 |

Note:
(1)High Particle Count, semi transparent particles
(2)High Particle Count, semi transparent particles
(3)High Particle Count, semi transparent particles

TABLE 66

MFI results for Block E formulations stored for two weeks at 25° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| E-1 | 8449 | 2187 | 211 | 44 | 0 |
| E-2 | 42779 | 10836 | 966 | 111 | 33 |
| E-3(1) | 103557 | 11791 | 588 | 100 | 33 |
| E-4 | 47565 | 6928 | 322 | 56 | 0 |
| E-5 | 18020 | 2065 | 144 | 0 | 0 |
| E-6 | 66850 | 3431 | 344 | 89 | 22 |
| E-7 | 29778 | 7839 | 1332 | 178 | 33 |
| E-8 | 12013 | 2232 | 344 | 78 | 11 |
| E-9 | 12435 | 2365 | 322 | 56 | 11 |
| E-10 | 15022 | 3309 | 455 | 78 | 0 |
| E-11 | 22661 | 5030 | 1121 | 189 | 11 |
| E-12 | 31754 | 8127 | 1532 | 155 | 11 |

Note:
(1)High Particle Count, semi transparent particles

TABLE 67

MFI results for Block E formulations stored for four weeks at 5° C.

| Form. Block | Total Particle Conc. (#/mL) | ≥2 μm (#/mL) | ≥5 μm (#/mL) | ≥10 μm (#/mL) | ≥25 μm (#/mL) |
|---|---|---|---|---|---|
| E-1 | 3853 | 699 | 33 | 11 | 0 |
| E-2 | 6151 | 1244 | 155 | 44 | 0 |
| E-3 | 5118 | 1110 | 155 | 56 | 0 |
| E-4 | 5529 | 1088 | 78 | 11 | 11 |
| E-5 | 4741 | 755 | 78 | 22 | 0 |
| E-6 | 6318 | 2209 | 755 | 155 | 0 |
| E-7 | 2587 | 444 | 67 | 44 | 0 |
| E-8(1) | 28192 | 9321 | 380 | 19 | 0 |
| E-9 | 5096 | 744 | 78 | 67 | 22 |
| E-10 | 51118 | 1599 | 255 | 78 | 22 |
| E-11 | 8671 | 2176 | 300 | 0 | 0 |
| E-12 | 17654 | 4630 | 733 | 33 | 0 |

Note:
(1)Need Time stamp, 79%-insufficient sample caused bottom right screen Schlieren lines due to illumination error and bubble in beginning- Imaging Capillary Isoelectric Focusing (icIEF)

The chemical stability of the Block E formulations was evaluated by measuring the charge variants present in the formulation after being subjected to storage conditions. These samples were frozen and shipped on dry ice prior to analysis. Results are reported in Tables 68-71 below.

TABLE 68 icIEF results for Block E formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| E-1 | 4.4 | 5.6 | 7.8 | 14.4 | 12.7 | 14.7 | 14.2 | 11.6 | 7.5 | 4.6 | 1.7 | 0.6 |
| E-2 | 4.3 | 6.5 | 7.4 | 12.7 | 13.7 | 14.8 | 14.0 | 11.6 | 8.3 | 4.5 | 1.8 | 0.4 |
| E-3 | 4.5 | 7.2 | 6.7 | 12.3 | 14.5 | 15.3 | 14.1 | 11.5 | 7.3 | 4.2 | 1.7 | 0.6 |
| E-4 | 5.2 | 7.4 | 6.3 | 12.2 | 14.0 | 15.3 | 13.4 | 11.6 | 7.6 | 4.5 | 2.1 | 0.4 |
| E-5 | 4.5 | 7.3 | 6.9 | 11.8 | 14.8 | 14.5 | 14.2 | 11.2 | 7.6 | 4.4 | 2.0 | 0.6 |
| E-6 | 4.2 | 6.5 | 6.5 | 12.0 | 15.1 | 15.0 | 13.9 | 11.6 | 7.7 | 4.5 | 2.2 | 0.9 |
| E-7 | 4.8 | 6.8 | 7.6 | 11.8 | 14.4 | 14.8 | 13.9 | 11.5 | 7.4 | 4.5 | 1.9 | 0.6 |
| E-8 | 4.6 | 6.7 | 6.9 | 11.8 | 13.1 | 15.8 | 13.4 | 11.7 | 7.4 | 4.9 | 2.5 | 1.2 |
| E-9 | 4.3 | 6.6 | 7.4 | 12.5 | 13.8 | 15.6 | 13.8 | 11.6 | 7.7 | 4.5 | 1.8 | 0.4 |
| E-10 | 4.6 | 6.6 | 8.0 | 12.5 | 14.4 | 14.7 | 13.6 | 11.8 | 7.6 | 4.3 | 1.6 | 0.3 |
| E-11 | 3.6 | 6.6 | 7.8 | 11.9 | 14.5 | 15.4 | 14.1 | 11.5 | 7.8 | 4.6 | 1.8 | 0.3 |
| E-12 | 4.4 | 6.9 | 7.9 | 12.5 | 14.5 | 15.0 | 13.6 | 11.4 | 7.2 | 4.6 | 1.7 | 0.3 |

TABLE 69 icIEF results for Block E formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| E-1 | 4.4 | 7.1 | 7.1 | 15.0 | 11.9 | 15.3 | 13.5 | 11.1 | 7.9 | 4.4 | 1.8 | 0.5 |
| E-2 | 5.2 | 7.2 | 8.0 | 12.7 | 13.5 | 15.1 | 12.7 | 11.1 | 7.7 | 4.2 | 1.8 | 0.6 |

TABLE 69-continued icIEF results for Block E formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| E-3 | 4.9 | 7.9 | 6.8 | 11.6 | 15.0 | 15.3 | 13.3 | 11.6 | 6.9 | 4.2 | 1.8 | 0.8 |
| E-4 | 5.2 | 7.5 | 6.6 | 12.4 | 14.4 | 14.3 | 14.2 | 11.3 | 7.1 | 4.3 | 2.1 | 0.6 |
| E-5 | 5.1 | 6.3 | 7.7 | 12.8 | 14.0 | 15.1 | 14.1 | 11.2 | 7.4 | 4.1 | 1.7 | 0.5 |
| E-6 | 4.7 | 7.2 | 6.6 | 12.3 | 14.3 | 15.5 | 13.1 | 11.2 | 7.2 | 4.8 | 2.3 | 1.0 |
| E-7 | 4.9 | 7.7 | 8.0 | 11.9 | 14.4 | 15.5 | 13.1 | 11.2 | 7.0 | 4.1 | 1.7 | 0.5 |
| E-8 | 4.7 | 7.1 | 6.9 | 11.8 | 14.4 | 14.7 | 13.8 | 11.1 | 7.4 | 4.7 | 2.5 | 1.0 |
| E-9 | 4.7 | 6.6 | 7.7 | 13.1 | 14.5 | 14.8 | 14.1 | 11.1 | 6.9 | 4.2 | 1.7 | 0.6 |
| E-10 | 5.4 | 7.4 | 8.6 | 13.1 | 14.9 | 15.3 | 13.0 | 10.6 | 6.4 | 3.7 | 1.4 | 0.1 |
| E-11 | 5.6 | 8.3 | 8.4 | 12.6 | 14.7 | 14.9 | 13.6 | 9.6 | 6.5 | 3.8 | 1.6 | 0.4 |
| E-12 | 5.8 | 8.0 | 8.5 | 13.1 | 15.8 | 14.6 | 13.0 | 9.9 | 6.1 | 3.5 | 1.4 | 0.3 |

TABLE 70 icIEF results for Block E formulations after storage for two weeks at 25° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| E-1 | 5.5 | 6.7 | 8.4 | 14.1 | 12.3 | 15.5 | 13.1 | 10.7 | 7.3 | 4.1 | 1.7 | 0.7 |
| E-2 | 4.6 | 6.6 | 8.0 | 12.8 | 14.1 | 15.0 | 12.7 | 11.5 | 7.8 | 4.4 | 1.9 | 0.5 |
| E-3 | 4.7 | 7.6 | 6.7 | 11.7 | 14.9 | 15.3 | 13.7 | 10.9 | 7.7 | 4.3 | 2.0 | 0.6 |
| E-4 | 5.0 | 6.4 | 7.9 | 12.0 | 14.4 | 14.9 | 14.0 | 11.4 | 7.3 | 4.2 | 2.0 | 0.6 |
| E-5 | 4.9 | 6.3 | 7.7 | 12.4 | 14.8 | 15.1 | 13.4 | 11.2 | 7.6 | 4.2 | 1.9 | 0.6 |
| E-6 | 4.9 | 5.9 | 7.5 | 12.1 | 14.5 | 14.7 | 13.9 | 11.1 | 7.6 | 4.5 | 2.3 | 1.0 |
| E-7 | 4.5 | 6.9 | 7.9 | 11.8 | 14.3 | 15.1 | 14.4 | 10.9 | 7.4 | 4.4 | 1.8 | 0.6 |
| E-8 | 4.5 | 6.6 | 7.3 | 11.9 | 14.3 | 14.7 | 13.6 | 11.8 | 7.3 | 4.7 | 2.3 | 0.9 |
| E-9 | 4.4 | 6.5 | 7.3 | 12.4 | 14.4 | 15.7 | 13.5 | 11.5 | 7.8 | 4.5 | 1.7 | 0.5 |
| E-10 | 4.9 | 6.8 | 7.9 | 12.8 | 14.9 | 14.4 | 13.3 | 11.0 | 7.8 | 4.2 | 1.7 | 0.3 |
| E-11 | 5.1 | 6.7 | 8.2 | 12.2 | 14.4 | 14.9 | 13.5 | 11.1 | 7.2 | 4.4 | 1.8 | 0.5 |
| E-12 | 5.3 | 7.2 | 8.4 | 12.9 | 14.7 | 14.9 | 13.1 | 11.2 | 6.2 | 4.3 | 1.6 | 0.3 |

TABLE 71 icIEF results for Block E formulations after storage for four weeks at 5° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| E-1 | 5.1 | 6.6 | 7.2 | 14.2 | 11.8 | 15.2 | 13.7 | 11.4 | 7.9 | 4.5 | 2.0 | 0.5 |
| E-2 | 4.4 | 5.9 | 8.3 | 12.5 | 13.8 | 14.6 | 14.1 | 11.1 | 8.4 | 4.6 | 1.9 | 0.5 |
| E-3 | 4.7 | 6.3 | 7.5 | 12.2 | 14.2 | 15.8 | 13.9 | 10.9 | 7.7 | 4.3 | 1.9 | 0.6 |
| E-4 | 4.9 | 6.1 | 8.4 | 11.4 | 14.1 | 15.6 | 12.8 | 11.6 | 7.6 | 4.5 | 2.2 | 0.8 |
| E-5 | 4.7 | 6.0 | 7.7 | 12.4 | 14.5 | 14.8 | 13.8 | 11.3 | 7.7 | 4.5 | 2.0 | 0.6 |
| E-6 | 4.5 | 7.0 | 6.9 | 11.9 | 14.1 | 14.7 | 14.0 | 11.5 | 7.5 | 4.6 | 2.3 | 1.0 |
| E-7 | 4.3 | 6.8 | 7.8 | 11.8 | 14.4 | 14.7 | 14.0 | 11.5 | 7.7 | 4.6 | 1.9 | 0.6 |
| E-8 | 4.6 | 6.7 | 7.1 | 11.4 | 14.8 | 14.1 | 13.8 | 11.1 | 7.9 | 4.8 | 2.5 | 1.1 |
| E-9 | 4.1 | 6.2 | 7.6 | 11.9 | 14.3 | 14.9 | 14.3 | 11.7 | 7.8 | 4.7 | 2.0 | 0.6 |
| E-10 | 4.3 | 6.8 | 7.3 | 12.6 | 14.5 | 15.0 | 13.8 | 11.2 | 7.8 | 4.5 | 1.8 | 0.4 |
| E-11 | 4.9 | 6.8 | 7.8 | 11.0 | 14.4 | 15.3 | 13.8 | 11.0 | 7.8 | 4.5 | 2.1 | 0.5 |
| E-12 | 4.4 | 6.4 | 8.5 | 12.0 | 14.8 | 14.1 | 13.9 | 11.0 | 8.0 | 4.6 | 1.8 | 0.5 |

Discussion

The aflibercept formulations of Block E are physically and chemically stable.

Example 7—Aflibercept Formulations Free of Both Buffers and Organic Co-Solvents

This example describes experiments to evaluate aflibercept formulations that are free of a buffer and free of an organic co-solvent (Block F). Additionally, it was intended to investigate the behavior of mixtures of sucrose and NaCl across the same pH range of 5.5 to 7.0 in terms of aflibercept stability. Table 72, below, shows an exemplary set of such formulations.

TABLE 72

| Form No. | aflibercept | pH | Sucrose (mM) | NaCl (mM) |
|---|---|---|---|---|
| F-1 | 40 mg/ml | 5.5 | 200 | 40 |
| F-2 | 40 mg/ml | 5.5 | 270 | 0 |
| F-3 | 40 mg/ml | 6.0 | 200 | 40 |
| F-4 | 40 mg/ml | 6.0 | 270 | 0 |
| F-5 | 40 mg/ml | 6.2 | 200 | 40 |
| F-6 | 40 mg/ml | 6.2 | 0 | 150 |
| F-7 | 40 mg/ml | 7.0 | 270 | 0 |
| F-8 | 40 mg/ml | 6.2 | 150 | 75 |
| F-9 | 40 mg/ml | 6.5 | 200 | 40 |
| F-10 | 40 mg/ml | 6.5 | 270 | 0 |

TABLE 72-continued

| Form No. | aflibercept | pH | Sucrose (mM) | NaCl (mM) |
|---|---|---|---|---|
| F-11 | 40 mg/ml | 7.0 | 200 | 40 |
| F-12 | 40 mg/ml | 7.0 | 270 | 0 |
| F-13 | 40 mg/ml | 5.5 | 0 | 150 |
| F-14 | 40 mg/ml | 6.0 | 0 | 150 |
| F-15 | 40 mg/ml | 6.5 | 0 | 150 |

Concentration, pH, and Osmolality

The aflibercept concentration (mg/mL), pH, and osmolality (mOSm) of the Block F formulations were evaluated at t0. Results are reported in Table 73 below.

TABLE 73

| Form No. | Final Concentration (mg/mL) | Final pH | Final Osmolality (mOsm/Kg) |
|---|---|---|---|
| F-1 | 39.1 | 5.51 | 321 |
| F-2 | 39.71 | 5.57 | 312 |
| F-3 | 39.32 | 5.97 | 307 |
| F-4 | 38.96 | 5.97 | 311 |
| F-5 | 39.85 | 5.27 | 314 |
| F-6 | 39.71 | 7.06 | 291 |
| F-7 | 39.29 | 6.20 | 316 |
| F-8 | 39.77 | 6.26 | 337 |
| F-9 | 39.85 | 6.52 | 319 |
| F-10 | 39.45 | 6.45 | 318 |
| F-11 | 39.74 | 6.90 | 315 |
| F-12 | 39.52 | 6.91 | 316 |
| F-13 | 39.45 | 5.49 | 292 |
| F-14 | 39.66 | 5.98 | 288 |
| F-15 | 39.56 | 6.51 | 292 |

Size Exclusion Chromatography

The stability of the Block F formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Tables 74-77 below.

TABLE 74

SEC results for Block F formulations at T = 0

| Form No. | Rel. Area (%) HMW | Rel. Area (%) Main Peak | Rel. Area (%), After Main Peak |
|---|---|---|---|
| F-1 | 0.93 | 99.07 | 0 |
| F-2 | 0.93 | 99.07 | 0 |
| F-3 | 0.96 | 99.04 | 0 |
| F-4 | 0.88 | 99.12 | 0 |
| F-5 | 0.95 | 99.05 | 0 |
| F-6 | 1.01 | 98.99 | 0 |
| F-7 | 1.09 | 98.91 | 0 |
| F-8 | 1.05 | 98.95 | 0 |
| F-9 | 1.03 | 98.97 | 0 |
| F-10 | 1.20 | 98.80 | 0 |
| F-11 | 1.10 | 98.90 | 0 |
| F-12 | 1.36 | 98.64 | 0 |
| F-13 | 1.34 | 98.66 | 0 |
| F-14 | 1.54 | 98.46 | 0 |
| F-15 | 1.34 | 98.66 | 0 |

TABLE 75

SEC results for Block F formulations after one week at 40° C.

| Form No. | Rel. Area (%) HMW | Rel. Area (%) Main Peak | Rel. Area (%), After Main Peak |
|---|---|---|---|
| F-1 | 1.85 | 98.15 | 0 |
| F-2 | 1.06 | 98.94 | 0 |
| F-3 | 1.81 | 98.19 | 0 |
| F-4 | 1.38 | 98.62 | 0 |
| F-5 | 1.99 | 98.01 | 0 |
| F-6 | 3.15 | 96.85 | 0 |
| F-7 | 1.67 | 98.33 | 0 |
| F-8 | 2.17 | 97.83 | 0 |
| F-9 | 2.12 | 97.88 | 0 |
| F-10 | 1.96 | 98.04 | 0 |
| F-11 | 2.24 | 97.76 | 0 |
| F-12 | 2.26 | 97.74 | 0 |
| F-13 | 4.78 | 95.22 | 0 |
| F-14 | 3.33 | 96.67 | 0 |
| F-15 | 2.98 | 97.02 | 0 |

TABLE 76

SEC results for Block F formulations two weeks at 25° C.

| Form No. | Rel. Area (%) HMW | Rel. Area (%) Main Peak | Rel. Area (%), After Main Peak |
|---|---|---|---|
| F-1 | 1.29 | 98.71 | 0 |
| F-2 | 1.09 | 98.91 | 0 |
| F-3 | 1.35 | 98.65 | 0 |
| F-4 | 1.30 | 98.70 | 0 |
| F-5 | 1.48 | 98.52 | 0 |
| F-6 | 1.91 | 98.09 | 0 |
| F-7 | 1.43 | 98.57 | 0 |
| F-8 | 1.43 | 98.57 | 0 |
| F-9 | 1.54 | 98.46 | 0 |
| F-10 | 1.62 | 98.38 | 0 |
| F-11 | 1.71 | 98.29 | 0 |
| F-12 | 1.83 | 98.17 | 0 |
| F-13 | 1.37 | 98.63 | 0 |
| F-14 | 1.30 | 98.70 | 0 |
| F-15 | 1.48 | 98.52 | 0 |

TABLE 77

SEC results for Block F formulations after four weeks at 5° C.

| Form No. | Rel. Area (%) HMW | Rel. Area (%) Main Peak | Rel. Area (%), After Main Peak |
|---|---|---|---|
| F-1 | 0.92 | 99.08 | 0 |
| F-2 | 0.86 | 99.14 | 0 |
| F-3 | 0.99 | 99.01 | 0 |
| F-4 | 1.02 | 98.98 | 0 |
| F-5 | 1.13 | 98.87 | 0 |
| F-6 | 1.42 | 98.58 | 0 |
| F-7 | 1.07 | 98.93 | 0 |
| F-8 | 1.05 | 98.95 | 0 |
| F-9 | 1.16 | 98.84 | 0 |
| F-10 | 1.14 | 98.86 | 0 |
| F-11 | 1.30 | 98.70 | 0 |
| F-12 | 1.33 | 98.67 | 0 |
| F-13 | 1.00 | 99.00 | 0 |
| F-14 | 0.99 | 99.01 | 0 |
| F-15 | 1.14 | 98.86 | 0 |

The initial monomer levels were near 99, as it was for the other blocks. At 40° C., some of the formulations show somewhat larger increases in aggregation, but these are the formulations containing only NaCl.

After two weeks at 25° C., the losses were again fairly minimal, as was observed for the previous blocks. Slightly lower monomer levels were seen near pH 7. At 5° C., the aggregate contents were about 1%, reflecting only sight losses from T=0.

Micro-Flow Imaging

The stability of the Block F formulations was evaluated by measuring the particles present in the formulation after being subjected to storage conditions. These samples were also shipped frozen on dry ice prior to evaluation. Results are reported in Tables 78-81 below.

TABLE 78

MFI results for Block F formulations at T = 0

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| F-1 | 36606 | 8793 | 1488 | 200 | 0 |
| F-2 | 72224 | 15855 | 2776 | 466 | 56 |
| F-3 | 43057 | 9682 | 1643 | 289 | 22 |
| F-4 | 30899 | 7028 | 1221 | 200 | 0 |
| F-5 | 29301 | 6084 | 1255 | 189 | 11 |
| F-6 (1) | 24919 | 5335 | 803 | 121 | 30 |
| F-7 | 88434 | 28690 | 6895 | 1088 | 22 |
| F-8 | 33908 | 7028 | 1166 | 178 | 11 |
| F-9 | 23838 | 4774 | 722 | 211 | 44 |
| F-10 (2) | 45354 | 9184 | 1413 | 138 | 0 |
| F-11 | 20041 | 3575 | 389 | 11 | 0 |
| F-12 | 32931 | 5707 | 933 | 100 | 11 |
| F-13 | 18020 | 2898 | 378 | 67 | 0 |
| F-14 | 77098 | 23716 | 5429 | 722 | 22 |
| F-15 | 29189 | 5551 | 799 | 67 | 0 |

Note:
(1) Due to low sample volume- stopped at 70%
(2) Bubble during illumination >> Lowsample volume
n.a.—not applicable

TABLE 79

MFI results for Block F formulations stored for one week at 40° C.

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| F-1 | 57779 | 10959 | 1821 | 255 | 67 |
| F-2 | 23349 | 5885 | 988 | 233 | 67 |
| F-3 | 56192 | 13113 | 1921 | 266 | 89 |
| F-4 | 33786 | 6362 | 910 | 167 | 11 |
| F-5 | 53638 | 4275 | 1399 | 167 | 11 |
| F-6 | 11580 | 3375 | 600 | 133 | 33 |
| F-7 | 6640 | 1699 | 278 | 56 | 22 |
| F-8 | 30877 | 6273 | 600 | 44 | 11 |
| F-9 | 45244 | 11414 | 1599 | 455 | 22 |
| F-10 | 59911 | 11070 | 2065 | 455 | 56 |
| F-11 | 39304 | 8038 | 988 | 167 | 0 |
| F-12 | 28179 | 5174 | 699 | 144 | 22 |
| F-13 | 35540 | 8150 | 1443 | 389 | 67 |
| F-14 | 32443 | 6640 | 1066 | 266 | 22 |
| F-15 | 32276 | 5751 | 755 | 22 | 0 |

TABLE 80

MFI results for Block F formulations stored for two weeks at 25° C.

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| F-1 | 29967 | 7228 | 1366 | 222 | 67 |
| F-2 | 28756 | 6517 | 1066 | 189 | 33 |
| F-3 | 38549 | 8860 | 1410 | 355 | 33 |
| F-4 | 25415 | 5996 | 866 | 100 | 0 |
| F-5 | 28257 | 6262 | 822 | 56 | 11 |
| F-6 | 35718 | 9848 | 1554 | 89 | 0 |
| F-7 | 12200 | 1712 | 291 | 146 | 36 |
| F-8 | 13912 | 3020 | 378 | 11 | 0 |
| F-9 | 6628 | 1166 | 133 | 11 | 0 |
| F-10 (1) | 35241 | 7150 | 866 | 89 | 0 |
| F-11 | 8316 | 1765 | 366 | 33 | 11 |
| F-12 | 31510 | 5363 | 666 | 100 | 0 |
| F-13 | 23605 | 5962 | 1221 | 233 | 11 |
| F-14 | 16421 | 4785 | 1133 | 167 | 0 |
| F-15 | 12724 | 2809 | 400 | 56 | 0 |

Note:
(1) Schileren Lines observed detected post-MVSS analysis, Time stamp filter used.

TABLE 81

MFI results for Block F formulations stored for four weeks at 5° C.

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| F-1 | 34397 | 8738 | 1488 | 167 | 44 |
| F-2 | 12424 | 2465 | 444 | 33 | 11 |
| F-3 | 34541 | 8993 | 1765 | 500 | 144 |
| F-4 | 25470 | 6118 | 1088 | 100 | 0 |
| F-5 | 37328 | 8982 | 1810 | 222 | 44 |
| F-6 | 62387 | 19930 | 4208 | 799 | 33 |
| F-7 | 17865 | 3620 | 588 | 89 | 0 |
| F-8 | 24360 | 5474 | 844 | 167 | 11 |
| F-9 | 11347 | 2598 | 444 | 67 | 0 |
| F-10 | 26092 | 4585 | 588 | 33 | 0 |
| F-11 | 17409 | 3686 | 633 | 100 | 22 |
| F-12 | 20241 | 4075 | 555 | 78 | 0 |
| F-13 | 40836 | 10714 | 2476 | 344 | 11 |
| F-14 | 23138 | 4108 | 677 | 122 | 11 |
| F-15 | 23749 | 5207 | 844 | 56 | 11 |

Imaging Capillary Isoelectric Focusing (icIEF)

The chemical stability of the Block F formulations was evaluated by measuring the charge variants present in the formulation after being subjected to storage conditions. These samples were frozen and shipped on dry ice prior to analysis. Results are reported in Tables 82-85 below.

TABLE 82 icIEF results for Block F formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| F-1 | 4.3 | 5.8 | 8.0 | 11.7 | 13.6 | 14.9 | 14.2 | 11.3 | 8.2 | 4.8 | 2.4 | 0.8 |
| F-2 | 4.5 | 6.0 | 7.3 | 12.2 | 14.1 | 14.5 | 13.7 | 11.6 | 7.4 | 5.4 | 2.5 | 0.8 |
| F-3 | 4.3 | 7.1 | 6.2 | 11.7 | 14.8 | 14.7 | 14.1 | 11.7 | 7.7 | 5.0 | 2.3 | 0.6 |

TABLE 82-continued icIEF results for Block F formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| F-4  | 4.8 | 6.4 | 7.3 | 12.5 | 14.7 | 13.1 | 15.1 | 11.1 | 7.4 | 4.8 | 2.4 | 0.7 |
| F-5  | 4.2 | 5.9 | 7.5 | 12.3 | 14.5 | 14.8 | 13.9 | 11.8 | 7.7 | 4.8 | 2.2 | 0.6 |
| F-6  | 4.5 | 6.1 | 7.7 | 12.1 | 14.3 | 15.0 | 13.4 | 11.7 | 7.8 | 4.6 | 2.1 | 0.7 |
| F-7  | 4.2 | 6.5 | 7.3 | 12.1 | 14.1 | 15.6 | 13.6 | 11.9 | 7.6 | 4.7 | 1.9 | 0.5 |
| F-8  | 4.3 | 7.5 | 6.3 | 12.1 | 14.3 | 14.9 | 14.3 | 11.3 | 7.8 | 4.8 | 1.9 | 0.5 |
| F-9  | 4.4 | 6.4 | 7.2 | 11.8 | 14.1 | 15.0 | 14.1 | 11.2 | 8.1 | 4.8 | 2.1 | 0.7 |
| F-10 | 4.3 | 6.0 | 7.8 | 11.7 | 14.0 | 15.3 | 13.8 | 11.6 | 7.9 | 4.8 | 2.3 | 0.6 |
| F-11 | 4.2 | 6.9 | 6.9 | 12.2 | 14.0 | 15.4 | 14.0 | 11.3 | 8.0 | 4.5 | 1.9 | 0.6 |
| F-12 | 4.4 | 6.7 | 6.9 | 12.0 | 14.9 | 14.8 | 14.2 | 11.4 | 8.0 | 4.5 | 1.9 | 0.4 |
| F-13 | 4.5 | 6.2 | 6.8 | 12.8 | 14.1 | 14.6 | 13.7 | 12.0 | 7.9 | 4.7 | 2.1 | 0.5 |
| F-14 | 4.3 | 6.2 | 7.3 | 12.0 | 14.4 | 15.4 | 13.8 | 11.4 | 7.8 | 4.6 | 2.2 | 0.6 |
| F-15 | 4.8 | 6.4 | 7.2 | 12.6 | 13.3 | 15.1 | 13.8 | 11.4 | 7.9 | 4.6 | 2.1 | 0.7 |

TABLE 83 icIEF results for Block F formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| F-1  | 4.5 | 7.1 | 6.2 | 11.7 | 14.3 | 14.8 | 13.8 | 11.2 | 8.0 | 5.1 | 2.5 | 0.9 |
| F-2  | 4.5 | 6.2 | 7.5 | 12.0 | 14.1 | 15.0 | 13.7 | 11.7 | 7.2 | 5.0 | 2.4 | 0.7 |
| F-3  | 4.9 | 7.1 | 7.1 | 11.6 | 14.2 | 14.9 | 13.7 | 11.0 | 7.6 | 4.9 | 2.3 | 0.7 |
| F-4  | 4.8 | 6.4 | 7.3 | 12.5 | 14.7 | 15.1 | 13.1 | 11.1 | 7.4 | 4.8 | 2.2 | 0.7 |
| F-5  | 4.9 | 6.6 | 7.3 | 12.0 | 14.3 | 15.0 | 13.6 | 11.4 | 7.4 | 4.7 | 2.1 | 0.6 |
| F-6  | 5.7 | 7.3 | 7.9 | 13.4 | 14.1 | 15.3 | 13.4 | 10.4 | 6.5 | 4.0 | 1.6 | 0.5 |
| F-7  | 4.8 | 7.1 | 7.2 | 12.7 | 14.7 | 14.8 | 13.8 | 10.8 | 7.2 | 4.5 | 1.9 | 0.4 |
| F-8  | 4.9 | 6.6 | 7.4 | 12.0 | 14.3 | 15.3 | 13.5 | 11.3 | 7.3 | 4.8 | 2.1 | 0.6 |
| F-9  | 5.4 | 7.1 | 7.5 | 11.5 | 14.3 | 15.1 | 13.9 | 10.6 | 7.3 | 4.6 | 2.0 | 0.6 |
| F-10 | 5.0 | 8.3 | 6.9 | 11.9 | 14.4 | 15.3 | 12.8 | 11.3 | 7.4 | 4.3 | 1.9 | 0.5 |
| F-11 | 5.5 | 8.2 | 6.4 | 13.4 | 14.1 | 14.5 | 13.6 | 10.6 | 6.7 | 4.4 | 1.9 | 0.7 |
| F-12 | 5.1 | 8.0 | 7.3 | 13.8 | 14.9 | 14.5 | 13.6 | 10.6 | 6.5 | 3.8 | 1.5 | 0.3 |
| F-13 | 4.3 | 6.2 | 6.9 | 11.6 | 14.0 | 15.9 | 14.3 | 11.7 | 7.5 | 4.7 | 2.3 | 0.7 |
| F-14 | 4.5 | 6.1 | 7.9 | 11.6 | 14.8 | 14.9 | 13.6 | 11.6 | 7.4 | 4.6 | 2.2 | 0.7 |
| F-15 | 4.9 | 6.8 | 7.4 | 12.4 | 14.6 | 15.1 | 13.7 | 11.0 | 7.2 | 4.2 | 2.0 | 0.7 |

TABLE 84 icIEF results for Block F formulations after storage for two weeks at 25° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| F-1  | 4.6 | 5.9 | 7.5 | 11.8 | 13.9 | 14.7 | 13.8 | 11.7 | 7.9 | 5.0 | 2.4 | 0.8 |
| F-2  | 4.8 | 6.0 | 7.6 | 12.3 | 14.2 | 14.4 | 14.1 | 11.3 | 7.8 | 4.8 | 2.1 | 0.6 |
| F-3  | 4.2 | 5.9 | 7.6 | 12.2 | 14.1 | 14.6 | 14.1 | 11.7 | 7.8 | 4.8 | 2.3 | 0.7 |
| F-4  | 4.3 | 6.0 | 7.5 | 12.3 | 14.3 | 15.4 | 13.6 | 11.4 | 7.6 | 4.8 | 2.1 | 0.6 |
| F-5  | 4.8 | 6.2 | 7.7 | 11.7 | 14.5 | 14.9 | 13.4 | 11.4 | 7.8 | 4.8 | 2.2 | 0.7 |
| F-6  | 4.8 | 6.5 | 7.9 | 12.3 | 14.1 | 14.4 | 14.0 | 11.3 | 7.4 | 4.5 | 2.1 | 0.8 |
| F-7  | 4.4 | 6.2 | 7.5 | 11.7 | 14.6 | 14.7 | 14.3 | 11.9 | 7.4 | 4.7 | 2.0 | 0.7 |
| F-8  | 4.5 | 6.1 | 7.0 | 12.7 | 14.0 | 14.4 | 13.9 | 11.9 | 7.8 | 4.7 | 2.1 | 0.8 |
| F-9  | 4.8 | 6.1 | 7.7 | 11.7 | 13.9 | 14.9 | 13.7 | 11.4 | 7.8 | 4.8 | 2.3 | 0.8 |
| F-10 | 4.5 | 6.0 | 7.7 | 12.3 | 14.5 | 15.0 | 13.8 | 11.4 | 7.6 | 4.7 | 2.1 | 0.6 |
| F-11 | 5.1 | 7.9 | 6.7 | 12.0 | 13.8 | 15.8 | 13.5 | 11.1 | 7.6 | 4.4 | 1.8 | 0.5 |
| F-12 | 5.2 | 6.8 | 7.5 | 12.1 | 14.2 | 14.9 | 13.8 | 11.3 | 7.3 | 4.4 | 2.0 | 0.6 |
| F-13 | 4.3 | 5.8 | 7.3 | 11.6 | 14.5 | 14.9 | 14.5 | 11.4 | 7.6 | 4.9 | 2.4 | 1.0 |
| F-14 | 4.5 | 6.3 | 7.3 | 12.2 | 14.3 | 15.0 | 13.8 | 11.8 | 7.7 | 4.6 | 2.0 | 0.6 |
| F-15 | 4.7 | 6.8 | 7.2 | 12.2 | 14.6 | 14.7 | 13.8 | 11.7 | 7.4 | 4.6 | 1.9 | 0.5 |

TABLE 85 icIEF results for Block F formulations after storage for four weeks at 5° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| F-1 | 3.7 | 6.2 | 7.4 | 11.8 | 14.3 | 15.4 | 14.1 | 11.4 | 7.8 | 4.8 | 2.3 | 0.8 |
| F-2 | 4.8 | 5.9 | 7.8 | 11.5 | 14.6 | 14.6 | 14.1 | 11.5 | 7.8 | 4.8 | 2.1 | 0.6 |
| F-3 | 4.3 | 6.1 | 7.2 | 12.5 | 14.3 | 14.5 | 14.1 | 11.9 | 7.6 | 4.8 | 2.1 | 0.6 |
| F-4 | 4.6 | 6.0 | 7.9 | 12.5 | 13.5 | 15.0 | 14.0 | 11.4 | 7.8 | 4.7 | 2.1 | 0.5 |
| F-5 | 4.5 | 6.3 | 7.6 | 11.5 | 14.7 | 15.0 | 13.7 | 11.4 | 7.8 | 4.8 | 2.2 | 0.6 |
| F-6 | 4.6 | 6.1 | 7.5 | 11.8 | 14.5 | 15.2 | 13.8 | 11.3 | 7.9 | 4.6 | 2.1 | 0.6 |
| F-7 | 4.5 | 6.1 | 7.7 | 11.7 | 14.1 | 15.1 | 13.9 | 11.8 | 7.6 | 4.9 | 2.1 | 0.5 |
| F-8 | 4.4 | 6.6 | 7.4 | 11.6 | 14.2 | 15.7 | 13.7 | 11.2 | 7.9 | 4.5 | 2.0 | 0.6 |
| F-9 | 4.1 | 6.5 | 7.6 | 11.9 | 14.0 | 15.2 | 14.1 | 11.3 | 7.8 | 4.8 | 2.1 | 0.6 |
| F-10 | 4.3 | 6.3 | 7.5 | 12.2 | 13.6 | 15.3 | 14.0 | 11.2 | 8.3 | 4.8 | 2.0 | 0.6 |
| F-11 | 4.4 | 7.2 | 6.4 | 12.3 | 13.8 | 15.5 | 14.2 | 11.5 | 7.7 | 4.7 | 1.8 | 0.6 |
| F-12 | 4.5 | 6.7 | 6.9 | 12.3 | 14.3 | 14.7 | 14.0 | 11.7 | 7.4 | 4.7 | 2.3 | 0.6 |
| F-13 | 4.2 | 6.8 | 7.0 | 12.7 | 14.0 | 14.9 | 14.3 | 11.1 | 8.1 | 4.5 | 1.9 | 0.5 |
| F-14 | 4.5 | 6.2 | 7.2 | 11.9 | 14.5 | 14.6 | 14.0 | 11.5 | 7.8 | 4.7 | 2.3 | 0.8 |
| F-15 | 4.6 | 6.2 | 7.3 | 11.6 | 14.7 | 14.6 | 13.5 | 11.7 | 7.9 | 4.6 | 2.3 | 0.8 |

Discussion

The aflibercept formulations of Block F are physically and chemically stable.

Example 8—Aflibercept Formulations

This example describes experiments to evaluate aflibercept formulations with various excipient combinations (Block G). Formulations in Block G include those that are free of a buffer; free of an organic co-solvent; include a sugar other than sucrose, include a polyol; include a surfactant other than polysorbate 20 (e.g. in buffer-free formulations); include $CaCl_2$) as a stabilizer; and have a high concentration of aflibercept. Table 86, below, shows an exemplary set of such formulations.

Concentration, pH, and Osmolality

The aflibercept concentration (mg/mL), pH, and osmolality (mOSm) of the Block G formulations were evaluated at t0. Results are reported in Table 87 below.

TABLE 87

| Form No. | Final Concentration (mg/mL) | Final pH | Final Osmolality (mOsm/Kg) |
|---|---|---|---|
| G-1 | 78.13 | 6.23 | 354 |
| G-2 | 117.44 | 6.26 | 360 |
| G-3 | 40.02 | 6.24 | 300 |
| G-4 | 78.55 | 6.23 | 330 |
| G-5 | 118.49 | 6.23 | 361 |
| G-6 | 39.63 | 6.22 | 298 |
| G-7 | 39.27 | 6.22 | 298 |
| G-8 | 39.83 | 6.21 | 293 |
| G-9 | 39.71 | 6.21 | 300 |
| G-10 | 39.70 | 6.28 | 332 |
| G-11 | 38.97 | 6.22 | 320 |
| G-12 | 39.56 | 6.27 | 296 |

TABLE 86

| Form No. | aflibercept | pH | Sucrose (mM) | NaCl (mM) | Surfactant (wt %) | Other |
|---|---|---|---|---|---|---|
| G-1 | 40 mg/ml | 6.2 | 200 | 40 | 0 | 10 mM His |
| G-2 | 80 mg/ml | 6.2 | 200 | 40 | 0 | 10 mM His |
| G-3 | 120 mg/ml | 6.2 | 200 | 40 | 0 | 10 mM His |
| G-4 | 40 mg/ml | 6.2 | 200 | 40 | 0.03% PS 20 | None |
| G-5 | 80 mg/ml | 6.2 | 200 | 40 | 0.03% PS 20 | None |
| G-6 | 120 mg/ml | 6.2 | 200 | 40 | 0.03% PS 20 | None |
| G-7 | 40 mg/ml | 6.2 | 200 | 40 | 0.06% PS 20 | None |
| G-8 | 40 mg/ml | 6.2 | 200 | 40 | 0.03% PS 80 | None |
| G-9 | 40 mg/ml | 6.2 | 200 | 40 | 0.06% PS 80 | None |
| G-10 | 40 mg/ml | 6.2 | 200 | 40 | 0.1% F-68 | None |
| G-11 | 40 mg/ml | 6.2 | 0 | 40 | 0 | 200 mM trehalose |
| G-12 | 40 mg/ml | 6.2 | 0 | 40 | 0 | 200 mM lactose |
| G-13 | 40 mg/ml | 6.2 | 0 | 40 | 0 | 200 mM sorbitol |
| G-14 | 40 mg/ml | 6.2 | 0 | 40 | 0 | 200 mM glycine |
| G-15 | 40 mg/ml | 6.2 | 0 | 40 | 0 | 200 mM xylitol |
| G-16 | 40 mg/ml | 6.2 | 170 | 40 | 0 | 50 mM phosphate |
| G-17 | 40 mg/ml | 6.2 | 170 | 40 | 0 | 50 mM His |
| G-18 | 40 mg/ml | 6.2 | 270 | 0 | 0.06% PS 80 | None |
| G-19 | 40 mg/ml | 6.2 | 200 | 40 | 0 | 1% PG |
| G-20 | 40 mg/ml | 6.2 | 200 | 40 | 0 | 1% glycerol |
| G-21 | 40 mg/ml | 6.2 | 170 | 40 | 0 | 5% glycerol |
| G-22 | 40 mg/ml | 6.2 | 200 | 0 | 0 | 20 mM glycine |
| G-23 | 40 mg/ml | 6.2 | 200 | 20 | 0 | 10 mM $CaCl_2$ |
| G-24 | 40 mg/ml | 6.2 | 200 | 20 | 0.03% PS 20 | 10 mM $CaCl_2$ |

TABLE 87-continued

| Form No. | Final Concentration (mg/mL) | Final pH | Final Osmolality (mOsm/Kg) |
|---|---|---|---|
| G-13 | 40.39 | 6.24 | 286 |
| G-14 | 39.47 | 6.18 | 298 |
| G-15 | 39.73 | 6.26 | 377 |
| G-16 | 39.63 | 6.23 | 354 |
| G-17 | 38.65 | 6.24 | 313 |
| G-18 | 39.59 | 6.28 | 467 |
| G-19 | 39.76 | 6.25 | 436 |
| G-20 | 39.52 | 6.21 | 945 |
| G-21 | 39.21 | 6.22 | 354 |
| G-22 | 39.21 | 6.21 | 300 |
| G-23 | 39.28 | 6.29 | 295 |
| G-24 | 78.13 | 6.23 | 354 |

Size Exclusion Chromatography

The stability of the Block G formulations was evaluated by measuring the amount of non-degraded aflibercept present in the formulation at time 0 (t0) and after being subjected to storage conditions. Size Exclusion Chromatography was conducted on the formulations and the percentage of protein present in the main peak (non-degraded aflibercept) in each formulation is reported in Tables 88-91 below.

TABLE 88

SEC results for Block G formulations at T = 0

| Form No. | Rel. Area (%) HMW) | Rel. Area (%) Main Peak | Rel. Area (%), After Main Peak |
|---|---|---|---|
| G-1 | 1.02 | 98.98 | 0.00 |
| G-2 | 1.16 | 98.84 | 0.00 |
| G-3 | 1.34 | 98.66 | 0.00 |
| G-4 | 1.10 | 98.90 | 0.00 |
| G-5 | 1.45 | 98.55 | 0.00 |
| G-6 | 1.51 | 98.49 | 0.00 |
| G-7 | 1.11 | 98.89 | 0.00 |
| G-8 | 1.11 | 98.89 | 0.00 |
| G-9 | 1.08 | 98.92 | 0.00 |
| G-10 | 1.09 | 98.91 | 0.00 |
| G-11 | 1.07 | 98.93 | 0.00 |
| G-12 | 1.16 | 98.84 | 0.00 |
| G-13 | 1.12 | 98.88 | 0.00 |
| G-14 | 0.98 | 99.02 | 0.00 |
| G-15 | 1.10 | 98.90 | 0.00 |
| G-16 | 0.98 | 99.02 | 0.00 |
| G-17 | 0.90 | 99.10 | 0.00 |
| G-18 | 1.01 | 98.99 | 0.00 |
| G-19 | 1.03 | 98.97 | 0.00 |
| G-20 | 1.04 | 98.96 | 0.00 |
| G-21 | 1.00 | 99.00 | 0.00 |
| G-22 | 0.96 | 99.04 | 0.00 |
| G-23 | 0.99 | 99.01 | 0.00 |
| G-24 | 0.98 | 99.02 | 0.00 |

TABLE 89

SEC results for Block G formulations after one week at 40° C.

| Form No. | Rel. Area (%) HMW) | Rel. Area (%) Main Peak | Rel. Area (%), After Main Peak |
|---|---|---|---|
| G-1 | 1.90 | 98.10 | 0.00 |
| G-2 | 2.81 | 97.19 | 0.00 |
| G-3 | 3.83 | 96.17 | 0.00 |
| G-4 | 2.12 | 97.88 | 0.00 |
| G-5 | 3.24 | 96.76 | 0.00 |
| G-6 | 4.34 | 95.66 | 0.00 |
| G-7 | 2.23 | 97.77 | 0.00 |
| G-8 | 2.14 | 97.86 | 0.00 |
| G-9 | 2.19 | 97.81 | 0.00 |
| G-10 | 2.14 | 97.86 | 0.00 |
| G-11 | 2.05 | 97.95 | 0.00 |
| G-12 | 2.42 | 97.58 | 0.00 |
| G-13 | 2.41 | 97.59 | 0.00 |
| G-14 | 2.31 | 97.69 | 0.00 |
| G-15 | 2.47 | 97.53 | 0.00 |
| G-16 | 1.94 | 98.06 | 0.00 |
| G-17 | 1.76 | 98.24 | 0.00 |
| G-18 | 1.82 | 98.18 | 0.00 |
| G-19 | 2.22 | 97.78 | 0.00 |
| G-20 | 2.05 | 97.95 | 0.00 |
| G-21 | 1.78 | 98.22 | 0.00 |
| G-22 | 1.82 | 98.18 | 0.00 |
| G-23 | 1.94 | 98.06 | 0.00 |
| G-24 | 1.99 | 98.01 | 0.00 |

TABLE 90

SEC results for Block G formulations two weeks at 25° C.

| Form No. | Rel. Area (%) HMW) | Rel. Area (%) Main Peak | Rel. Area (%), After Main Peak |
|---|---|---|---|
| G-1 | 1.05 | 98.95 | 0.00 |
| G-2 | 1.31 | 98.69 | 0.00 |
| G-3 | 1.59 | 98.41 | 0.00 |
| G-4 | 1.19 | 98.81 | 0.00 |
| G-5 | 1.58 | 98.42 | 0.00 |
| G-6 | 1.86 | 98.14 | 0.00 |
| G-7 | 1.23 | 98.77 | 0.00 |
| G-8 | 1.19 | 98.81 | 0.00 |
| G-9 | 1.20 | 98.80 | 0.00 |
| G-10 | 1.22 | 98.78 | 0.00 |
| G-11 | 1.25 | 98.75 | 0.00 |
| G-12 | 1.42 | 98.58 | 0.00 |
| G-13 | 1.25 | 98.75 | 0.00 |
| G-14 | 1.10 | 98.90 | 0.00 |
| G-15 | 1.25 | 98.75 | 0.00 |
| G-16 | 1.08 | 98.92 | 0.00 |
| G-17 | 0.87 | 99.13 | 0.00 |
| G-18 | 1.19 | 98.81 | 0.00 |
| G-19 | 1.21 | 98.79 | 0.00 |
| G-20 | 1.18 | 98.82 | 0.00 |
| G-21 | 1.18 | 98.82 | 0.00 |
| G-22 | 1.14 | 98.86 | 0.00 |
| G-23 | 1.07 | 98.93 | 0.00 |
| G-24 | 1.12 | 98.88 | 0.00 |

TABLE 91

SEC results for Block G formulations after four weeks at 5° C.

| Form No. | Rel. Area (%) HMW) | Rel. Area (%) Main Peak | Rel. Area (%), After Main Peak |
|---|---|---|---|
| G-1 | 0.96 | 99.04 | 0.00 |
| G-2 | 1.18 | 98.82 | 0.00 |
| G-3 | 1.40 | 98.60 | 0.00 |
| G-4 | 1.15 | 98.85 | 0.00 |
| G-5 | 1.44 | 98.56 | 0.00 |
| G-6 | 1.63 | 98.37 | 0.00 |
| G-7 | 1.19 | 98.81 | 0.00 |
| G-8 | 1.13 | 98.87 | 0.00 |
| G-9 | 1.15 | 98.85 | 0.00 |
| G-10 | 1.13 | 98.87 | 0.00 |
| G-11 | 1.11 | 98.89 | 0.00 |
| G-12 | 1.20 | 98.80 | 0.00 |
| G-13 | 1.14 | 98.86 | 0.00 |
| G-14 | 0.99 | 99.01 | 0.00 |
| G-15 | 1.15 | 98.85 | 0.00 |
| G-16 | 0.98 | 99.02 | 0.00 |
| G-17 | 0.87 | 99.13 | 0.00 |

TABLE 91-continued

SEC results for Block G formulations after four weeks at 5° C.

| Form No. | Rel. Area (%) HMW) | Rel. Area (%) Main Peak | Rel. Area (%), After Main Peak |
|---|---|---|---|
| G-18 | 1.06 | 98.94 | 0.00 |
| G-19 | 1.10 | 98.90 | 0.00 |
| G-20 | 1.08 | 98.92 | 0.00 |
| G-21 | 1.06 | 98.94 | 0.00 |
| G-22 | 1.05 | 98.95 | 0.00 |
| G-23 | 1.02 | 98.98 | 0.00 |
| G-24 | 1.03 | 98.97 | 0.00 |

At t=0 monomer contents are near 99%. Upon 40° C. storage, the monomer contents varied around 98%. After two weeks at 25° C., there appears some higher level of aggregation at higher protein concentrations. As with other blocks, the losses at 5° C. after four weeks are insignificant.

Micro-Flow Imaging

The stability of the Block G formulations was evaluated by measuring the particles present in the formulation after being subjected to storage conditions. These samples were also shipped frozen on dry ice prior to evaluation. Results are reported in Tables 92-95 below.

TABLE 92

MFI results for Block G formulations at T = 0

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| G-1 | 17143 | 3986 | 511 | 67 | 0 |
| G-2 | 37283 | 7494 | 844 | 100 | 0 |
| G-3 | 20250 | 3333 | 422 | 46 | 11 |
| G-4 | 4996 | 866 | 111 | 11 | 0 |
| G-5 | 11536 | 1654 | 100 | 44 | 11 |
| G-6 | 9876 | 1484 | 114 | 23 | 0 |
| G-7 | 4119 | 500 | 0 | 0 | 0 |
| G-8 | 3986 | 400 | 0 | 0 | 0 |
| G-9 | 3764 | 744 | 67 | 11 | 0 |
| G-10 | 7594 | 1266 | 167 | 22 | 11 |
| G-11 | 7872 | 1477 | 200 | 11 | 0 |
| G-12 | 13224 | 2121 | 233 | 22 | 11 |
| G-13 | 9215 | 1665 | 189 | 33 | 0 |
| G-14 | 15178 | 3231 | 477 | 89 | 0 |
| G-15 | 10759 | 1677 | 211 | 11 | 11 |
| G-16 | 12902 | 2110 | 189 | 33 | 0 |
| G-17 | 11247 | 1776 | 178 | 33 | 0 |
| G-18 | 10925 | 999 | 155 | 22 | 0 |
| G-19 | 8316 | 1299 | 255 | 100 | 11 |
| G-20 | 8449 | 1099 | 167 | 11 | 0 |
| G-21 | 11991 | 2032 | 155 | 11 | 0 |
| G-22 | 14511 | 2387 | 244 | 67 | 0 |
| G-23 | 24948 | 4341 | 344 | 78 | 0 |
| G-24 | 10570 | 1899 | 167 | 22 | 11 |

Note:
for most samples non-detected MVSS Schlieren lines were observed for most samples. High concentration samples (G3 and G6, @ 120 mgmL) had detectable shlieren lines which is expected.

TABLE 93

MFI results for Block G formulations stored for one week at 40° C.

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| G-1 | 38982 | 7583 | 744 | 78 | 22 |
| G-2 | 28701 | 8472 | 1288 | 167 | 11 |
| G-3 | 10204 | 1377 | 133 | 33 | 11 |
| G-4 | 9504 | 2098 | 422 | 89 | 22 |
| G-5 | 41403 | 2498 | 78 | 11 | 0 |
| G-6 | 7640 | 571 | 91 | 23 | 0 |
| G-7 | 18675 | 3853 | 799 | 289 | 78 |
| G-8 | 6728 | 1188 | 178 | 67 | 22 |
| G-9 | 8749 | 1621 | 178 | 56 | 56 |
| G-10 | 12635 | 2321 | 244 | 67 | 0 |
| G-11 | 26780 | 4186 | 355 | 78 | 11 |
| G-12 | 60600 | 14778 | 2321 | 366 | 33 |
| G-13 | 61854 | 13501 | 1732 | 278 | 44 |
| G-14 | 63386 | 16033 | 1910 | 155 | 22 |
| G-15 | 22395 | 4841 | 489 | 22 | 0 |
| G-16 | 24959 | 5296 | 1188 | 144 | 22 |
| G-17 | 39060 | 7039 | 811 | 100 | 33 |
| G-18 | 1999 | 222 | 22 | 22 | 22 |
| G-19 | 57158 | 12158 | 1887 | 155 | 11 |
| G-20 | 34641 | 4785 | 644 | 111 | 22 |
| G-21 | 37850 | 7250 | 1343 | 333 | 11 |
| G-22 | 25204 | 5207 | 1155 | 178 | 22 |
| G-23 | 26014 | 5019 | 755 | 133 | 33 |
| G-24 | 3742 | 977 | 333 | 111 | 11 |

TABLE 94

MFI results for Block G formulations stored for two weeks at 25° C.

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| G-1 | 27935 | 5263 | 666 | 89 | 0 |
| G-2 | 12546 | 3397 | 355 | 44 | 22 |
| G-3 | 7697 | 1576 | 320 | 57 | 11 |
| G-4 | 8505 | 1477 | 189 | 78 | 11 |
| G-5 | 3930 | 699 | 78 | 11 | 0 |
| G-6 | 7970 | 1028 | 57 | 11 | 0 |
| G-7 | 5152 | 1055 | 133 | 11 | 0 |
| G-8 | 3386 | 533 | 44 | 22 | 11 |
| G-9 | 10148 | 2631 | 1210 | 322 | 11 |
| G-10 | 2842 | 777 | 122 | 11 | 0 |
| G-11 | 14123 | 2698 | 289 | 67 | 11 |
| G-12 | 21873 | 7261 | 1732 | 533 | 11 |
| G-13 | 26181 | 6728 | 844 | 67 | 22 |
| G-14 | 13756 | 3797 | 555 | 67 | 22 |
| G-15 | 8727 | 2065 | 311 | 67 | 11 |
| G-16 | 2687 | 400 | 111 | 56 | 11 |
| G-17 | 7972 | 1821 | 444 | 78 | 0 |
| G-18 | 8749 | 1377 | 200 | 78 | 11 |
| G-19 | 6129 | 1521 | 289 | 22 | 0 |
| G-20 | 3575 | 600 | 200 | 33 | 11 |
| G-21 | 11336 | 1921 | 355 | 56 | 0 |
| G-22 | 8727 | 2298 | 366 | 44 | 0 |
| G-23 | 12435 | 2098 | 466 | 89 | 11 |
| G-24 | 10270 | 2620 | 677 | 100 | 0 |

TABLE 95

MFI results for Block G formulations stored for four weeks at 5° C.

| Form. Block | Particle Conc. (#/mL) | ≥2 μm (#/mL) | ≥5 μm (#/mL) | ≥10 μm (#/mL) | ≥25 μm (#/mL) |
|---|---|---|---|---|---|
| G-1 | 11702 | 2709 | 444 | 22 | 0 |
| G-2 | 21839 | 5474 | 1055 | 189 | 33 |
| G-3 | 8506 | 2261 | 285 | 91 | 11 |
| G-4 | 5529 | 977 | 100 | 44 | 11 |
| G-5 | 10514 | 2587 | 511 | 155 | 33 |
| G-6 | 1715 | 422 | 0 | 0 | 0 |
| G-7 | 13979 | 2443 | 300 | 122 | 33 |
| G-8 | 8194 | 1510 | 89 | 33 | 11 |
| G-9 | 6029 | 1299 | 289 | 78 | 11 |
| G-10 | 16621 | 3253 | 389 | 56 | 11 |
| G-11 | 9548 | 2176 | 344 | 44 | 11 |
| G-12 | 4241 | 1510 | 311 | 89 | 0 |
| G-13 | 18309 | 4363 | 577 | 144 | 0 |
| G-14 | 8383 | 2376 | 455 | 133 | 22 |
| G-15 | 13035 | 3353 | 600 | 67 | 11 |
| G-16 | 8827 | 1932 | 600 | 155 | 22 |
| G-17 | 3509 | 744 | 244 | 67 | 11 |
| G-18 | 7050 | 1155 | 100 | 0 | 0 |
| G-19 | 13201 | 3520 | 1088 | 189 | 11 |
| G-20 | 10570 | 2254 | 289 | 56 | 0 |
| G-21 | 4463 | 888 | 133 | 11 | 0 |
| G-22 | 8716 | 1732 | 200 | 44 | 11 |
| G-23 | 4486 | 988 | 211 | 33 | 0 |
| G-24 | 1976 | 422 | 67 | 22 | 11 |

Imaging Capillary Isoelectric Focusing (icIEF)

The chemical stability of the Block G formulations was evaluated by measuring the charge variants present in the formulation after being subjected to storage conditions. These samples were frozen and shipped on dry ice prior to analysis. Results are reported in Tables 96-99 below.

TABLE 96 icIEF results for Block G formulations at T = 0

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| G-1 | 4.5 | 6.0 | 7.0 | 11.7 | 14.2 | 15.1 | 13.6 | 11.3 | 8.6 | 4.6 | 2.4 | 0.9 |
| G-2 | 3.4 | 6.3 | 6.8 | 12.6 | 14.6 | 15.9 | 13.1 | 11.2 | 8.8 | 4.5 | 2.1 | 0.6 |
| G-3 | 4.6 | 6.5 | 7.9 | 11.6 | 14.3 | 14.5 | 13.8 | 10.6 | 8.9 | 4.6 | 2.1 | 0.6 |
| G-4 | 4.4 | 6.1 | 7.6 | 11.9 | 13.9 | 14.9 | 13.9 | 11.5 | 7.8 | 4.8 | 2.3 | 0.8 |
| G-5 | 4.2 | 5.9 | 7.7 | 11.9 | 14.6 | 15.3 | 13.5 | 11.4 | 8.1 | 4.7 | 2.1 | 0.6 |
| G-6 | 4.5 | 6.0 | 6.9 | 12.5 | 14.4 | 15.1 | 13.6 | 11.9 | 7.7 | 4.6 | 2.0 | 0.6 |
| G-7 | 4.3 | 6.0 | 7.2 | 11.8 | 14.2 | 14.4 | 14.0 | 11.8 | 7.9 | 5.1 | 2.6 | 0.8 |
| G-8 | 4.3 | 6.4 | 7.3 | 11.7 | 14.5 | 14.4 | 14.0 | 11.7 | 7.9 | 4.9 | 2.2 | 0.7 |
| G-9 | 4.3 | 6.5 | 6.9 | 12.0 | 13.9 | 14.9 | 14.2 | 11.6 | 7.9 | 4.9 | 2.2 | 0.7 |
| G-10 | 4.4 | 6.4 | 6.8 | 11.9 | 13.9 | 14.6 | 14.5 | 11.7 | 7.6 | 5.1 | 2.4 | 0.7 |
| G-11 | 4.7 | 6.4 | 6.9 | 12.0 | 14.3 | 15.2 | 13.6 | 11.4 | 8.0 | 4.8 | 2.2 | 0.6 |
| G-12 | 5.1 | 7.0 | 7.0 | 13.4 | 14.1 | 14.6 | 12.4 | 9.6 | 8.4 | 5.0 | 2.5 | 0.9 |
| G-13 | 4.4 | 6.2 | 6.8 | 12.2 | 14.2 | 15.2 | 13.6 | 12.1 | 7.6 | 4.9 | 2.2 | 0.6 |
| G-14 | 3.8 | 5.9 | 7.5 | 12.2 | 14.3 | 14.7 | 13.8 | 11.3 | 8.3 | 5.1 | 2.4 | 0.8 |
| G-15 | 4.0 | 6.5 | 6.4 | 12.1 | 14.3 | 15.0 | 13.8 | 11.8 | 7.9 | 5.0 | 2.4 | 0.8 |
| G-16 | 4.4 | 6.2 | 6.9 | 12.1 | 14.0 | 15.5 | 13.9 | 11.1 | 8.1 | 5.0 | 2.0 | 0.6 |
| G-17 | 4.1 | 6.2 | 6.7 | 12.2 | 13.6 | 16.0 | 13.3 | 11.8 | 8.7 | 4.2 | 2.4 | 0.7 |
| G-18 | 4.6 | 6.5 | 7.3 | 11.9 | 14.7 | 14.6 | 14.0 | 11.5 | 7.7 | 4.7 | 2.0 | 0.5 |
| G-19 | 4.6 | 6.1 | 7.0 | 11.9 | 14.4 | 14.9 | 13.6 | 11.3 | 7.9 | 4.9 | 2.4 | 0.8 |
| G-20 | 4.2 | 7.3 | 5.6 | 12.3 | 15.2 | 14.4 | 14.0 | 11.4 | 7.8 | 4.7 | 2.1 | 0.7 |
| G-21 | 4.3 | 6.2 | 7.4 | 11.8 | 14.0 | 15.3 | 14.1 | 11.7 | 7.5 | 5.0 | 2.1 | 0.7 |
| G-22 | 4.5 | 7.1 | 6.3 | 12.4 | 13.9 | 14.9 | 13.4 | 11.8 | 7.7 | 4.8 | 2.4 | 0.7 |
| G-23 | 4.4 | 6.3 | 7.3 | 11.4 | 14.3 | 15.0 | 13.9 | 11.8 | 7.7 | 5.0 | 2.3 | 0.8 |
| G-24 | 4.2 | 6.0 | 7.7 | 11.6 | 14.4 | 14.6 | 14.4 | 11.2 | 8.1 | 4.9 | 2.2 | 0.6 |

TABLE 97 icIEF results for Block G formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| G-1 | 4.0 | 6.4 | 7.5 | 12.2 | 14.4 | 15.3 | 14.0 | 11.5 | 7.8 | 4.3 | 2.2 | 0.5 |
| G-2 | 4.9 | 6.9 | 7.7 | 12.2 | 14.6 | 14.8 | 13.7 | 9.8 | 8.6 | 4.3 | 2.0 | 0.6 |
| G-3 | 4.6 | 6.5 | 7.5 | 11.8 | 14.9 | 15.1 | 13.2 | 10.4 | 8.4 | 4.6 | 2.2 | 0.6 |
| G-4 | 4.9 | 7.3 | 6.6 | 12.3 | 14.4 | 14.8 | 13.8 | 10.9 | 7.4 | 4.7 | 2.2 | 0.7 |
| G-5 | 4.9 | 6.4 | 7.1 | 12.6 | 14.4 | 15.7 | 12.9 | 11.1 | 7.2 | 4.8 | 2.3 | 0.7 |
| G-6 | 4.5 | 6.7 | 6.4 | 13.1 | 14.6 | 15.5 | 13.1 | 11.3 | 7.3 | 4.8 | 2.1 | 0.6 |
| G-7 | 4.5 | 7.2 | 6.0 | 12.8 | 13.9 | 15.1 | 13.7 | 11.5 | 7.5 | 4.7 | 2.3 | 0.6 |
| G-8 | 4.8 | 6.3 | 7.4 | 11.5 | 14.5 | 14.5 | 13.4 | 11.3 | 7.5 | 4.9 | 2.6 | 1.2 |
| G-9 | 5.0 | 6.7 | 7.1 | 11.8 | 14.4 | 14.6 | 13.5 | 11.7 | 7.3 | 5.0 | 2.1 | 0.6 |
| G-10 | 4.9 | 6.5 | 7.1 | 12.0 | 14.5 | 14.9 | 13.5 | 10.8 | 7.6 | 5.0 | 2.3 | 0.7 |

TABLE 97-continued icIEF results for Block G formulations after storage for one week at 40° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| G-11 | 4.5 | 6.3 | 7.6 | 11.9 | 14.7 | 15.0 | 13.9 | 10.8 | 7.7 | 4.8 | 2.2 | 0.7 |
| G-12 | 5.9 | 7.1 | 7.8 | 12.2 | 15.3 | 14.2 | 13.1 | 9.1 | 7.6 | 5.0 | 2.1 | 0.6 |
| G-13 | 5.1 | 6.4 | 7.7 | 11.9 | 14.3 | 14.6 | 13.7 | 11.4 | 7.5 | 4.7 | 2.1 | 0.6 |
| G-14 | 3.4 | 6.4 | 7.8 | 11.9 | 14.9 | 15.1 | 13.5 | 11.6 | 7.6 | 4.8 | 2.3 | 0.7 |
| G-15 | 4.1 | 6.3 | 6.8 | 13.0 | 14.2 | 14.9 | 14.1 | 11.5 | 7.6 | 4.7 | 2.1 | 0.6 |
| G-16 | 4.9 | 6.9 | 6.7 | 12.5 | 14.5 | 14.9 | 13.7 | 11.4 | 7.1 | 4.6 | 2.1 | 0.7 |
| G-17 | 4.9 | 7.1 | 6.9 | 11.8 | 14.4 | 14.7 | 13.8 | 11.4 | 8.4 | 3.9 | 2.2 | 0.6 |
| G-18 | 4.9 | 6.9 | 7.2 | 12.7 | 14.0 | 15.4 | 13.1 | 11.3 | 7.2 | 4.5 | 2.1 | 0.7 |
| G-19 | 4.8 | 6.2 | 7.1 | 12.4 | 14.2 | 14.9 | 13.2 | 11.6 | 7.7 | 4.8 | 2.3 | 0.9 |
| G-20 | 4.9 | 6.6 | 7.4 | 12.0 | 14.3 | 15.3 | 13.7 | 11.2 | 7.3 | 4.7 | 2.0 | 0.6 |
| G-21 | 4.9 | 6.8 | 6.7 | 12.5 | 14.6 | 14.9 | 13.6 | 11.4 | 7.3 | 4.8 | 2.0 | 0.6 |
| G-22 | 4.5 | 6.9 | 7.0 | 12.9 | 14.2 | 14.8 | 14.3 | 11.0 | 7.4 | 4.5 | 1.9 | 0.6 |
| G-23 | 4.3 | 7.0 | 6.8 | 12.4 | 14.0 | 15.1 | 14.5 | 10.8 | 7.8 | 4.7 | 2.0 | 0.6 |
| G-24 | 4.9 | 6.8 | 6.6 | 11.9 | 14.6 | 14.9 | 13.6 | 10.9 | 7.5 | 4.8 | 2.6 | 0.9 |

TABLE 98 icIEF results for Block G formulations after storage for two weeks at 25° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| G-1 | 4.3 | 6.2 | 7.6 | 11.8 | 14.1 | 15.0 | 14.0 | 11.2 | 8.0 | 4.5 | 2.5 | 0.8 |
| G-2 | 4.0 | 6.5 | 7.0 | 12.3 | 14.7 | 15.5 | 13.6 | 10.1 | 8.8 | 4.5 | 2.3 | 0.7 |
| G-3 | 4.6 | 6.0 | 7.9 | 11.8 | 14.1 | 14.3 | 14.1 | 10.4 | 8.8 | 4.7 | 2.5 | 1.0 |
| G-4 | 4.5 | 6.1 | 7.8 | 11.8 | 14.4 | 14.6 | 13.5 | 12.3 | 7.7 | 4.8 | 2.0 | 0.6 |
| G-5 | 4.5 | 6.5 | 7.1 | 12.2 | 14.4 | 14.8 | 13.9 | 11.4 | 7.7 | 4.8 | 2.0 | 0.6 |
| G-6 | 4.5 | 6.3 | 6.8 | 12.3 | 14.3 | 15.0 | 13.4 | 12.2 | 7.4 | 4.9 | 2.3 | 0.6 |
| G-7 | 4.3 | 6.4 | 7.4 | 11.5 | 14.5 | 14.5 | 13.9 | 11.4 | 8.1 | 4.8 | 2.4 | 0.7 |
| G-8 | 4.6 | 6.4 | 7.4 | 11.6 | 14.5 | 15.1 | 13.5 | 11.7 | 7.9 | 4.8 | 2.0 | 0.5 |
| G-9 | 4.4 | 6.6 | 6.8 | 12.2 | 14.3 | 14.5 | 13.7 | 11.8 | 7.6 | 5.0 | 2.5 | 0.8 |
| G-10 | 4.5 | 6.5 | 6.8 | 12.5 | 13.7 | 14.7 | 14.0 | 11.3 | 8.1 | 4.8 | 2.4 | 0.8 |
| G-11 | 3.7 | 6.2 | 7.2 | 12.3 | 14.3 | 15.4 | 13.8 | 11.6 | 7.9 | 4.8 | 2.2 | 0.7 |
| G-12 | 5.6 | 7.0 | 7.8 | 11.9 | 15.7 | 13.2 | 13.6 | 9.1 | 7.7 | 5.3 | 2.3 | 0.9 |
| G-13 | 4.3 | 6.3 | 7.1 | 12.3 | 13.9 | 14.9 | 13.8 | 11.9 | 7.7 | 4.9 | 2.2 | 0.7 |
| G-14 | 3.5 | 6.2 | 7.5 | 12.2 | 14.0 | 15.2 | 13.7 | 11.7 | 8.0 | 5.0 | 2.3 | 0.7 |
| G-15 | 4.6 | 5.9 | 7.6 | 11.8 | 14.4 | 14.1 | 13.9 | 11.6 | 7.8 | 5.0 | 2.4 | 0.8 |
| G-16 | 4.6 | 6.6 | 7.3 | 12.1 | 14.3 | 14.6 | 13.8 | 11.1 | 7.9 | 4.8 | 2.2 | 0.8 |
| G-17 | 4.8 | 6.1 | 7.1 | 12.3 | 13.9 | 14.6 | 13.8 | 11.8 | 8.5 | 4.1 | 2.4 | 0.7 |
| G-18 | 4.6 | 6.3 | 7.6 | 11.8 | 14.6 | 15.4 | 13.7 | 11.7 | 7.4 | 4.6 | 1.9 | 0.4 |
| G-19 | 4.8 | 7.1 | 6.6 | 11.8 | 13.9 | 15.1 | 13.9 | 11.1 | 7.9 | 4.9 | 2.2 | 0.7 |
| G-20 | 4.3 | 5.9 | 7.7 | 11.7 | 14.6 | 15.0 | 13.6 | 11.5 | 7.6 | 5.0 | 2.3 | 0.8 |
| G-21 | 4.7 | 6.2 | 7.3 | 12.1 | 14.0 | 15.3 | 13.3 | 11.3 | 8.1 | 5.0 | 2.1 | 0.7 |
| G-22 | 4.2 | 6.6 | 7.9 | 11.5 | 14.5 | 14.6 | 14.6 | 11.3 | 7.6 | 4.7 | 2.0 | 0.5 |
| G-23 | 4.9 | 6.1 | 7.5 | 11.4 | 14.6 | 14.8 | 13.5 | 11.7 | 7.6 | 4.9 | 2.1 | 0.6 |
| G-24 | 4.3 | 6.5 | 7.1 | 12.4 | 14.0 | 15.1 | 13.9 | 11.6 | 7.6 | 5.0 | 2.0 | 0.6 |

TABLE 99 icIEF results for Block G formulations after storage for four weeks at 5° C.

| Formulation Block | Rel. Area (%) Smoothing (Group) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| G-1 | 4.5 | 6.7 | 6.6 | 12.4 | 14.1 | 14.5 | 13.9 | 11.6 | 8.3 | 4.4 | 2.2 | 0.8 |
| G-2 | 4.3 | 6.4 | 7.2 | 12.0 | 14.7 | 15.2 | 13.3 | 10.7 | 8.8 | 4.6 | 2.2 | 0.7 |
| G-3 | 4.9 | 6.1 | 7.1 | 12.2 | 14.6 | 14.8 | 13.8 | 11.3 | 7.9 | 4.6 | 2.2 | 0.6 |
| G-4 | 4.5 | 6.2 | 7.5 | 11.9 | 14.1 | 14.4 | 13.4 | 12.1 | 7.7 | 5.0 | 2.3 | 0.8 |
| G-5 | 4.5 | 6.1 | 7.6 | 11.6 | 14.3 | 14.5 | 13.8 | 11.8 | 7.8 | 4.8 | 2.3 | 0.8 |
| G-6 | 4.4 | 6.4 | 6.8 | 12.0 | 14.3 | 15.1 | 13.7 | 11.7 | 8.0 | 4.9 | 2.2 | 0.7 |
| G-7 | 4.4 | 6.2 | 6.9 | 12.3 | 14.2 | 15.0 | 13.9 | 11.8 | 7.7 | 4.8 | 2.2 | 0.6 |
| G-8 | 4.6 | 6.3 | 7.1 | 12.0 | 14.2 | 14.5 | 13.6 | 11.6 | 7.8 | 4.9 | 2.5 | 0.9 |
| G-9 | 4.4 | 6.4 | 7.0 | 12.2 | 14.1 | 14.8 | 13.8 | 11.6 | 8.1 | 4.8 | 2.3 | 0.7 |
| G-10 | 4.5 | 6.3 | 7.1 | 11.6 | 14.1 | 14.9 | 14.0 | 12.0 | 7.6 | 4.9 | 2.3 | 0.6 |
| G-11 | 4.4 | 6.0 | 7.2 | 11.8 | 14.2 | 14.9 | 13.7 | 11.3 | 8.2 | 5.0 | 2.4 | 0.8 |
| G-12 | 5.5 | 6.8 | 7.2 | 12.9 | 14.3 | 14.7 | 13.1 | 9.1 | 8.3 | 5.1 | 2.2 | 0.7 |
| G-13 | 4.6 | 6.4 | 6.8 | 12.2 | 14.0 | 14.4 | 14.8 | 11.5 | 7.8 | 4.9 | 2.1 | 0.6 |

TABLE 99-continued icIEF results for Block G formulations after storage for four weeks at 5° C.

| Formulation | Rel. Area (%) Smoothing (Group) | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| G-14 | 3.1 | 6.1 | 8.0 | 11.5 | 14.6 | 14.7 | 14.2 | 11.7 | 7.9 | 5.0 | 2.2 | 0.8 |
| G-15 | 4.5 | 6.3 | 7.0 | 12.4 | 13.9 | 14.7 | 14.1 | 11.4 | 8.1 | 4.9 | 2.1 | 0.7 |
| G-16 | 4.3 | 6.5 | 7.4 | 11.4 | 14.5 | 14.9 | 14.2 | 11.3 | 7.9 | 4.7 | 2.2 | 0.7 |
| G-17 | 4.4 | 6.0 | 7.4 | 11.8 | 13.8 | 14.8 | 14.2 | 11.6 | 8.7 | 4.2 | 2.5 | 0.8 |
| G-18 | 4.6 | 6.4 | 7.0 | 12.1 | 14.7 | 14.7 | 13.6 | 11.3 | 8.1 | 4.7 | 2.0 | 0.6 |
| G-19 | 4.3 | 6.5 | 7.0 | 12.0 | 14.1 | 15.0 | 13.8 | 11.3 | 8.1 | 5.0 | 2.3 | 0.8 |
| G-20 | 4.3 | 6.4 | 7.2 | 11.8 | 14.2 | 14.5 | 13.9 | 12.0 | 7.6 | 4.9 | 2.3 | 0.8 |
| G-21 | 4.5 | 6.1 | 7.5 | 11.4 | 14.7 | 14.5 | 13.9 | 11.8 | 7.9 | 5.0 | 2.1 | 0.7 |
| G-22 | 4.4 | 6.2 | 7.3 | 11.4 | 14.6 | 15.1 | 13.7 | 11.8 | 7.7 | 4.9 | 2.3 | 0.7 |
| G-23 | 4.3 | 6.3 | 7.2 | 11.7 | 14.3 | 14.6 | 13.7 | 11.9 | 7.8 | 4.9 | 2.3 | 0.8 |
| G-24 | 4.5 | 6.2 | 7.6 | 11.9 | 14.3 | 15.2 | 13.9 | 11.3 | 7.7 | 4.8 | 2.0 | 0.5 |

Discussion

The aflibercept formulations of Block G are physically and chemically stable.

Example 9—Factors Contributing to SEC Stability at 40° C. for 1 Week

A PLS1 model used the monomer content after storage at 40° C. for one week as the endpoint. Two of the 112 formulations (A-2 and F-13) were found to be outliers. The correlation coefficient for the calibration set is 0.89 and the r-value for the validation set is 0.74, which is reasonable for a data set that is this large and diverse. Significant factors were determined to be sucrose, NaCl, PS 20, PEG 3350, His, Gly, $MgCl_2$, $CaCl_2$, protein, and pH.

Figure 1:
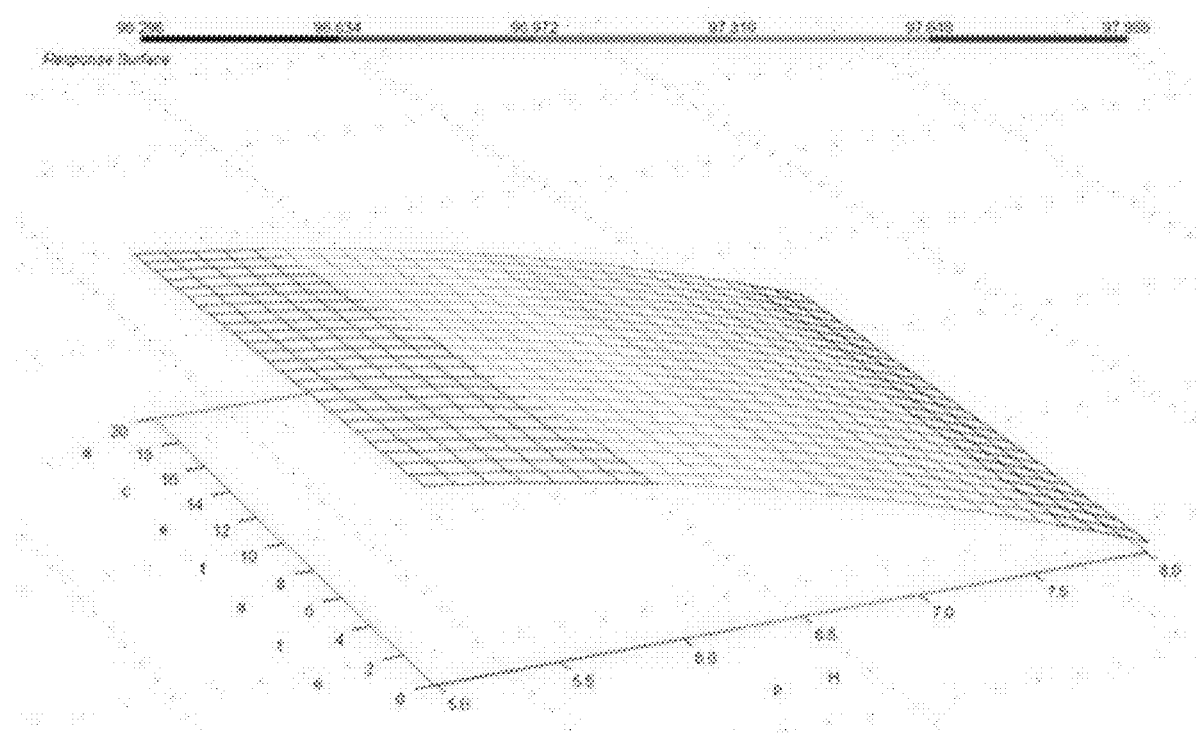
FIG. 1 is a graphic showing the effect of pH and acetate according to a PLS1 model using monomer content after one week at 40° C. as the endpoint. The protein concentration was fixed at 40 mg/mL.
Figure 2:
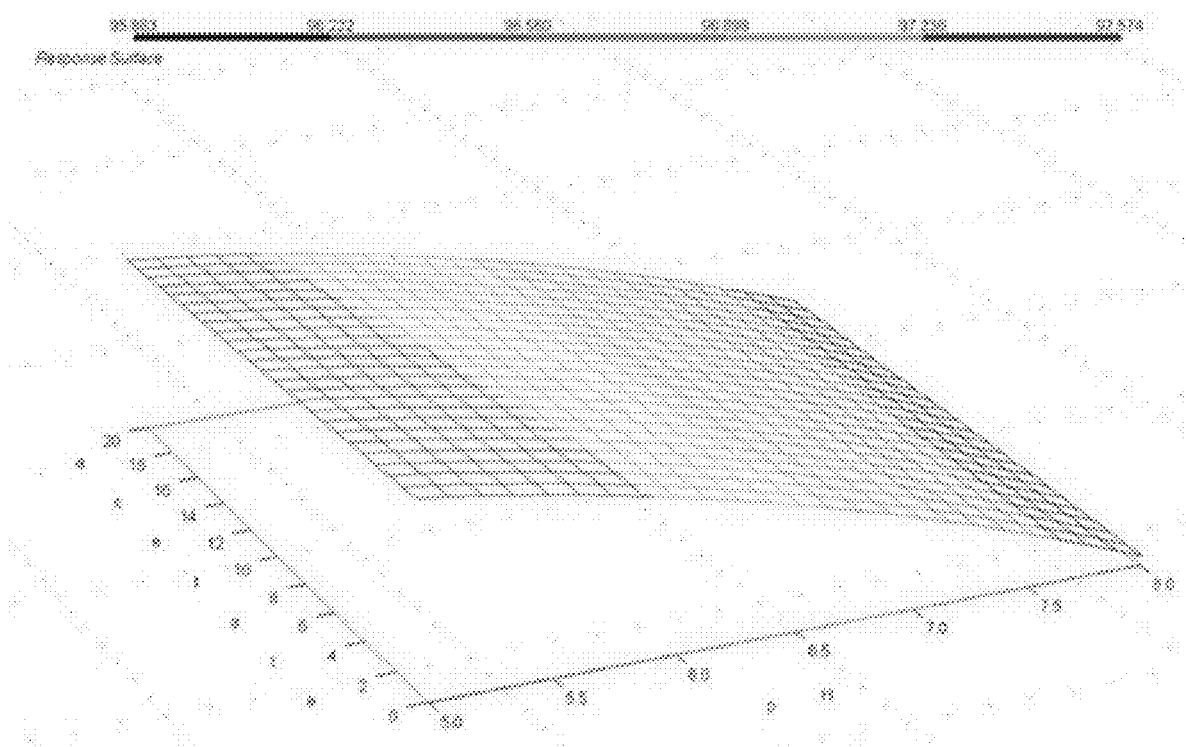
FIG. 2 is a graphic showing the effect of pH and acetate in the presence of 100 mM NaCl according to the PLS1 model using monomer content after one week at 40° C. as the endpoint. The protein concentration was fixed at 40 mg/mL.

The model predicts that the optimal pH for a buffer-free formulation would be 5.0 to 6.0 (see front edge of surface in FIG. 1). The addition of acetate has little impact on stability, except a slight narrowing of the optimal pH range to about 5.0 to 5.5. Adding NaCl has no effect on the pH-acetate profile (FIG. 2), suggesting that the degree of ionization (i.e., buffering capacity) is not impacting stability.

Figure 3:
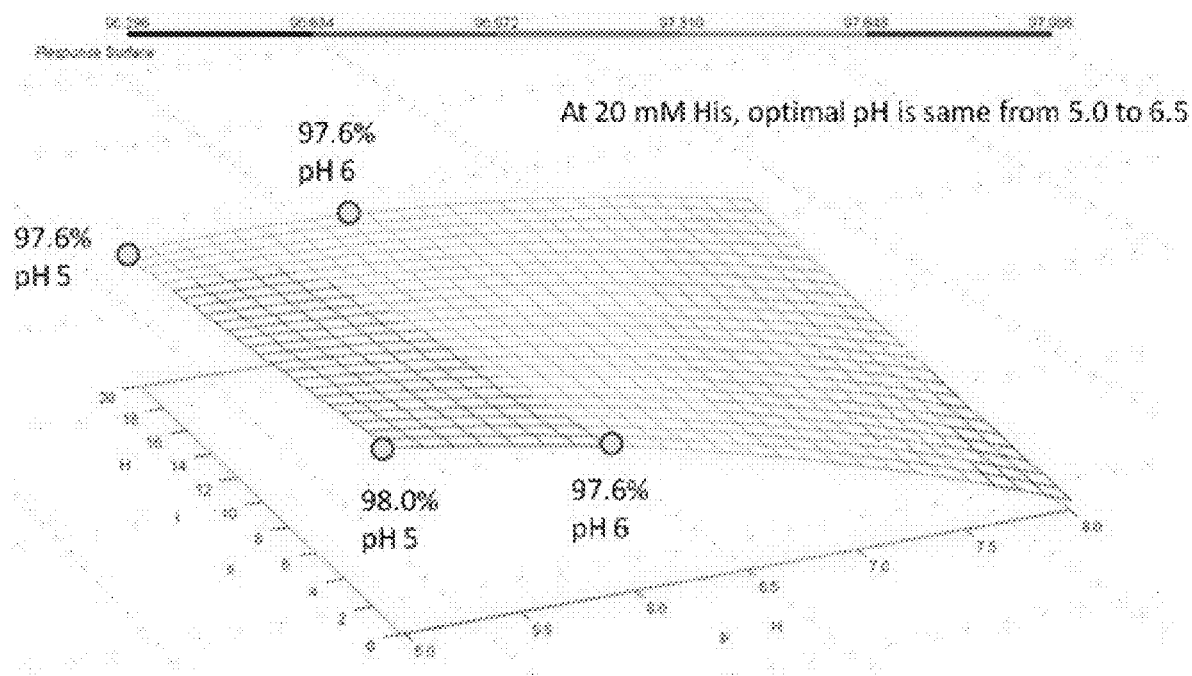
FIG. 3 is a graphic showing the effect of pH and His according to the PLS1 model using monomer content after one week at 40° C. as the endpoint. The protein concentration was fixed at 40 mg/mL.
Figure 4:
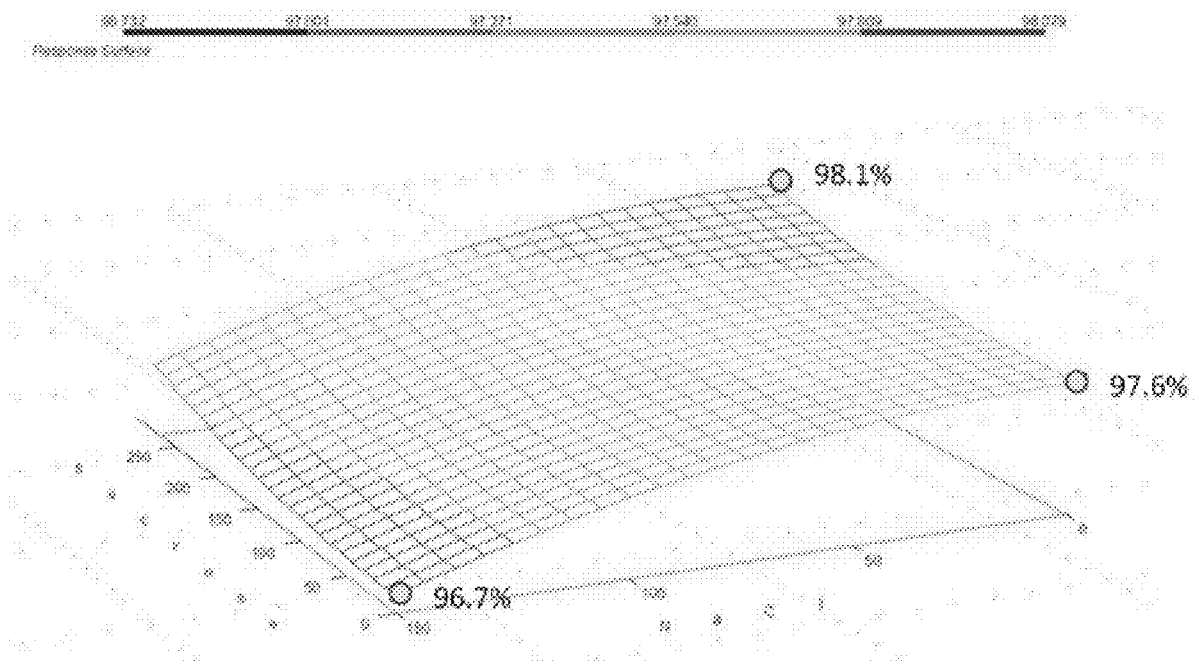
FIG. 4 is a graphic showing the effect of sucrose and NaCl according to the PLS1 model using monomer content after one week at 40° C. as the endpoint. The protein concentration was fixed at 40 mg/mL, the pH at 5.5, and His at 20 mM.

Using His as the buffer, one obtains a broader pH optimum, extending from about 5.0 to about 6.5 (FIG. 3). If one fixes the pH at 5.5 in 20 mM His buffer, the effects of NaCl and sucrose can be observed (FIG. 4). There is substantial stabilization by sucrose, but only a modest improvement with NaCl.

Figure 5:
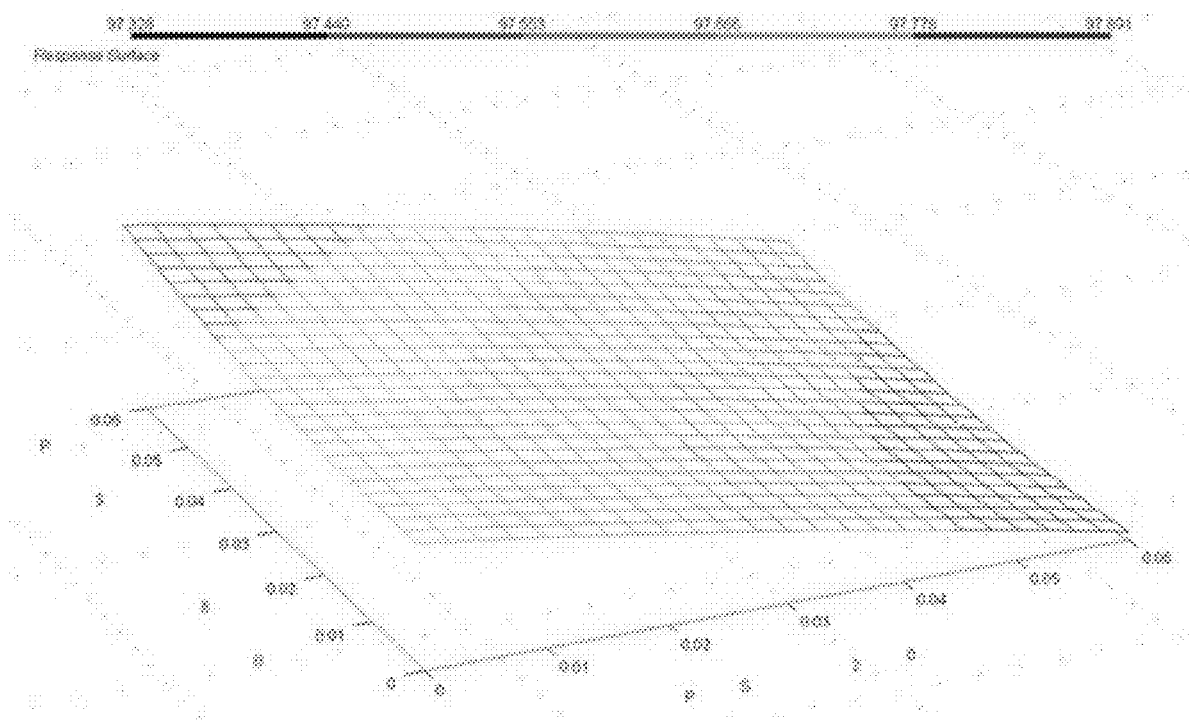
FIG. 5 is a graphic showing the effect of PS20 and PS80 according to the PLS1 model using monomer content after one week at 40° C. as the endpoint. The protein concentration was fixed at 40 mg/mL, the pH at 5.5, and His at 10 mM.
Figure 6:
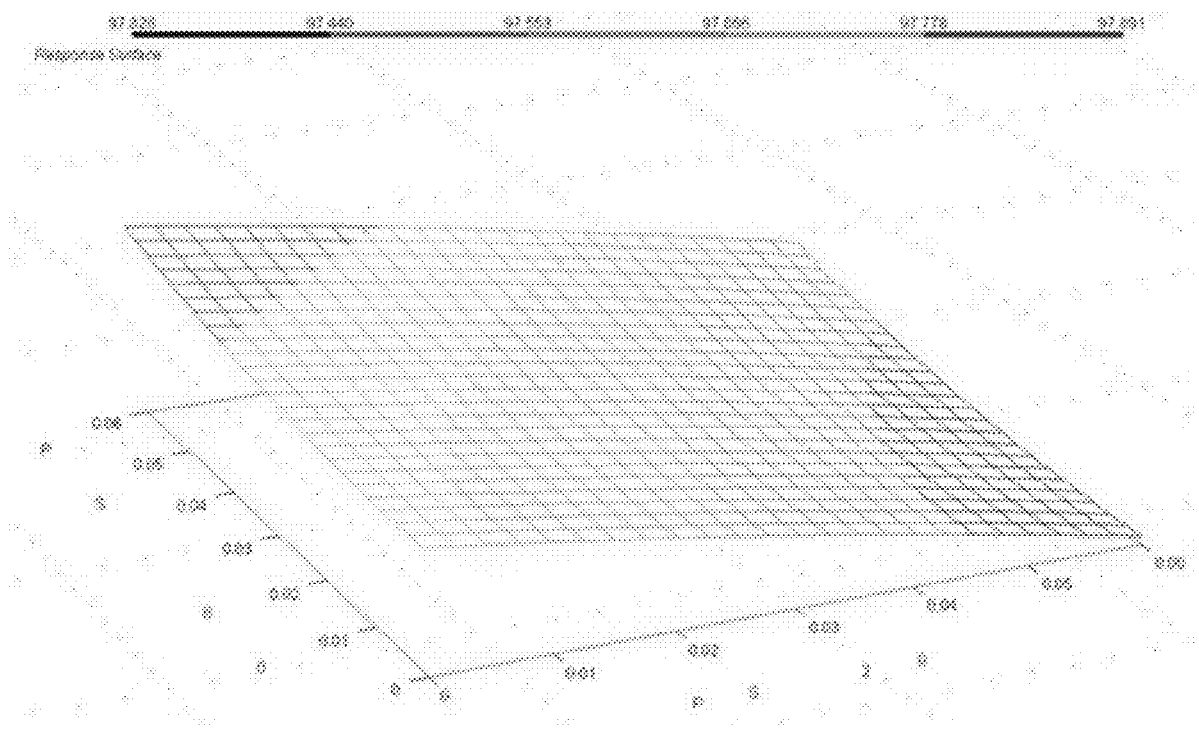
FIG. 6 is a graphic showing the effect of glycerol and PEG 3350 according to the PLS1 model using monomer content after one week at 40° as the endpoint. The protein concentration was fixed at 40 mg/mL, the pH at 5.5, and His at 0 mM.

The impact of co-solvents is an important consideration, given the overall formulation strategy. Here the effects of PS 20 and PS 80 can be seen (FIG. 5). There is a slight stabilization predicted for PS 80, but a slight destabilization for PS 20. On the other hand, PEG 3350 does not contribute to stabilization and is likely destabilizing, while glycerol was found to provide a sizable improvement in storage stability, at least at higher concentrations (FIG. 6).

Figure 7:
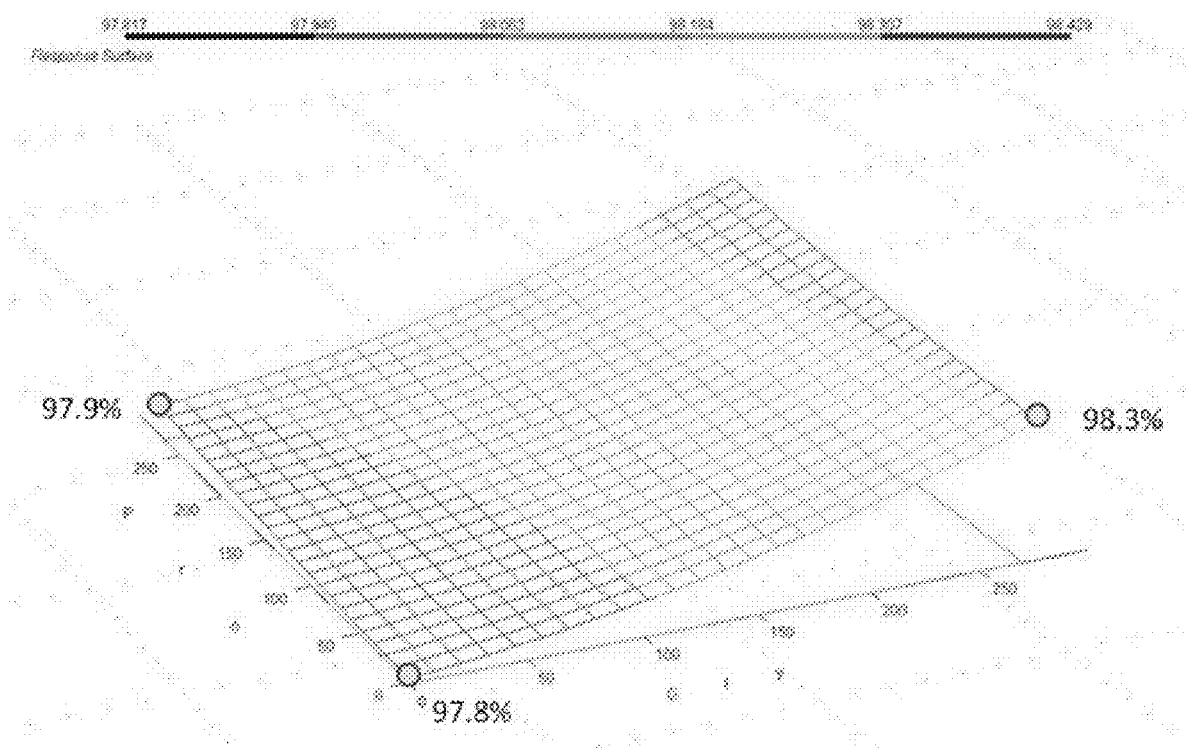
FIG. 7 is a graphic showing the effect of Gly and Pro according to the PLS1 model using monomer content after one week at 40° C. as the endpoint. The protein concentration was fixed at 40 mg/mL, the pH at 5.5, and His at 0 mM.
Figure 8:
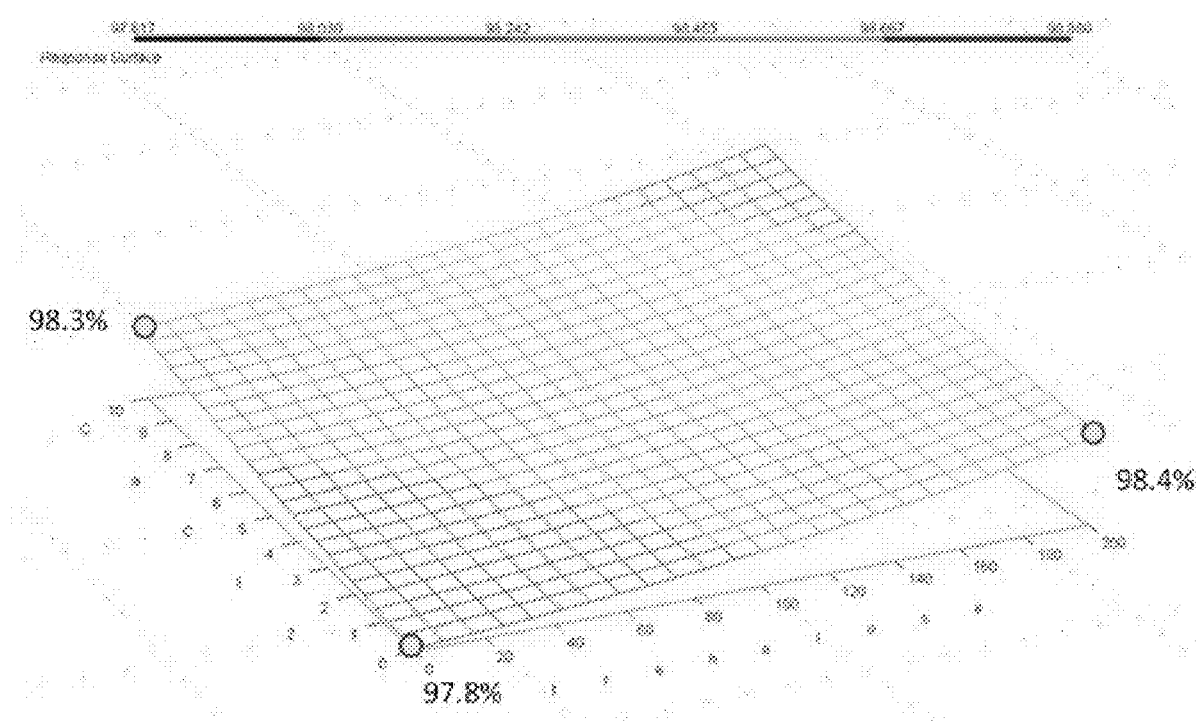
FIG. 8 is a graphic showing the effect of trehalose and calcium chloride according to the PLS1 model using monomer content after one week at 40° C. as the endpoint. The protein concentration was fixed at 40 mg/mL, the pH at 5.5, and His at 0 mM.

The effects of amino acids are seen in FIG. 7, where glycine (Gly) appears to be a good stabilizer for aflibercept, while the stabilizing effect of proline (Pro) is only slight. Finally, a response surface for trehalose and $CaCl_2$) is present (FIG. 8). $CaCl_2$) was found to be a good stabilizer, even when added at only 10 mM concentration. The trend for trehalose is similar to what was seen for sucrose, suggesting that sugars may be good choices for stabilization of aflibercept, as evidenced by storage at elevated temperature.

Overall, the PLS analysis of the t1 w/40° C. SEC data found that the optimal pH for a buffer-free formulation would be 5.0 to 6.0. In the presence of acetate or His buffer, this narrows to 5.0 to about 5.5. Of the two, His appears to be the best buffer. Of the stabilizers, sucrose appears to be quite effective, but other sugars, like trehalose may work just as well. Amino acids, especially, Gly, could also be effective stabilizers. There is evidence that some of the co-solvents tested (glycerol, polysorbate 80) may improve storage stability. PEG 3350 and PS 20 were actually destabilizing to some degree.

Example 10—Factors Contributing to SEC Stability at 25° C. for 2 Weeks

A PLS1 model used the monomer content by after two weeks at 25° C. as the endpoint. All of the 112 formulations were included and the model indicates that the significant factors are sucrose, PEG 3350, His, ArgHCl, $CaCl_2$), and pH. The correlation coefficient for the calibration set is 0.82, while the r-value for the validation set is 0.73, so the model quality is similar, but slightly lower than the last model.

Figure 9:
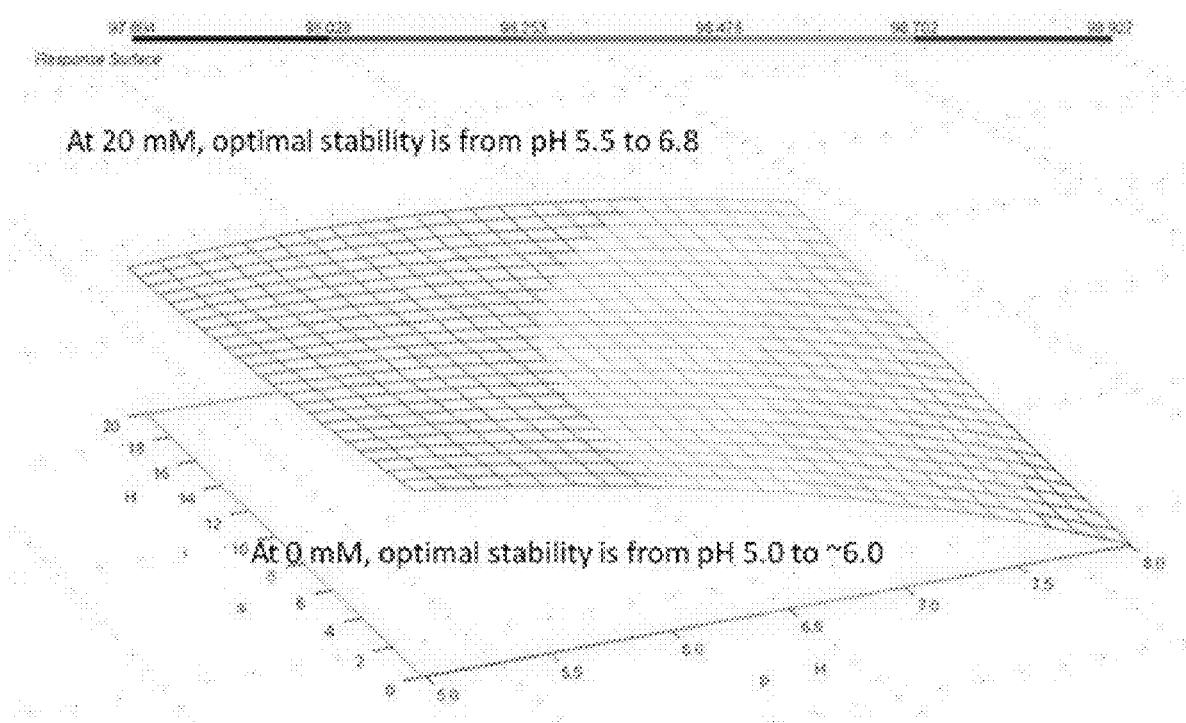
FIG. 9 is a graphic showing the effect of pH and His according to the PLS1 model using monomer content after two weeks at 25° C. as the endpoint. The protein concentration was fixed at 40 mg/mL.
Figure 10:
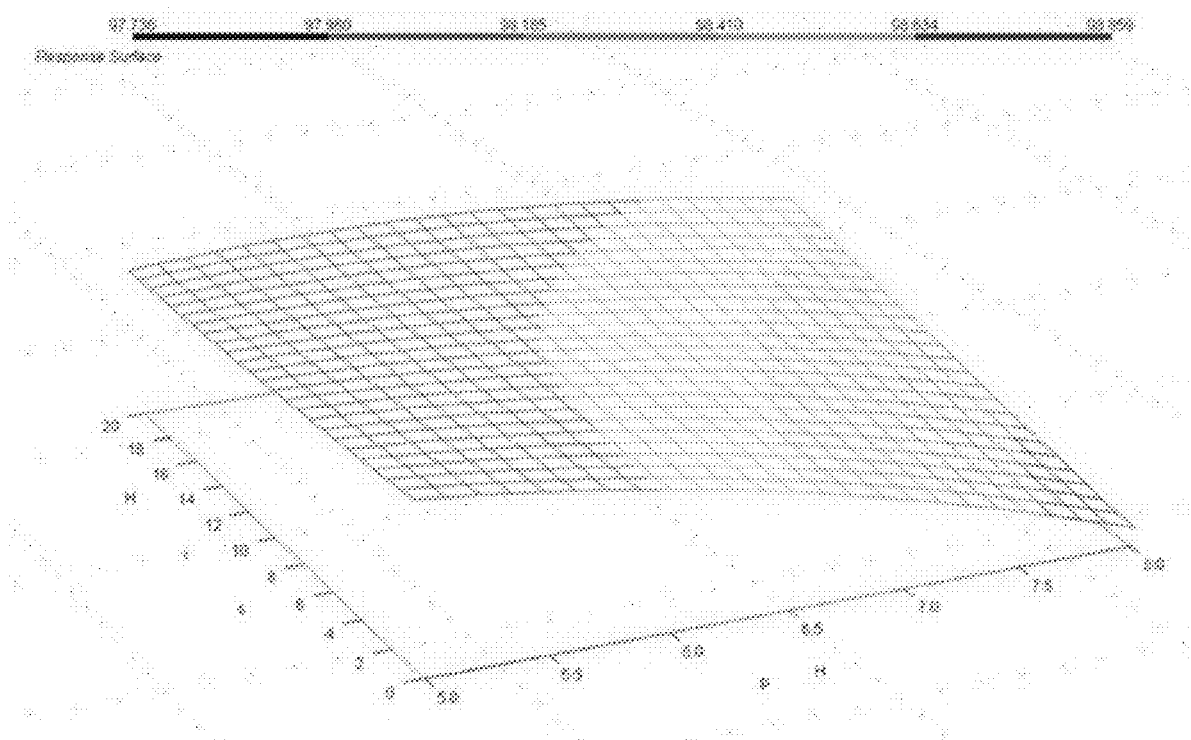
FIG. 10 is a graph showing the effect of pH and His in the presence of 100 mM NaCl according to the PLS1 model using monomer content after two weeks at 25° C. as the endpoint. The protein concentration was fixed at 40 mg/mL.
Figure 11:
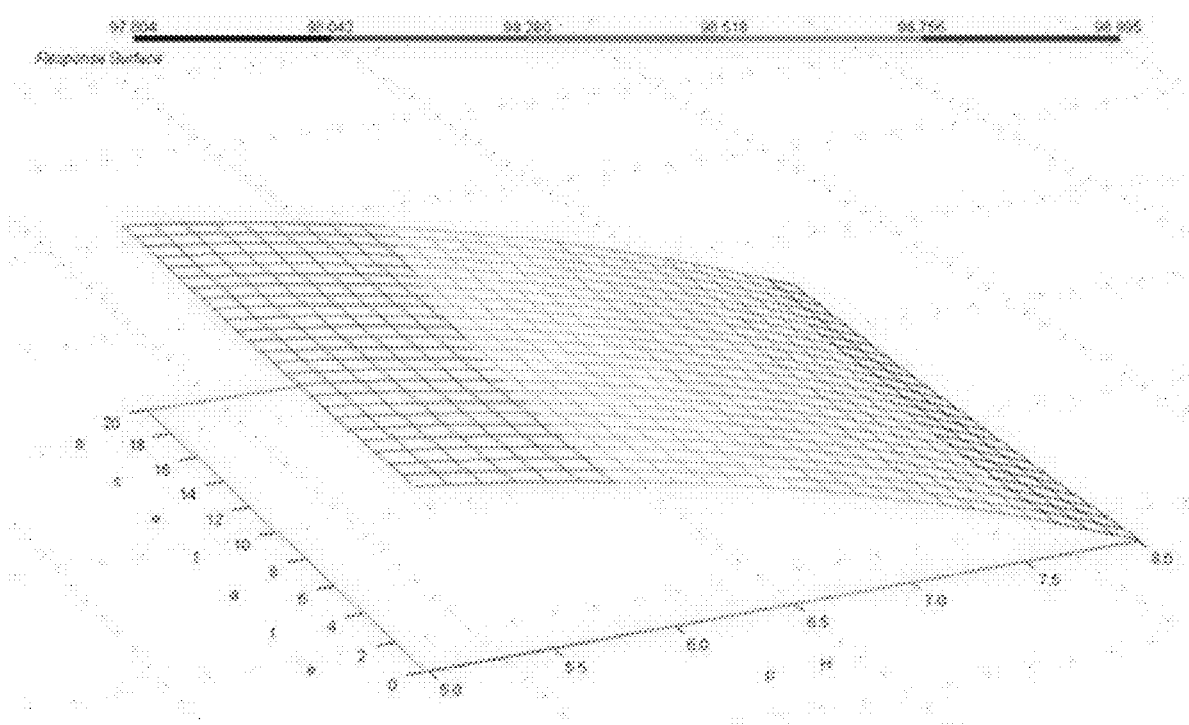
FIG. 11 is a graph showing the effect of pH and acetate according to the PLS1 model using monomer content after two weeks at 25° C. as the endpoint. The protein concentration was fixed at 40 mg/mL.
Figure 12:
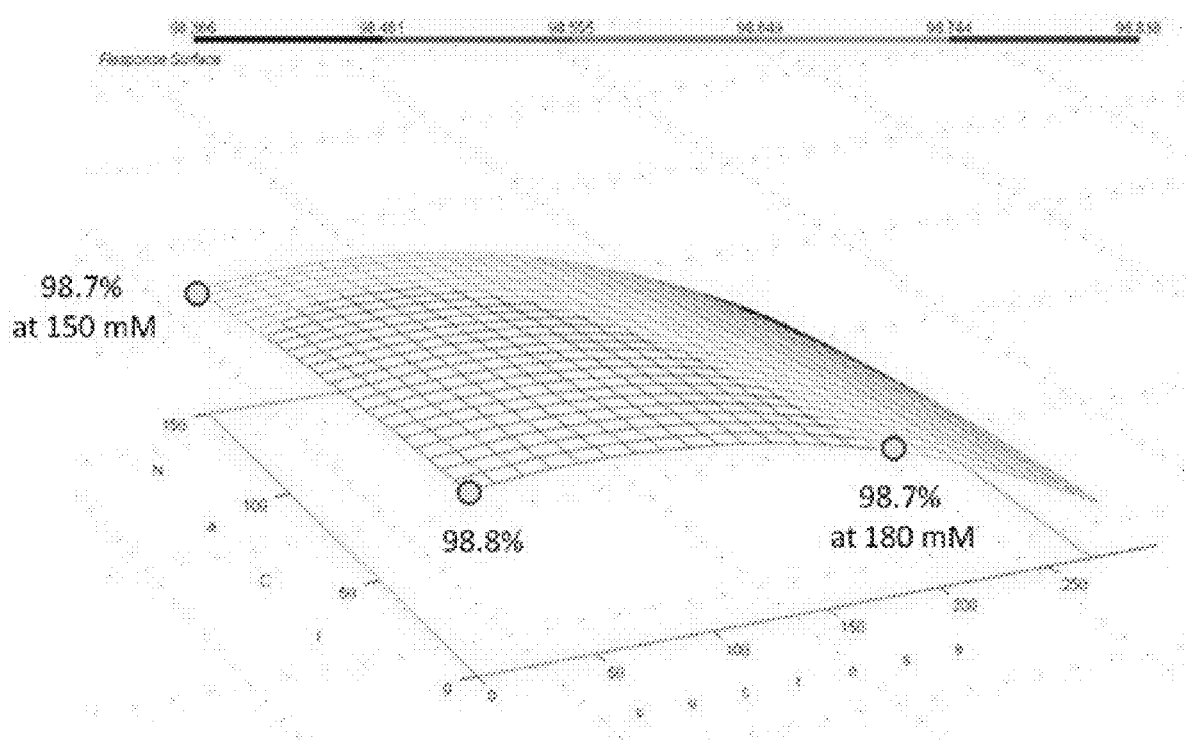
FIG. 12 is a graph showing the effect of NaCl and sucrose according to the PLS1 model using monomer content after two weeks at 25° C. as the endpoint. The protein concentration was fixed at 40 mg/mL, the pH at 6.0, and the His at 20 mM.
Figure 13:
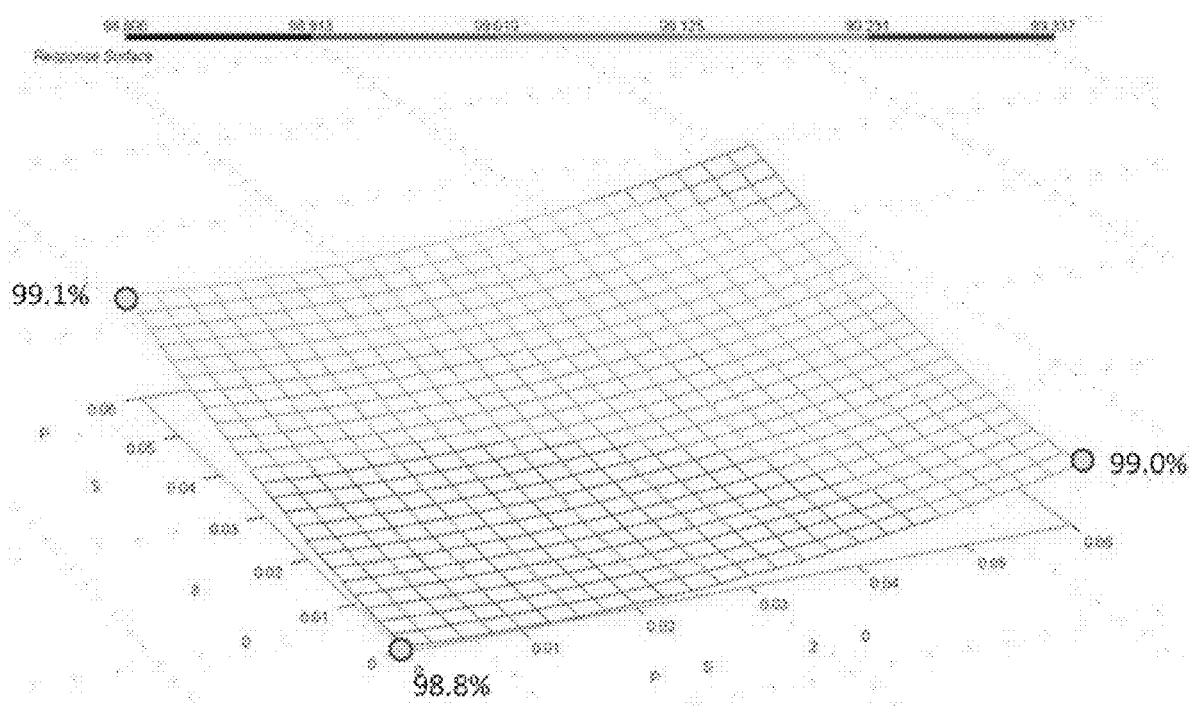
FIG. 13 is a graphic showing the effect of PS20 and PS80 according to the PLS1 model using monomer content after two weeks at 25° C. as the endpoint. The protein concentration was fixed at 40 mg/mL, the pH 6.0, and His at 20 mM.
Figure 14:
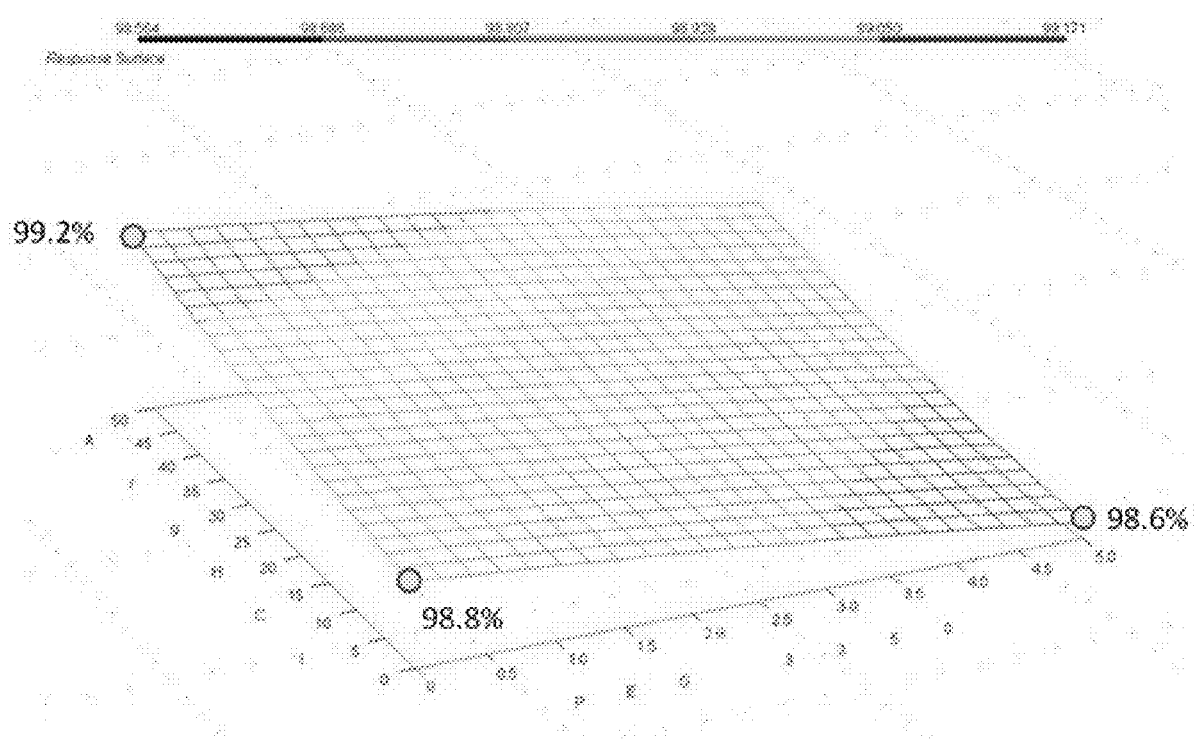
FIG. 14 is a graphic showing the effect of ArgHCl and PEG 3350 according to the PLS1 model using monomer content after two weeks at 25° C. as the endpoint. The protein concentration was fixed at 40 mg/mL, the pH at 6.0, and His at 20 mM.
Figure 15:
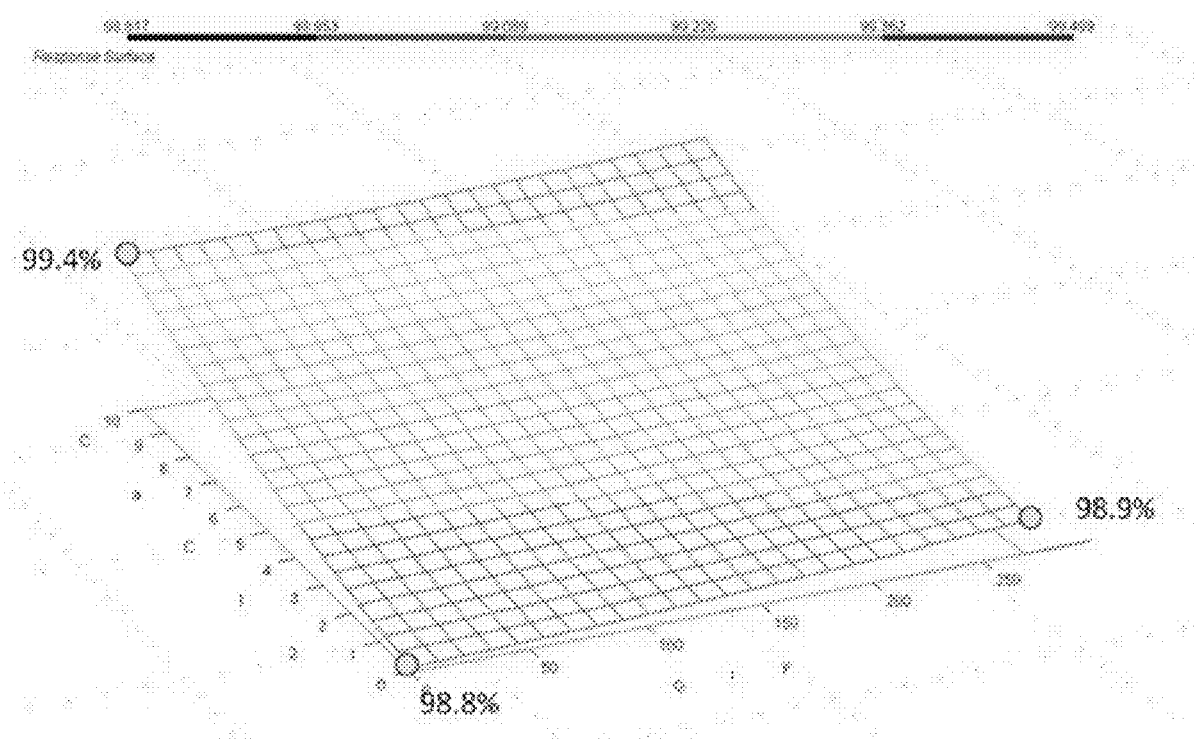
FIG. 15 is a graphic showing the effect of calcium chloride and glycine according to the PLS1 model using monomer content after two weeks at 25° C. as the endpoint. The protein concentration was fixed at 40 mg/mL, the pH at 6.0, and His at 20 mM.
Figure 16:
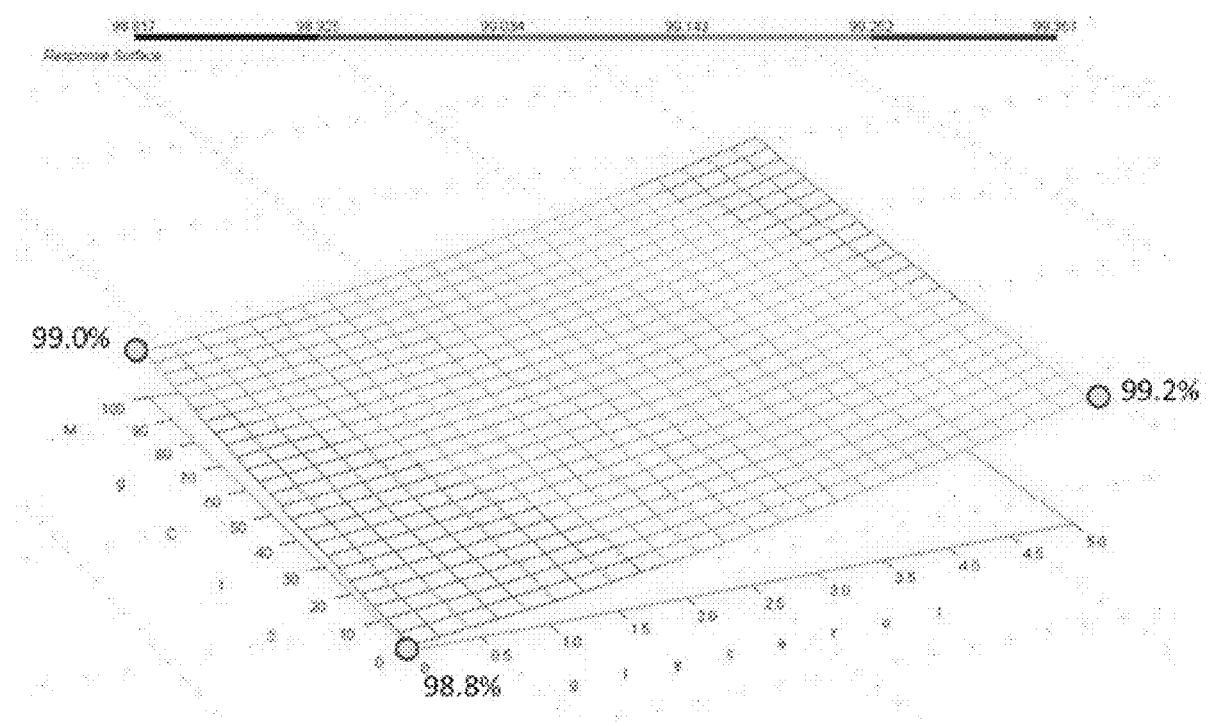
FIG. 16 is a graphic showing the effect of magnesium chloride and glycerol according to the PLS1 model using monomer content after two weeks at 25° C. as the endpoint. The protein concentration was fixed at 40 mg/mL, the pH at 6.0, and the His at 20 mM.

This PLS1 model predicts that the optimal pH range for a buffer-free formulation is from 5.0 to 6.0 (FIG. 9). In the presence of 20 mM His, this range expands upwards to 6.8. As with the previous model, the presence of 100 mM NaCl has virtually no effect on the pH-buffer stability profile (FIG. 10). Using acetate as the buffer has a more limited effect than when using His (FIG. 11), although the slightly larger pH range in the presence of buffer is observed The stability in the presence of NaCl is nearly constant until the concentration exceeds about 100 mM or 120 mM (FIG. 12). Similarly, stability with sucrose is maintained until greater 180 mM. Both PS 20 and PS 80 are predicted to have a modest stabilization effect on aflibercept during storage at 25° C. (FIG. 13). On the other hand, PEG 3350 is destabilizing (FIG. 14). The amino acid, ArgHCl, displays some ability to stabilize the protein (FIG. 14), while the effect of Gly is relatively weak (FIG. 15). Again, $CaCl_2$) was found to be a good stabilizer during storage. In the last response surface, glycerol was found to be comparable to ArgHCl as a stabilizer (FIG. 16), while $MgCl_2$ was a weaker stabilizer.

The PLS analysis of the 25° C. SEC data indicates that the optimal pH for a buffer-free formulation is between about 5.0 and about 6.0. The range appears to broaden if one uses 20 mM His buffer. His appears to be superior to acetate as a buffer system in this model. Stability is maintained in the presence of sucrose concentrations up to about 180 mM. There appears to be storage stabilization by different co-solvents, like glycerol and polysorbates (but not PEG 3350). Of the amino acids, ArgHCl is the most effective stabilizer.

Finally, increased stability is seen with the levels of CaCl$_2$) evaluated (and higher amounts may also be stabilizing) and with increasing amounts of MgCl$_2$.

Example 11—Factors Contributing to SEC Stability at 5° C. for 4 Weeks

A PLS1 model employed the monomer content after storage for four weeks at 5° C. (a suitable storage condition of aflibercept according to the Eylea package insert) as the endpoint. All formulations were included and the significant factors were determined to be sucrose, PS 20, PS 80, PEG 3350, tris, ArgHCl, Pro, MgCl$_2$, dextran, and pH. The r-value for the calibration set was 0.88, while the correlation coefficient for the validation set was 0.79.

Figure 17:
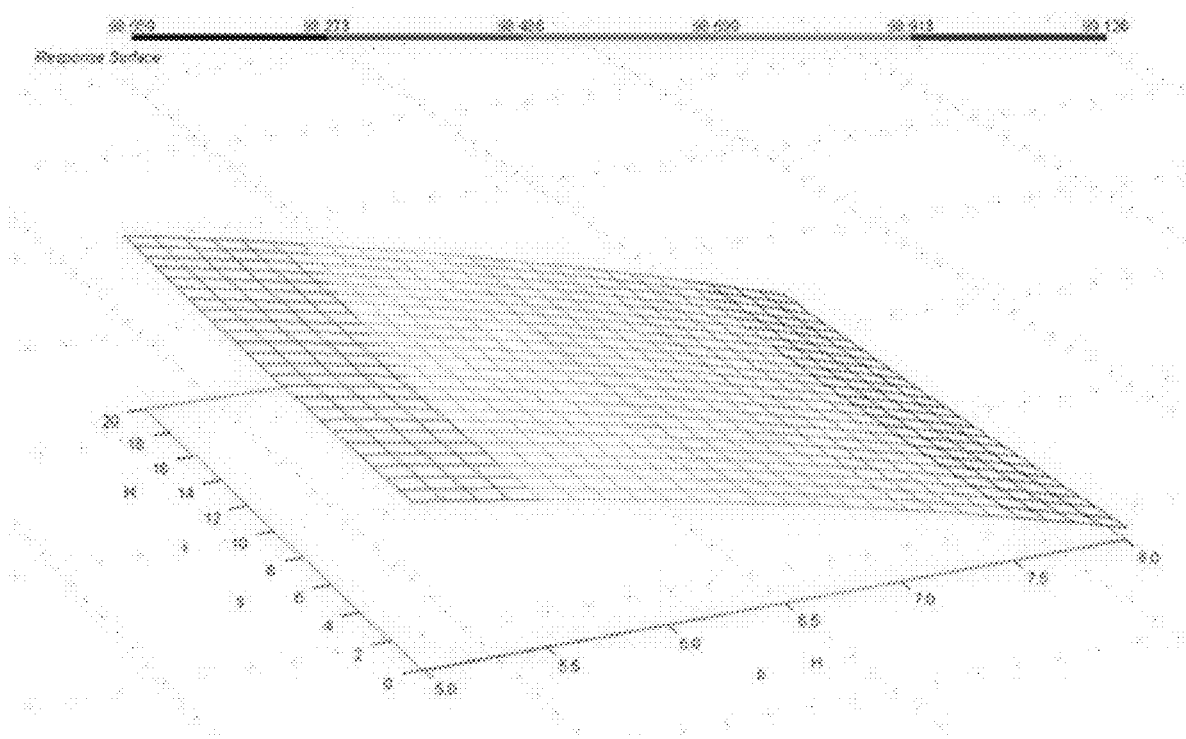
FIG. 17 is a graphic showing the effect of pH and His according to the PSL1 model using monomer content after four weeks at 5° C. as the endpoint. The protein concentration was fixed at 40 mg/mL.
Figure 18:
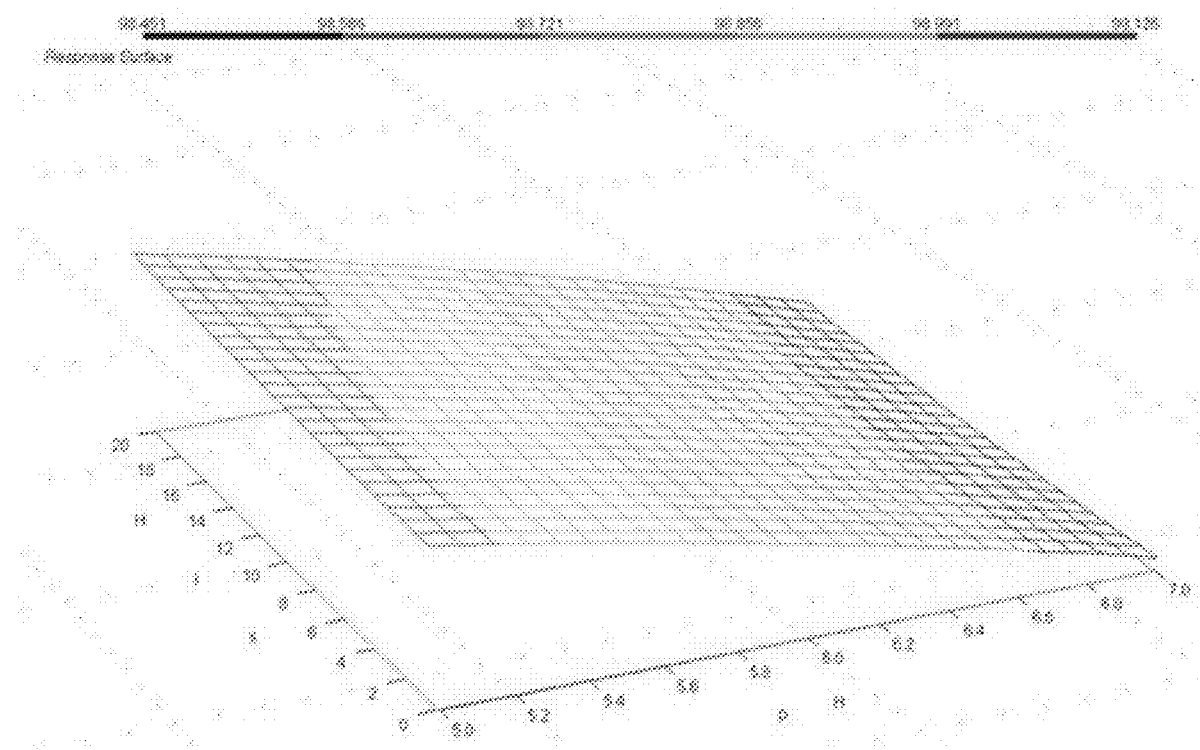
FIG. 18 is a graphic showing the effect of pH (down to pH 7.0) and His according to the PLS1 model using monomer content after four weeks at 5° C. as the endpoint. The protein concentration was fixed at 40 mg/mL.
Figure 19:
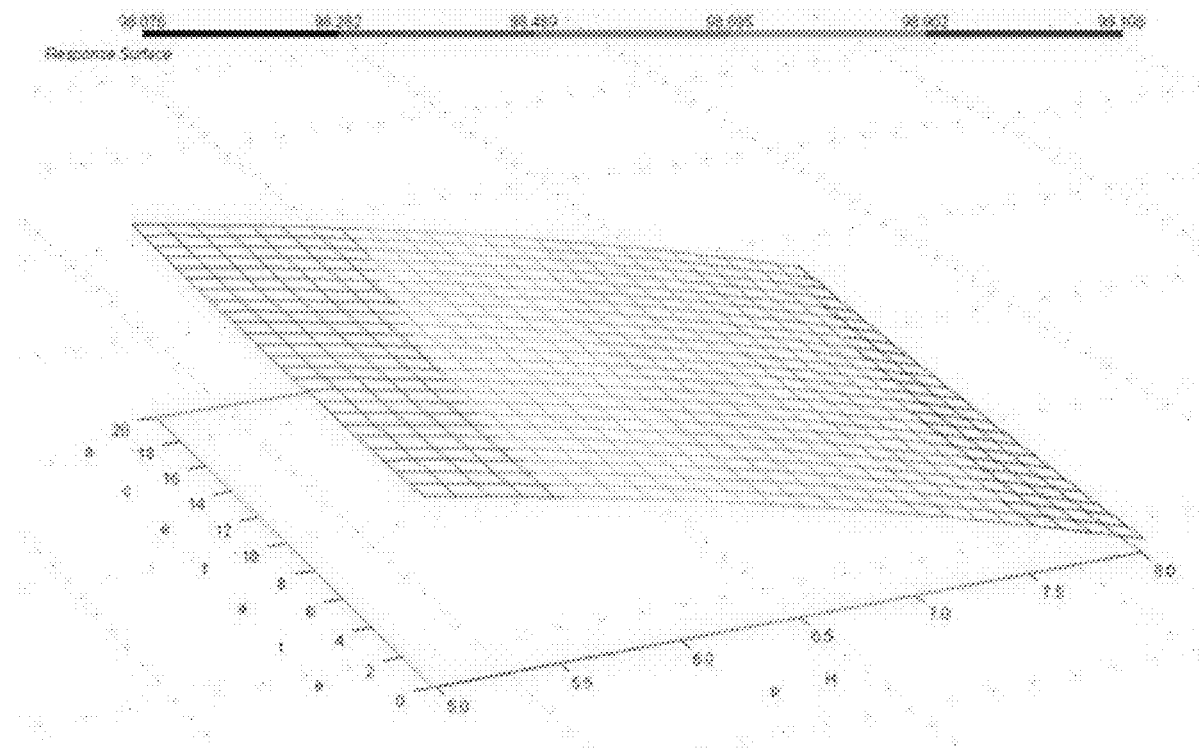
FIG. 19 is a graphic showing the effect of pH and acetate according to the PLS1 model using monomer content after four weeks at 5° C. as the endpoint. The protein concentration was fixed at 40 mg/mL.
Figure 20:
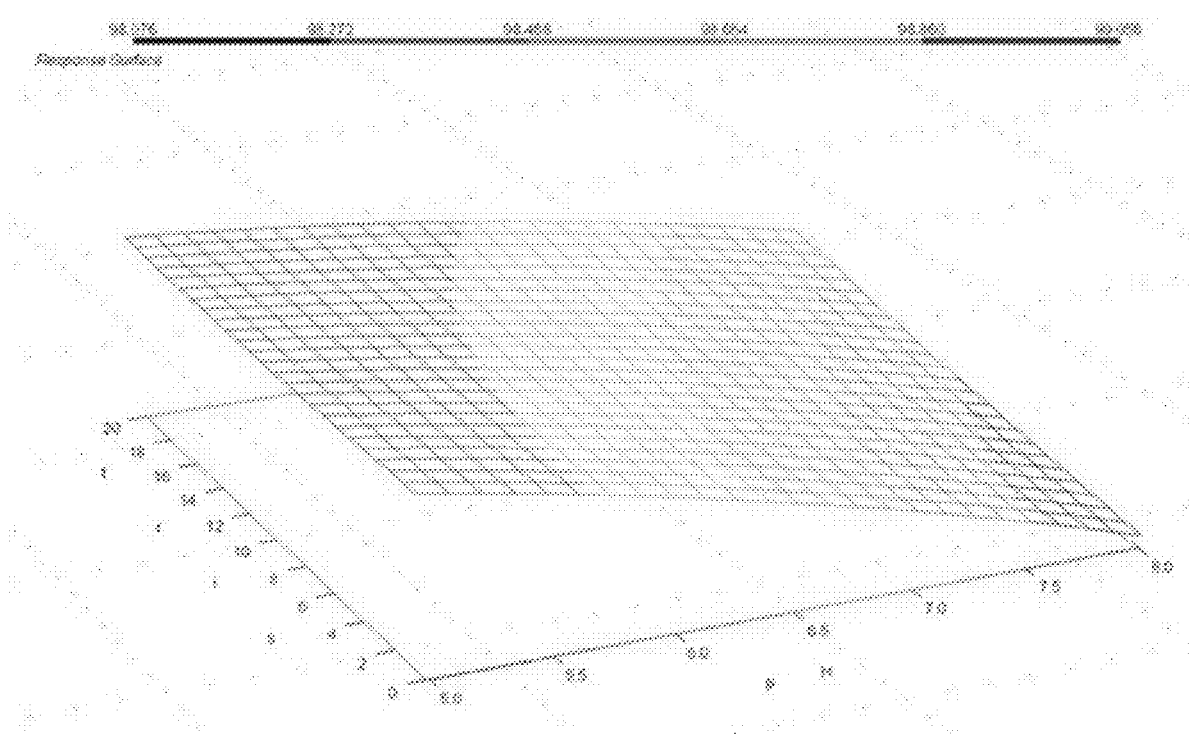
FIG. 20 is a graphic showing the effect of pH and Tris according to the PLS1 model using monomer content after four weeks at 5° C. as the endpoint. The protein concentration was fixed at 40 mg/mL.

The PLS1 model indicates that the optimal pH for a buffer-free formulation is 5.0 to 5.5 under these conditions, with a slightly extended range (maybe to 5.7) in the presence of 20 mM His (FIG. 17). The pH-His response surface is expended to remove the clearly unstable conditions >pH 7 (FIG. 18). This zoomed in view suggests that the best pH conditions may be <5.5. With acetate as the buffer, the profile is quite similar to that with His, suggesting that either buffer may be sufficient (FIG. 19). The model also predicts tris as having a significant effect, but this is in relation to stabilization at elevated pH, where the stability profile is the poorest (FIG. 20). It would not be suitable for a formulation between pH 5 and 6.

Figure 21:
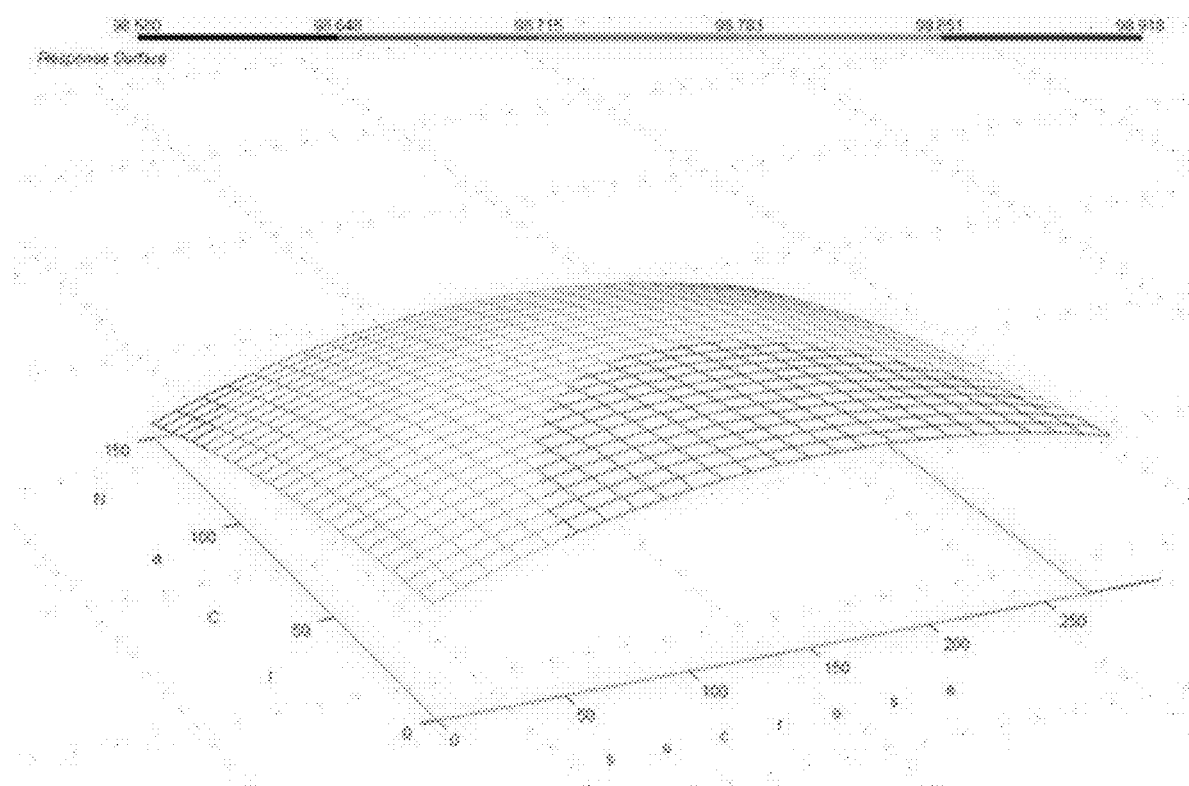
FIG. 21 is a graphic showing the effect of NaCl and sucrose according to the PLS1 model using monomer content after four weeks at 5° C. as the endpoint. The protein concentration was fixed at 40 mg/mL and pH at 6.0.
Figure 22:
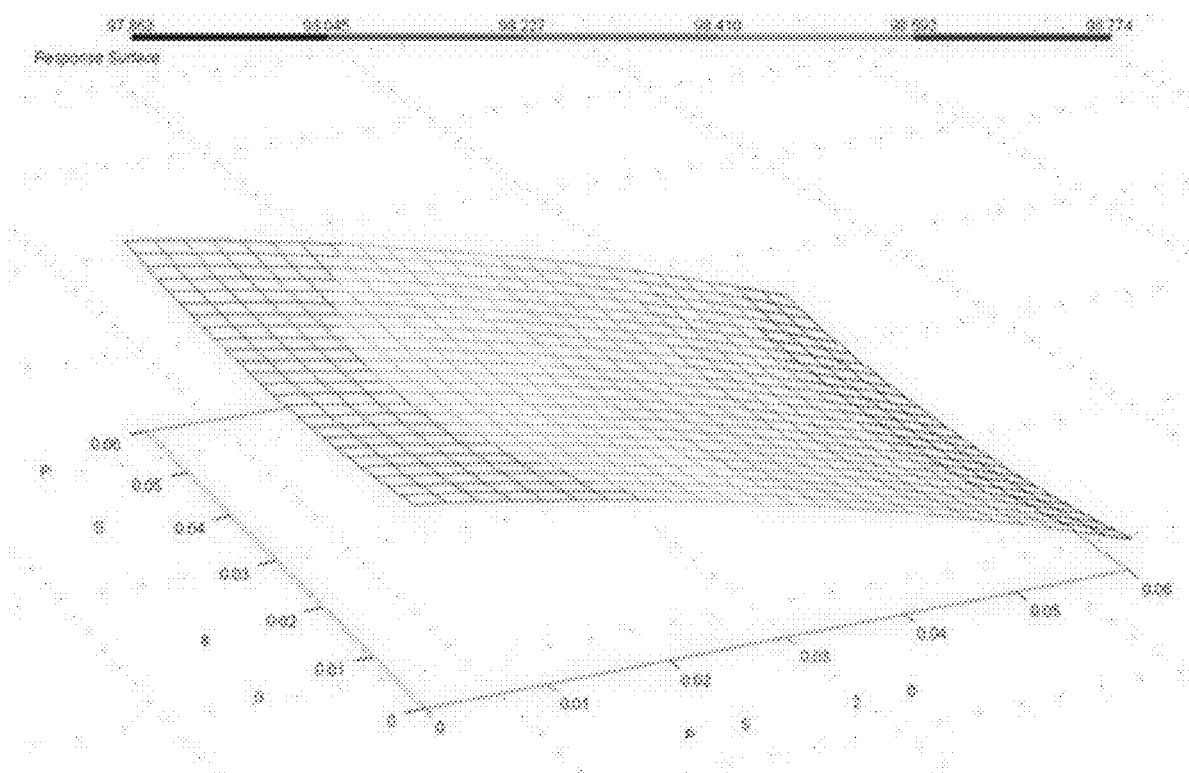
FIG. 22 is a graphic showing the effect of PS20 and PS80 according to the PLS1 model using monomer content after four weeks at 5° C. as the endpoint. The protein concentration was fixed at 40 mg/mL and pH at 6.0.
Figure 23:
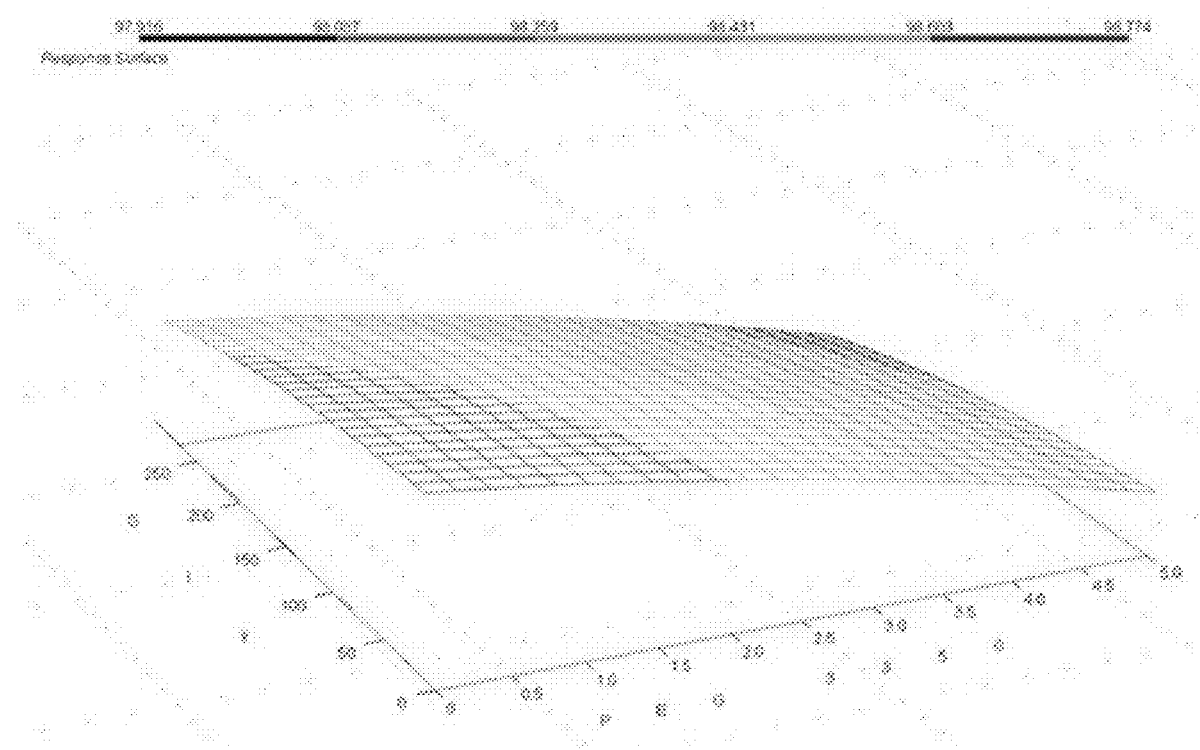
FIG. 23 is a graphic showing the effect of PEG 3360 and Gly according to the PLS1 model using monomer content after four weeks at 5° C. as the endpoint. The protein concentration was fixed at 40 mg/mL and pH 6.0.

Sucrose is found to be a stabilizer, especially at concentrations between 50-200 mM, while destabilization is predicted for NaCl, especially at concentrations above 50 mM (FIG. 21). The effects of the two polysorbates, PS 20 and PS 80, are shown in FIG. 22. The range is very small, so effectively neither excipient impacts the stability profile of aflibercept at 5° C. The effect of PEG 3350 is again detrimental to storage stability (FIG. 23), while Gly has only a small effect, primarily at concentrations below 200 mM. The effects of other amino acids (Pro, ArgHCl) are similar to what was seen for Gly (FIG. 24).

Figure 25:
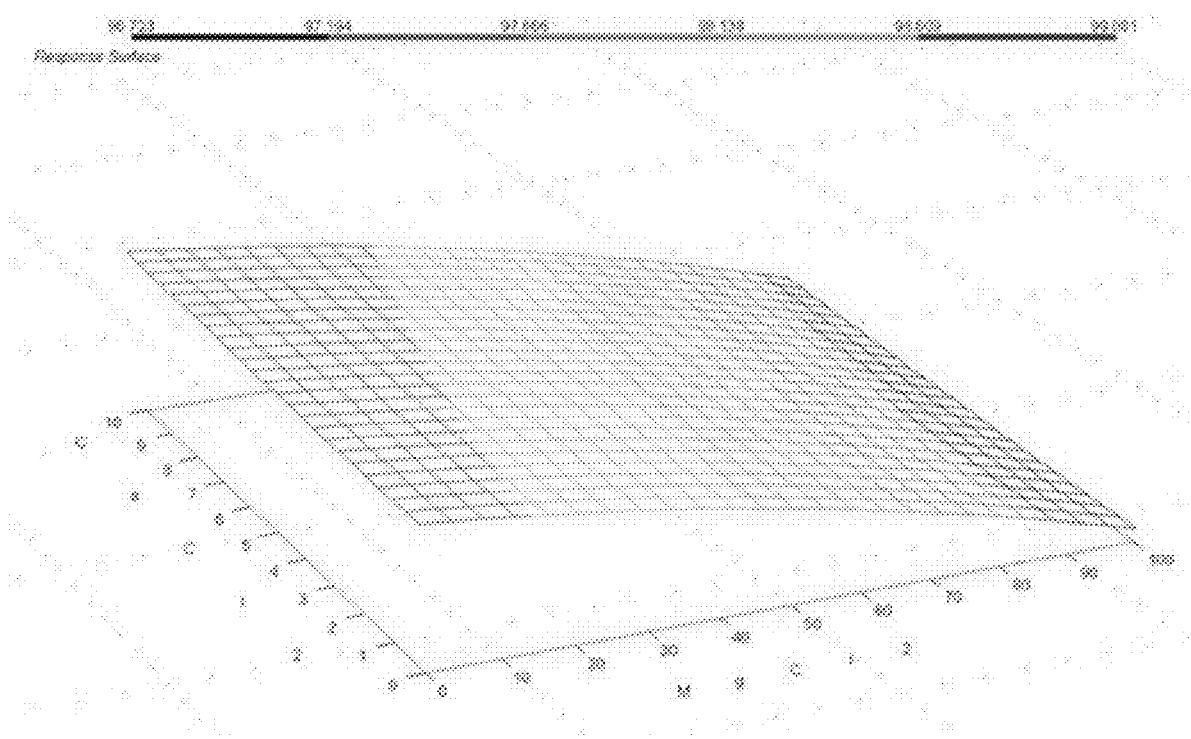
FIG. 25 is a graphic showing the effect of magnesium chloride and calcium chloride according to the PLS1 model using monomer content after four weeks at 5° C. as the endpoint. The protein concentration was fixed at 40 mg/mL and pH at 6.0.
Figure 26:
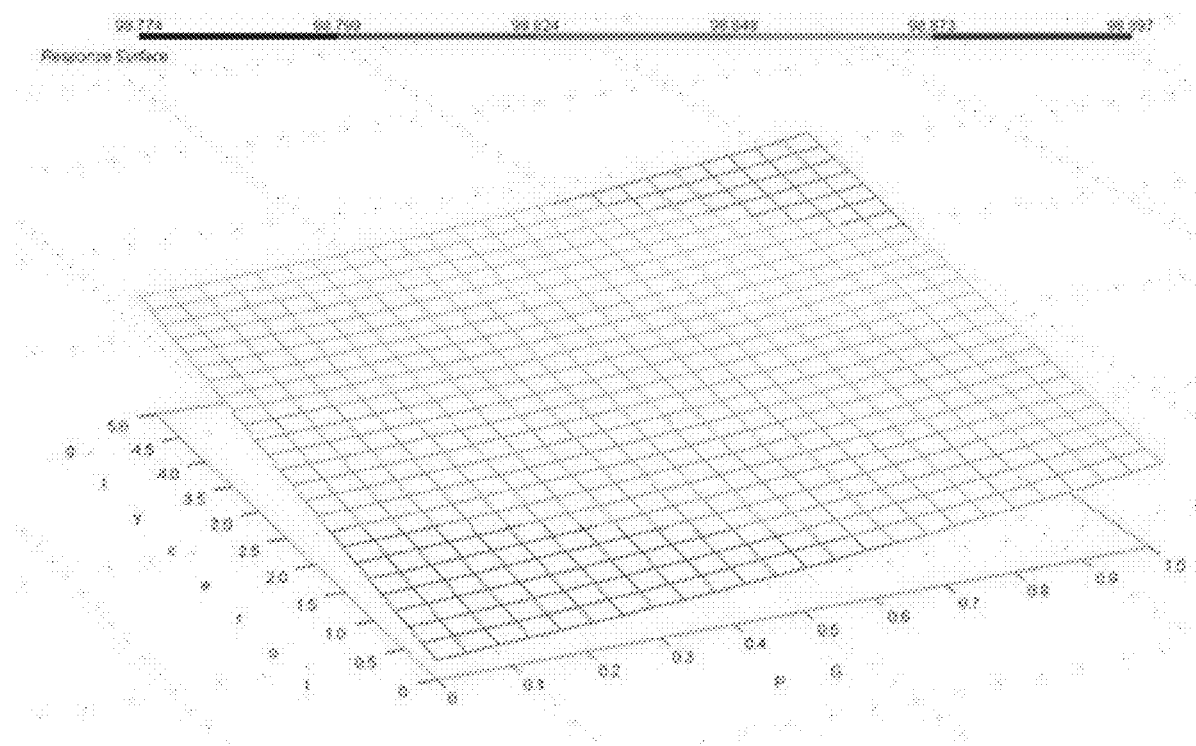
FIG. 26 is a graphic showing the effect of propylene glycol (PG) and glycerol according to the PLS1 model using monomer content after four weeks at 5° C. as the endpoint. The protein concentration was fixed at 40 mg/mL and pH at 6.0.
Figure 27:
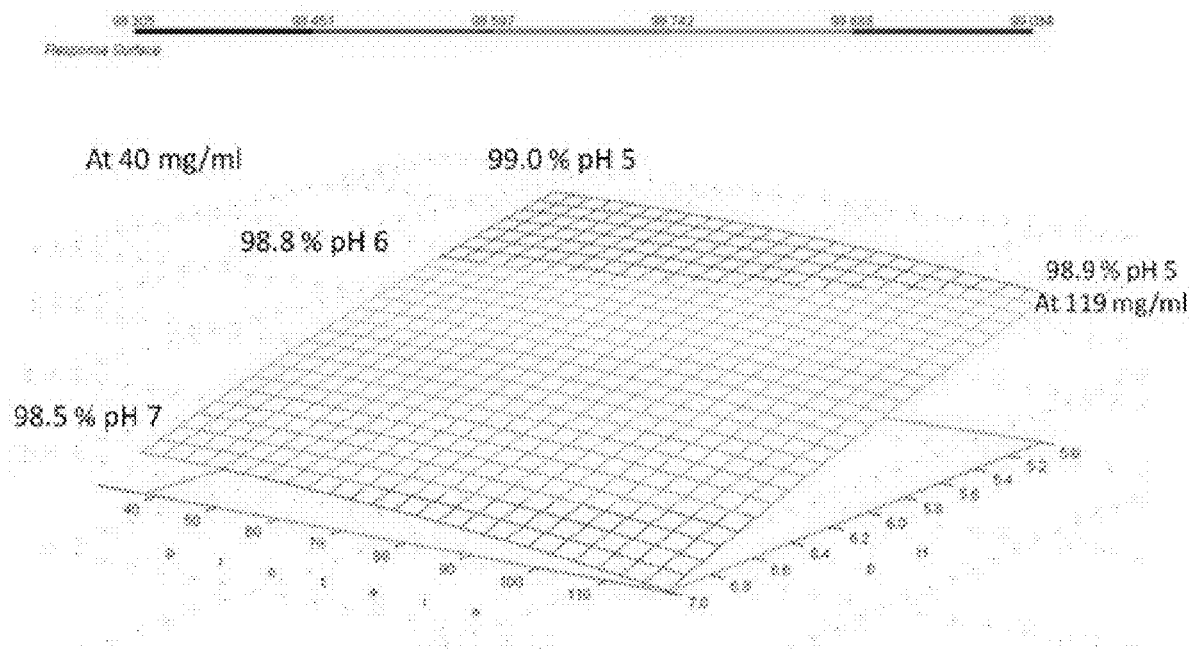
FIG. 27 is a graphic showing the effect of pH and protein concentration according to the PLS1 model using monomer content after four weeks at 5° C. as the endpoint.

The storage stability is decreased in the presence of MgCl$_2$ according this model, while CaCl$_2$) provide stabilization at 10 mM (FIG. 25), similar to what previous models are forecast. The impact of the co-solvents PG and glycerol are seen in FIG. 26. Both were found to increase stability during storage at 5 C. Finally, the effect of protein concentration was examined, as it was marked as being a significant factor. Not surprisingly, the stability decreases slightly at higher protein concentrations (FIG. 27), which would be expected for an aggregation process. However, the losses are quite small.

Overall, the PLS1 model for the 5° C. SEC data on storage stability find the best stability is <pH 6.0, preferably below 5.5. Both His and acetate appears to be good buffer choices. Sucrose is an effective stabilizer, while salts and amino acids contribute less to stability. The one ionic compound that appears to be of value in stabilizing the protein is CaCl$_2$). Most of the co-solvents tested appear to provide stabilization, except PEG 3350, which is destabilizing, and polysorbates that have little effect.

Example 12—Factors Contributing to Particle Stability

A PLS2 model was constructed using the total particles concentration (counts per mL) at all three time points (t1 w/40° C., t2 w/25° C., t4 w/5° C.). All of the formulations were considered, but a number were identified as outliers, especially within Block C, where many of the samples were damaged due to agitation upon shipping on blue ice. The model has some scatter, with a correlation coefficient of 0.74 for the calibration set and 0.56 for the validation set, but it still shows a clear trend of particle levels as a function of formulation composition.

Figure 28:
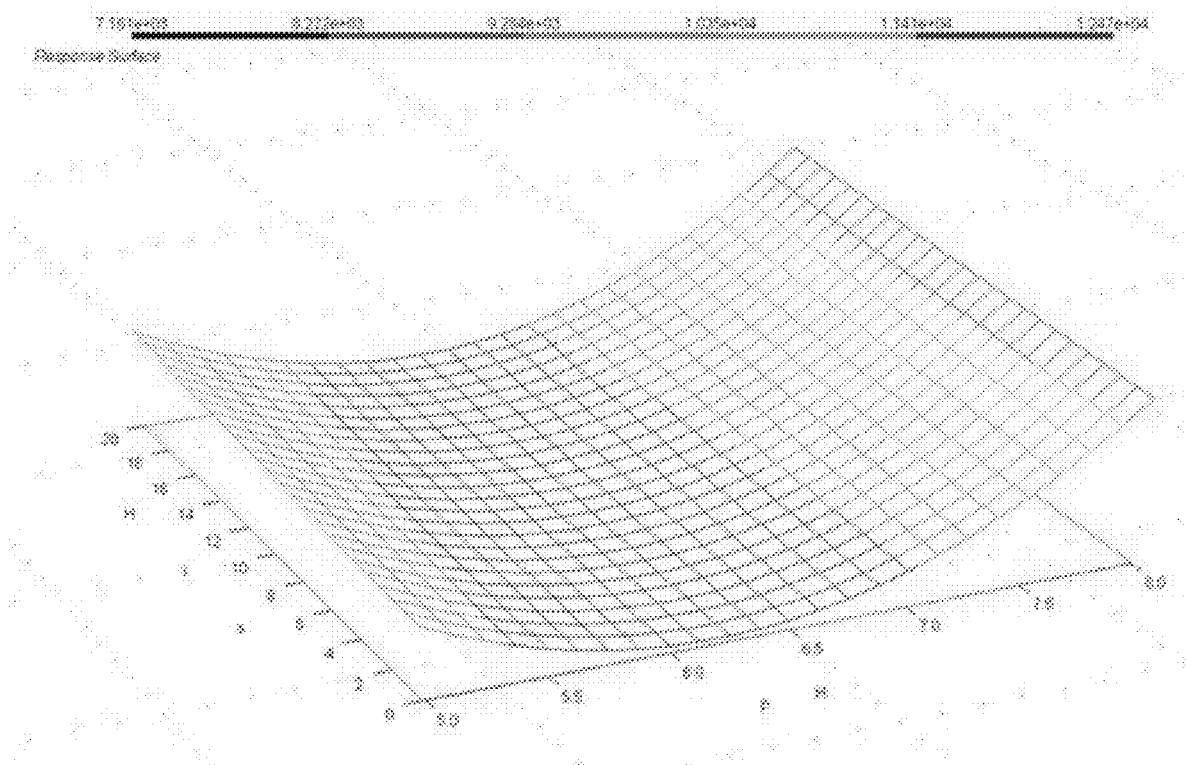
FIG. 28 is a graphic showing the effect of pH and His according to the PLS2 model using the total particle concentration (counts per mL) at t1 w/40° C., t2 w/25° C., and t4 w/5° C. as the endpoints. The protein concentration was fixed at 40 mg/mL.
Figure 29:
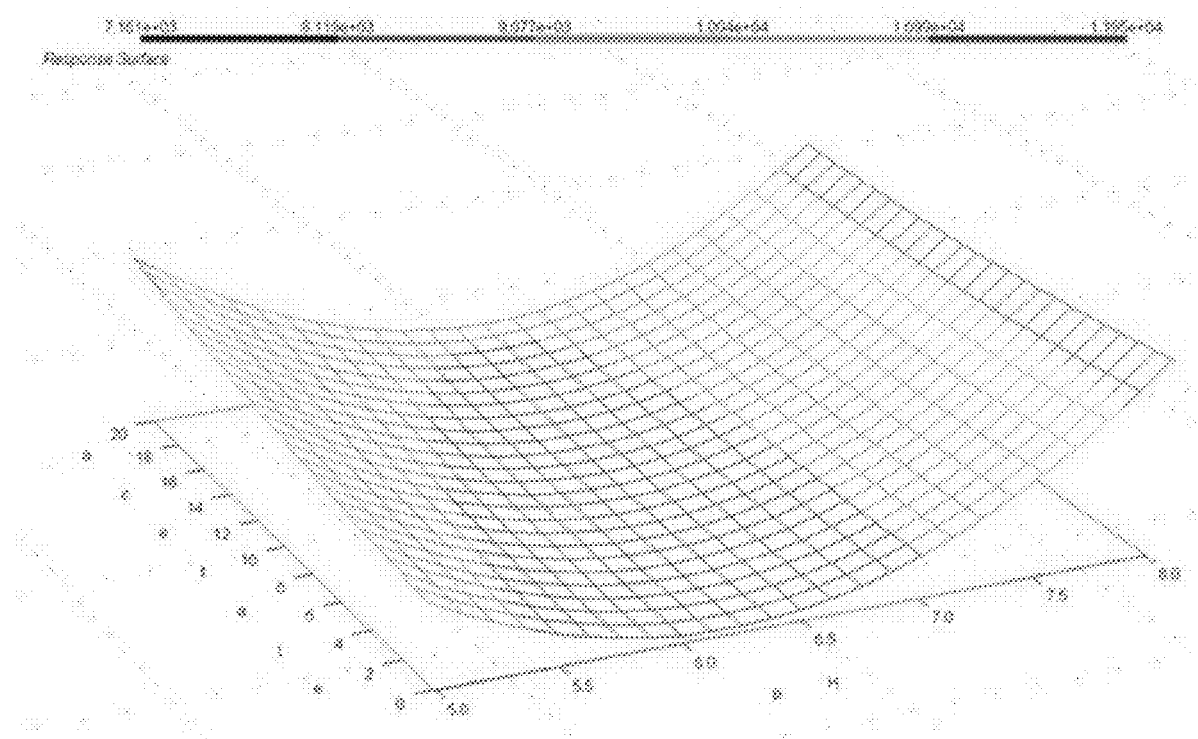
FIG. 29 is a graphic showing the effect of pH and acetate according to the PLS2 model using the total particle concentration (counts per mL) at t1 w/40° C., t2 w/25° C., and t4 w/5° C. as the endpoints. The protein concentration was fixed at 40 mg/mL.
Figure 30:
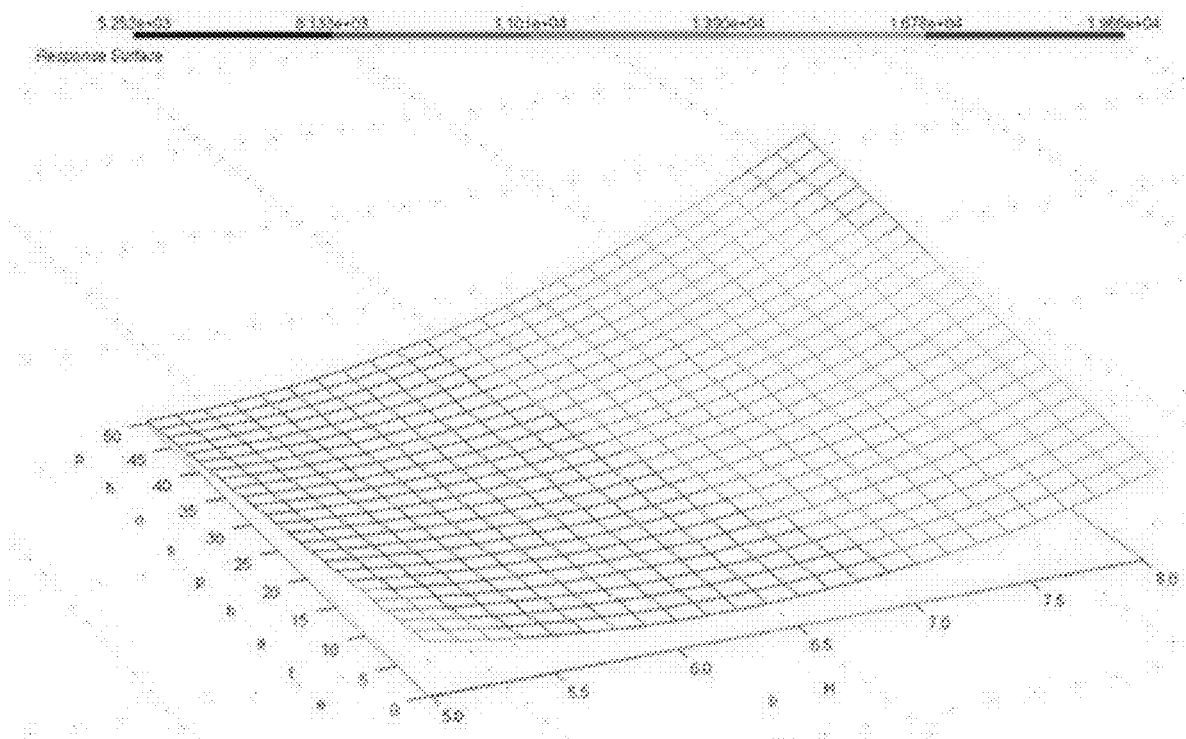
FIG. 30 is a graphic showing the effect of pH and phosphate according to the PSL2 model using the total particle concentration (counts per mL) at t1 w/40° C., t2 w/25° C., and t4 w/5° C. as the endpoints. The protein concentration was fixed at 40 mg/mL.

The response surface for pH and His shows a clear minimum corresponding to the optimal pH of about 6.2 for minimizing particle formation (FIG. 28). Addition of His results in a slight increase in particle levels, as is seen for acetate (FIG. 29), but the increases are quite small for both buffers. Use of phosphate buffer shows a sizable increase in particles when employed at higher pH conditions (FIG. 30), but little, if any effect at lower pH except for shifting the pH optimum towards pH 5.0.

Figure 31:
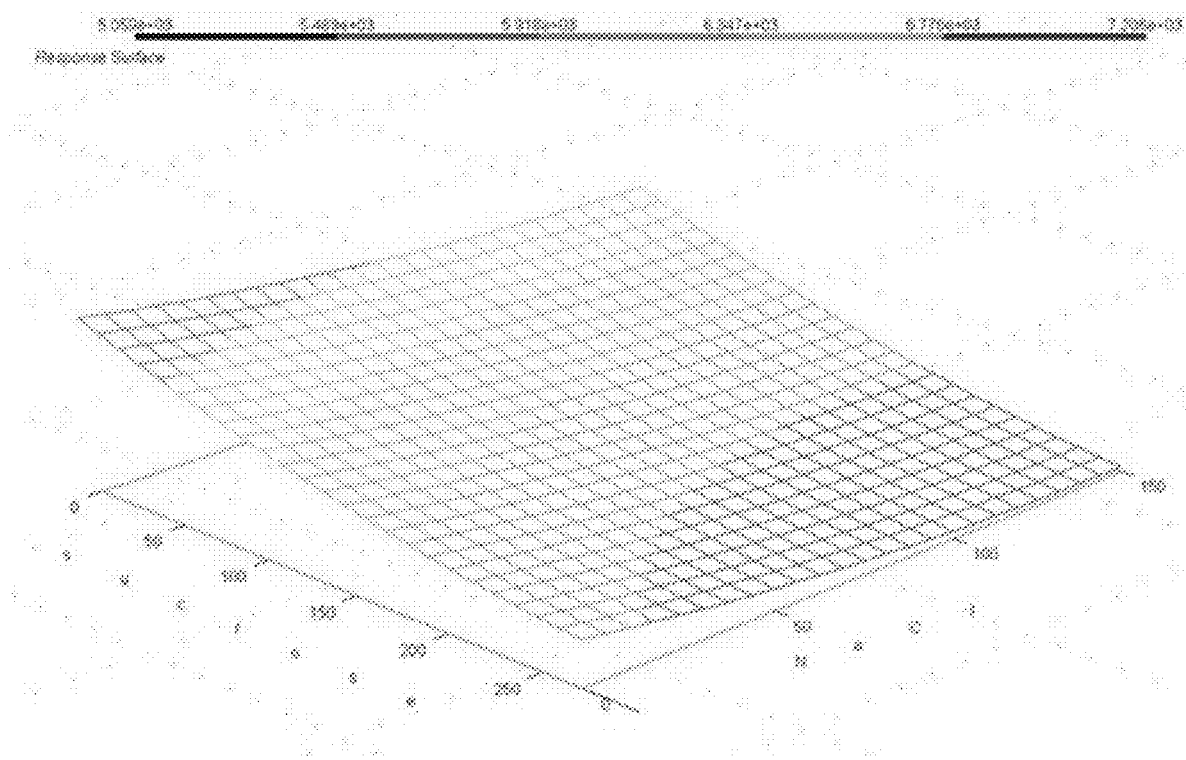
FIG. 31 is a graphic showing the effect of sucrose and NaCl according to the PSL2 model using the total particle concentration (counts per mL) at t1 w/40° C., t2 w/25° C., and t4 w/5° C. as the endpoints. The protein concentration was fixed at 40 mg/mL.
Figure 32:
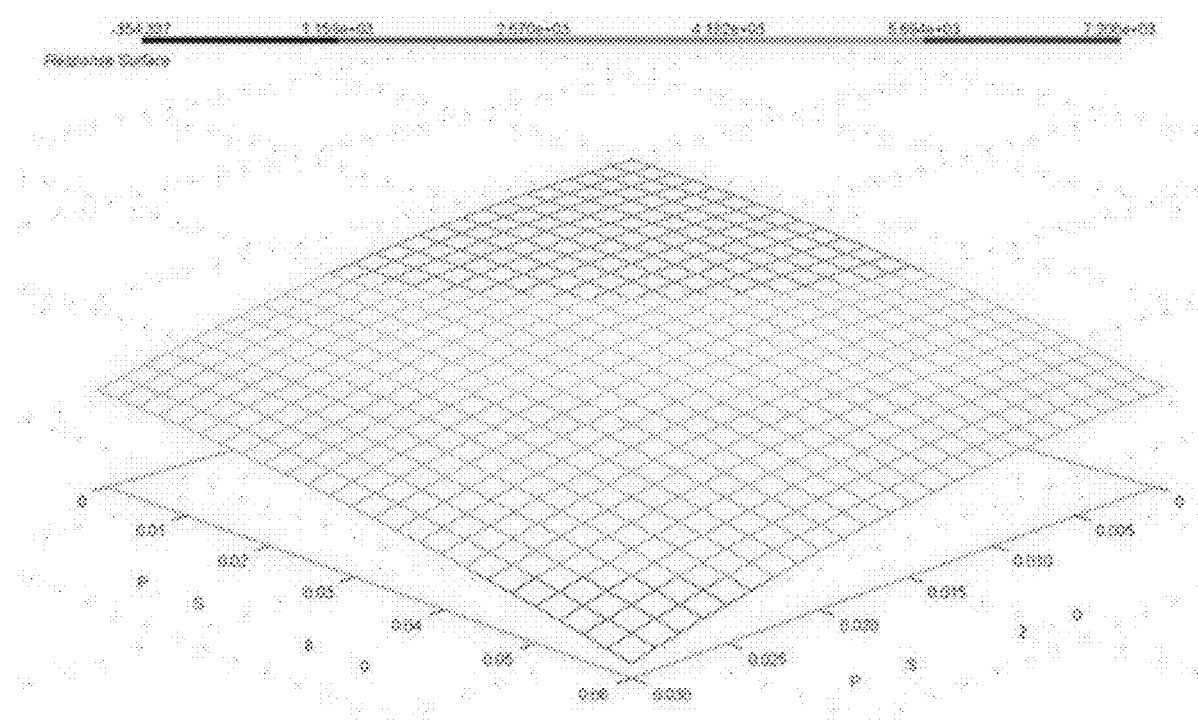
FIG. 32 is a graphic showing the effect of PS20 and PS80 according to the PSL2 model using the total particle concentration (counts per mL) at t1 w/40° C., t2 w/25° C., and t4 w/5° C. as the endpoints. The protein concentration was fixed at 40 mg/mL and the pH set at 6.0.
Figure 33:
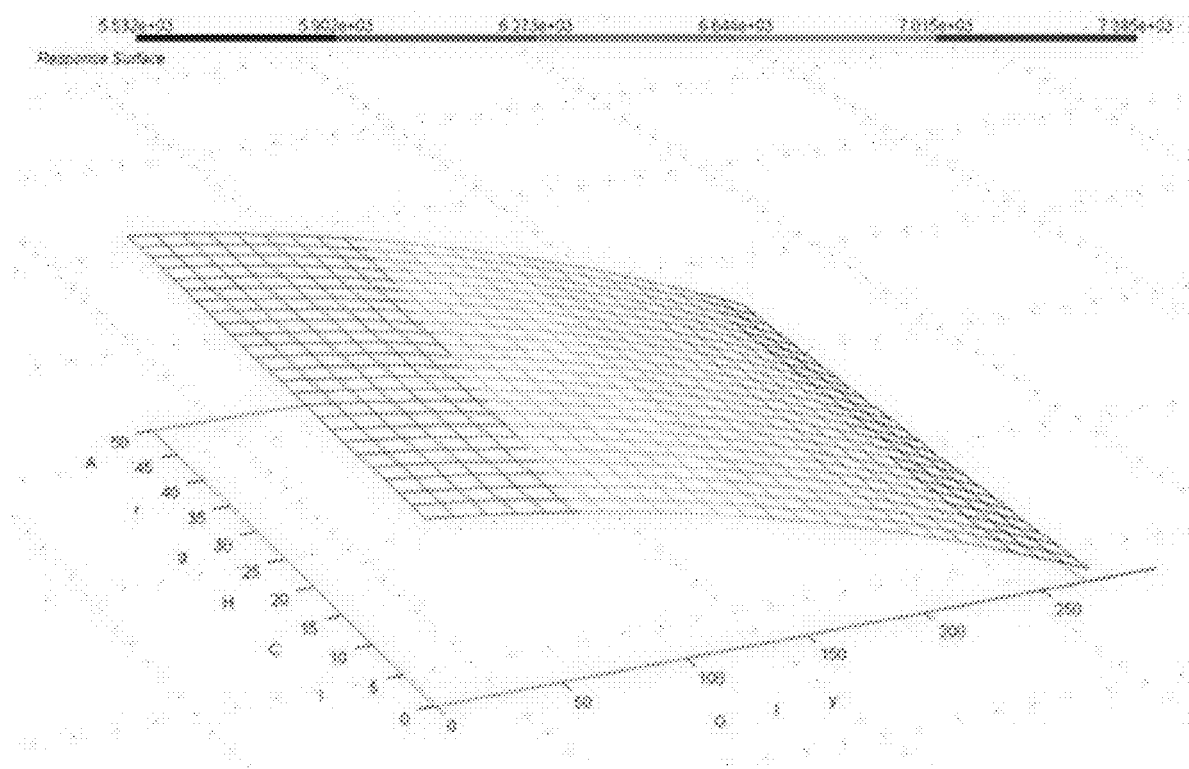
FIG. 33 is a graphic showing the effect of glycine and ArgHCl according to the PSL2 model using the total particle concentration (counts per mL) at t1 w/40° C., t2 w/25° C., and t4 w/5° C. as the endpoints. The protein concentration was fixed at 40 mg/mL and the pH set at 6.0.
Figure 34:
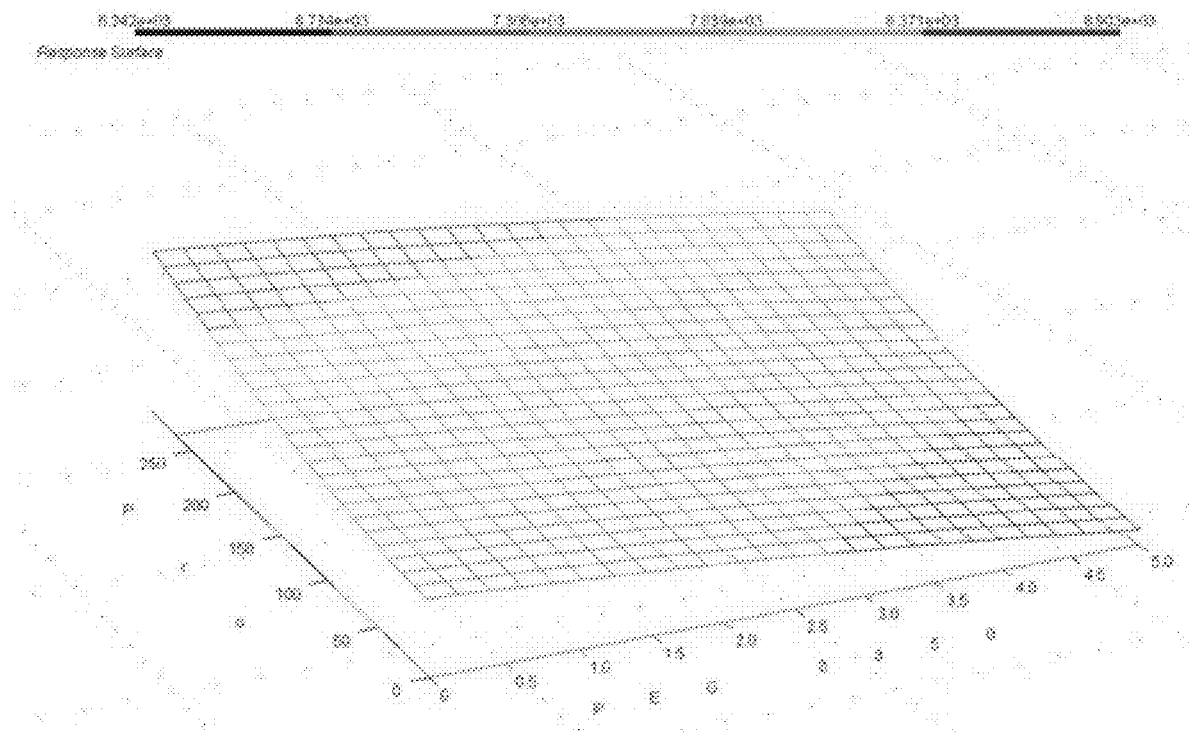
FIG. 34 is a graphic showing the effect of proline and PEG 3350 according to the PLS2 model using the total particle concentration (counts per mL) at t1 w/40° C., t2 w/25° C., and t4 w/5° C. as the endpoints. The protein concentration was fixed at 40 mg/mL and the pH set at 6.0.
Figure 35:
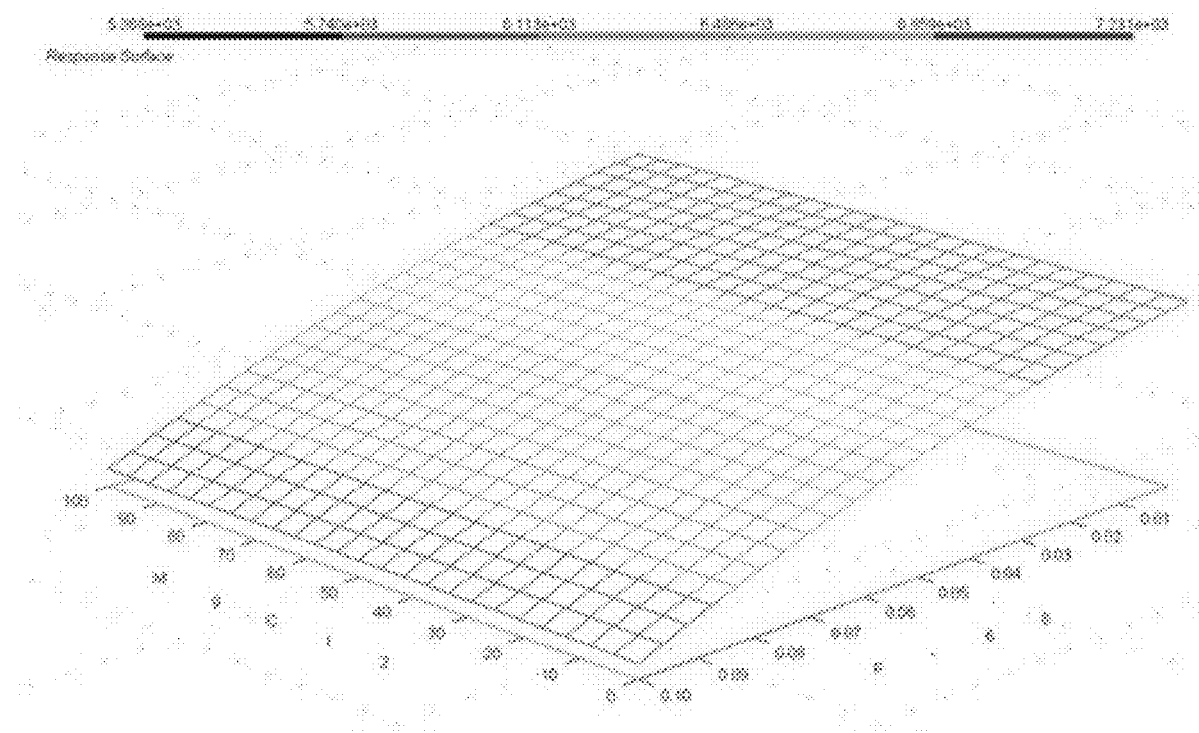
FIG. 35 is a graphic showing the effect of Pluronic F-68 and magnesium chloride according to the PLS2 model using the total particle concentration (counts per mL) at t1 w/40° C., t2 w/25° C., and t4 w/5° C. as the endpoints. The protein concentration was fixed at 40 mg/mL and the pH set at 6.0.

Addition of both sucrose and NaCl result in modest decreases in the levels of SVPs at pH 6.0 (FIG. 31). Reductions in particle counts are even greater when using polysorbate surfactants (PS 20, PS 80) (FIG. 32). In general, amino acids were not very effective at reducing the amounts of SVPs. While Gly showed some degree of stabilization, ArgHCl has essentially no effect (FIG. 33), while Pro actually increased particle levels (FIG. 34). Like its effect on aggregate levels measured by SEC, PEG 3350 reduced particle levels somewhat (FIG. 34). The non-ionic, polymeric surfactant Pluronic F-68 (poloxamer 188) also reduced particle levels, while MgCl$_2$ has no impact (FIG. 35).

Figure 36:
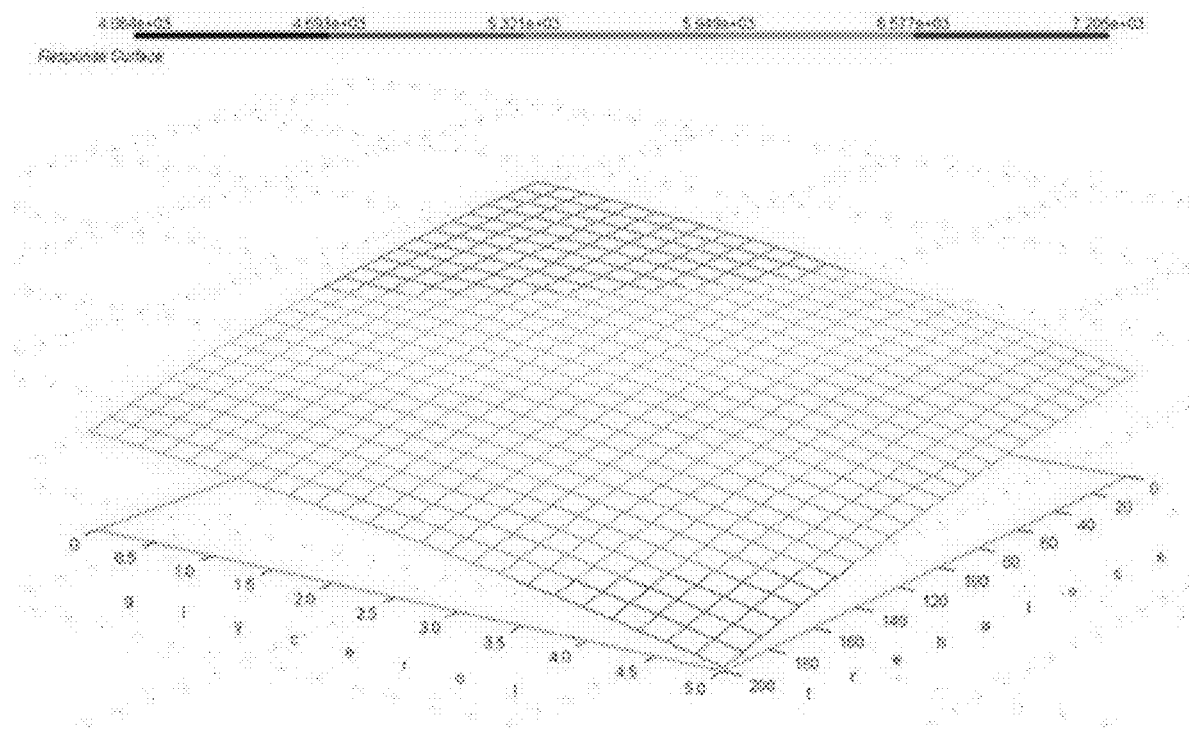
FIG. 36 is a graphic showing the effect of trehalose and glycerol according to the PLS2 model using the total particle concentration (counts per mL) at t1 w/40° C., t2 w/25° C., and t4 w/5° C. as the endpoints. The protein concentration was fixed at 40 mg/mL and the pH set at pH 6.0.
Figure 37:
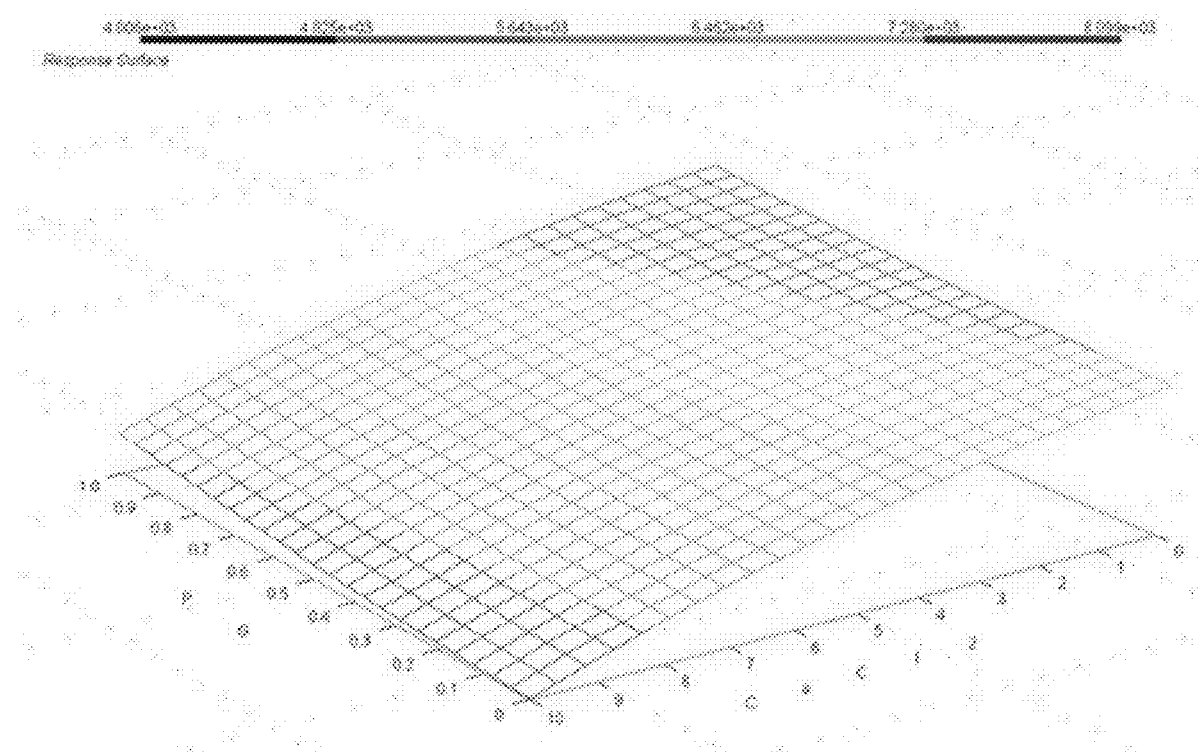
FIG. 37 is a graphic showing the effect of propylene glycol (PG) and calcium chloride according to the PLS2 model using the total particle concentration (counts per mL) at t1 w/40° C., t2 w/25° C., and t4 w/5° C. as the endpoints. The protein concentration was fixed at 40 mg/mL and the pH set at 6.0.

According to this model, trehalose and glycerol both reduced particle levels somewhat (FIG. 36), comparable to what was seen with sucrose and NaCl. By comparison, propylene glycol (PG) did not impact SVP levels, while CaCl$_2$) did provide some degree of stabilization (FIG. 37).

Overall, the PLS2 model for total particles concentration (counts per mL) indicates that the optimal pH is near 6.3, although the range is roughly from 5.5. to 7.0. Both acetate and His were seen to increase particle levels slightly, but neither altered the optimal pH significantly. Co-solvents/surfactants were mostly effective at lowering SVP levels. PS 20 and PS 80 were more effective than F-68 and glycerol, which were more effective than PEG 3350, which was more effective than PG). Of the amino acids, only Gly showed any appreciable effect on reducing particle formation. Sucrose and trehalose, along with NaCl and CaCl$_2$) effectively reduced SVP levels to some degree. Other sugars and polyols are expected to have similar stabilizing effects.

Example 13—Factors Contributing to Chemical Stability

The average measured isoelectric points for each of the 12 peaks in the icIEF data for the formulations in the blocks above is listed in Table 100 below. The measured pI values for each feature were used, along with the relative areas listed above, to calculate the average pI value for each sample. Then, for each stored sample, these were compared to the values at T=0. This was the metric used for the PLS modeling. The best model used data from samples stored at 5° C. In all cases, a number of formulations were marked as outliers.

TABLE 100

| Formulation | Avg. pI for each icIEF peak | | | | | | | | | | | |
|---|---|---|---|---|---|---|---|---|---|---|---|---|
| Block | 1 | 2 | 3 | 4 | 5 | 6 | 7 | 8 | 9 | 10 | 11 | 12 |
| Block A | 6.69 | 6.77 | 6.87 | 6.96 | 7.05 | 7.16 | 7.27 | 7.39 | 7.55 | 7.73 | 7.96 | 8.18 |
| Block B | 6.66 | 6.74 | 6.84 | 6.93 | 7.02 | 7.12 | 7.24 | 7.35 | 7.50 | 7.64 | 7.84 | 8.07 |
| Block C | 6.66 | 6.74 | 6.84 | 6.92 | 7.01 | 7.11 | 7.22 | 7.34 | 7.47 | 7.67 | 7.86 | 8.07 |
| Block D | 6.76 | 6.84 | 6.93 | 7.01 | 7.10 | 7.20 | 7.32 | 7.44 | 7.57 | 7.83 | 8.01 | 8.19 |
| Block E | 6.77 | 6.85 | 6.94 | 7.03 | 7.11 | 7.22 | 7.34 | 7.46 | 7.59 | 7.73 | 7.91 | 8.11 |
| Block F | 6.65 | 6.73 | 6.83 | 6.91 | 7.01 | 7.11 | 7.22 | 7.35 | 7.49 | 7.64 | 7.84 | 8.07 |
| Block G | 6.65 | 6.74 | 6.83 | 6.92 | 7.01 | 7.10 | 7.22 | 7.34 | 7.47 | 7.64 | 7.83 | 8.07 |

A PLS1 model was constructed using the change or difference in average pI value for samples stored at 5° C. as the endpoint. The model quality was lower than for the previous models, but the results still are sufficient to allow some indication of the effect of various factors, especially pH and buffers. Likely, these would be the most influential on chemical processes leading to differences in pI value.

Figure 38:
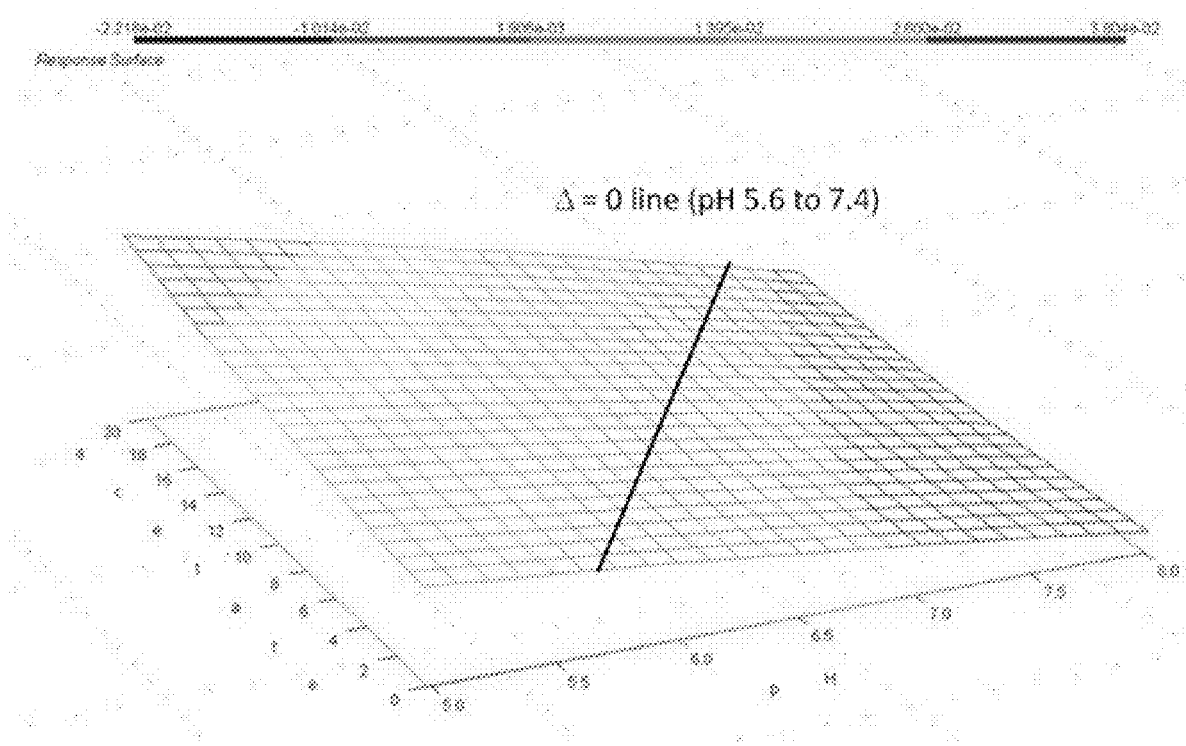
FIG. 38 is a graphic showing the effect of pH and acetate according to the PLS1 model using the difference in average pI value at t4 w/5° C. (compared to t0) as the endpoint. The protein concentration is fixed at 40 mg/mL.
Figure 39:
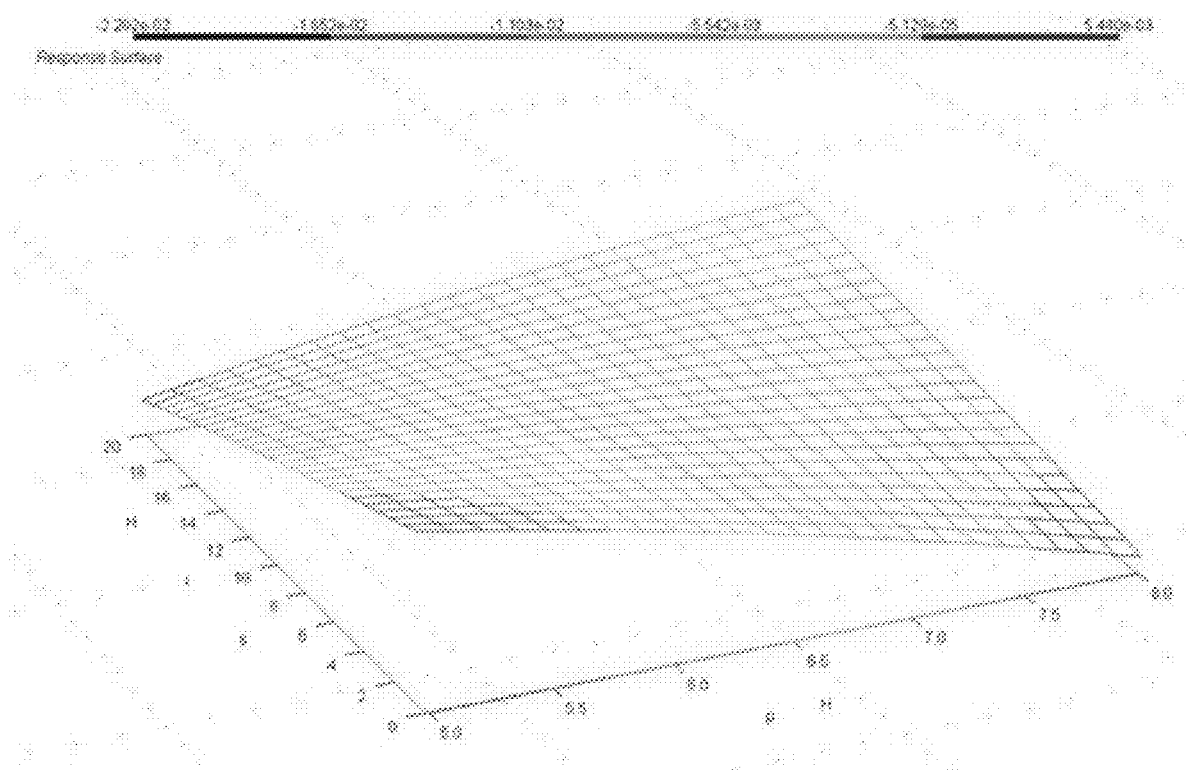
FIG. 39 is a graphic showing the e Effect of pH and His according to the PLS1 model using the difference in average pI value at t4 w/5° C. (compared to t0) as the endpoint. The protein concentration is fixed at 40 mg/mL.
Figure 40:
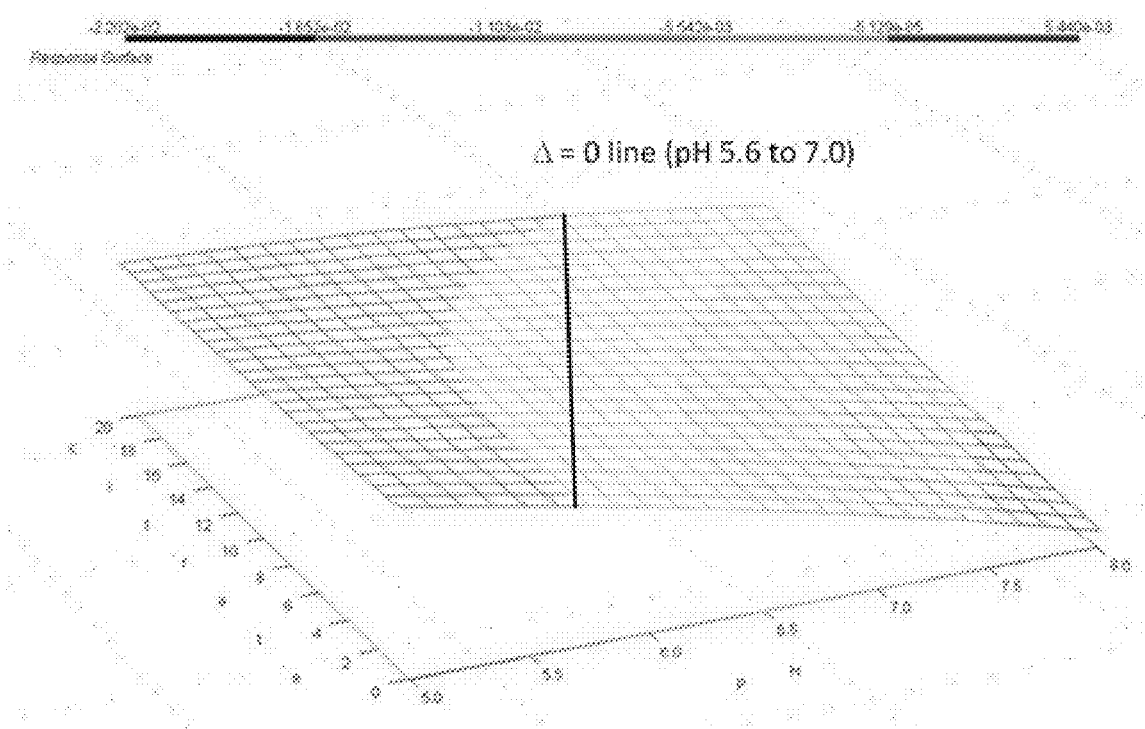
FIG. 40 is a graphic showing the effect of pH and citrate according to the PLS1 model using the difference in average pI value at t4 w/5° C. (compared to t0) as the endpoint. The protein concentration is fixed at 40 mg/mL.

FIG. 38 shows the response surface for pH and acetate. A line has been drawn in to mark the line where no change in pI (Δ) value occurs. In a buffer-free system, the model predicts the optimal pH is close to 5.6. In the presence of 20 mM acetate, this value shifts all the way to 7.4. A similar trend is seen for using citrate buffer (FIG. 40). However, with His buffer, the effect of pH on A is evened out, but does not reach 0 at a concentration of 20 mM (FIG. 39).

Figure 41:
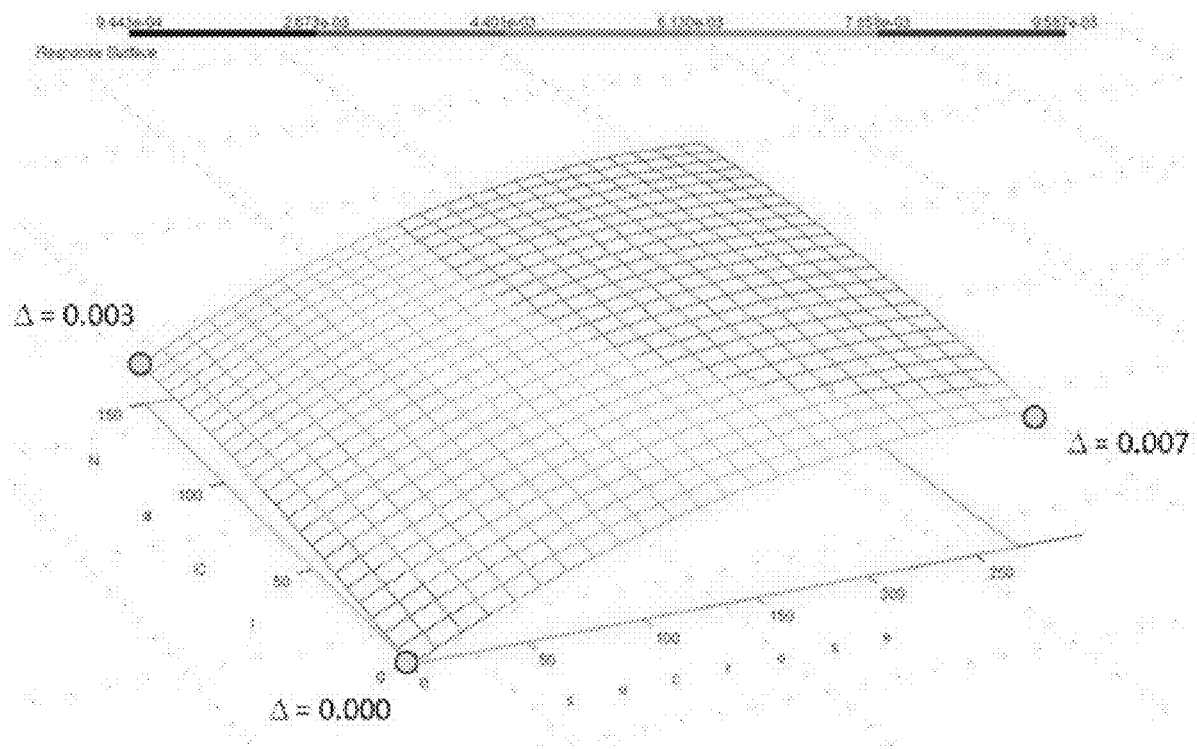
FIG. 41 is a graphic showing the effect of sucrose and NaCl according to the PLS1 model using the difference in average pI value at t4 w/5° C. (compared to t0) as the endpoint. The protein concentration is fixed at 40 mg/mL and the pH is set to 5.6.
Figure 42:
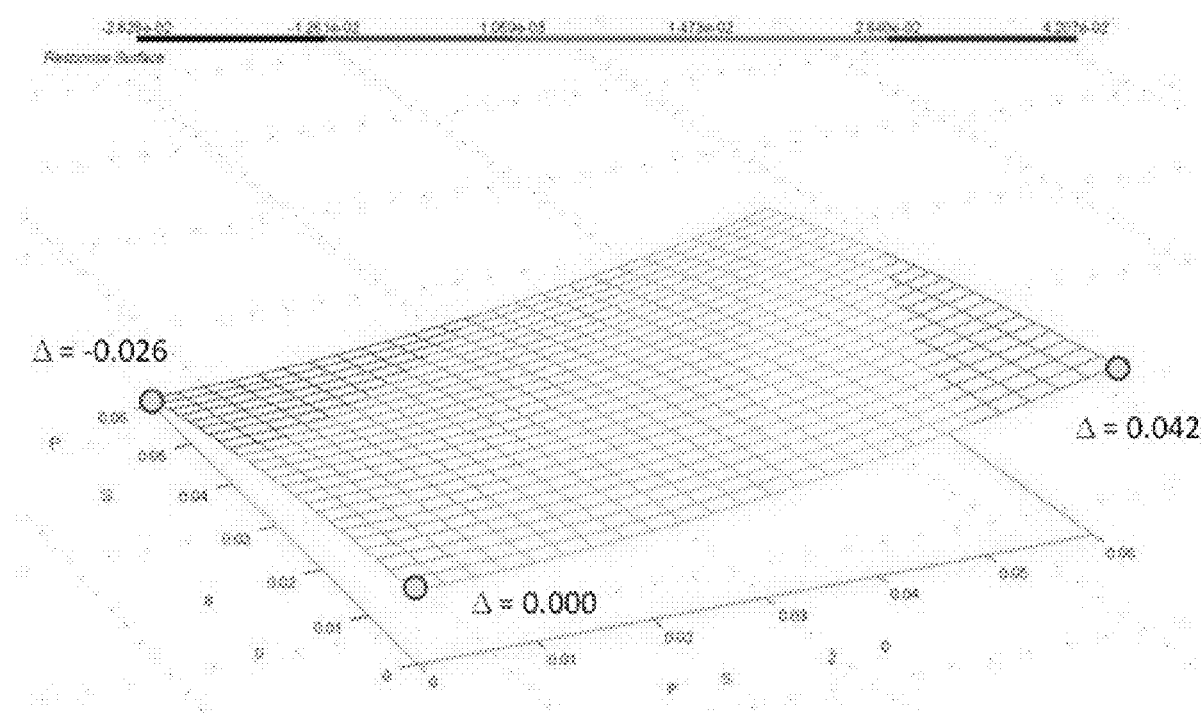
FIG. 42 is a graphic showing the effect of PS 20 and PS 80 according to the PLS1 model using the difference in average pI value at t4 w/5° C. (compared to t0) as the endpoint. The protein concentration is fixed at 40 mg/mL and the pH is set to 5.6.
Figure 43:
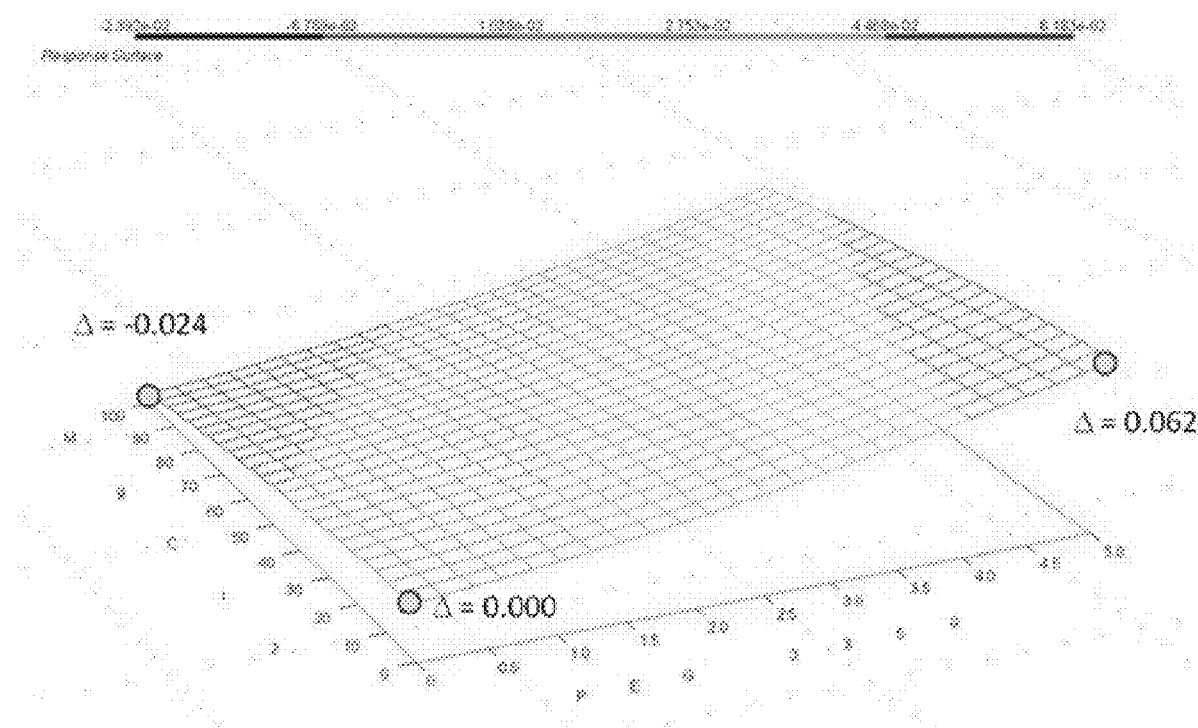
FIG. 43 is a graphic showing the effect of PEG 3350 and $MgCl_2$ according to the PLS1 model using the difference in average pI value at t4 w/5° C. (compared to t0) as the endpoint. The protein concentration is fixed at 40 mg/mL and the pH is set to 5.6.
Figure 44:
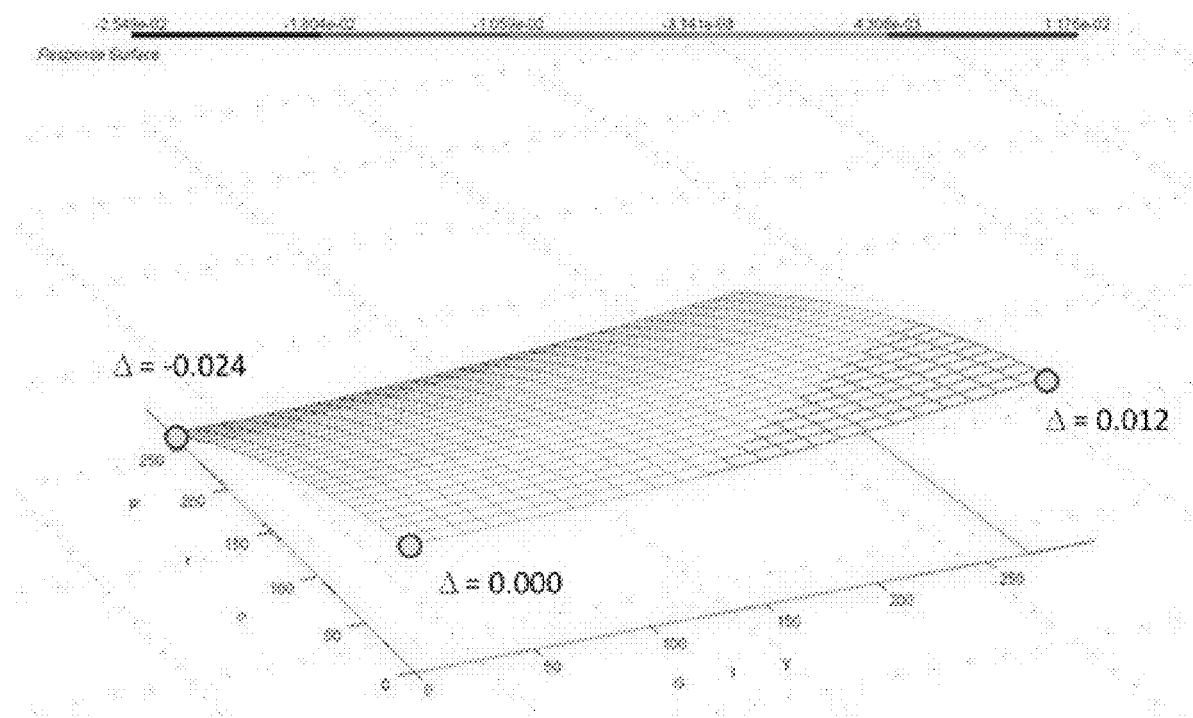
FIG. 44 is a graphic showing the effect of Gly and Pro according to the PLS1 model using the difference in average pI value at t4 w/5° C. (compared to t0) as the endpoint. The protein concentration is fixed at 40 mg/mL and the pH is set to 5.6.
Figure 45:
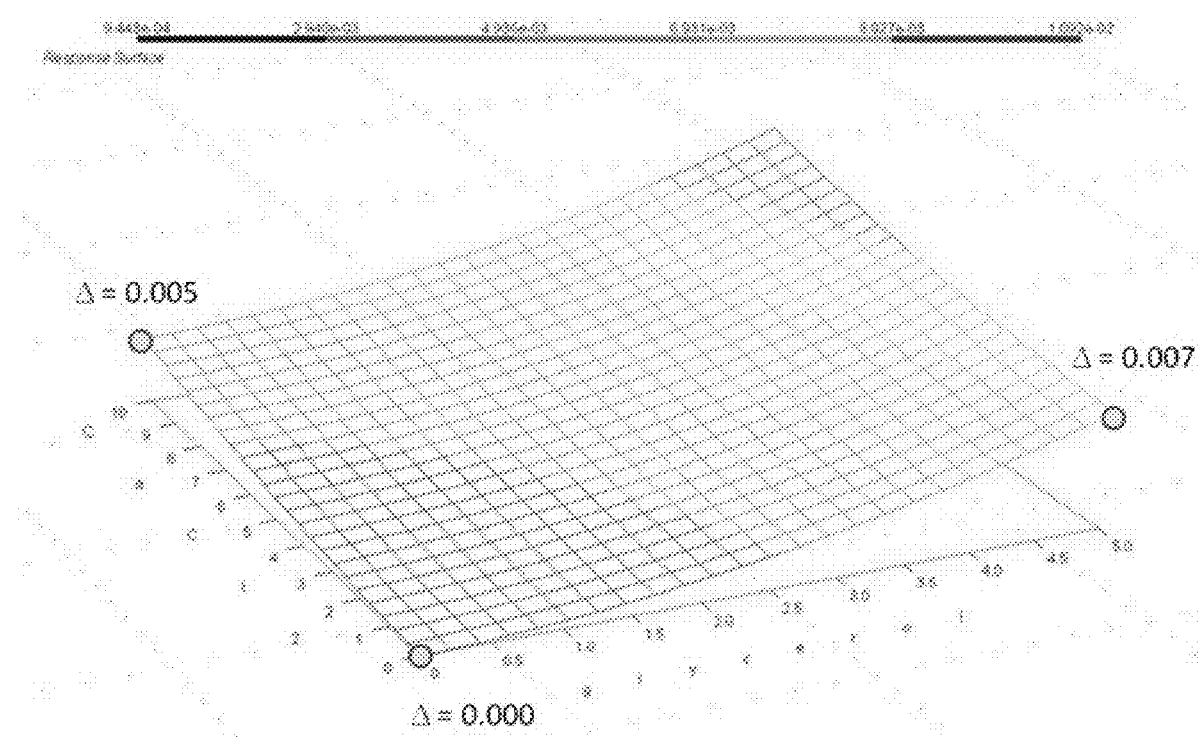
FIG. 45 is a graphic showing the effect of glycerol and $CaCl_2$ according to the PLS1 model using the difference in average pI value at t4 w/5° C. (compared to t0) as the endpoint. The protein concentration is fixed at 40 mg/mL and the pH is set to 5.6.

In the response surfaces of FIGS. 42-46, the pH is set at 5.6, the point where A is effectively zero. This allows the relative impact of an excipient to be evaluated quantitatively (at least within the error of the model). For sucrose and NaCl, each lead to a slight, but almost imperceptible rise in A (FIG. 41). By comparison, both PS 20 and PS 80 exhibit a much bigger effect on A, although they trend in opposite directions (FIG. 42). PEG 3350 has an even larger effect on A (FIG. 43), indicating that co-solvents, in general, facilitate chemical degradation seen by icIEF. MgCl$_2$ also leads to a relatively sizable change in A (FIG. 43), unlike NaCl. The effect of Pro is nearly identical to that of MgCl$_2$ (FIG. 44), while Gly trends in the opposite direction.

Figure 46:
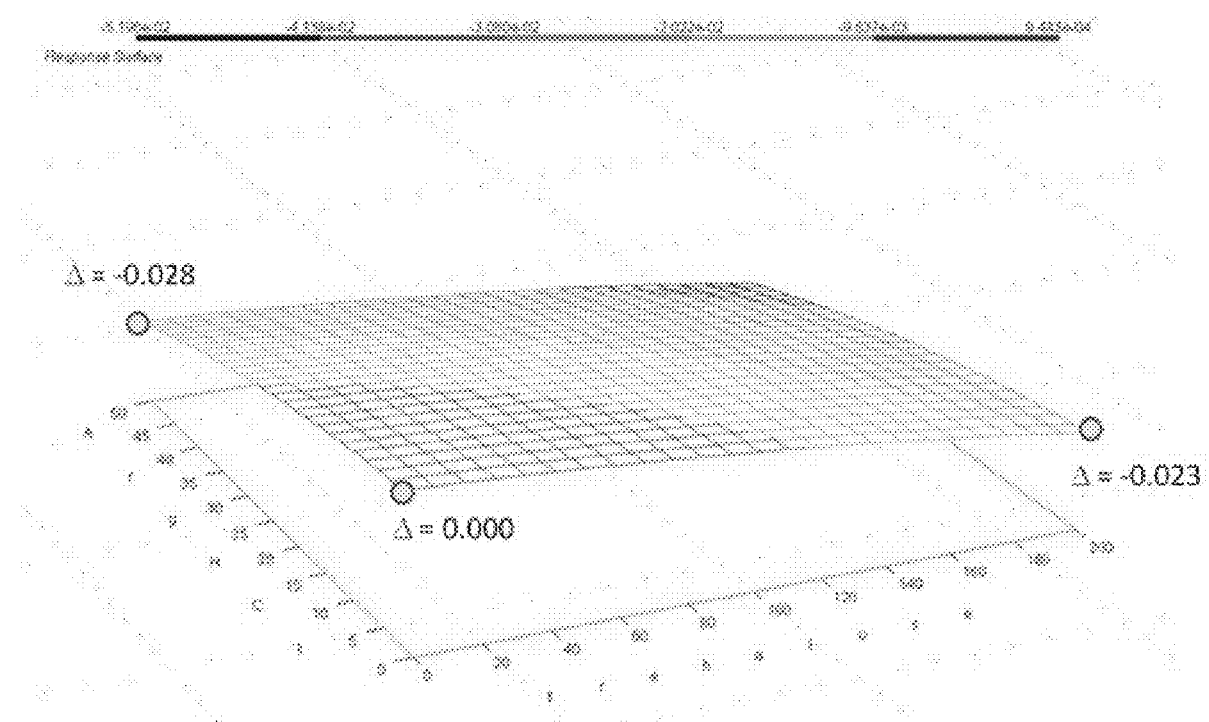
FIG. 46 is a graphic showing the effect of ArgHCl and trehalose according to the PLS1 model using the difference in average pI value at t4 w/5° C. (compared to t0) as the endpoint. The protein concentration is fixed at 40 mg/mL and the pH is set to 5.6.

Glycerol appears to have the smallest effect on A of the co-solvents, while CaCl$_2$ has little impact as well (FIG. 45), much like the effects seen with sucrose and NaCl. Finally, trehalose appears to have a larger impact on A than sucrose, while ArgHCl has an effect much like that of Pro (FIG. 46).

Example 14—Discussion of Formulations and Stability

The stability of the formulations from the blocks were evaluated.

Physical Stability by Size Exclusion Chromatography

An examination of the most stable formulations after one week at 40° C. shows that 49 of the 110 novel formulations surpassed the stability exhibited on average by the Eylea formulation. Among these, the two most stable (F-2 and F-4) were buffer-free and co-solvent-free. Formulation B-2 is buffer-free, while formulations D-1 and D-2 were co-solvent-free. This summary indicates that both general strategies for obtaining a stable, formulation are viable, at least in terms of storage stability. Most of these formulations are based on sucrose, but Gly and Pro both were found to provide significant stabilization.

TABLE 101

List of fifteen most stable formulations after one week at 40° C. based on monomer content by SEC

| Form No. | SEC (%) Main Peak 1 Week, 40° C. |
|---|---|
| F-2 | 98.94 |
| F-4 | 98.62 |
| B-2 | 98.56 |
| D-1 | 98.46 |
| D-2 | 98.36 |
| F-7 | 98.33 |
| E-1 | 98.32 |
| D-9 | 98.28 |
| C-2 | 98.25 |
| G-17 | 98.24 |
| G-21 | 98.22 |
| D-7 | 98.20 |
| F-3 | 98.19 |
| G-22 | 98.18 |
| G-18 | 98.18 |

TABLE 102

List of fifteen most stable formulations after four weeks at 5° C. based on monomer content by SEC

| Form No. | SEC (%) Main Peak 4 Week, 5° C. |
|---|---|
| F-2 | 99.14 |
| G-17 | 99.13 |
| F-1 | 99.08 |
| G-1 | 99.04 |
| G-16 | 99.02 |
| F-3 | 99.01 |
| F-14 | 99.01 |
| G-14 | 99.01 |
| F-13 | 99.00 |
| G-23 | 98.98 |
| F-4 | 98.98 |
| G-24 | 98.97 |
| G-22 | 98.95 |
| F-8 | 98.95 |

When one considers 5° C. storage for four weeks, 47 of the 110 formulations outperform the average of the two Eylea compositions. Interestingly, two of the most stable at 5° C. (F-1 and F-2) were also one of the most stable at 40° C. Included in this list, are seven formulations that are buffer-free and co-solvent-free. The optimal pH is mostly 6.0 to 6.3 in these preparations. Again, sucrose is a good stabilizer, although the addition of 10 mM CaCl$_2$ appears to be beneficial. On this list, formulations from Block A were not listed, as they contained no tonicity modifiers, but many of them exhibited relatively high stability indicating that an aflibercept formulation can be buffered with one the buffers in Block A.

The results of storage at 5° C. are particularly relevant since the Eylea package insert states "EYLEA should be refrigerated at 2° C. to 8° C. (36° F. to 46° F.). Do Not Freeze." Thus, formulations that are stable at 5° C., including a biosimilar of Eylea, are suitable for commercial use.
Discussion The results of the stability studies show that the pH range at which aflibercept is physically stable also provides chemical stability.

Seven blocks of formulations, encompassing over 110 discrete formulations of aflibercept were prepared and evaluated for storage stability at various temperatures in comparison with the current Eylea formulation. Many of the new formulations appear to exhibit greater stability than the Eylea composition. Stability was measured using SEC, MFI, and icIEF. The stability as determined by SEC was examined using PLS modeling for each of the storage temperatures. While the outcomes from the three models differed to some degree, they provided a mostly coherent description of the most stable formulations. The optimal pH appears to be between 5.0 and 6.0.

For buffered formulations, both acetate and His appear to be suitable choices for buffers, based on their effects on stability and their buffering capacities in this pH range.

Sucrose appears to be potent stabilizer, while many of the co-solvents tested appear to provide some stabilization as well in terms of recovery of monomer as measured by SEC upon storage. Of the co-solvents, PEG 3350 appears to be the least favorable, while PS 20, PS 80, and glycerol would be the better choices. However, PEG provided stability at lower temperatures (e.g. 5° C.) indicating that it may suitable for aflibercept since Eylea requires storage at 2-8° C. Trehalose may also be a good choice for a stabilizer. Amino acids provide some degree of stabilization, with Gly being the most consistent in terms of stabilization performance. $CaCl_2$), at a concentration of 10 mM, appears to provide a measurable improvement in storage stability. Without being limited to any particular theory, this stability is a result of $Ca^{2+}$ binding to aflibercept and providing conformational stability.

In terms of subvisible particle formation, the optimal pH range was from 5.5 to 7.0, more preferably at about 6.3. So, the range overlaps with optimal range determined by SEC analysis. Again, for buffered formulations, acetate and His appear to be favorable buffer choices. Co-solvents appear to reduce SVP formation upon storage, along with sucrose, trehalose, NaCl, and $CaCl_2$.

Chemical stability was assessed using icIEF, where small, but discernible differences in pI were observed upon storage. PLS analysis of these differences produced a poorer quality model, but still allowed one to discern that the optimal pH was near 5.6, at least for a buffer-free system. Inclusion of a buffer has a small effect, but tends to shift the optimal pH upward. Sucrose, NaCl, and $CaCl_2$) appears to be favorable stabilizers, while glycerol is predicted to be the most effective co-solvent.

Overall, these studies provide a basis for the conclusion that the formulations of aflibercept disclosed herein will be commercially viable. In addition, these results indicate that an aflibercept formulation that is buffer-free, a co-solvent-free, or both buffer-free and a co-solvent-free is technically achievable.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An aqueous formulation comprising:
   a. about 30 mg/mL to about 50 mg/mL aflibercept;
   b. between about 1 mM and about 250 mM sucrose; and
   c. polysorbate, polyethylene glycol (PEG), or combinations thereof,
   wherein the formulation is free of buffer, the pH of the formulation is about 5.5 to about 7.0, and the formulation is stable at 25° C. for 2 weeks or 40° C. for 1 week.

2. The aqueous formulation of claim 1, wherein the polysorbate is polysorbate 20.

3. The aqueous formulation of claim 1, wherein the polyethylene glycol (PEG) is PEG 3350.

4. The aqueous formulation of claim 2, wherein the aqueous formulation comprises about 0.03% polysorbate 20.

5. The aqueous formulation of claim 1, further comprising a salt.

6. The aqueous formulation of claim 3, wherein the aqueous formulation comprises between about 1% and about 5% PEG 3350.

7. The aqueous formulation of claim 1, wherein the formulation is suitable for ophthalmic administration.

8. The aqueous formulation of claim 5, wherein the salt comprises sodium chloride, magnesium chloride, calcium chloride, or combinations thereof.

9. The aqueous formulation of claim 8, wherein the salt comprises sodium chloride.

10. The aqueous formulation of claim 9, wherein the aqueous formulation comprises about 40 mM to about 150 mM sodium chloride.

11. The aqueous formulation of claim 10, wherein the aqueous formulation comprises about 40 mM sodium chloride.

12. The aqueous formulation of claim 10, wherein the aqueous formulation comprises about 75 mM sodium chloride.

13. The aqueous formulation of claim 10, wherein the aqueous formulation comprises about 150 mM sodium chloride.

14. The aqueous formulation of claim 1, wherein the aqueous formulation comprises about 150 mM sucrose.

15. The aqueous formulation of claim 1, wherein the aqueous formulation comprises about 200 mM sucrose.

16. The aqueous formulation of claim 1, wherein the aqueous formulation comprises about 250 mM sucrose.

17. The aqueous formulation of claim 1, wherein the aqueous formulation comprises polysorbate and polyethylene glycol.

18. An aqueous formulation comprising:
    a. about 30 mg/mL to about 50 mg/mL aflibercept;
    b. between about 25 mM and about 280 mM of an amino acid; and
    c. polysorbate,
    wherein the formulation is free of buffer, the pH of the formulation is about 6.0 to about 7.0, and the formulation is stable at 25° C. for 2 weeks or 40° C. for 1 week.

19. The aqueous formulation of claim 18, wherein the amino acid comprises glycine, arginine, or proline.

20. The aqueous formulation of claim 18, wherein the amino acid comprises glycine.

21. The aqueous formulation of claim 18, wherein the amino acid comprises about 270 mM glycine.

22. The aqueous formulation of claim 18, wherein the amino acid comprises arginine.

23. The aqueous formulation of claim 18, wherein the amino acid comprises between about 25 mM and 50 mM arginine.

24. The aqueous formulation of claim 18, wherein the amino acid comprises proline.

25. The aqueous formulation of claim 18, wherein the amino acid comprises about 270 mM proline.

26. The aqueous formulation of claim 18, wherein the aqueous formulation further comprises a salt.

27. The aqueous formulation of claim 26, wherein the salt comprises between about 40 mM and about 150 mM sodium chloride.

28. The aqueous formulation of claim 26, wherein the salt comprises between about 75 mM and 100 mM magnesium chloride.

29. The aqueous formulation of claim 18, wherein the aqueous formulation further comprises dextran.

30. The aqueous formulation of claim 18, wherein the aqueous formulation comprises 0.03% polysorbate 20.

\* \* \* \* \*